(12) United States Patent  
Simpson et al.

(10) Patent No.: US 7,761,130 B2
(45) Date of Patent: Jul. 20, 2010

(54) DUAL ELECTRODE SYSTEM FOR A CONTINUOUS ANALYTE SENSOR

(75) Inventors: Peter C. Simpson, Encinitas, CA (US); James H. Brauker, San Diego, CA (US); Paul V. Goode, Cherry Hill, NJ (US); Apurv U. Kamath, San Diego, CA (US); James R. Petisce, San Diego, CA (US); Kum Ming Woo, San Diego, CA (US); Melissa A. Nicholas, San Diego, CA (US); Robert J. Boock, San Diego, CA (US); Monica A. Rixman, San Diego, CA (US); John Burd, San Diego, CA (US); Rathbun K. Rhodes, Madison, WI (US); Mark A. Tapsak, Orangeville, PA (US)

(73) Assignee: DexCom, Inc., San Diego, CA (US)

( * ) Notice: Subject to any disclaimer, the term of this patent is extended or adjusted under 35 U.S.C. 154(b) by 136 days.

(21) Appl. No.: 11/692,154

(22) Filed: Mar. 27, 2007

(65) Prior Publication Data

US 2007/0213611 A1    Sep. 13, 2007

Related U.S. Application Data

(63) Continuation-in-part of application No. 11/543,539, filed on Oct. 4, 2006, now Pat. No. 7,467,003, which is a continuation-in-part of application No. 11/004,561, filed on Dec. 3, 2004.

(60) Provisional application No. 60/527,323, filed on Dec. 5, 2003, provisional application No. 60/587,787, filed on Jul. 13, 2004.

(51) Int. Cl.
    *A61B 5/00* (2006.01)
(52) U.S. Cl. .................. 600/345; 600/347; 600/365
(58) Field of Classification Search .............. None
    See application file for complete search history.

(56) References Cited

U.S. PATENT DOCUMENTS

| 1,564,641 | A | 12/1925 | St. James |
| 2,402,306 | A | 6/1946 | Turkel |

(Continued)

FOREIGN PATENT DOCUMENTS

EP        0 098 592        1/1984

(Continued)

OTHER PUBLICATIONS

Atanasov, et al. 1994. Biosensor for continuous glucose monitoring. Biotechnology and Bioengineering 43:262-266.

(Continued)

*Primary Examiner*—Robert L Nasser
(74) *Attorney, Agent, or Firm*—Knobbe Martens Olson & Bear LLP

(57) ABSTRACT

Disclosed herein are systems and methods for a continuous analyte sensor, such as a continuous glucose sensor. One such system utilizes first and second working electrodes to measure analyte or non-analyte related signal, both of which electrode include an interference domain.

21 Claims, 24 Drawing Sheets

U.S. PATENT DOCUMENTS

| | | |
|---|---|---|
| 3,210,578 A | 10/1965 | Sherer |
| 3,775,182 A | 11/1973 | Patton et al. |
| 3,791,871 A | 2/1974 | Rowley |
| 3,826,244 A | 7/1974 | Salcman et al. |
| 3,838,033 A | 9/1974 | Mindt et al. |
| 3,898,984 A | 8/1975 | Mandel et al. |
| 3,933,593 A | 1/1976 | Sternberg |
| 3,943,918 A | 3/1976 | Lewis |
| 3,957,613 A | 5/1976 | Macur |
| 3,982,530 A | 9/1976 | Storch |
| 4,052,754 A | 10/1977 | Homsy |
| 4,067,322 A | 1/1978 | Johnson |
| 4,240,889 A | 12/1980 | Yoda et al. |
| 4,253,469 A | 3/1981 | Aslan |
| 4,255,500 A | 3/1981 | Hooke |
| 4,340,457 A | 7/1982 | Kater |
| 4,378,016 A | 3/1983 | Loeb |
| 4,402,694 A | 9/1983 | Ash et al. |
| 4,403,984 A | 9/1983 | Ash et al. |
| 4,431,004 A | 2/1984 | Bessman et al. |
| 4,442,841 A | 4/1984 | Uehara et al. |
| 4,484,987 A | 11/1984 | Gough |
| 4,494,950 A | 1/1985 | Fischell |
| 4,545,382 A | 10/1985 | Higgins et al. |
| 4,554,927 A | 11/1985 | Fussell |
| 4,571,292 A | 2/1986 | Liu et al. |
| 4,578,215 A | 3/1986 | Bradley |
| 4,650,547 A | 3/1987 | Gough |
| 4,655,880 A | 4/1987 | Liu |
| 4,671,288 A | 6/1987 | Gough |
| 4,672,970 A | 6/1987 | Uchida et al. |
| 4,680,268 A | 7/1987 | Clark, Jr. |
| 4,685,463 A | 8/1987 | Williams |
| 4,703,756 A | 11/1987 | Gough et al. |
| 4,711,245 A | 12/1987 | Higgins |
| 4,721,677 A | 1/1988 | Clark |
| 4,726,381 A | 2/1988 | Jones |
| 4,731,726 A | 3/1988 | Allen |
| 4,757,022 A | 7/1988 | Shults et al. |
| 4,763,658 A | 8/1988 | Jones |
| 4,776,944 A | 10/1988 | Janata et al. |
| 4,786,657 A | 11/1988 | Hammar et al. |
| 4,787,398 A | 11/1988 | Garcia et al. |
| 4,795,542 A | 1/1989 | Ross et al. |
| 4,805,625 A | 2/1989 | Wyler |
| 4,810,470 A | 3/1989 | Burkhardt et al. |
| 4,813,424 A | 3/1989 | Wilkins |
| 4,822,336 A | 4/1989 | DiTraglia |
| 4,852,573 A | 8/1989 | Kennedy |
| 4,858,615 A | 8/1989 | Meinema |
| 4,861,830 A | 8/1989 | Ward, Jr. |
| 4,871,440 A | 10/1989 | Nagata et al. |
| 4,886,740 A | 12/1989 | Vadgama |
| 4,890,620 A | 1/1990 | Gough |
| 4,909,908 A | 3/1990 | Ross et al. |
| 4,919,141 A | 4/1990 | Zier et al. |
| 4,953,552 A | 9/1990 | DeMarzo |
| 4,955,861 A | 9/1990 | Enegren et al. |
| 4,970,145 A | 11/1990 | Bennetto et al. |
| 4,973,320 A | 11/1990 | Brenner et al. |
| 4,974,929 A | 12/1990 | Curry |
| 4,975,175 A | 12/1990 | Karube et al. |
| 4,994,167 A | 2/1991 | Shults et al. |
| 5,034,112 A | 7/1991 | Murase et al. |
| 5,050,612 A | 9/1991 | Matsumura |
| 5,063,081 A | 11/1991 | Cozzette et al. |
| 5,068,536 A | 11/1991 | Rosenthal |
| 5,089,112 A | 2/1992 | Skotheim et al. |
| 5,137,028 A | 8/1992 | Nishimura |
| 5,140,985 A | 8/1992 | Schroeder et al. |
| 5,155,149 A | 10/1992 | Atwater et al. |
| 5,165,407 A | 11/1992 | Wilson et al. |
| 5,183,549 A | 2/1993 | Joseph et al. |
| 5,198,771 A | 3/1993 | Fidler et al. |
| 5,200,051 A | 4/1993 | Cozzette et al. |
| 5,202,261 A * | 4/1993 | Musho et al. .......... 204/403.09 |
| 5,212,050 A | 5/1993 | Mier et al. |
| 5,242,835 A | 9/1993 | Jensen |
| 5,249,576 A | 10/1993 | Goldberger et al. |
| 5,250,439 A | 10/1993 | Musho et al. |
| 5,262,305 A | 11/1993 | Heller et al. |
| 5,264,104 A | 11/1993 | Gregg et al. |
| 5,266,179 A | 11/1993 | Nankai et al. |
| 5,269,891 A | 12/1993 | Colin |
| 5,281,319 A | 1/1994 | Kaneko et al. |
| 5,282,848 A | 2/1994 | Schmitt |
| 5,284,140 A | 2/1994 | Allen et al. |
| 5,286,364 A | 2/1994 | Yacynych et al. |
| 5,298,144 A | 3/1994 | Spokane |
| 5,299,571 A | 4/1994 | Mastrototaro |
| 5,307,263 A | 4/1994 | Brown |
| 5,310,469 A | 5/1994 | Cunningham et al. |
| 5,312,361 A | 5/1994 | Zadini et al. |
| 5,316,008 A | 5/1994 | Suga et al. |
| 5,322,063 A | 6/1994 | Allen et al. |
| 5,330,634 A | 7/1994 | Wong et al. |
| 5,331,555 A | 7/1994 | Hashimoto et al. |
| 5,337,747 A | 8/1994 | Neftel |
| 5,352,348 A | 10/1994 | Young et al. |
| 5,354,449 A | 10/1994 | Band et al. |
| 5,356,786 A | 10/1994 | Heller et al. |
| 5,372,133 A | 12/1994 | Hogen |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,411,866 A | 5/1995 | Luong |
| 5,425,717 A | 6/1995 | Mohiuddin |
| 5,428,123 A | 6/1995 | Ward et al. |
| 5,438,984 A | 8/1995 | Schoendorfer |
| 5,462,051 A | 10/1995 | Oka et al. |
| 5,462,645 A | 10/1995 | Albery et al. |
| 5,466,575 A | 11/1995 | Cozzette et al. |
| 5,469,846 A | 11/1995 | Khan |
| 5,474,552 A | 12/1995 | Palti |
| 5,476,094 A | 12/1995 | Allen et al. |
| 5,476,776 A | 12/1995 | Wilkins |
| 5,482,473 A | 1/1996 | Lord et al. |
| 5,486,776 A | 1/1996 | Chiang |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,507,288 A | 4/1996 | Bocker et al. |
| 5,513,636 A | 5/1996 | Palti |
| 5,531,878 A | 7/1996 | Vadgama et al. |
| 5,540,828 A | 7/1996 | Yacynych |
| 5,564,439 A | 10/1996 | Picha |
| 5,568,806 A | 10/1996 | Cheney, II et al. |
| 5,569,186 A | 10/1996 | Lord et al. |
| 5,571,395 A | 11/1996 | Park et al. |
| 5,582,184 A | 12/1996 | Ericson et al. |
| 5,582,497 A | 12/1996 | Noguchi |
| 5,586,553 A | 12/1996 | Halili et al. |
| 5,593,852 A | 1/1997 | Heller et al. |
| 5,605,152 A | 2/1997 | Slate et al. |
| 5,611,900 A | 3/1997 | Worden |
| 5,624,537 A | 4/1997 | Turner et al. |
| 5,653,863 A | 8/1997 | Genshaw et al. |
| 5,660,163 A | 8/1997 | Schulman et al. |
| 5,665,222 A | 9/1997 | Heller et al. |
| 5,676,820 A | 10/1997 | Wang et al. |
| 5,682,884 A | 11/1997 | Hill |
| 5,683,562 A | 11/1997 | Schaffar et al. |

| | | | | | | |
|---|---|---|---|---|---|---|
| 5,686,829 | A | 11/1997 | Girault | 6,274,285 | B1 | 8/2001 | Gries et al. |
| 5,695,623 | A | 12/1997 | Michel et al. | 6,275,717 | B1 | 8/2001 | Gross et al. |
| 5,703,359 | A | 12/1997 | Wampler, III | 6,284,478 | B1 | 9/2001 | Heller et al. |
| 5,707,502 | A | 1/1998 | McCaffrey et al. | 6,293,925 | B1 | 9/2001 | Safabash et al. |
| 5,711,861 | A | 1/1998 | Ward et al. | 6,294,281 | B1 | 9/2001 | Heller |
| 5,735,273 | A | 4/1998 | Kurnik et al. | 6,299,583 | B1 | 10/2001 | Eggers et al. |
| 5,741,634 | A | 4/1998 | Nozoe et al. | 6,300,002 | B1 | 10/2001 | Webb et al. |
| 5,743,262 | A | 4/1998 | Lepper, Jr. et al. | 6,325,979 | B1 | 12/2001 | Hahn et al. |
| 5,746,898 | A | 5/1998 | Preidel | 6,326,160 | B1 | 12/2001 | Dunn et al. |
| 5,749,832 | A | 5/1998 | Vadgama et al. | 6,329,161 | B1 | 12/2001 | Heller et al. |
| 5,756,632 | A | 5/1998 | Ward et al. | 6,343,225 | B1 | 1/2002 | Clark, Jr. |
| 5,776,324 | A | 7/1998 | Usala | 6,356,776 | B1 | 3/2002 | Berner et al. |
| 5,777,060 | A | 7/1998 | Van Antwerp | 6,360,888 | B1 | 3/2002 | Melver et al. |
| 5,791,344 | A | 8/1998 | Schulman et al. | 6,368,141 | B1 | 4/2002 | Van Antwerp et al. |
| 5,795,453 | A | 8/1998 | Gilmartin | 6,368,274 | B1 | 4/2002 | Van Antwerp et al. |
| 5,795,774 | A | 8/1998 | Matsumoto et al. | 6,407,195 | B2 | 6/2002 | Sherman et al. |
| 5,800,420 | A | 9/1998 | Gross | 6,413,393 | B1 | 7/2002 | Van Antwerp et al. |
| 5,807,375 | A | 9/1998 | Gross et al. | 6,413,396 | B1 | 7/2002 | Yang et al. |
| 5,833,603 | A | 11/1998 | Kovacs et al. | 6,418,332 | B1 | 7/2002 | Mastrototaro et al. |
| 5,837,454 | A | 11/1998 | Cozzette et al. | 6,424,847 | B1 | 7/2002 | Mastrototaro et al. |
| 5,851,197 | A | 12/1998 | Marano et al. | 6,442,413 | B1 | 8/2002 | Silver |
| 5,863,400 | A | 1/1999 | Drummond et al. | 6,459,917 | B1 | 10/2002 | Gowda et al. |
| 5,879,373 | A | 3/1999 | Roper et al. | 6,461,496 | B1 | 10/2002 | Feldman et al. |
| 5,882,494 | A | 3/1999 | Van Antwerp | 6,465,066 | B1 | 10/2002 | Rule et al. |
| 5,914,026 | A | 6/1999 | Blubaugh, Jr. et al. | 6,466,810 | B1 | 10/2002 | Ward et al. |
| 5,928,130 | A | 7/1999 | Schmidt | 6,475,750 | B1 | 11/2002 | Han et al. |
| 5,931,814 | A | 8/1999 | Alex et al. | 6,477,395 | B2 | 11/2002 | Schulman et al. |
| 5,932,175 | A | 8/1999 | Knute et al. | 6,484,045 | B1 | 11/2002 | Holker et al. |
| 5,954,643 | A | 9/1999 | Van Antwerp et al. | 6,484,046 | B1 | 11/2002 | Say et al. |
| 5,954,954 | A | 9/1999 | Houck et al. | 6,498,043 | B1 | 12/2002 | Schulman et al. |
| 5,957,854 | A | 9/1999 | Besson et al. | 6,498,941 | B1 | 12/2002 | Jackson |
| 5,961,451 | A | 10/1999 | Reber et al. | 6,510,329 | B2 | 1/2003 | Heckel |
| 5,964,993 | A | 10/1999 | Blubaugh et al. | 6,512,939 | B1 | 1/2003 | Colvin et al. |
| 5,965,380 | A | 10/1999 | Heller et al. | 6,514,718 | B2 | 2/2003 | Heller et al. |
| 5,972,199 | A | 10/1999 | Heller | 6,520,326 | B2 | 2/2003 | McIvor et al. |
| 5,976,085 | A | 11/1999 | Kimball et al. | 6,542,765 | B1 | 4/2003 | Guy et al. |
| 5,985,129 | A | 11/1999 | Gough et al. | 6,546,268 | B1 | 4/2003 | Ishikawa et al. |
| 5,999,848 | A | 12/1999 | Gord et al. | 6,547,839 | B2 | 4/2003 | Zhang et al. |
| 6,001,067 | A * | 12/1999 | Shults et al. ............. 600/584 | 6,551,496 | B1 | 4/2003 | Moles et al. |
| 6,011,984 | A | 1/2000 | Van Antwerp et al. | 6,553,241 | B2 | 4/2003 | Mannheimer et al. |
| 6,013,113 | A | 1/2000 | Mika | 6,553,244 | B2 | 4/2003 | Lesho et al. |
| 6,030,827 | A | 2/2000 | Davis et al. | 6,558,320 | B1 | 5/2003 | Causey |
| 6,051,389 | A * | 4/2000 | Ahl et al. .................. 435/10 | 6,558,351 | B1 | 5/2003 | Steil et al. |
| 6,059,946 | A | 5/2000 | Yukawa et al. | 6,560,471 | B1 | 5/2003 | Heller et al. |
| 6,074,775 | A | 6/2000 | Gartstein et al. | 6,561,978 | B1 | 5/2003 | Conn et al. |
| 6,081,735 | A | 6/2000 | Diab et al. | 6,565,509 | B1 | 5/2003 | Say et al. |
| 6,081,736 | A | 6/2000 | Colvin et al. | 6,569,309 | B2 | 5/2003 | Otsuka et al. |
| 6,083,710 | A | 7/2000 | Heller et al. | 6,579,498 | B1 | 6/2003 | Eglise |
| 6,088,608 | A | 7/2000 | Schulman et al. | 6,579,690 | B1 | 6/2003 | Bonnecaze et al. |
| 6,091,975 | A | 7/2000 | Daddona et al. | 6,585,763 | B1 | 7/2003 | Keilman et al. |
| 6,093,156 | A | 7/2000 | Cunningham et al. | 6,587,705 | B1 | 7/2003 | Berner et al. |
| 6,093,172 | A | 7/2000 | Funderburk et al. | 6,594,514 | B2 | 7/2003 | Berner et al. |
| 6,117,290 | A | 9/2000 | Say | 6,595,919 | B2 | 7/2003 | Berner et al. |
| 6,119,028 | A | 9/2000 | Schulman et al. | 6,607,658 | B1 | 8/2003 | Heller et al. |
| 6,120,676 | A | 9/2000 | Heller et al. | 6,612,984 | B1 | 9/2003 | Kerr |
| 6,121,009 | A | 9/2000 | Heller et al. | 6,613,379 | B2 | 9/2003 | Ward et al. |
| 6,122,536 | A | 9/2000 | Sun et al. | 6,615,078 | B1 | 9/2003 | Burson et al. |
| 6,134,461 | A | 10/2000 | Say et al. | 6,618,934 | B1 | 9/2003 | Feldman et al. |
| 6,144,869 | A | 11/2000 | Berner et al. | 6,633,772 | B2 | 10/2003 | Ford et al. |
| 6,144,871 | A | 11/2000 | Saito et al. | 6,642,015 | B2 | 11/2003 | Vachon et al. |
| 6,162,611 | A | 12/2000 | Heller et al. | 6,653,091 | B1 | 11/2003 | Dunn et al. |
| 6,175,752 | B1 * | 1/2001 | Say et al. .................. 600/345 | 6,654,625 | B1 | 11/2003 | Say et al. |
| 6,175,753 | B1 | 1/2001 | Menkes et al. | 6,673,596 | B1 | 1/2004 | Sayler et al. |
| 6,180,416 | B1 | 1/2001 | Kurnik et al. | 6,689,265 | B2 | 2/2004 | Heller et al. |
| 6,212,416 | B1 | 4/2001 | Ward et al. | 6,721,587 | B2 | 4/2004 | Gough |
| 6,214,185 | B1 | 4/2001 | Offenbacher et al. | 6,730,200 | B1 | 5/2004 | Stewart et al. |
| 6,219,574 | B1 | 4/2001 | Cormier et al. | 6,737,158 | B1 | 5/2004 | Thompson |
| 6,233,471 | B1 | 5/2001 | Berner et al. | 6,741,877 | B1 | 5/2004 | Shults et al. |
| 6,248,067 | B1 | 6/2001 | Causey, III et al. | 6,743,635 | B2 | 6/2004 | Neel et al. |
| 6,256,522 | B1 | 7/2001 | Schultz | 6,784,274 | B2 | 8/2004 | van Antwerp et al. |
| 6,259,937 | B1 | 7/2001 | Schulman et al. | 6,793,632 | B2 | 9/2004 | Sohrab |
| 6,264,825 | B1 | 7/2001 | Blackburn et al. | 6,801,041 | B2 | 10/2004 | Karinka et al. |
| 6,268,161 | B1 | 7/2001 | Han et al. | 6,802,957 | B2 | 10/2004 | Jung et al. |

| | | | | | |
|---|---|---|---|---|---|
| 6,809,507 B2 | 10/2004 | Morgan et al. | 2003/0188427 A1 | 10/2003 | Say et al. |
| 6,809,653 B1 | 10/2004 | Mann et al. | 2003/0199744 A1 | 10/2003 | Buse et al. |
| 6,862,465 B2 | 3/2005 | Shults et al. | 2003/0199745 A1 | 10/2003 | Burson et al. |
| 6,881,551 B2 | 4/2005 | Heller et al. | 2003/0203498 A1 | 10/2003 | Neel et al. |
| 6,892,085 B2 | 5/2005 | McIvor et al. | 2003/0211050 A1 | 11/2003 | Majeti et al. |
| 6,893,552 B1 | 5/2005 | Wang et al. | 2003/0211625 A1 | 11/2003 | Cohan |
| 6,895,263 B2 | 5/2005 | Shin et al. | 2003/0225324 A1 | 12/2003 | Anderson et al. |
| 6,895,265 B2 | 5/2005 | Silver | 2003/0225437 A1 | 12/2003 | Ferguson |
| 6,931,327 B2 | 8/2005 | Goode et al. | 2003/0228681 A1 | 12/2003 | Ritts et al. |
| 6,932,894 B2 | 8/2005 | Mao et al. | 2003/0235817 A1 | 12/2003 | Bartkowiak et al. |
| 6,965,791 B1 | 11/2005 | Hitchcock et al. | 2004/0006263 A1 | 1/2004 | Anderson et al. |
| 6,972,080 B1 | 12/2005 | Tomioka et al. | 2004/0023253 A1 | 2/2004 | Kunwar et al. |
| 7,003,336 B2 | 2/2006 | Holker et al. | 2004/0023317 A1 | 2/2004 | Motamedi et al. |
| 7,003,341 B2 | 2/2006 | Say et al. | 2004/0063167 A1 | 4/2004 | Kaastrup et al. |
| 7,008,979 B2 | 3/2006 | Schottman et al. | 2004/0074785 A1 | 4/2004 | Holker |
| 7,033,322 B2 | 4/2006 | Silver | 2004/0078219 A1 | 4/2004 | Kaylor |
| 7,060,059 B2 | 6/2006 | Keith et al. | 2004/0106857 A1 | 6/2004 | Gough |
| 7,070,580 B2 | 7/2006 | Nielsen | 2004/0111017 A1 | 6/2004 | Say et al. |
| 7,074,307 B2 | 7/2006 | Simpson et al. | 2004/0138543 A1 | 7/2004 | Russell et al. |
| 7,078,582 B2 | 7/2006 | Stebbings et al. | 2004/0173472 A1 | 9/2004 | Jung et al. |
| 7,098,803 B2 | 8/2006 | Mann et al. | 2004/0176672 A1 | 9/2004 | Silver et al. |
| 7,110,803 B2 | 9/2006 | Shults et al. | 2004/0180391 A1 | 9/2004 | Gratzl et al. |
| 7,115,884 B1 | 10/2006 | Walt et al. | 2004/0204687 A1 | 10/2004 | Morgensen |
| 7,120,483 B2 | 10/2006 | Russell et al. | 2004/0224001 A1 | 11/2004 | Pacetti et al. |
| 7,136,689 B2 | 11/2006 | Shults et al. | 2004/0234575 A1 | 11/2004 | Horres et al. |
| 7,153,265 B2 | 12/2006 | Vachon | 2004/0242982 A1 | 12/2004 | Sakata et al. |
| 7,190,988 B2 | 3/2007 | Say et al. | 2004/0248282 A1 | 12/2004 | Sobha et al. |
| 7,192,450 B2 | 3/2007 | Brauker et al. | 2004/0254433 A1 | 12/2004 | Bandis |
| 7,207,974 B2 | 4/2007 | Safabash et al. | 2005/0006122 A1 | 1/2005 | Burnette |
| 7,248,906 B2 | 7/2007 | Dirac et al. | 2005/0027182 A1 | 2/2005 | Siddiqui et al. |
| 7,267,665 B2 | 9/2007 | Steil et al. | 2005/0031689 A1 | 2/2005 | Shults et al. |
| 7,279,174 B2 | 10/2007 | Pacetti et al. | 2005/0033132 A1 | 2/2005 | Shults et al. |
| 7,310,544 B2 | 12/2007 | Brister et al. | 2005/0038332 A1 | 2/2005 | Saidara et al. |
| 7,335,286 B2 | 2/2008 | Abel et al. | 2005/0051427 A1 | 3/2005 | Brauker et al. |
| 7,336,984 B2 | 2/2008 | Gough et al. | 2005/0056551 A1* | 3/2005 | White et al. ............. 205/777.5 |
| 7,357,793 B2 | 4/2008 | Pacetti | 2005/0070770 A1 | 3/2005 | Dirac et al. |
| 7,366,556 B2* | 4/2008 | Brister et al. ............... 600/347 | 2005/0077584 A1 | 4/2005 | Uhland et al. |
| 7,379,765 B2 | 5/2008 | Petisce et al. | 2005/0079200 A1 | 4/2005 | Rathenow et al. |
| 7,381,184 B2 | 6/2008 | Funderburk et al. | 2005/0107677 A1 | 5/2005 | Ward et al. |
| 7,399,277 B2 | 7/2008 | Saidara et al. | 2005/0112169 A1 | 5/2005 | Brauker et al. |
| 7,424,318 B2 | 9/2008 | Brister et al. | 2005/0115832 A1* | 6/2005 | Simpson et al. ........ 204/403.09 |
| 7,460,898 B2 | 12/2008 | Brister et al. | 2005/0118344 A1 | 6/2005 | Pacetti |
| 7,467,003 B2 | 12/2008 | Brister et al. | 2005/0119720 A1 | 6/2005 | Gale et al. |
| 7,471,972 B2 | 12/2008 | Rhodes et al. | 2005/0139489 A1 | 6/2005 | Davies et al. |
| 7,494,465 B2 | 2/2009 | Brister et al. | 2005/0143675 A1 | 6/2005 | Neel et al. |
| 7,497,827 B2 | 3/2009 | Brister et al. | 2005/0154272 A1 | 7/2005 | Dirac et al. |
| 2001/0016682 A1 | 8/2001 | Berner et al. | 2005/0176136 A1* | 8/2005 | Burd et al. ................ 435/287.2 |
| 2002/0019022 A1 | 2/2002 | Dunn et al. | 2005/0176678 A1 | 8/2005 | Horres et al. |
| 2002/0023852 A1 | 2/2002 | McIvor et al. | 2005/0195930 A1 | 9/2005 | Spital et al. |
| 2002/0042090 A1 | 4/2002 | Heller et al. | 2005/0197554 A1 | 9/2005 | Polcha |
| 2002/0042561 A1 | 4/2002 | Schulman et al. | 2005/0242479 A1 | 11/2005 | Petisce et al. |
| 2002/0045808 A1 | 4/2002 | Ford et al. | 2005/0245795 A1 | 11/2005 | Goode et al. |
| 2002/0065453 A1 | 5/2002 | Lesho et al. | 2005/0245799 A1 | 11/2005 | Brauker et al. |
| 2002/0084196 A1 | 7/2002 | Liamos et al. | 2005/0258037 A1 | 11/2005 | Hajizadeh et al. |
| 2002/0099997 A1 | 7/2002 | Piret | 2005/0272989 A1 | 12/2005 | Shah et al. |
| 2002/0119711 A1 | 8/2002 | Van Antwerp et al. | 2006/0003398 A1 | 1/2006 | Heller et al. |
| 2002/0177763 A1 | 11/2002 | Burns et al. | 2006/0015020 A1* | 1/2006 | Neale et al. ................. 600/309 |
| 2002/0188185 A1 | 12/2002 | Sohrab | 2006/0019327 A1 | 1/2006 | Brister et al. |
| 2003/0004457 A1 | 1/2003 | Andersson | 2006/0036140 A1 | 2/2006 | Brister et al. |
| 2003/0006669 A1 | 1/2003 | Pei et al. | 2006/0036141 A1 | 2/2006 | Kamath et al. |
| 2003/0009093 A1 | 1/2003 | Silver | 2006/0047095 A1 | 3/2006 | Pacetti |
| 2003/0032874 A1 | 2/2003 | Rhodes et al. | 2006/0067908 A1 | 3/2006 | Ding |
| 2003/0036773 A1 | 2/2003 | Whitehurst et al. | 2006/0078908 A1 | 4/2006 | Pitner et al. |
| 2003/0050546 A1 | 3/2003 | Desai et al. | 2006/0079740 A1 | 4/2006 | Silver et al. |
| 2003/0065254 A1 | 4/2003 | Schulman et al. | 2006/0134165 A1 | 6/2006 | Pacetti |
| 2003/0076082 A1 | 4/2003 | Morgan et al. | 2006/0142651 A1 | 6/2006 | Brister et al. |
| 2003/0088166 A1 | 5/2003 | Say et al. | 2006/0171980 A1 | 8/2006 | Helmus et al. |
| 2003/0097082 A1 | 5/2003 | Purdy et al. | 2006/0173444 A1 | 8/2006 | Choy et al. |
| 2003/0100040 A1 | 5/2003 | Bonnecaze et al. | 2006/0177379 A1 | 8/2006 | Asgari |
| 2003/0130616 A1 | 7/2003 | Steil et al. | 2006/0183871 A1 | 8/2006 | Ward et al. |
| 2003/0134347 A1 | 7/2003 | Heller et al. | 2006/0183984 A1 | 8/2006 | Dobbles et al. |
| 2003/0138674 A1 | 7/2003 | Zeikus et al. | 2006/0183985 A1 | 8/2006 | Brister et al. |
| 2003/0187338 A1 | 10/2003 | Say et al. | 2006/0189856 A1 | 8/2006 | Petisce et al. |

| | | |
|---|---|---|
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0229512 A1* | 10/2006 | Petisce et al. ............ 600/347 |
| 2006/0258761 A1* | 11/2006 | Boock et al. ............... 521/50 |
| 2006/0263839 A1 | 11/2006 | Ward et al. |
| 2006/0269586 A1 | 11/2006 | Pacetti |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2007/0007133 A1 | 1/2007 | Mang et al. |
| 2007/0032718 A1 | 2/2007 | Shults et al. |
| 2007/0038044 A1 | 2/2007 | Dobbles et al. |
| 2007/0129524 A1 | 6/2007 | Sunkara |
| 2007/0135698 A1 | 6/2007 | Shah et al. |
| 2007/0163880 A1 | 7/2007 | Woo et al. |
| 2007/0173709 A1* | 7/2007 | Petisce et al. ............ 600/345 |
| 2007/0173710 A1* | 7/2007 | Petisce et al. ............ 600/345 |
| 2007/0173711 A1 | 7/2007 | Shah et al. |
| 2007/0200254 A1 | 8/2007 | Curry |
| 2007/0200267 A1 | 8/2007 | Tsai |
| 2007/0202672 A1 | 8/2007 | Curry |
| 2007/0203966 A1 | 8/2007 | Brauker et al. |
| 2007/0208246 A1 | 9/2007 | Brauker et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0233013 A1 | 10/2007 | Schoenberg |
| 2007/0259217 A1 | 11/2007 | Logan |
| 2007/0275193 A1 | 11/2007 | DeSimone et al. |
| 2007/0299385 A1 | 12/2007 | Santini et al. |
| 2007/0299409 A1 | 12/2007 | Whitbourne et al. |
| 2008/0021008 A1 | 1/2008 | Pacetti et al. |
| 2008/0021666 A1 | 1/2008 | Goode et al. |
| 2008/0027301 A1 | 1/2008 | Ward et al. |
| 2008/0033269 A1 | 2/2008 | Zhang |
| 2008/0034972 A1 | 2/2008 | Gough et al. |
| 2008/0045824 A1 | 2/2008 | Tapsak et al. |
| 2008/0183061 A1 | 7/2008 | Goode et al. |
| 2008/0188731 A1 | 8/2008 | Brister et al. |
| 2008/0194935 A1 | 8/2008 | Brister et al. |
| 2008/0194938 A1 | 8/2008 | Brister et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0275313 A1 | 11/2008 | Brister et al. |
| 2008/0296155 A1 | 12/2008 | Shults et al. |
| 2009/0045055 A1 | 2/2009 | Rhodes et al. |
| 2009/0076356 A1 | 3/2009 | Simpson |
| 2009/0076360 A1 | 3/2009 | Brister et al. |
| 2009/0099436 A1 | 4/2009 | Brister et al. |
| 2009/0124879 A1 | 5/2009 | Brister et al. |
| 2009/0143660 A1 | 6/2009 | Brister et al. |

FOREIGN PATENT DOCUMENTS

| | | |
|---|---|---|
| EP | 0 127 958 | 12/1984 |
| EP | 0 284 518 | 9/1988 |
| EP | 0 320 109 | 6/1989 |
| EP | 0 353 328 | 2/1990 |
| EP | 0 390 390 | 10/1990 |
| EP | 0 476 980 | 3/1992 |
| EP | 0 838 230 | 4/1998 |
| EP | 1 077 634 | 2/2001 |
| FR | 2656423 | 6/1991 |
| FR | 2760962 | 9/1998 |
| GB | 2149918 | 6/1985 |
| JP | 02002913 | 1/1990 |
| JP | 3-293556 | 12/1991 |
| WO | WO 89/02720 | 4/1989 |
| WO | WO 91/09302 | 6/1991 |
| WO | WO 93/14693 | 8/1993 |
| WO | WO 93/23744 | 11/1993 |
| WO | WO 94/22367 | 10/1994 |
| WO | WO 96/25089 | 2/1995 |
| WO | WO 96/14026 | 5/1996 |
| WO | WO 97/01986 | 1/1997 |
| WO | WO 97/06727 | 2/1997 |
| WO | WO 98/24358 | 6/1998 |
| WO | WO 98/38906 | 9/1998 |
| WO | WO 99/56613 | 4/1999 |
| WO | WO 99/58051 | 11/1999 |
| WO | WO 00/19887 | 4/2000 |
| WO | WO 00/32098 | 6/2000 |
| WO | WO 00/33065 | 6/2000 |
| WO | WO 00/59373 | 10/2000 |
| WO | WO 00/074753 | 12/2000 |
| WO | WO 01/58348 | 8/2001 |
| WO | WO 01/88524 A1 | 11/2001 |
| WO | WO 01/88534 A2 | 11/2001 |
| WO | WO 06/105146 | 10/2006 |

OTHER PUBLICATIONS

Bani Amer, M. M. 2002. An accurate amperometric glucose sensor based glucometer with eliminated cross-sensitivity. J Med Eng Technol 26(5):208-213.

Choleau, et al. 2002. Calibration of a subcutaneous amperometric glucose sensor implanted for 7 days in diabetic patients. Part 1. Effect of measurement uncertainties on the determination of sensor sensitivity and background current . Biosensors and Bioelectronics 17:641-646.

Choleau, et al. 2002. Calibration of a subcutaneous amperometric glucose sensor implanted for 7 days in diabetic patients. Part 2. Superiority of the one-point calibration method. Biosensors and Bioelectronics 17:647-654.

Ernst, et al. 2002. Reliable glucose monitoring through the use of microsystem technology. Anal. Bioanal. Chem. 373:758-761.

Fare, et al. 1998. Functional characterization of a conducting polymer-based immunoassay system. Biosensors & Bioelectronics 13(3-4):459-470.

Feldman, B.; Brazg, R.; Schwartz, S.; Weinstein, R. 2003. A continuous glucose sensor based on wired enzyme technology—results from a 3-day trial in patients with type 1 diabetes. Diabetes Technol Ther 5(5):769-779.

Gilligan, B. C.; Shults, M.; Rhodes, R. K.; Jacobs, P. G.; Brauker, J. H.; Pintar, T. J.; Updike, S. J. 2004, Feasibility of continuous long-term glucose monitoring from a subcutaneous glucose sensor in humans. Diabetes Technol Ther 6:378-386.

Gilligan, et al. 1994. Evaluation of a subcutaneous glucose sensor out to 3 months in a dog model. Diabetes Care 17(8):882-887.

Harrison, et al. 1988. Characterization of perfluorosulfonic acid polymer coated enzyme electrodes and a miniaturized integrated potentiostat for glucose analysis in whole blood. Anal. Chem. 60:2002-2007.

Hunter, I., Jones, L., Kanigan, T., Brenan, C., Sanbol, L. Sosnowski, L. 2000. Minimally Invasive Glucose Sensor and Insulin Delivery System. MIT Home Automation and Healthcare Consortium. Progress Report No. 25.

Jeong, et al. 2003. In vivo calibration of the subcutaneous amperometric glucose sensors using a non-enzyme electrode. Biosensors and Bioelectronics 19:313-319.

Johnson, et al. 1992. In vivo evaluation of an electroenzymatic glucose sensor implanted in subcutaneous tissue. Biosensors & Bioelectronics 7:709-714.

Matsumoto et al. 1998. A micro-planar amperometeric glucose sensor unsusceptible to interference species. Sensors and Actuators B 49:68-72.

Matsumoto, et al. 2001. A long-term lifetime amperometric glucose sensor with a perfluorocarbon polymer coating. Biosens Bioelectron 16:271-276.

McGrath, M. J.; Iwuoha, E. I.; Diamond, D.; Smyth, M. R. 1995. The use of differential measurements with a glucose biosensor for interference compensation during glucose determinations by flow injection analysis. Biosens Bioelectron 10:937-943.

Memoli, A.; Annesini, M. C.; Mascini, M.; Papale, S.; Petralito, S. 2002. A comparison between different immobilised glucoseoxidase-based electrodes. J Pharm Biomed Anal 29:1045-1052.

Moatti-Sirat, D, et al. 1992. Evaluating in vitro and in vivo the interference of ascorbate and acetaminophen on glucose detection by a needle-type glucose sensor. Biosensors and Bioelectronics 7:345-352.

Moatti-Sirat, D.; Capron, F.; Poitout, V.; Reach, G.; Bindra, D. S.; Zhang, Y.; Wilson, G. S.; Thevenot, D. R. 1992. Towards continuous glucose monitoring: in vivo evaluation of a miniaturized glucose sensor implanted for several days in rat subcutaneous tissue. Diabetologia 35:224-230.

Ohara, T. J.; Rajagopalan, R.; Heller, A. 1994. "Wired" enzyme electrodes for amperometric determination of glucose or lactate in the presence of interfering substances. Anal Chem 66:2451-2457.

Palmisano, et al. 2000. Simultaneous monitoring of glucose and lactate by an interference and cross-talk free dual electrode amperometric biosensor based on electropolymerized thin films. Biosensors & Bioelectronics 15:531-539.

Postlethwaite, et al. 1996. Interdigitated array electrode as an alternative to the rotated ring-disk electrode for determination of the reaction products of dioxygen reduction. Analytical Chemistry 68:2951-2958.

Rhodes, et al. 1994. Prediction of pocket-portable and implantable glucose enzyme electrode performance from combined species permeability and digital simulation analysis. Analytical Chemistry 66(9):1520-1529.

Tierney, M. J.; Garg, S.; Ackerman, N. R.; Fermi, S. J.; Kennedy, J.; Lopatin, M.; Potts, R. O.; Tamada, J. A. 2000. Effect of acetaminophen on the accuracy of glucose measurements obtained with the GlucoWatch biographer. Diabetes Technol Ther 2:199-207.

Turner, A.P.F. 1988. Amperometric biosensor based on mediator-modified electrodes. Methods in Enzymology 137:90-103.

Updike, et al. 1982. Implanting the glucose enzyme electrode: Problems, progress, and alternative solutions. Diabetes Care 5(3):207-212.

Ward, et al. 2000. Rise in background current over time in a subcutaneous glucose sensor in the rabbit: Relevance to calibration and accuracy. Biosensors & Bioelectronics 15:53-61.

Ward, W. K.; Wood, M. D.; Troupe, J. E. 2000. Understanding Spontaneous Output Fluctuations of an Amperometric Glucose Sensor: Effect of Inhalation Anesthesia and e of a Nonenzyme Containing Electrode. ASAIO Journal 540-546.

Wilkins, et al. 1995. Integrated implantable device for long-term glucose monitoring. Biosens. Bioelectron 10:485-494.

Wilson, et al. 1992. Progress toward the development of an implantable sensor for glucose. Clin. Chem. 38(9):1613-1617.

Zhang, et al. 1994. Elimination of the acetaminophen interference in an implantable glucose sensor. Analytical Chemistry 66(7):1183-1188.

ISR and WO for PCT/US06/38820 filed Oct. 4, 2006.

ISR and WO PCT/US04/40476.

U.S. Appl. No. 09/447,227, filed , Nov. 22, 1999, (See Image File Wrapper).

Brooks, et al. "Development of an on-line glucose sensor for fermentation monitoring," Biosensors, 3:45-56 (1987/88).

Godsland, et al. 2001. Maximizing the Success Rate of Minimal Model Insulin Sensitivity Measurement in Humans: The Importance of Basal Glucose Levels. The Biochemical Society and the Medical Research Society, 1-9.

Heller, "Electrical wiring of redox enzymes," Acc. Chem. Res., 23:128-134 (1990).

Kerner, et al. "The function of a hydrogen peroxide-detecting electroenzymatic glucose electrode is markedly impaired in human sub-cutaneous tissue and plasma," Biosensors & Bioelectronics, 8:473-482 (1993).

Koschinsky, et al. 1998. New approach to technical and clinical evaluation of devices for self-monitoring of blood glucose. Diabetes Care 11(8): 619-619.

Mastrototaro, et al. "An electroenzymatic glucose sensor fabricated on a flexible substrate," Sensors and Actuators B, 5:139-44 (1991).

Pickup, et al. "Implantable glucose sensors: choosing the appropriate sensor strategy," *Biosensors*, 3:335-346 (1987/88).

Pickup, et al. "In vivo molecular sensing in diabetes mellitus: an implantable glucose sensor with direct electron transfer," *Diabetologia*, 32:213-217 (1989).

Rebrin, et al. "Automated feedback control of subcutaneous glucose concentration in diabetic dogs," Diabetologia, 32:573-76 (1989).

Shaw, et al. "In vitro testing of a simply constructed, highly stable glucose sensor suitable for implantation in diabetic patients," Biosensors & Bioelectronics, 6:401-406 (1991).

Turner and Pickup, "Diabetes mellitus: biosensors for research and management," Biosensors, 1:85-115 (1985).

Wagner, et al. 1998. Continuous amperometric monitoring of glucose in a brittle diabetic chimpanzee with a miniature subcutaneous electrode. Proc. Natl. Acad. Sci. A, 95:6379-6382.

Office Action dated Dec. 26, 2007 in U.S. Appl. No. 11/021,046.
Office Action dated Dec. 12, 007 in U.S. Appl. No. 11/543,707.
Office Action mailed May 18, 2007 in U.S. Appl. No. 11/543,707.
Office Action mailed May 23, 2007 in U.S. Appl. No. 11/543,539.
Office Action mailed Dec. 12, 2007 in U.S. Appl. No. 11/543,539.
Office Action mailed May 18, 2007 in U.S. Appl. No. 11/543,683.
Office Action mailed Dec. 12, 2007 in U.S. Appl. No. 11/543,683.
Office Action mailed Jun. 5, 2007 in U.S. Appl. No. 11/543,734.
Office Action mailed Dec. 17, 2007 in U.S. Appl. No. 11/543,734.
Office Action dated Nov. 1, 2007 in U.S. Appl. No. 11/034,343.
Office Action dated Sep. 21, 2007 in U.S. Appl. No. 10/838,912.
Office Action dated May 17, 2007 in U.S. Appl. No. 11/077,759.
Office Action dated Jan. 28, 2008 in U.S. Appl. No. 11/077,715.
Office Action dated Jul. 26, 2007 in U.S. Appl. No. 11/077,715.
Office Action dated Apr. 10, 2007 in U.S. Appl. No. 11/077,715.
Office Action dated Oct. 31, 2006 in U.S. Appl. No. 11/077,715.
Office Action dated Oct. 9, 2007 in U.S. Appl. No. 11/077,883.
Office Action dated Sep. 18, 2007 in U.S. Appl. No. 11/078,230.
Office Action dated Jul. 27, 2007 in U.S. Appl. No. 11/077,714.
Office Action dated Apr. 10, 2007 in U.S. Appl. No. 11/077,714.
Office Action dated Oct. 11, 2006 in U.S. Appl. No. 11/077,714.
Office Action dated Jan. 10, 2008 in U.S. Appl. No. 11/077,714.
Office Action dated Jan. 30, 2007 in U.S. Appl. No. 11/077,763.
Office Action dated Jan. 3, 2008 in U.S. Appl. No. 11/157,746.
Office Action dated Oct. 4, 2006 in U.S. Appl. No. 11/334,876.
Office Action dated Sep. 25, 2007 in U.S. Appl. No. 11/334,876.

IPRP for PCT/US04/40476 filed Dec. 3, 2004.

Armour et al. Dec. 1990. Application of Chronic Intravascular Blood Glucose Sensor in Dogs. Diabetes 39:1519-1526.

Bellucci et al. Jan. 1986. Electrochemical behaviour of graphite-epoxy composite materials (GECM) in aqueous salt solutions, Journal of Applied Electrochemistry, 16(1):15-22.

Bindra et al. 1991. Design and in Vitro Studies of a Needle-Type Glucose Senso for Subcutaneous Monitoring. Anal. Chem 63:1692-96.

Bobbioni-Harsch et al. 1993. Lifespan of subcutaneous glucose sensors and their performances during dynamic glycaemia changes in rats, J. Biomed. Eng. 15:457-463.

Bode, B. W. 2000. Clinical utility of the continuous glucose monitoring system. Diabetes Technol Ther, 2(Suppl 1):S35-41.

Cass et al. "Ferrocene-mediated enzyme electrodes for amperometric determination of glucose," Anal. Chem., 36:667-71 (1984).

Chia et al. 2004. Glucose sensors: toward closed loop insulin delivery. Endocrinol Metab Clin North Am 33:175-95.

Clark et al. 1987. Configurational cyclic voltammetry: increasing the specificity and reliablity of implanted electrodes, IEEE/Ninth Annual Conference of the Engineering in Medicine and Biology Society, pp. 0782-0783.

Davies, et al. 1992. Polymer membranes in clinical sensor applications. I. An overview of membrane function, Biomaterials, 13(14):971-978.

El Degheidy et al. 1986. Optimization of an implantable coated wire glucose sensor. J. Biomed Eng. 8:121-129.

Fischer et al. 1995. Hypoglycaemia-warning by means of subcutaneous electrochemical glucose sensors: an animal study, Horm. Metab. Rese. 27:53.

Frost et al. 2002. Implantable chemical sensors for real-time clinical monitoring: Progress and challenges. Current Opinion in Chemical Biology 6:633-641.

Gouda et al., Jul. 4, 2003. Thermal inactivation of glucose oxidase, The Journal of Biological Chemistry, 278(27):24324-24333.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," Diabetes Care, 17(5): 387-396.

Heller, A. 1992. Electrical Connection of Enzyme Redox Centers to Electrodes. J. Phys. Chem. 96:3579-3587.

Hicks, 1985. In Situ Monitoring, Clinical Chemistry, 31(12):1931-1935.

Hu, et al. 1993. A needle-type enzyme-based lactate sensor for in vivo monitoring, Analytica Chimica Acta, 281:503-511.

Johnson (1991). "Reproducible electrodeposition of biomolecules for the fabrication of miniature electroenzymatic biosensors," Sensors and Actuators B, 5:85-89.

Kawagoe et al. 1991. Enzyme-modified organic conducting salt microelectrode, Anal. Chem. 63:2961-2965.

Maidan et al. 1992. Elimination of Electrooxidizable Interferent-Produced Currents in Amperometric Biosensors, Analytical Chemistry, 64:2889-2896.

McKean, et al. Jul. 7, 1988. A Telemetry Instrumentation System for Chronically Implanted Glucose and Oxygen Sensors. Transactions on Biomedical Engineering 35:526-532.

Moatti-Sirat et al., Reduction of acetaminophen interference in glucose sensors by a composite Nafion membrane: demonstration in rats and man, Diabetologia 37(6):610-616, Jun. 1994.

Morff et al. 1990. Microfabrication of reproducible, economical, electroenzymatic glucose sensors, Annual International Conference of the IEEE Engineering in Medicine and Biology Society, 12(2):0483-0484.

Murphy, et al. 1992. Polymer membranes in clinical sensor applications. II. The design and fabrication of permselective hydrogels for electrochemical devices, Biomaterials, 13(14):979-990.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Pishko et al. "Amperometric glucose microelectrodes prepared through immobilization of glucose oxidase in redox hydrogels," Anal. Chem., 63:2268-72 (1991).

Poitout, et al. 1991. In Vitro and in Vivo Evaluation in Dogs of a Miniaturized Glucose Sensor, ASAIO Transactions, 37:M298-M300.

Reach et al. 1992. Can continuous glucose monitoring be used for the treatment of diabetes? Analytical Chemistry 64(5):381-386.

Sakakida et al. 1993. Ferrocene-Mediated Needle Type Glucose Sensor Covered with Newly Designed Biocompatible Membran, Sensors and Actuators B 13-14:319-322.

Shichiri et al. 1983. Glycaemic Control in Pancreatectomized Dogs with a Wearable Artificial Endocrine Pancreas. Diabetologia 24:179-184.

Shichiri et al. 1985. Needle-type Glucose Sensor for Wearable Artificial Endocrine Pancreas in Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shichiri et al., 1989. Membrane Design For Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sokol et al. 1980, Immobilized-enzyme rate-determination method for glucose analysis, Clin. Chem. 26(1):89-92.

Sternberg et al. 1988. Study and Development of Multilayer Needle-type Enzyme-based Glucose Microsensors. Biosensors 4:27-40.

Thome et al. 1995. Can the decrease in subcutaneous glucose concentration precede the decrease in blood glucose level? Proposition for a push-pull kinetics hypothesis, Horm. Metab. Res. 27:53, X-abstract.

Thomé -Duret et al. 1996. Modification of the sensitivity of glucose sensor implanted into subcutaneous tissue. Diabetes Metabolism, 22:174-178.

Thompson et al., In Vivo Probes: Problems and Perspectives, Department of Chemistry, University of Toronto, Canada, pp. 255-261, 1986.

Updike et al. 1979. Continuous glucose monitor based on an immobilized enzyme electrode detector. J Lab Clin Med, 93(4):518-527.

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.

Ward et al. 1999. Assessment of chronically implanted subcutaneous glucose sensors in dogs: The effect of surrounding fluid masses. ASAIO Journal, 45:555-561.

Yang et al (1996). "A glucose biosensor based on an oxygen electrode: In-vitro performances in a model buffer solution and in blood plasma," Biomedical Instrumentation & Technology, 30:55-61.

Zhang et al (1993). Electrochemical oxidation of $H_2O_2$ on Pt and Pt + Ir electrodes in physiological buffer and its applicability to $H_2O_2$-based biosensors. J. Electroanal. Chem., 345:253-271.

Zhu et al. (1994). "Fabrication and characterization of glucose sensors based on a microarray H2O2 electrode." Biosensors & Bioelectronics, 9: 295-300.

Official Action in European App. No. 04812899.5, dated Oct. 8, 2008.

Supplementary European Search Report for App. No. 04812899.5, dated May 8, 2008.

Invitation to Pay Additional Fees for PCT/US07/080228, filed Oct. 2, 2007.

IPRP for PCT/US06/38820 filed Oct. 4, 2006.

IPRP for PCT/US07/080228, filed Oct. 2, 2007.

ISR and WO for PCT/US07/080228, filed Oct. 2, 2007.

Office Action dated Mar. 31, 2008 in U.S. Appl. No. 11/077,759.
Office Action dated Apr. 21, 2008 in U.S. Appl. No. 11/077,643.
Office Action dated May 1, 2008 in U.S. Appl. No. 11/157,746.
Office Action dated May 5, 2008 in U.S. Appl. No. 11/078,232.
Office Action dated May 12, 2008 in U.S. Appl. No. 11/077,715.
Office Action dated Jun. 19, 2008 in U.S. Appl. No. 11/021,162.
Office Action dated Jun. 23, 2008 in U.S. Appl. No. 11/021,046.
Office Action dated Jun. 26, 2008 in U.S. Appl. No. 11/157,365.
Office Action dated Jun. 30, 2008 in U.S. Appl. No. 11/360,252.
Office Action dated Jul. 10, 2008 in U.S. Appl. No. 11/077,759.
Office Action dated Aug. 11, 2008 in U.S. Appl. No. 11/360,819.
Office Action dated Sep. 5, 2008 in U.S. Appl. No. 11/078,230.
Office Action dated Sep. 12, 2008 in U.S. Appl. No. 10/991,353.
Office Action dated Sep. 16, 2008 in U.S. Appl. No. 11/077,714.
Office Action dated Sep. 18, 2008 in U.S. Appl. No. 11/077,883.
Office Action dated Sep. 18, 2008 in U.S. Appl. No. 11/439,630.
Office Action dated Oct. 1, 2008 in U.S. Appl. No. 11/077,643.
Office Action dated Oct. 8, 2008 in U.S. Appl. No. 10/896,637.
Office Action dated Nov. 12, 2008 in U.S. Appl. No. 11/078,232.
Office Action dated Nov. 12, 2008, 2008 in U.S. Appl. No. 11/077,715.
Office Action dated Nov. 28, 2008 in U.S. Appl. No. 11/333,837.
Office Action dated Nov. 28, 2008 in U.S. Appl. No. 11/360,250.
Office Action dated Dec. 26, 2008 in U.S. Appl. No. 11/360,819.
Office Action dated Dec. 30, 2008 in U.S. Appl. No. 11/034,343.
Office Action dated Jan. 7, 2009 in U.S. Appl. No. 11/157,365.
Office Action dated Jan. 26, 2009 in U.S. Appl. No. 11/078,230.
Office Action dated Jan. 29, 2009, in U.S. Appl. No. 11/360,252.
Office Action dated Feb. 4, 2009 in U.S. Appl. No. 11/021,046.
Office Action dated Feb. 23, 2009 in U.S. Appl. No. 11/439,630.
Office Action dated Mar. 4, 2009 in U.S. Appl. No. 10/991,353.
Office Action dated Mar. 5, 2009 in U.S. Appl. No. 10/896,637.
Office Action dated Mar. 5, 2009 in U.S. Appl. No. 11/078,232.
Office Action dated Mar. 11, 2009 in U.S. Appl. No. 11/077,643.
Office Action dated Apr. 6, 2009 in U.S. Appl. No. 11/077,883.

Office Action dated Apr. 16, 2009 in U.S. Appl. No. 11/077,714.
Office Action dated May 26, 2009 in U.S. Appl. No. 11/077,759.
Final Office Action dated Jun. 15, 2009 in U.S. Appl. No. 11/360,250.
Office Action dated Jun. 29, 2009 in U.S. Appl. No. 11/333,837.
Office Action dated Jul. 20, 2009 in U.S. Appl. No. 10/896,637.
Office Action dated Jul. 21, 2009 in U.S. Appl. No. 11/078,232.
Office Action dated Jul. 21, 2009 in U.S. Appl. No. 11/157,365.
Office Action dated Jul. 23, 2009, in U.S. Appl. No. 11/360,252.
US 7,530,950, 05/2009, Brister et al. (withdrawn)

* cited by examiner

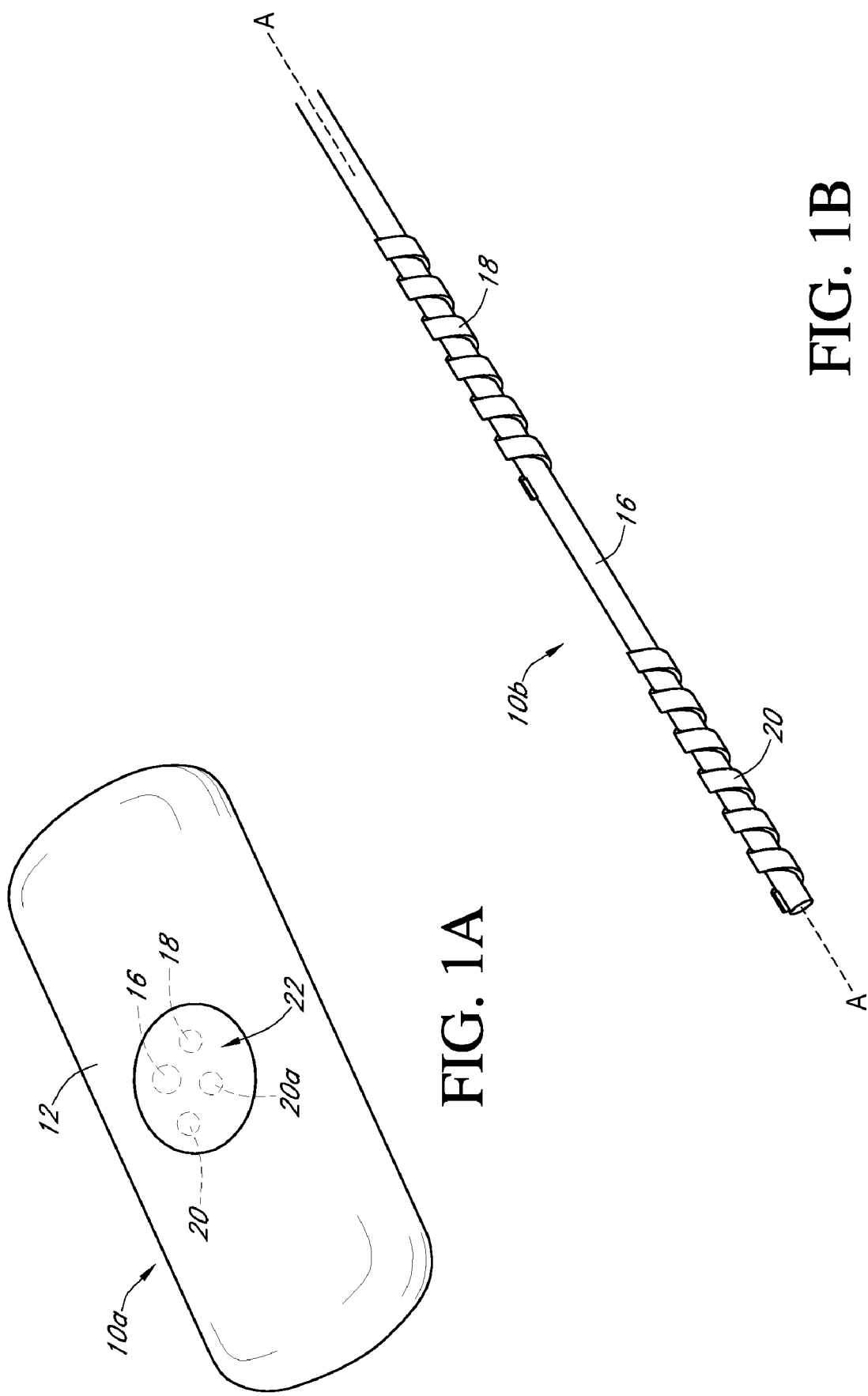

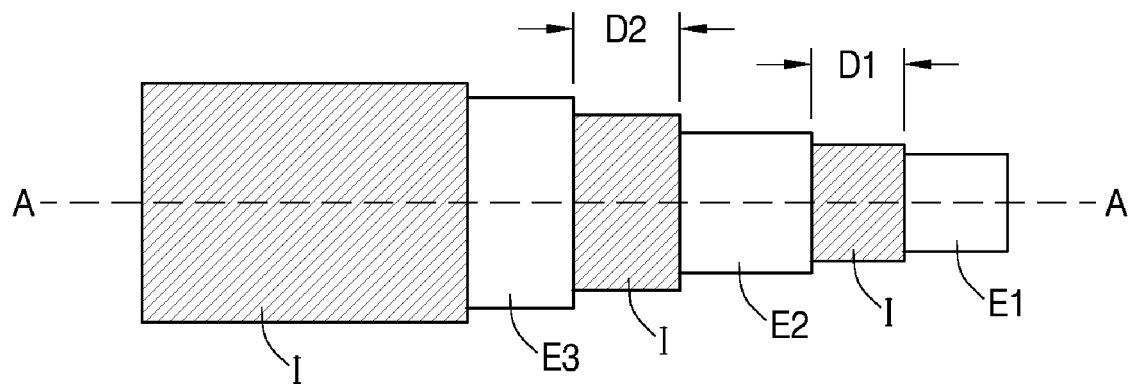
FIG. 7A$_1$
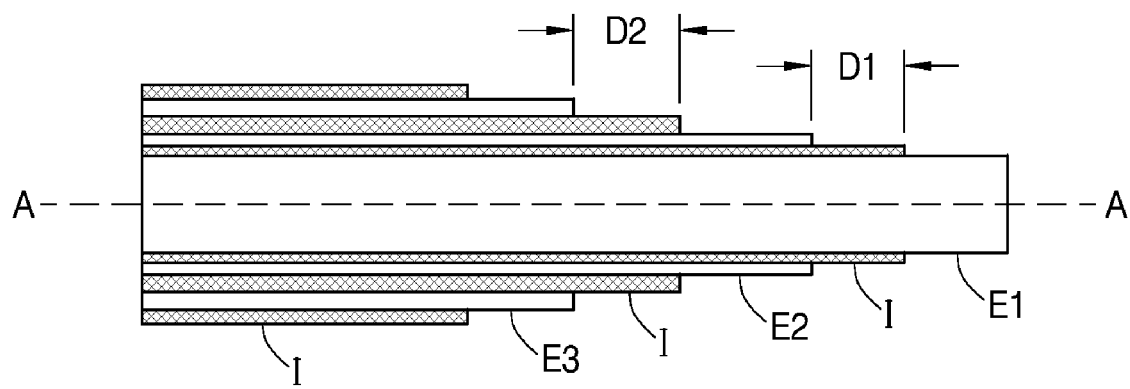
FIG. 7A$_2$

DUAL ELECTRODE SYSTEM FOR A CONTINUOUS ANALYTE SENSOR

CROSS-REFERENCE TO RELATED APPLICATIONS

This application is a continuation-in-part of U.S. application Ser. No. 11/543,539 filed Oct. 4, 2006, now U.S. Pat. No. 7,467,003, which is a continuation-in-part of U.S. application Ser. No. 11/004,561 filed Dec. 3, 2004, which claims the benefit of U.S. Provisional Application No. 60/527,323 filed Dec. 5, 2003, U.S. Provisional Application No. 60/587,787 filed Jul. 13, 2004, and U.S. Provisional Application No. 60/614,683 filed Sep. 30, 2004. Each of the aforementioned applications is incorporated by reference herein in its entirety, and each is hereby expressly made a part of this specification.

FIELD OF THE INVENTION

The present invention relates generally to systems and methods for measuring an analyte concentration in a host.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyper- or hypo-glycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

SUMMARY OF THE INVENTION

A variety of continuous glucose sensors have been developed for detecting and/or quantifying glucose concentration in a host. These sensors have typically required one or more blood glucose measurements, or the like, from which to calibrate the continuous glucose sensor to calculate the relationship between the current output of the sensor and blood glucose measurements, to provide meaningful values to a patient or doctor. Unfortunately, continuous glucose sensors are conventionally also sensitive to non-glucose related changes in the baseline current and sensitivity over time, for example, due to changes in a host's metabolism, maturation of the tissue at the biointerface of the sensor, interfering species which cause a measurable increase or decrease in the signal, or the like. Therefore, in addition to initial calibration, continuous glucose sensors should be responsive to baseline and/or sensitivity changes over time, which requires recalibration of the sensor. Consequently, users of continuous glucose sensors have typically been required to obtain numerous blood glucose measurements daily and/or weekly in order to maintain calibration of the sensor over time.

The preferred embodiments provide improved calibration techniques that utilize electrode systems and signal processing that provides measurements useful in simplifying and updating calibration that allows the patient increased convenience (for example, by requiring fewer reference glucose values) and confidence (for example, by increasing accuracy of the device).

In a first aspect, an analyte sensor configured for measuring an analyte in a host is provided, the sensor comprising: a first working electrode disposed beneath an active enzymatic portion of a sensor membrane; and a second working electrode disposed beneath an inactive-enzymatic portion of a sensor membrane or a non-enzymatic portion of a sensor membrane, wherein the sensor membrane comprises an interference domain located over the first working electrode and the second working electrode, wherein the interference domain is configured to substantially block flow of at least one interfering species.

In an embodiment of the first aspect, the interference domain is configured to substantially block at least one interferent selected from the group consisting of acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

In an embodiment of the first aspect, the interference domain is configured to substantially block at least one interferent selected from the group consisting of hydrogen peroxide, reactive oxygen species, and reactive nitrogen species.

In an embodiment of the first aspect, the interference domain is configured to substantially block at least one non-constant noise causing interferent.

In an embodiment of the first aspect, the interference domain comprises an auxiliary electrode comprising a conductive material, wherein the auxiliary electrode is configured to modify an electrochemical interferant such that the electrochemical interferent is rendered substantially electrochemically non-reactive at the working electrode In an embodiment of the first aspect, the auxiliary electrode comprises a form selected from the group consisting of a mesh, a grid, and a plurality of spaced wires.

In an embodiment of the first aspect, the auxiliary electrode comprises a polymer, wherein the polymer comprises a material that is permeable to an electrochemical interferant.

In an embodiment of the first aspect, the interference domain comprises a blend of at least one hydrophilic component and at least one hydrophobic component, wherein the interference domain is configured such that the sensor provides an equivalent analyte signal response to at least one interferent that does not substantially affect accuracy of an in vivo analyte concentration measurement, and wherein the sensor is configured to provide a linear response to analyte concentration, in vivo within in a physiological range.

In an embodiment of the first aspect, an amount of the hydrophobic component is greater than an amount of the hydrophilic component.

In an embodiment of the first aspect, the blend of at least one hydrophilic component and at least one hydrophobic component comprises at least one hydrophilic substituent of a polymer and at least one hydrophobic substituent of a polymer.

In an embodiment of the first aspect, the hydrophilic component and the hydrophobic component each comprise at least one cellulosic derivative.

In an embodiment of the first aspect, the cellulosic derivative comprises at least one of cellulose acetate and cellulose acetate butyrate.

In an embodiment of the first aspect, the interference domain comprises a silicone material configured to allow transport of an analyte therethrough.

In an embodiment of the first aspect, the silicone material comprises a blend of a silicone elastomer and a hydrophilic copolymer.

In an embodiment of the first aspect, the hydrophilic copolymer comprises hydroxy substituents.

In an embodiment of the first aspect, the hydrophilic copolymer comprises a PLURONIC® polymer.

In an embodiment of the first aspect, the silicone material has a micellar jacket structure.

In an embodiment of the first aspect, the interference domain comprises a polyurethane.

In an embodiment of the first aspect, the interference domain comprises a polymer having pendant ionic groups.

In an embodiment of the first aspect, the interference domain comprises a polymer membrane having a predetermined pore size that restricts diffusion of high molecular weight species.

In an embodiment of the first aspect, the high molecular weight species comprise at least one of glucose and ascorbic acid.

In an embodiment of the first aspect, the sensor is configured to be subcutaneously implanted.

In an embodiment of the first aspect, the sensor is configured to be intravascularly implanted.

In an embodiment of the first aspect, the sensor comprises an architecture with at least one dimension less than about 1 mm.

In an embodiment of the first aspect, the interference domain is configured to substantially block passage therethrough of at least one interferent such that an equivalent glucose signal response of the interferent is less than about 60 mg/dl.

In an embodiment of the first aspect, an equivalent glucose signal response of the interferent is less than about 30 mg/dL.

In an embodiment of the first aspect, the equivalent glucose signal response of the interferent is less than about 10 mg/dL.

In an embodiment of the first aspect, the membrane comprises at least one compound selected from the group consisting of Nafion, sulfonated polyether sulfone, polyamino-phenol and polypyrrole.

In an embodiment of the first aspect, the membrane comprises at least one enzyme configured to metabolize at least one interferent, wherein the enzyme is selected from the group consisting of a peroxidase and an oxidase.

In an embodiment of the first aspect, the interference domain comprises a sorbent having an affinity for an interfering species.

In a second aspect, an analyte sensor configured for measuring glucose in a host is provided, the sensor comprising: a first working electrode configured to generate a first signal indicative of glucose and non-glucose related electroactive compounds having a first oxidation potential; and a second working electrode configured to generate a second signal indicative of non-glucose related electroactive compounds having the first oxidation potential; and electronics configured to process the first signal and the second signal, wherein the sensor further comprises at least two mechanisms configured to substantially block or substantially eliminate noise in the sensor signal, the mechanisms comprising a first mechanism disposed on the sensor and configured to reduce or substantially block interferants from reaching the first working electrode and the second working electrode, and a second mechanism in the electronics comprising programming configured to process the first signal to substantially eliminate the signal associated with the non-glucose related electroactive compounds therefrom.

In an embodiment of the second aspect, the first mechanism comprises an interference domain.

In an embodiment of the second aspect, the first mechanism comprises a mechanism configured to increase flow around at least a portion of the sensor.

In an embodiment of the second aspect, the first mechanism comprises a physical spacer.

In an embodiment of the second aspect, the first mechanism comprises at least one mechanism selected from the group consisting of a hydrogel, a scavenging agent, a bioactive agent, a shedding layer, and an interferent scavenger.

In an embodiment of the second aspect, the first mechanism comprises an auxiliary electrode configured to electrochemically modify electrochemical interferants to render them substantially non-electroactively reactive at the first working electrode and the second working electrode.

In an embodiment of the second aspect, the non-glucose related electroactive compounds having a first oxidation potential comprise non-constant non-glucose related compounds.

In a third aspect, a method for providing a substantially noise-free signal for a glucose sensor implanted in a host is provided, the method comprising: implanting a glucose sensor in a host, the glucose sensor comprising: a first working electrode disposed beneath an active enzymatic portion of a sensor membrane; and a second working electrode disposed beneath an inactive-enzymatic or a non-enzymatic portion of a sensor membrane, wherein the sensor is configured to substantially block one or more interferants from reaching the first working electrode and the second working electrode; generating a first signal indicative of glucose and non-glucose related electroactive compounds having a first oxidation potential; generating a second signal indicative of non-glucose related electroactive compounds having the first oxidation potential; and processing the first signal to substantially eliminate the signal associated with the non-glucose related electroactive compounds therefrom.

BRIEF DESCRIPTION OF THE DRAWINGS

FIG. 1A is a perspective view of a continuous analyte sensor, including an implantable body with a membrane system disposed thereon FIG. 1B is an expanded view of an alternative embodiment of a continuous analyte sensor, illustrating the in vivo portion of the sensor.

FIG. 7A1 is a schematic of one embodiment of a coaxial sensor having axis A-A.

FIG. 7A2 is a cross-section of the sensor shown in FIG. 7A1.

DETAILED DESCRIPTION OF THE PREFERRED EMBODIMENT

Figure 1C:
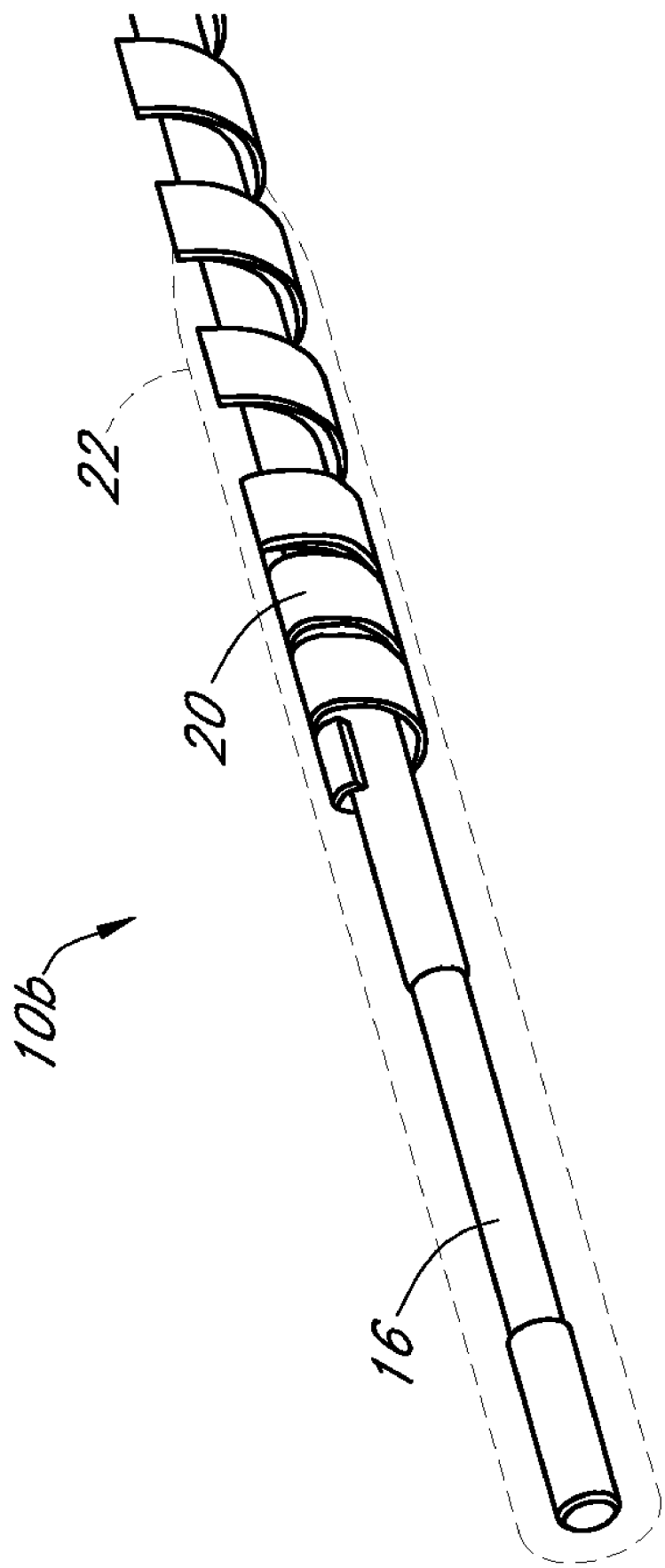
FIG. 1C is an expanded view of another alternative embodiment of a continuous analyte sensor, illustrating the in vivo portion of the sensor.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotimidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A, S, C, E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "continuous glucose sensor" as used herein is a broad term, and is to be given its ordinary and customary meaning to a person of ordinary skill in the art (and it is not to be limited to a special or customized meaning), and refers without limitation to a device that continuously or continually measures glucose concentration, for example, at time intervals ranging from fractions of a second up to, for example, 1, 2, or 5 minutes, or longer. It should be understood that continuous glucose sensors can continually measure glucose concentration without requiring user initiation and/or interaction for each measurement, such as described with reference to U.S. Pat. No. 6,001,067, for example.

The phrase "continuous glucose sensing" as used herein is a broad term, and is to be given its ordinary and customary meaning to a person of ordinary skill in the art (and it is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "biological sample" as used herein is a broad term, and is to be given its ordinary and customary meaning to a person of ordinary skill in the art (and it is not to be limited to a special or customized meaning), and refers without limitation to a sample of a host body, for example, blood, interstitial fluid, spinal fluid, saliva, urine, tears, sweat, tissue, and the like.

The term "host" as used herein is a broad term, and is to be given its ordinary and customary meaning to a person of ordinary skill in the art (and it is not to be limited to a special or customized meaning), and refers without limitation to plants or animals, for example humans.

The term "biointerface membrane" as used herein is a broad term, and is to be given its ordinary and customary meaning to a person of ordinary skill in the art (and it is not to be limited to a special or customized meaning), and refers without limitation to a permeable or semi-permeable membrane that can include one or more domains and is typically constructed of materials of a few microns thickness or more, which can be placed over the sensing region to keep host cells (for example, macrophages) from gaining proximity to, and thereby damaging the membrane system or forming a barrier cell layer and interfering with the transport of glucose across the tissue-device interface.

The term "membrane system" as used herein is a broad term, and is to be given its ordinary and customary meaning to a person of ordinary skill in the art (and it is not to be limited to a special or customized meaning), and refers without limitation to a permeable or semi-permeable membrane that can be comprised of one or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "domain" as used herein is a broad term, and is to be given its ordinary and customary meaning to a person of ordinary skill in the art (and it is not to be limited to a special or customized meaning), and refers without limitation to regions of a membrane that can be layers, uniform or non-uniform gradients (for example, anisotropic), functional aspects of a material, or provided as portions of the membrane.

The term "copolymer" as used herein is a broad term, and is to be given its ordinary and customary meaning to a person of ordinary skill in the art (and it is not to be limited to a special or customized meaning), and refers without limitation to polymers having two or more different repeat units and includes copolymers, terpolymers, tetrapolymers, and the like.

The term "sensing region" as used herein is a broad term, and is to be given its ordinary and customary meaning to a person of ordinary skill in the art (and it is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electrochemically reactive surface at one location on the body and an electronic connection at another location on the body, and a membrane system affixed to the body and covering the electrochemically reactive surface. In another embodiment, the sensing region generally comprises a non-conductive body, a working electrode (anode), a reference electrode (optionally can be remote from the sensing region), an insulator disposed therebetween, and a multi-domain membrane affixed to the body and covering the electrochemically reactive surfaces of the working and optionally reference electrodes.

The term "electrochemically reactive surface" as used herein is a broad term, and is to be given its ordinary and customary meaning to a person of ordinary skill in the art (and it is not to be limited to a special or customized meaning), and refers without limitation to the surface of an electrode where an electrochemical reaction takes place. In one embodiment, a working electrode measures hydrogen peroxide creating a measurable electronic current.

The term "electrochemical cell" as used herein is a broad term, and is to be given its ordinary and customary meaning to a person of ordinary skill in the art (and it is not to be limited to a special or customized meaning), and refers without limitation to a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "electrode" as used herein is a broad term, and is to be given its ordinary and customary meaning to a person of ordinary skill in the art (and it is not to be limited to a special or customized meaning), and refers without limitation to a conductor through which electricity enters or leaves something such as a battery or a piece of electrical equipment. In one embodiment, the electrodes are the metallic portions of a sensor (e.g., electrochemically reactive surfaces) that are exposed to the extracellular milieu, for detecting the analyte. In some embodiments, the term electrode includes the conductive wires or traces that electrically connect the electrochemically reactive surface to connectors (for connecting the sensor to electronics) or to the electronics.

The term "enzyme" as used herein is a broad term, and is to be given its ordinary and customary meaning to a person of ordinary skill in the art (and it is not to be limited to a special or customized meaning), and refers without limitation to a protein or protein-based molecule that speeds up a chemical reaction occurring in a living thing. Enzymes may act as catalysts for a single reaction, converting a reactant (also called an analyte herein) into a specific product. In one exemplary embodiment of a glucose oxidase-based glucose sensor, an enzyme, glucose oxidase (GOX) is provided to react with glucose (the analyte) and oxygen to form hydrogen peroxide.

The term "co-analyte" as used herein is a broad term, and is to be given its ordinary and customary meaning to a person of ordinary skill in the art (and it is not to be limited to a special or customized meaning), and refers without limitation to a molecule required in an enzymatic reaction to react with the analyte and the enzyme to form the specific product being measured. In one exemplary embodiment of a glucose sensor, an enzyme, glucose oxidase (GOX) is provided to react with glucose and oxygen (the co-analyte) to form hydrogen peroxide.

The term "constant analyte" as used herein is a broad term, and is to be given its ordinary and customary meaning to a person of ordinary skill in the art (and it is not to be limited to a special or customized meaning), and refers without limitation to an analyte that remains relatively constant over a time period, for example over an hour to a day as compared to other variable analytes. For example, in a person with diabetes, oxygen and urea may be relatively constant analytes in particular tissue compartments relative to glucose, which is known to oscillate from about 40 to about 400 mg/dL during a 24-hour cycle. Although analytes such as oxygen and urea are known to oscillate to a lesser degree, for example due to physiological processes in a host, they are substantially constant, relative to glucose, and can be digitally filtered, for example low pass filtered, to minimize or eliminate any relatively low amplitude oscillations. Constant analytes other than oxygen and urea are also contemplated.

The term "proximal" as used herein is a broad term, and is to be given its ordinary and customary meaning to a person of ordinary skill in the art (and it is not to be limited to a special or customized meaning), and refers without limitation to near to a point of reference such as an origin or a point of attachment. For example, in some embodiments of a membrane system that covers an electrochemically reactive surface, the electrolyte domain is located more proximal to the electrochemically reactive surface than the resistance domain.

The term "distal" as used herein is a broad term, and is to be given its ordinary and customary meaning to a person of ordinary skill in the art (and it is not to be limited to a special or customized meaning), and refers without limitation to spaced relatively far from a point of reference, such as an origin or a point of attachment. For example, in some embodiments of a membrane system that covers an electrochemically reactive surface, a resistance domain is located more distal to the electrochemically reactive surfaces than the electrolyte domain.

The term "substantially" as used herein is a broad term, and is to be given its ordinary and customary meaning to a person of ordinary skill in the art (and it is not to be limited to a special or customized meaning), and refers without limitation to a sufficient amount that provides a desired function. For example, the interference domain of the preferred embodiments is configured to resist a sufficient amount of interfering species such that tracking of glucose levels can be achieved, which may include an amount greater than 50 percent, an amount greater than 60 percent, an amount greater than 70 percent, an amount greater than 80 percent, or an amount greater than 90 percent of interfering species.

The term "computer" as used herein is a broad term, and is to be given its ordinary and customary meaning to a person of ordinary skill in the art (and it is not to be limited to a special or customized meaning), and refers without limitation to machine that can be programmed to manipulate data.

The term "modem" as used herein is a broad term, and is to be given its ordinary and customary meaning to a person of ordinary skill in the art (and it is not to be limited to a special or customized meaning), and refers without limitation to an electronic device for converting between serial data from a computer and an audio signal suitable for transmission over a telecommunications connection to another modem.

The terms "processor module" and "microprocessor" as used herein are broad terms, and are to be given their ordinary and customary meaning to a person of ordinary skill in the art (and they are not to be limited to a special or customized meaning), and refer without limitation to a computer system, state machine, processor, or the like designed to perform arithmetic and logic operations using logic circuitry that responds to and processes the basic instructions that drive a computer.

The term "ROM" as used herein is a broad term, and is to be given its ordinary and customary meaning to a person of ordinary skill in the art (and it is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM" as used herein is a broad term, and is to be given its ordinary and customary meaning to a person of ordinary skill in the art (and it is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter" as used herein is a broad term, and is to be given its ordinary and customary meaning to a person of ordinary skill in the art (and it is not to be limited to a special or customized meaning), and refers without limitation to hardware and/or software that converts analog electrical signals into corresponding digital signals.

The term "RF transceiver" as used herein is a broad term, and is to be given its ordinary and customary meaning to a person of ordinary skill in the art (and it is not to be limited to a special or customized meaning), and refers without limitation to a radio frequency transmitter and/or receiver for transmitting and/or receiving signals.

The terms "raw data stream" and "data stream" as used herein are broad terms, and are to be given their ordinary and customary meaning to a person of ordinary skill in the art (and they are not to be limited to a special or customized meaning), and refer without limitation to an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer. In some embodiments, raw data includes one or more values (e.g., digital value) representative of the current flow integrated over time (e.g., integrated value), for example, using a charge counting device, or the like.

The term "counts" as used herein is a broad term, and is to be given its ordinary and customary meaning to a person of ordinary skill in the art (and it is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "electronic circuitry" as used herein is a broad term, and is to be given its ordinary and customary meaning to a person of ordinary skill in the art (and it is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat" as used herein is a broad term, and is to be given its ordinary and customary meaning to a person of ordinary skill in the art (and it is not to be limited to a special or customized meaning), and refers without limitation to an electrical system that applies a potential between the working and reference electrodes of a two- or three-electrode cell at a preset value and measures the current flow through the working electrode. Typically, the potentiostat forces whatever current is necessary to flow between the working and reference or counter electrodes to keep the desired potential, as long as the needed cell voltage and current do not exceed the compliance limits of the potentiostat.

The terms "operably connected" and "operably linked" as used herein are broad terms, and are to be given their ordinary and customary meaning to a person of ordinary skill in the art (and they are not to be limited to a special or customized meaning), and refer without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "smoothing" and "filtering" as used herein are broad terms, and are to be given their ordinary and customary meaning to a person of ordinary skill in the art (and they are not to be limited to a special or customized meaning), and refer without limitation to modification of a set of data to make it smoother and more continuous and remove or diminish outlying points, for example, by performing a moving average of the raw data stream.

The term "algorithm" as used herein is a broad term, and is to be given its ordinary and customary meaning to a person of ordinary skill in the art (and it is not to be limited to a special or customized meaning), and refers without limitation to the computational processes (for example, programs) involved in transforming information from one state to another, for example using computer processing.

The term "regression" as used herein is a broad term, and is to be given its ordinary and customary meaning to a person of ordinary skill in the art (and it is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "pulsed amperometric detection" as used herein is a broad term, and is to be given its ordinary and customary meaning to a person of ordinary skill in the art (and it is not to be limited to a special or customized meaning), and refers without limitation to an electrochemical flow cell and a controller, which applies the potentials and monitors current generated by the electrochemical reactions. The cell can include one or multiple working electrodes at different applied potentials. Multiple electrodes can be arranged so that they face the chromatographic flow independently (parallel configuration), or sequentially (series configuration).

The term "calibration" as used herein is a broad term, and is to be given its ordinary and customary meaning to a person of ordinary skill in the art (and it is not to be limited to a special or customized meaning), and refers without limitation to the relationship and/or the process of determining the relationship between the sensor data and corresponding reference data, which may be used to convert sensor data into meaningful values substantially equivalent to the reference. In some embodiments, namely in continuous analyte sensors, calibration may be updated or recalibrated over time if changes in the relationship between the sensor and reference data occur, for example due to changes in sensitivity, baseline, transport, metabolism, or the like.

The term "sensor analyte values" and "sensor data" as used herein are broad terms, and are to be given their ordinary and customary meaning to a person of ordinary skill in the art (and they are not to be limited to a special or customized meaning), and refer without limitation to data received from a continuous analyte sensor, including one or more time-spaced sensor data points.

The term "reference analyte values" and "reference data" as used herein are broad terms, and are to be given their ordinary and customary meaning to a person of ordinary skill in the art (and they are not to be limited to a special or customized meaning), and refer without limitation to data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or an YSI (Yellow Springs Instruments) test, for example.

The term "matched data pairs" as used herein is a broad term, and is to be given its ordinary and customary meaning to a person of ordinary skill in the art (and it is not to be limited to a special or customized meaning), and refers without limitation to reference data (for example, one or more reference analyte data points) matched with substantially time corresponding sensor data (for example, one or more sensor data points).

The terms "interferants" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor so as to produce a signal that does not accurately represent the analyte measurement. In one example of an electrochemical sensor, interfering species are compounds with an oxidation potential that overlaps with that of the analyte to be measured, producing a false positive signal. In another example of an electrochemical sensor, interfering species are substantially non-constant compounds (e.g., the concentration of an interfering species fluctuates over time). Interfering species include but are not limited to compounds with electroactive acidic, amine or sulfhydryl groups, urea, lacetic acid, phosphates, citrates, peroxides, amino acids, amino acid precursors or break-down products, nitric oxide (NO), NO-donors, NO-precursors, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid electroactive species produced during cell metabolism and/or wound healing, electroactive species that arise during body pH changes and the like. Interferents that cause constant and/or non-constant noise are included in the definitions of "interferants" and "interfering species".

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, the interference domain of some embodiments is configured to substantially block a sufficient amount of interfering species such that tracking of glucose levels can be achieved, which may include an amount greater than 50 percent, an amount greater than 60 percent, an amount greater than 70 percent, an amount greater than 80 percent, and an amount greater than 90 percent of interfering species.

The term "bifunctional" as used herein is a broad term, and is to be given its ordinary and customary meaning to a person of ordinary skill in the art (and it is not to be limited to a special or customized meaning), and refers without limitation to having or serving two functions. For example, in a needle-type analyte sensor, a metal wire is bifunctional because it provides structural support and acts as an electrical conductor.

The term "function" as used herein is a broad term, and is to be given its ordinary and customary meaning to a person of ordinary skill in the art (and it is not to be limited to a special or customized meaning), and refers without limitation to an action or use for which something is suited or designed.

The term "electrical conductor" as used herein is a broad term, and is to be given its ordinary and customary meaning to a person of ordinary skill in the art (and is not to be limited to a special or customized meaning) and refers without limitation to materials that contain movable charges of electricity. When an electric potential difference is impressed across separate points on a conductor, the mobile charges within the conductor are forced to move, and an electric current between those points appears in accordance with Ohm's law.

Accordingly, the term "electrical conductance" as used herein is a broad term, and is to be given its ordinary and customary meaning to a person of ordinary skill in the art (and is not to be limited to a special or customized meaning) and refers without limitation to the propensity of a material to behave as an electrical conductor. In some embodiments, the term refers to a sufficient amount of electrical conductance (e.g., material property) to provide a necessary function (electrical conduction).

The terms "insulative properties," "electrical insulator" and "insulator" as used herein are broad terms, and are to be given their ordinary and customary meaning to a person of ordinary skill in the art (and is not to be limited to a special or customized meaning) and refers without limitation to the tendency of materials that lack mobile charges to prevent movement of electrical charges between two points. In one exemplary embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The term "structural support" as used herein is a broad term, and is to be given its ordinary and customary meaning to a person of ordinary skill in the art (and is not to be limited to a special or customized meaning) and refers without limitation to the tendency of a material to keep the sensor's structure stable or in place. For example, structural support can include "weight bearing" as well as the tendency to hold the parts or components of a whole structure together. A variety of materials can provide "structural support" to the sensor.

The term "diffusion barrier" as used herein is a broad term, and is to be given its ordinary and customary meaning to a person of ordinary skill in the art (and is not to be limited to a special or customized meaning) and refers without limitation to something that obstructs the random movement of compounds, species, atoms, molecules, or ions from one site in a medium to another. In some embodiments, a diffusion barrier is structural, such as a wall that separates two working electrodes and substantially prevents diffusion of a species from one electrode to the other. In some embodiments, a diffusion barrier is spatial, such as separating working electrodes by a distance sufficiently large enough to substantially prevent a species at a first electrode from affecting a second electrode. In other embodiments, a diffusion barrier can be temporal, such as by turning the first and second working electrodes on and off, such that a reaction at a first electrode will not substantially affect the function of the second electrode.

The terms "integral," "integrally," "integrally formed," integrally incorporated," "unitary" and "composite" as used herein are broad terms, and are to be given their ordinary and customary meaning to a person of ordinary skill in the art (and they are not to be limited to a special or customized meaning), and refer without limitation to the condition of being composed of essential parts or elements that together make a whole. The parts are essential for completeness of the whole. In one exemplary embodiment, at least a portion (e.g., the in vivo portion) of the sensor is formed from at least one platinum wire at least partially covered with an insulative coating, which is at least partially helically wound with at least one additional wire, the exposed electroactive portions of which are covered by a membrane system (see description of FIG. 1B or 9B); in this exemplary embodiment, each element of the sensor is formed as an integral part of the sensor (e.g., both functionally and structurally).

The term "coaxial" as used herein is a broad term, and is to be given its ordinary and customary meaning to a person of ordinary skill in the art (and it is not to be limited to a special or customized meaning), and refers without limitation to having a common axis, having coincident axes or mounted on concentric shafts.

The term "twisted" as used herein is a broad term, and is to be given its ordinary and customary meaning to a person of ordinary skill in the art (and it is not to be limited to a special or customized meaning), and refers without limitation to united by having one part or end turned in the opposite direction to the other, such as, but not limited to the twisted strands of fiber in a string, yarn, or cable.

The term "helix" as used herein is a broad term, and is to be given its ordinary and customary meaning to a person of ordinary skill in the art (and it is not to be limited to a special or customized meaning), and refers without limitation to a spiral or coil, or something in the form of a spiral or coil (e.g. a corkscrew or a coiled spring). In one example, a helix is a mathematical curve that lies on a cylinder or cone and makes a constant angle with the straight lines lying in the cylinder or cone. A "double helix" is a pair of parallel helices intertwined about a common axis, such as but not limited to that in the structure of DNA.

The term "in vivo portion" as used herein is a broad term, and is to be given its ordinary and customary meaning to a person of ordinary skill in the art (and it is not to be limited to a special or customized meaning), and refers without limitation to a portion of a device that is to be implanted or inserted into the host. In one exemplary embodiment, an in vivo portion of a transcutaneous sensor is a portion of the sensor that is inserted through the host's skin and resides within the host.

The terms "background," "baseline," and "noise" as used herein are broad terms, and are to be given their ordinary and customary meaning to a person of ordinary skill in the art (and is not to be limited to a special or customized meaning), and refer without limitation to a component of an analyte sensor signal that is not related to the analyte concentration. In one example of a glucose sensor, the noise (e.g., background) is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation $y=mx+b$, the value of b represents the baseline of the signal. In general, noise (e.g., background) comprises components related to constant and non-constant factors (e.g., constant noise and non-constant noise), including interfering species.

The term "constant noise" and "constant background" as used herein are broad terms, and are to be given their ordinary and customary meaning to a person of ordinary skill in the art (and it is not to be limited to a special or customized meaning), and refer without limitation to the component of the noise signal that remains relatively constant over time. For example, certain electroactive compounds found in the human body are relatively constant factors (e.g., baseline of the host's physiology) and do not significantly adversely affect accuracy of the calibration of the glucose concentration (e.g., they can be relatively constantly eliminated using the equation $y=mx+b$). In some circumstances, constant background noise can slowly drift over time (e.g., increases or decreases), however this drift need not adversely affect the accuracy of a sensor, for example, because a sensor can be calibrated and re-calibrated and/or the drift measured and compensated for.

The term "non-constant noise" or non-constant background" as used herein are broad terms, and are to be given their ordinary and customary meaning to a person of ordinary skill in the art (and it is not to be limited to a special or customized meaning), and refer without limitation to a component of the background signal that is relatively non-constant, for example, transient and/or intermittent. For example, certain electroactive compounds, are relatively non-constant (e.g., intermittent interferents due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The terms "inactive enzyme" or "inactivated enzyme" as used herein are broad terms, and are to be given their ordinary and customary meaning to a person of ordinary skill in the art (and it is not to be limited to a special or customized meaning), and refer without limitation to an enzyme (e.g., glucose oxidase, GOx) that has been rendered inactive (e.g., "killed" or "dead") and has no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The term "non-enzymatic" as used herein is a broad term, and is to be given their ordinary and customary meaning to a person of ordinary skill in the art (and it is not to be limited to a special or customized meaning), and refers without limitation to a lack of enzyme activity. In some embodiments, a "non-enzymatic" membrane portion contains no enzyme; while in other embodiments, the "non-enzymatic" membrane portion contains inactive enzyme. In some embodiments, an enzyme solution containing inactive enzyme or no enzyme is applied.

The term "GOx" as used herein is a broad term, and is to be given their ordinary and customary meaning to a person of ordinary skill in the art (and it is not to be limited to a special or customized meaning), and refers without limitation to the enzyme Glucose Oxidase (e.g., GOx is an abbreviation).

The term "mechanism" as used herein is a broad term, and is to be given their ordinary and customary meaning to a person of ordinary skill in the art (and it is not to be limited to a special or customized meaning), and refers without limitation to a process, technique, or system for achieving a result. The term is not limited by the processes, techniques, or systems described herein, but also includes any process, technique, or system that can achieve a stated result.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Overview

Noise

Generally, implantable sensors measure a signal (e.g., counts) related to an analyte of interest in a host. For example, an electrochemical sensor can measure glucose, creatinine, or urea in a host, such as an animal, especially a human. Generally, the signal is converted mathematically to a numeric value indicative of analyte status, such as analyte concentration. However, it is not unusual for a sensor to experience a certain level of noise. The term "noise" generally refers to a signal detected by the sensor that is substantially non-analyte related (e.g., non-glucose related). In other words, things other than the analyte concentration substantially cause noise. Noise is clinically important because it can reduce sensor performance, such as by making the analyte concentration appear higher or lower than the actual concentration. For example, if a host is hyperglycemic (e.g., blood sugar too high, greater than ~120 mg/dl) or euglycemic (e.g., ~80-120 mg/dl), noise can cause the host's blood sugar to appear higher than it truly is, which can lead to improper treatment decisions, such as to give the host an excessive insulin dose. An excessive insulin dose, in some circumstances, can lead to a dangerous hypoglycemic state (e.g., blood sugar too low, less than ~80 mg/dl). In the case of a hypoglycemic host, noise can cause the hosts blood sugar to appear euglycemic or even hyperglycemic, which can also lead to improper treatment decisions, such as not eating when necessary or taking insulin, for example. Accordingly, since noise can cause error and reduce sensor performance, noise reduction is desirable.

Noise is comprised of two components, constant noise and non-constant noise, and can be caused by a variety of factors, ranging from mechanical factors to biological factors. For example, it is known that macro- or micro-motion, ischemia, pH changes, temperature changes, pressure, stress, or even unknown mechanical, electrical, and/or biochemical sources can cause noise. In general, "constant noise" (sometimes referred to as constant background or baseline) is caused by factors that are relatively stable over time, including but not limited to electroactive species that arise from generally constant (e.g., daily) metabolic processes. In contrast, "non-constant noise" (sometimes referred to as non-constant background) is caused by transient events, such as during wound healing or in response to an illness, or due to ingestion (e.g., some drugs). In particular, noise can be caused by a variety of interfering species (constant or non-constant). Interfering species can be compounds, such as drugs that have been administered to the host, or products of various host metabolic processes. Exemplary interferents include but are not limited to a variety of drugs (e.g., acetaminophen), $H_2O_2$ from exterior sources, reactive metabolic species (e.g., reactive oxygen and nitrogen species, some hormones, etc.). In some circumstances, constant noise-causing factors can have an affect on the sensor signal similar to non-constant noise-causing factors, such as when the concentration of a constant noise-causing factor temporarily increases, such as due to temporary lack of lymph flow (see discussion of intermittent sedentary noise).

In some experiments of implantable glucose sensors, it was observed that noise increased when some hosts are intermittently sedentary, such as during sleep or sitting for extended periods. When the host began moving again, the noise quickly dissipated. Noise that occurs during intermittent, sedentary periods (sometimes referred to as intermittent sedentary noise) can occur during relatively inactive periods, such as sleeping. Non-constant, non-analyte-related factors can cause intermittent, sedentary noise, such as was observed in one exemplary study of non-diabetic individuals implanted with enzymatic-type glucose sensors built without enzyme. These sensors (without enzyme) could not react with or measure glucose and therefore provided a signal due to non-glucose effects (e.g., baseline, interferants, and/or noise). During sedentary periods (e.g., during sleep), extensive, sustained signal was observed on the sensors. Then, when the host got up and moved around, the signal rapidly corrected. Additional, in vitro experiments were conducted to determine if a sensor (e.g., electrode) component might have leached into the area surrounding the sensor, but none was detected. From these results, it is believed that a host-produced non-analyte related reactant was diffusing to the electrodes and producing the unexpected non-constant signal noise.

While not wishing to be bound by theory, it is believed that a concentration increase of electroactive interferants, such as electroactive metabolites from cellular metabolism and wound healing, can interfere with sensor function and cause noise observed during host sedentary periods. For example, local lymph pooling, which can occur when a part of the body is compressed or when the body is inactive, can cause, in part, this local build up of interferants (e.g., electroactive metabolites). Similarly, a local accumulation of wound healing metabolic products (e.g., at the site of sensor insertion) likely causes noise on the sensor. Interferants can include but are not limited to compounds with electroactive acidic, amine or sulfhydryl groups, urea, lacetic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing, for example. For a more complete discussion of noise and its sources, see co-pending U.S. patent application Ser. No. 11/503,367, filed Aug. 10, 2006 and entitled "ANALYTE SENSOR," herein incorporated by reference in its entirety.

Noise can be difficult to remove from the sensor signal by calibration using standard calibration equations (e.g., because the background of the signal does not remain constant). Noise can significantly adversely affect the accuracy of the calibration of the analyte signal. Additionally noise, as described herein, can occur in the signal of conventional sensors with electrode configurations that are not particularly designed to measure noise substantially equally at both active and in-active electrodes (e.g., wherein the electrodes are spaced and/or non symmetrical, noise may not be equally measured and therefore not easily removed using conventional dual electrode designs).

Noise can be recognized and/or analyzed in a variety of ways. In preferred embodiments, the sensor data stream is monitored, signal artifacts are detected and data processing is based at least in part on whether or not a signal artifact has been detected, such as described in U.S. Patent Publication No. US-2005-0043598-A1. Additional discussion can also be found in U.S. Patent Publication No. US-2007-0032706-A1, both herein incorporated by reference in their entirety.

Reduction of Noise

Figure 2A:
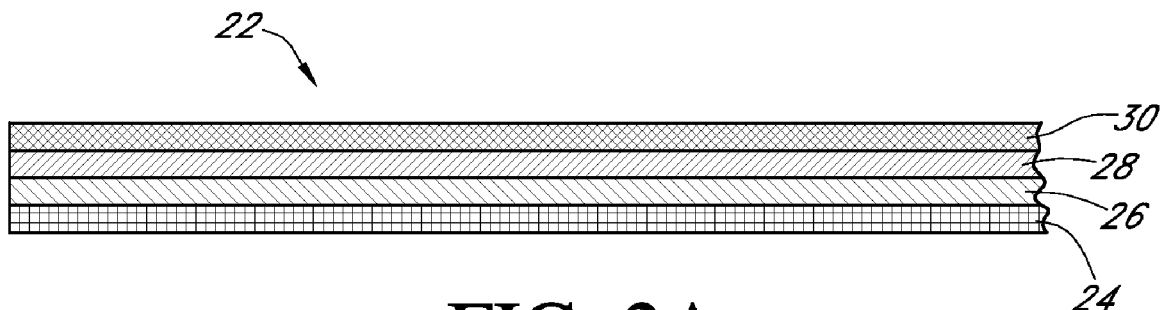
FIG. 2A is a schematic view of a membrane system in one embodiment, configured for deposition over the electroactive surfaces of the analyte sensor of FIG. 1A.
Figure 2B:
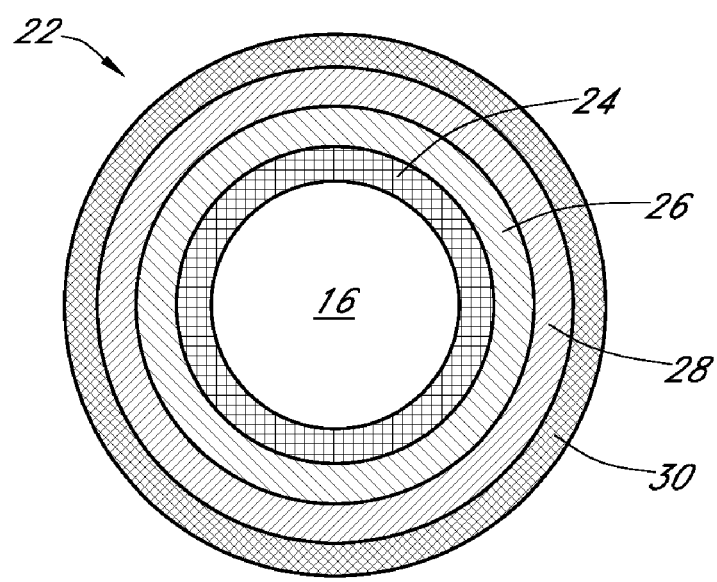
FIG. 2B is a schematic view of a membrane system in an alternative embodiment, configured for deposition over the electroactive surfaces of the analyte sensor of FIG. 1B.

Noise can be recognized and substantially reduced and/or eliminated by a variety of sensor configurations and/or methods, such as by using 1) sensor configurations that block and/or remove the interferent, or that specifically detect the noise and 2) mathematical algorithms that recognize and/or remove the signal noise component. The preferred embodiments provide devices and methods for reducing and/or eliminating noise, such as by blocking interferent passage to the sensor's electroactive surfaces, diluting and/or removing interferents around the sensor and mathematically determining and eliminating the noise signal component. Those knowledgeable in the art will recognize that the various sensor structures (e.g., multiple working electrodes, membrane interference domains, etc.), bioactive agents, algorithms and the like disclosed herein can be employed in a plurality of combinations, depending upon the desired effect and the noise reduction strategy selected. In preferred embodiments, the sensor comprises at least two working electrodes (one with and one without enzyme over its electroactive surface) and an interference domain configured to substantially block interferent passage therethrough, such that at least some interferent no longer has a substantial affect on sensor measurements (e.g., at either working electrode). The term "interference domain," as used herein is a broad term, and is to be given its ordinary and customary meaning to a person of ordinary skill in the art (and it is not to be limited to a special or customized meaning), and refers without limitation to any mechanism of the membrane system configured to reduce any kind of noise or interferants, such as constant and/or non-constant noise. "Noise-reducing mechanisms" as used herein is a broad term, and is to be given its ordinary and customary meaning to a person of ordinary skill in the art (and it is not to be limited to a special or customized meaning), and refers without limitation to any sensor system component configuration that reduces and/or eliminates noise on the sensor signal. Such structural configurations include but are not limited to electrode configurations (e.g., two or more working electrodes), membrane configurations (e.g., interference domain), algorithmic configurations (e.g., signal processing to remove an identified noise component of the signal), and he like. In some embodiments, the interference domain is a component of the membrane system, such as shown in FIGS. 2A and 2B. However, the interference domain can be disposed at any level (e.g., layer or domain) of the membrane system (e.g., more proximal or more distal to the electroactive surfaces than as shown in FIGS. 2A and 2B). In some other embodiments, the interference domain is combined with an additional membrane domain, such as the resistance domain or the enzyme domain. A detailed discussion of the use of two or more electrodes to detect and reduce and/or eliminate noise can be found elsewhere herein, especially the sections entitled "Preferred Sensor Components" and "Exemplary Continuous Sensor Configurations." A detailed discussion of noise-blocking interference domains can be found in the section entitled "Interference Domain."

Sensor Component Overview

The preferred embodiments provide a continuous analyte sensor that measures a concentration of the analyte of interest or a substance indicative of the concentration or presence of the analyte. In some embodiments, the analyte sensor is an invasive, minimally invasive, or non-invasive device, for example a subcutaneous, transdermal, or intravascular device. In some embodiments, the analyte sensor may analyze a plurality of intermittent biological samples. The analyte sensor may use any method of analyte-measurement, including enzymatic, chemical, physical, electrochemical, spectrophotometric, polarimetric, calorimetric, radiometric, or the like.

In general, analyte sensors provide at least one working electrode and at least one reference electrode, which are configured to measure a signal associated with a concentration of the analyte in the host, such as described in more detail below, and as appreciated by one skilled in the art. The output signal is typically a raw data stream that is used to provide a useful value of the measured analyte concentration in a host to the patient or doctor, for example. However, the analyte sensors of the preferred embodiments comprise at least one additional working electrode configured to measure at least one additional signal, as discussed elsewhere herein. For example, in some embodiments, the additional signal is associated with the baseline and/or sensitivity of the analyte sensor, thereby enabling monitoring of baseline and/or sensitivity changes that may occur in a continuous analyte sensor over time.

In general, continuous analyte sensors define a relationship between sensor-generated measurements (for example, current in nA or digital counts after A/D conversion) and a reference measurement (for example, mg/dL or mmol/L) that are meaningful to a user (for example, patient or doctor). In the case of an implantable enzyme-based electrochemical glucose sensor, the sensing mechanism generally depends on phenomena that are linear with glucose concentration, for example: (1) diffusion of glucose through a membrane system (for example, biointerface membrane and membrane system) situated between implantation site and the electrode surface, (2) an enzymatic reaction within the membrane system (for example, membrane system), and (3) diffusion of the $H_2O_2$ to the sensor. Because of this linearity, calibration of the sensor can be understood by solving an equation:

$$y=mx+b$$

where y represents the sensor signal (counts), x represents the estimated glucose concentration (mg/dL), m represents the sensor sensitivity to glucose (counts/mg/dL), and b represents the baseline signal (counts). Because both sensitivity m and baseline (background) b change over time in vivo calibration has conventionally required at least two independent, matched data pairs $(x_1, y_1; x_2, y_2)$ to solve for m and b and thus allow glucose estimation when only the sensor signal, y is available. Matched data pairs can be created by matching reference data (for example, one or more reference glucose data points from a blood glucose meter, or the like) with substantially time corresponding sensor data (for example, one or more glucose sensor data points) to provide one or more matched data pairs, such as described in co-pending U.S. Patent Publication No. US-2005-0027463-A1.

Accordingly, in some embodiments, the sensing region is configured to measure changes in sensitivity of the analyte sensor over time, which can be used to trigger calibration, update calibration, avoid inaccurate calibration (for example, calibration during unstable periods), and/or trigger filtering of the sensor data. Namely, the analyte sensor is configured to measure a signal associated with a non-analyte constant in the host. Preferably, the non-analyte constant signal is measured beneath the membrane system on the sensor. In one example of a glucose sensor, a non-glucose constant that can be measured is oxygen, wherein a measured change in oxygen transport is indicative of a change in the sensitivity of the glucose signal, which can be measured by switching the bias potential of the working electrode, an auxiliary oxygen-measuring electrode, an oxygen sensor, or the like, as described in more detail elsewhere herein.

Alternatively or additionally, in some embodiments, the sensing region is configured to measure changes in the amount of background noise (e.g., baseline) in the signal, which can be used to trigger calibration, update calibration, avoid inaccurate calibration (for example, calibration during unstable periods), and/or trigger filtering of the sensor data. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). Namely, the glucose sensor is configured to measure a signal associated with the baseline (all non-glucose related current generated) measured by sensor in the host. In some embodiments, an auxiliary electrode located beneath a non-enzymatic portion of the membrane system is used to measure the baseline signal. In some embodiments, the baseline signal is subtracted from the glucose signal (which includes the baseline) to obtain the signal contribution substantially only due to glucose. Subtraction may be accomplished electronically in the sensor using a differential amplifier, digitally in the receiver, and/or otherwise in the hardware or software of the sensor or receiver as is appreciated by one skilled in the art, and as described in more detail elsewhere herein.

One skilled in the art appreciates that the above-described sensitivity and baseline signal measurements can be combined to benefit from both measurements in a single analyte sensor.

Preferred Sensor Components

In general, sensors of the preferred embodiments describe a variety of sensor configurations, wherein each sensor generally comprises two or more working electrodes, a reference and/or counter electrode, an insulator, and a membrane system configured to substantially reduce and/or eliminate noise and/or interferents. In general, the sensors can be configured to continuously measure an analyte in a biological sample, for example, in subcutaneous tissue, in a host's blood flow, and the like. Although a variety of exemplary embodiments are shown, one skilled in the art appreciates that the concepts and examples here can be combined, reduced, substituted, or otherwise modified in accordance with the teachings of the preferred embodiments and/or the knowledge of one skilled in the art.

Preferably, each exemplary sensor design (e.g., FIGS. 1A, 1B, 7A through 9B, and 11) includes first and second working electrodes, wherein the working electrodes are formed from known materials. In some embodiments, the sensor is configured with an architecture smaller than about 1 mm in at least one dimension. For example, in some embodiments, each electrode is formed from a fine wire with a diameter of from about 0.001 or less to about 0.010 inches or more, for example, and is formed from, e.g. a plated insulator, a plated wire, or bulk electrically conductive material. In preferred embodiments, the working electrodes comprise wires formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, and the like), it can be advantageous to form the electrodes from plated wire (e.g. platinum on steel wire) or bulk metal (e.g. platinum wire). It is believed that electrodes formed from bulk metal wire provide superior performance (e.g. in contrast to deposited electrodes), including increased stability of assay, simplified manufacturability, resistance to contamination (e.g. which can be introduced in deposition processes), and improved surface reaction (e.g. due to purity of material) without peeling or delamination.

Preferably, the first working electrode is configured to measure the concentration of an analyte. In an enzymatic electrochemical sensor for detecting glucose, for example, the first working electrode measures the hydrogen peroxide produced by an enzyme catalyzed reaction of the analyte being detected and creates a measurable electronic current.

For example, in the detection of glucose wherein glucose oxidase (GOX) produces hydrogen peroxide as a byproduct, hydrogen peroxide ($H_2O_2$) reacts with the surface of the working electrode producing two protons ($2H^+$), two electrons ($2e^-$) and one molecule of oxygen ($O_2$), which produces the electronic current being detected.

Preferably, each exemplary sensor design (e.g., FIGS. 1A, 1B, 7A through 9B, and 11) includes at least one additional working electrode configured to measure a non-analyte-related signal (e.g., baseline, background, etc.), to measure another analyte (e.g., oxygen), to generate oxygen, and/or as a transport-measuring electrode, all of which are described in more detail elsewhere herein. In general, the additional working electrode(s) can be formed as described with reference to the first working electrode. In one embodiment, the auxiliary (additional) working electrode is configured to measure a background signal, including constant and non-constant analyte signal components.

Preferably, each exemplary sensor design (e.g., FIGS. 1A-1C, and 7A through 9B) includes a reference and/or counter electrode. In general, the reference electrode has a configuration similar to that described elsewhere herein with reference to the first working electrode, however may be formed from materials, such as silver, silver/silver chloride, calomel, and the like. In some embodiments, the reference electrode is integrally formed with the one or more working electrodes, however other configurations are also possible (e.g. remotely located on the host's skin, or otherwise in bodily fluid contact). In some exemplary embodiments (e.g., FIGS. 1B and 9B, the reference electrode is helically wound around other component(s) of the sensor system. In some alternative embodiments, the reference electrode is disposed remotely from the sensor, such as but not limited to on the host's skin, as described herein.

Preferably, each exemplary sensor design (e.g., FIGS. 1A-1C, 7A through 9B, and 11) includes an insulator (e.g., non-conductive material) or similarly functional component. In some embodiments, one or more electrodes are covered with an insulating material, for example, a non-conductive polymer. Dip-coating, spray-coating, vapor-deposition, or other coating or deposition techniques can be used to deposit the insulating material on the electrode(s). In some embodiments, the insulator is a separate component of the system (e.g., see FIG. 7E) and can be formed as is appreciated by one skilled in the art. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). In alternative embodiments, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa.

Preferably, each exemplary sensor design (e.g., FIGS. 1A-1C, 7A through 9B, and 11) includes exposed electroactive area(s). In embodiments wherein an insulator is disposed over one or more electrodes, a portion of the coated electrode(s) can be stripped or otherwise removed, for example, by hand, excimer lasing, chemical etching, laser ablation, grit-blasting (e.g. with sodium bicarbonate or other suitable grit), and the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g. a platinum electrode). Although a variety of "grit" materials can be used (e.g. sand, talc, walnut shell, ground plastic, sea salt, and the like), in some preferred embodiments, sodium bicarbonate is an advantageous grit-material because it is sufficiently hard to ablate, a coating (e.g., parylene) without damaging, an underlying conductor (e.g., platinum). One additional advantage of sodium bicarbonate blasting includes its polishing action on the metal as it strips the polymer layer, thereby eliminating a cleaning step that might otherwise be necessary. In some embodiments, the tip (e.g., end) of the sensor is cut to expose electroactive surface areas, without a need for removing insulator material from sides of insulated electrodes. In general, a variety of surfaces and surface areas can be exposed.

Preferably, each exemplary sensor design (e.g., FIGS. 1A-1C, 7A through 9B, and 11) includes a membrane system, such as those illustrated in FIGS. 2A and 2B. Preferably, a membrane system is deposited over at least a portion of the electroactive surfaces of the sensor (working electrode(s) and optionally reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface. Some examples of suitable membrane systems are described in U.S. Patent Publication No. US-2005-0245799-A1.

In general, the membrane system includes a plurality of domains, for example, one or more of an electrode domain 24, an interference domain 26, an enzyme domain 28 (for example, including glucose oxidase), and a resistance domain 30, as shown in FIGS. 2A and 2B, and can include a high oxygen solubility domain, and/or a bioprotective domain (not shown), such as is described in more detail in U.S. Patent Publication No. US-2005-0245799-A1, and such as is described in more detail below. While the embodiment illustrated in FIGS. 2A and 2B shows the interference domain between the electrode domain and the enzyme domain, the interference domain can be disposed more proximal or more distal to the electroactive surfaces. For example, in some embodiments, the interference domain is more distal to the electroactive surfaces than the enzyme domain. In some embodiments, the interference domain is the most distal layer/domain of the membrane system, relative to the electroactive surfaces. In some embodiments, the interference domain can be the most proximal domain/layer, relative to the electroactive surfaces. In still other embodiments, the interference can be combined with one or more other membrane domains/layers. For example, in some embodiments, the interference domain and the resistance domain are combined into a single domain that provides both interference blocking and control of analyte flux. In some embodiments, the membrane system includes one or more domains not illustrated in FIGS. 2A and 2B, such as but not limited to a bioprotective domain (e.g., cell disruptive domain) and the like. On skilled in the art appreciates that a wide variety of configurations and combinations encompassed by the preferred embodiments.

The membrane system can be deposited on the exposed electroactive surfaces using known thin film techniques (for example, vapor deposition, spraying, electro-depositing, dipping, or the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art.

In some embodiments, one or more domains of the membrane systems are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Patent Publication No. US-2005-0245799-A1 describes biointerface and membrane system configurations and materials that may be applied to the preferred embodiments.

Electrode Domain

In selected embodiments, the membrane system comprises an electrode domain 24 (FIGS. 2A-2B). The electrode domain is provided to ensure that an electrochemical reaction occurs between the electroactive surfaces of the working electrode and the reference electrode, and thus the electrode domain is preferably situated more proximal to the electroactive surfaces than the interference and/or enzyme domain. Preferably, the electrode domain includes a coating that maintains a layer of water at the electrochemically reactive surfaces of the sensor. In other words, the electrode domain is present to provide an environment between the surfaces of the working electrode and the reference electrode, which facilitates an electrochemical reaction between the electrodes. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain is formed of a curable mixture of a urethane polymer and a hydrophilic polymer. Particularly preferred coatings are formed of a polyurethane polymer having carboxylate or hydroxyl functional groups and non-ionic hydrophilic polyether segments, wherein the polyurethane polymer is crosslinked with a water-soluble carbodiimide (e.g., 1-ethyl-3-(3-dimethylaminopropyl)carbodiimide (EDC)) in the presence of polyvinylpyrrolidone and cured at a moderate temperature of about 50° C.

In some preferred embodiments, the electrode domain is formed from a hydrophilic polymer such as polyvinylpyrrolidone (PVP). An electrode domain formed from PVP has been shown to reduce break-in time of analyte sensors; for example, a glucose sensor utilizing a cellulosic-based interference domain such as described in more detail below. Additional description of using PVP to reduce break-in time can be found in co-pending U.S. patent application Ser. No. 11/654,140, filed Jan. 17, 2007 and entitled "MEMBRANES FOR ANALYTE SENSOR" and U.S. Patent Publication No. US-2006-0229512-A1, which are incorporated herein by reference in their entirety.

Preferably, the electrode domain is deposited by vapor deposition, spray coating, dip coating, or other thin film techniques on the electroactive surfaces of the sensor. In one preferred embodiment, the electrode domain is formed by dip-coating the electroactive surfaces in an electrode layer solution and curing the domain for a time of from about 15 minutes to about 30 minutes at a temperature of from about 40° C. to about 55° C. (and can be accomplished under vacuum (e.g., 20 to 30 mmHg)). In embodiments wherein dip-coating is used to deposit the electrode domain, a preferred insertion rate of from about 1 to about 3 inches per minute into the electrode layer solution, with a preferred dwell time of from about 0.5 to about 2 minutes in the electrode layer solution, and a preferred withdrawal rate of from about 0.25 to about 2 inches per minute from the electrode layer solution provide a functional coating. However, values outside of those set forth above can be acceptable or even desirable in certain embodiments, for example, depending upon solution viscosity and solution surface tension, as is appreciated by one skilled in the art. In one embodiment, the electroactive surfaces of the electrode system are dip-coated one time (one layer) and cured at 50° C. under vacuum for 20 minutes.

Although an independent electrode domain is described herein, in some embodiments sufficient hydrophilicity can be provided in the interference domain and/or enzyme domain (the domain adjacent to the electroactive surfaces) so as to provide for the full transport of ions in the aqueous environment (e.g. without a distinct electrode domain). In these embodiments, an electrode domain is not necessary.

Interference Domain

As discussed elsewhere herein, noise can occur during the first few hours or days after sensor implantation, such as during periods of inactivity (e.g., intermittent, sedentary noise), and is believed to be caused by a local increase in interferants (e.g., electroactive metabolites) that disrupts sensor function, resulting in apparent glucose signals that are generally unrelated to the host's glucose concentration. While not wishing to be bound by theory, it is believed that the noise intensity and/or number of intermittent, sedentary noise occurrences can be reduced or eliminated by reducing the local concentration of interferants, such as by incorporation of an interference domain 26 into the membrane system 22. In general, the term "interference domain" includes any noise-reducing mechanism that substantially blocks, reduces, eliminates, reacts with, or otherwise keeps an interferant from reacting at the working electrode(s). Additionally, the noise-reducing mechanisms described herein, including structures, membrane materials, bioactive agents, and the like, which can reduce the effect of interfering species (noise) on the sensor signal, can be considered at least a part of an "interference domain." Some examples of interference domain structures are described herein in this section entitled, "Interference Domain." However, other known interference domain structures can be implemented with the dual electrode sensor described herein. While the embodiments shown in FIGS. 2A and 2B show the interference domain 26 located between the electrode and enzyme domains, the interference domain can be disposed at any level of the membrane system (e.g., more proximal or more distal to the electroactive surfaces). For example, the interference domain can be disposed between the enzyme domain and the resistance domain, between the electroactive surfaces and the electrode domain, as the most exterior membrane domain, etc. In some embodiments, any domain of the membrane system can be configured to function as an interference domain or combined with the interference domain. For example, the enzyme domain and interference domain can be combined into an enzyme-interference domain that performs the functions of an enzyme domain and an interference domain. In one preferred embodiment, the sensor comprises two working electrodes (one with and one without enzyme) and a membrane system comprising an interference domain configured to substantially reduce noise caused by one or more endogenous or exogenous interferents.

As illustrated in FIGS. 2A and 2B, the membrane system of the preferred embodiments includes an interference domain 26. In some preferred embodiments, an interference domain 26 is provided that substantially restricts or blocks the flow of one or more interfering species therethrough. In some embodiments, the interference domain can be configured to reduce noise using, one, two or more noise-reducing mechanisms. For example, in some embodiments, the interference domain is configured to substantially block passage of at least one interfering species into the membrane system. In some embodiments, the interference domain is configured to substantially reduce the concentration of at least one interferent, such as by increasing fluid bulk, forming a fluid pocket, or promoting increased bulk fluid flow. In some other embodiments, the interference domain is configured to oxidize and/or reduce an interferent, such that the interferent no longer substantially affects the sensor. In some embodiments, the interference domain is configured to reduce noise by combining two or more noise-reducing mechanisms, as described below. Some known interfering species for a glucose sensor, as described in more detail herein, include acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. In some embodiments, the interference domain of the preferred embodiments is less permeable to one or more of the interfering species than to the measured species, e.g. the product of an enzymatic reaction that is measured at the electroactive surface(s), such as but not limited to $H_2O_2$.

Cellulosic Polymer Materials

In one embodiment, the interference domain 26 is formed from one or more cellulosic derivatives. Cellulosic derivatives can include, but are not limited to, cellulose esters and cellulose ethers. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like, as well as their copolymers and terpolymers with other cellulosic or non-cellulosic monomers. Cellulose is a polysaccharide polymer of β-D-glucose. While cellulosic derivatives are generally preferred, other polymeric polysaccharides having similar properties to cellulosic derivatives can also be employed in the preferred embodiments.

In one preferred embodiment, the interference domain 26 is formed from cellulose acetate butyrate. Cellulose acetate butyrate with a molecular weight of about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is employed. In certain embodiments, however, higher or lower molecular weights can be preferred. In some embodiments, a blend of two or more cellulose acetate butyrates having different molecular weights is preferred. While a "blend" as defined herein (a composition of two or more substances that are not substantially chemically combined with each other and are capable of being separated) is generally preferred, in certain embodiments a single polymer incorporating different constituents (e.g. separate constituents as monomeric units and/or substituents on a single polymer chain) can be employed instead. Additionally, a casting solution or dispersion of cellulose acetate butyrate at a wt. % of from about 5% to about 25%, preferably from about 5%, 6%, 7%, 8%, 9%, 10%, 11%, 12%, 13%, 14% or 15% to about 16%, 17%, 18%, 19%, 20%, 21%, 22%, 23%, 24% or 25%, and more preferably from about 5% to about 15% is preferred. Preferably, the casting solution includes a solvent or solvent system, for example an acetone:ethanol solvent system. Higher or lower concentrations can be preferred in certain embodiments. In alternative embodiments, a single solvent (e.g. acetone) is used to form a symmetrical membrane domain. A single solvent is used in casting solutions for forming symmetric membrane layer(s). A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g. functional groups). It can also be desirable to include additional substances in the casting solutions or dispersions, e.g. functionalizing agents, crosslinking agents, other polymeric substances, substances capable of modifying the hydrophilicity/hydrophobicity of the resulting layer, and the like.

In one alternative embodiment, the interference domain 26 is formed from cellulose acetate. Cellulose acetate with a molecular weight of about 30,000 daltons or less to about 100,000 daltons or more, preferably from about 35,000, 40,000, or 45,000 daltons to about 55,000, 60,000, 65,000, 70,000, 75,000, 80,000, 85,000, 90,000, or 95,000 daltons, and more preferably about 50,000 daltons is preferred. In some embodiments, a blend of two or more cellulose acetates having different molecular weights is preferred. Additionally, a casting solution or dispersion of cellulose acetate at a weight percent of about 3% to about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 8% is preferred. In certain embodiments, however, higher or lower molecular weights and/or cellulose acetate weight percentages can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries (e.g. functional groups). It can also be desirable to include additional substances in the casting solutions or dispersions such as described in more detail above.

In addition to forming an interference domain from only cellulose acetate(s) or only cellulose acetate butyrate(s), the interference domain 26 can be formed from combinations or blends of cellulosic derivatives, such as but not limited to cellulose acetate and cellulose acetate butyrate, or combinations of layer(s) of cellulose acetate and layer(s) of cellulose acetate butyrate. In some embodiments, a blend of cellulosic derivatives (for formation of an interference domain) includes up to about 10 wt. % or more of cellulose acetate. For example, about 1, 2, 3, 4, 5, 6, 7, 8, 9 wt. % or more cellulose acetate is preferred, in some embodiments. In some embodiments, the cellulosic derivatives blend includes from about 90 wt. % or less to about 100 wt. % cellulose acetate butyrate. For example, in some embodiments, the blend includes about 91, 92, 93, 94, 95, 96, 97, 98 or 99 wt. % cellulose acetate butyrate. In some embodiments, the cellulosic derivative blend includes from about 1.5, 2.0, 2.5, 3.0 or 3.5 wt. % cellulose acetate to about 98.5, 98.0, 97.5, 97.0 or 96.5 wt. % cellulose acetate butyrate. In other embodiments, the blend includes from about 4, 4.5, 5, 5.5, 6, 6.5, 7, 7.5 or 8 wt. % cellulose acetate to about 96, 95.5, 95, 94.5, 94, 93.3, 93, 92.5 or 92 wt. % cellulose acetate butyrate. In still other embodiments, the blend includes from about 8.5, 9.0, 9.5, 10.0, 10.5 or 11.0 wt. % cellulose acetate to about 91.5, 91.0, 90.5, 90, 89.5 or 89 wt. % cellulose acetate butyrate.

In some embodiments, preferred blends of cellulose acetate and cellulose acetate butyrate contain from about 1.5 parts or less to about 60 parts or more cellulose acetate butyrate to one part of cellulose acetate. In some embodiments, a blend contains from about 2 parts to about 40 parts cellulose acetate butyrate to one part cellulose acetate. In other embodiments, about 4, 6, 8, 10, 12, 14, 16, 18 or 20 parts cellulose acetate butyrate to one part cellulose acetate is preferred for formation of the interference domain 26. In still other embodiments, a blend having from 22, 24, 26, 28, 30, 32, 34, 36 or 38 parts cellulose acetate butyrate to one part cellulose acetate is preferred. As is discussed elsewhere herein, cellulose acetate butyrate is relatively more hydrophobic than cellulose acetate. Accordingly, the cellulose acetate/cellulose acetate butyrate blend contains substantially more hydrophobic than hydrophilic components.

Cellulose acetate butyrate is a cellulosic polymer having both acetyl and butyl groups, in addition to hydroxyl groups. Acetyl groups are more hydrophilic than butyl groups, and hydroxyl groups are more hydrophilic than both acetyl and butyl groups. Accordingly, the relative amounts of acetyl, butyl and hydroxyl groups can be used to modulate the hydrophilicity/hydrophobicity of the cellulose acetate butyrate of the cellulose acetate/cellulose acetate butyrate blend. A cellulose acetate butyrate can be selected based on the compound's relative amounts of acetate, butyrate and hydroxyl groups; and a cellulose acetate can be selected based on the compounds relative amounts of acetate and hydroxyl groups. For example, in some embodiments, a cellulose acetate butyrate having about 35% or less acetyl groups, about 10% to about 25% butyl groups, and hydroxyl groups making up the remainder is preferred for formation of the interference domain 26. In other embodiments a cellulose acetate butyrate having from about 25% to about 34% acetyl groups and from about 15 to about 20% butyl groups is preferred. In still other embodiments, the preferred cellulose acetate butyrate contains from about 28% to about 30% acetyl groups and from about 16 to about 18% butyl groups. In yet another embodiment, the cellulose acetate butyrate can have no acetate groups and from about 20% to about 60% butyrate groups. In yet another embodiment, the cellulose acetate butyrate has about 55% butyrate groups and no acetate groups.

While an asymmetric interference domain can be used in some alternative embodiments, a symmetrical interference domain 26 (e.g. of cellulosic-derivative blends, such as but not limited to blends of cellulose acetate components and cellulose acetate butyrate components) is preferred in some embodiments. Symmetrical membranes are uniform throughout their entire structure, without gradients of pore densities or sizes, or a skin on one side but not the other, for example. In various embodiments, a symmetrical interference domain 26 can be formed by the appropriate selection of a solvent (e.g. no anti-solvent is used), for making the casting solution. Appropriate solvents include solvents belonging to the ketone family that are able to solvate the cellulose acetate and cellulose acetate butyrate. The solvents include but are not limited to acetone, methyl ethyl ketone, methyl n-propyl ketone, cyclohexanone, and diacetone alcohol. Other solvents, such as furans (e.g. tetra-hydro-furan and 1,4-dioxane), may be preferred in some embodiments. In one exemplary embodiment, between about 7 wt. % and about 9 wt. % solids (e.g. a blend of cellulosic derivatives, such as cellulose acetate and cellulose acetate butyrate) are blended with a single solvent (e.g. acetone), to form the casting solution for a symmetrical interference domain. In another embodiment, from about 10 to about 15% solids are blended with acetone to form the casting solution. In yet another embodiment, from about 16 to about 18% solids are blended with acetone to form the casting solution. A relatively lower or greater weight percent of solids is preferred to form the casting solution, in some embodiments.

The casting solution can be applied either directly to the electroactive surface(s) of the sensor or on top of an electrode domain layer (if included in the membrane system). The casting solution can be applied using any known thin film technique, as discussed elsewhere herein. Additionally, in various embodiments, a symmetrical interference domain 26 includes at least one layer; and in some embodiments, two, three or more layers are formed by the sequential application and curing of the casting solution.

The concentration of solids in the casting solution can be adjusted to deposit a sufficient amount of solids on the electrode in one layer (e.g. in one dip or spray) to form a membrane layer with sufficient blocking ability, such that the equivalent glucose signal of an interferent (e.g. compounds with an oxidation or reduction potential that overlaps with that of the measured species (e.g. $H_2O_2$)), measured by the sensor, is about 60 mg/dL or less. For example, in some embodiments, the casting solution's percentage of solids is adjusted such that only a single layer (e.g. dip one time) is required to deposit a sufficient amount of the cellulose acetate/cellulose acetate butyrate blend to form a functional symmetric interference domain that substantially blocks passage therethrough of at least one interferent, such as but not limited to acetaminophen, ascorbic acid, dopamine, ibuprofen, salicylic acid, tolbutamide, tetracycline, creatinine, uric acid, ephedrine, L-dopa, methyl dopa and tolazamide. In some embodiments, the amount of interference domain material deposited by as single dip is sufficient to reduce the equivalent glucose signal of the interferant (e.g. measured by the sensor) to about 60 mg/dl or less. In preferred embodiments, the interferent's equivalent glucose signal response (measured by the sensor) is 50 mg/dl or less. In more preferred embodiments, the interferent produces an equivalent glucose signal response of 40 mg/dl or less. In still more preferred embodiments, the interferent produces an equivalent glucose signal response of less than about 30, 20 or 10 mg/dl. In one exemplary embodiment, the interference domain is configured to substantially block acetaminophen passage therethrough, wherein the equivalent glucose signal response of the acetaminophen is less than about 30 mg/dl.

In alternative embodiments, the interference domain is configured to substantially block a therapeutic dose of acetaminophen. The term "therapeutic dose" as used herein is a broad term, and is to be given its ordinary and customary meaning to a person of ordinary skill in the art (and is not to be limited to a special or customized meaning), and refers without limitation to the quantity of any substance required to effect the cure of a disease, to relieve pain, or that will correct the manifestations of a deficiency of a particular factor in the diet, such as the effective dose used with therapeutically applied compounds, such as drugs. For example, a therapeutic dose of acetaminophen can be an amount of acetaminophen required to relieve headache pain or reduce a fever. As a further example, 1,000 mg of acetaminophen taken orally, such as by swallowing two 500 mg tablets of acetaminophen, is the therapeutic dose frequently taken for headaches. In some embodiments, the interference membrane is configured to block a therapeutic dose of acetaminophen, wherein the equivalent glucose signal response of the acetaminophen is less than about 60 mg/dl. In a preferred embodiment, the interference membrane is configured to block a therapeutic dose of acetaminophen, wherein the equivalent glucose signal response of the acetaminophen is less than about 40 mg/dl. In a more preferred embodiment, the interference membrane is configured to block a therapeutic dose of acetaminophen, wherein the equivalent glucose signal response of the acetaminophen is less than about 30 mg/dl.

While not wishing to be bound by theory, it is believed that, with respect to symmetrical cellulosic-based membranes, there is an inversely proportional balance between interferent blocking and analyte sensitivity. Namely, changes to the interference domain configuration that increase interferent blocking can result in a corresponding decrease in sensor sensitivity. Sensor sensitivity is discussed in more detail elsewhere herein. It is believed that the balance between interferent blocking and sensor sensitivity is dependent upon the relative proportions of hydrophobic and hydrophilic components of the membrane layer (e.g. the interference domain), with sensors having more hydrophobic interference domains having increased interferent blocking but reduces sensitivity; and sensors having more hydrophilic interference domains having reduced interferent blocking but increased sensitivity. It is believed that the hydrophobic and hydrophilic components of the interference domain can be balanced, to promote a desired level of interferent blocking while at the same time maintaining a desired level of analyte sensitivity. The interference domain hydrophobe-hydrophile balance can be manipulated and/or maintained by the proper selection and blending of the hydrophilic and hydrophobic interference domain components (e.g. cellulosic derivatives having acetyl, butyryl, propionyl, methoxy, ethoxy, propoxy, hydroxyl, carboxymethyl, and/or carboxyethyl groups). For example, cellulose acetate is relatively more hydrophilic than cellulose acetate butyrate. In some embodiments, increasing the percentage of cellulose acetate (or reducing the percentage of cellulose acetate butyrate) can increase the hydrophilicity of the cellulose acetate/cellulose acetate butyrate blend, which promotes increased permeability to hydrophilic species, such as but not limited to glucose, $H_2O_2$ and some interferents (e.g. acetaminophen). In another embodiment, the percentage of cellulose acetate butyrate is increased to increase blocking of interferants, but less permeability to some desired molecules, such as $H_2O_2$ and glucose, is also reduced.

One method, of manipulating the hydrophobe-hydrophile balance of the interference domain, is to select the appropriate percentages of acetyl groups (relatively more hydrophilic than butyl groups), butyl groups (relatively more hydrophobic than acetyl groups) and hydroxyl groups of the cellulose acetate butyrate used to form the interference domain 26. For example, increasing the percentage of acetate groups on the cellulose acetate butyrate will make the cellulose acetate butyrate more hydrophilic. In another example, increasing the percentage of butyl groups on the cellulose acetate butyrate will make the cellulose acetate butyrate more hydrophobic. In yet another example, increasing the percentage of hydroxyl groups will increase the hydrophilicity of the cellulose acetate butyrate. Accordingly, the selection of a cellulose acetate butyrate that is more or less hydrophilic (or more or less hydrophobic) can modulate the over-all hydrophilicity of the cellulose acetate/cellulose acetate butyrate blend. In one exemplary embodiment, an interference domain can be configured to be relatively more hydrophobic (and therefore block interferants more strongly) by reducing the percentage of acetyl or hydroxyl groups or by increasing the percentage of butyl groups on the cellulose acetate butyrate used in the casting solution (while maintaining the relative ratio of cellulose acetate to cellulose acetate butyrate).

In some alternative embodiments, the interference domain is formed of a blend of cellulosic derivatives, wherein the hydrophilic and hydrophobic components of the interference domain are balanced, such that the glucose sensitivity is from about 1 pA/mg/dL to about 100 pA/mg/dL, and at least one interferent is sufficiently blocked from passage through the interference domain such that the equivalent glucose signal response of the at least one interferent is less than about 60 mg/dL. In a preferred embodiment, the glucose sensitivity is from about 5 pA/mg/dL to about 25 pA/mg/dL. In a more preferred embodiments, the glucose sensitivity is from about 5 pA/mg/dL to about 25 pA/mg/dL and the equivalent glucose signal response of the at least one interferent is less than about 40 mg/dL. In a still more preferred embodiments, the glucose sensitivity is from about 5 pA/mg/dL to about 25 pA/mg/dL and the equivalent glucose signal response of the at least one interferent is less than about 30 mg/dL. In some embodiments, the balance between hydrophilic and hydrophobic components of the interference domain can be achieved by adjusting the amounts of hydrophilic and hydrophobic components, relative to each other, as well as adjusting the hydrophilic and hydrophobic groups (e.g. acetyl, butyryl, propionyl, methoxy, ethoxy, propoxy, hydroxyl, carboxymethyl, and/or carboxyethyl groups) of the components themselves (e.g. cellulosic derivatives, such as but not limited to cellulose acetate and cellulose acetate butyrate).

In some alternative embodiments, additional polymers, such as Nafion®, can be used in combination with cellulosic derivatives to provide equivalent and/or enhanced function of the interference domain 26. As one example, a layer of a 5 wt. % Nafion® casting solution was applied over a previously applied (e.g. and cured) layer of 8 wt. % cellulose acetate, e.g. by dip coating at least one layer of cellulose acetate and subsequently dip coating at least one layer Nafion® onto a needle-type sensor such as described with reference to the preferred embodiments. Any number of coatings or layers formed in any order may be suitable for forming the interference domain of the preferred embodiments.

In some alternative embodiments, more than one cellulosic derivative can be used to form the interference domain 26 of the preferred embodiments. In general, the formation of the interference domain on a surface utilizes a solvent or solvent system, in order to solvate the cellulosic derivative(s) (or other polymer) prior to film formation thereon. In preferred embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method of deposition, its desired thickness, and the like. However, a percent solute of from about 1 wt. % to about 25 wt. % is preferably used to form the interference domain solution so as to yield an interference domain having the desired properties. The cellulosic derivative (or other polymer) used, its molecular weight, method of deposition, and desired thickness can be adjusted, depending upon one or more other of the parameters, and can be varied accordingly as is appreciated by one skilled in the art.

In some alternative embodiments, other polymer types that can be utilized for the interference domain 26 including polyurethanes, polymers having pendant ionic groups, and polymers having controlled pore size, for example. In one such alternative embodiment, the interference domain includes a thin, hydrophobic membrane that is non-swellable and restricts diffusion of high molecular weight species. The interference domain 26 is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Pat. No. 7,074,307, U.S. Patent Publication No. 2005-0176136-A1, U.S. Pat. No. 7,081,195, and U.S. Patent Publication No. 2005-0143635-A1. In some alternative embodiments, a distinct interference domain is not included.

In some embodiments, the interference domain 26 is deposited either directly onto the electroactive surfaces of the sensor or onto the distal surface of the electrode domain, for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes can also be desirable in certain embodiments, but thinner membranes are generally preferred because they have a lower impact on the rate of diffusion of hydrogen peroxide from the enzyme membrane to the electrodes. In some embodiments, the interference domain can be deposited either more proximal or more distal than the electrode domain, relative to the electroactive surfaces, depending upon the interference domain composition and membrane system configuration.

In general, the membrane systems of the preferred embodiments can be formed and/or deposited on the exposed electroactive surfaces (e.g. one or more of the working and reference electrodes) using known thin film techniques (for example, casting, spray coating, drawing down, electro-depositing, dip coating, and the like), however casting or other known application techniques can also be utilized. Preferably, the interference domain is deposited by spray or dip coating. In one exemplary embodiment of a needle-type (transcutaneous) sensor such as described herein, the interference domain is formed by dip coating the sensor into an interference domain solution using an insertion rate of from about 0.5 inch/min to about 60 inches/min, preferably 1 inch/min, a dwell time of from about 0 minute to about 2 minutes, preferably about 1 minute, and a withdrawal rate of from about 0.5 inch/minute to about 60 inches/minute, preferably about 1 inch/minute, and curing (drying) the domain from about 1 minute to about 30 minutes, preferably from about 3 minutes to about 15 minutes (and can be accomplished at room temperature or under vacuum (e.g. 20 to 30 mmHg)). In one exemplary embodiment including cellulose acetate butyrate interference domain, a 3-minute cure (i.e., dry) time is preferred between each layer applied. In another exemplary embodiment employing a cellulose acetate interference domain, a 15-minute cure (i.e., dry) time is preferred between each layer applied.

In some embodiments, the dip process can be repeated at least one time and up to 10 times or more. In other embodiments, only one dip is preferred. The preferred number of repeated dip processes depends upon the cellulosic derivative(s) used, their concentration, conditions during deposition (e.g. dipping) and the desired thickness (e.g., sufficient thickness to provide functional blocking of certain interferents), and the like. In some embodiments, 1 to 3 microns may be preferred for the interference domain thickness, however, values outside of these can be acceptable or even desirable in certain embodiments, for example, depending upon viscosity and surface tension, as is appreciated by one skilled in the art. In one exemplary embodiment, an interference domain is formed from three layers of cellulose acetate butyrate. In another exemplary embodiment, an interference domain is formed from 10 layers of cellulose acetate. In another embodiment, an interference domain is formed from 1 layer of a blend of cellulose acetate and cellulose acetate butyrate. In alternative embodiments, the interference domain can be formed using any known method and combination of cellulose acetate and cellulose acetate butyrate, as will be appreciated by one skilled in the art.

In some embodiments, the electroactive surface can be cleaned prior to application of the interference domain 26. In some embodiments, the interference domain 26 of the preferred embodiments can be useful as a bioprotective or biocompatible domain, namely, a domain that interfaces with host tissue when implanted in an animal (e.g. a human) due to its stability and biocompatibility.

Silicone/Hydrophilic Polymer Blend Materials

It is believed that incorporation of a silicone-hydrophilic polymer blend into the membrane system can substantially reduce and/or eliminate noise, such as by substantially blocking and/or slowing (e.g., reducing the diffusion rate) the passage of an interferent therethrough. In preferred embodiments, a sensor having two or more working electrodes, such as but not limited to those illustrated in FIGS. 1B, 7A1-9B and 11, includes a membrane system 22 wherein the interference domain comprises a blend of a silicone polymer with a hydrophilic polymer configured to reduce noise-causing species, such as constant and/or non-constant noise-causing species. In some embodiments, additional membrane domains/layers comprise a blend of a silicone polymer with a hydrophilic polymer configured to reduce noise-causing species. In some preferred embodiments, the sensor includes a silicone-hydrophilic polymer blend membrane domain and/or layer (e.g., an interference domain) comprising a micellar jacket structure (described elsewhere herein). While not wishing to be bound by theory, it is believed that membrane domains comprising a silicone-hydrophilic polymer blend can reduce noise by blocking and/or suppressing passage of at least one interfering species into the membrane system, while at the same time allowing for and/or promoting the transport of the analyte (e.g., glucose or other such water-soluble molecules, such as drugs).

By "hydrophilic polymer," it is meant that the polymer has an affinity for water, due to the presence of one or more hydrophilic substituents, and generally is primarily soluble in water or has a tendency to absorb water. In one example, the hydrophilic component of a hydrophilic polymer promotes the movement of water and/or compounds in the water (e.g., by diffusion or other means) through a membrane formed of the hydrophilic polymer, such as by lowering the thermodynamic barrier to movement of compounds in the water into the membrane.

In some embodiments, hydrophilic polymers include hydrophilic-hydrophobic polymers. Generally, the terms "hydrophilic-hydrophobic" and "hydrophobic-hydrophilic" are used interchangeably herein (are not meant to imply that either the hydrophilic or the hydrophobic substituents are the major component of the polymer) and refer to the property of having both hydrophilic and hydrophobic substituents and/or characteristics in a single molecule, such as, for example, a polymer.

The hydrophilic and hydrophobic substituents of a polymer can affect the polymer's behavior in certain circumstances, such as but not limited to silicone/hydrophilic-hydrophobic blend materials and micellar jackets, which are discussed elsewhere herein. Using PEO-PPO-PEO as an exemplary polymer, the polymer's major component (PEO) is hydrophilic and can provide an overall hydrophilic character to the molecule (e.g., the molecule generally behaves in a hydrophilic manner). However, the hydrophobic component (PPO) of the polymer makes it possible for the polymer to have some hydrophobic character (e.g., for portions of the molecule to behave in the manner of a hydrophobic molecule), in some situations. In some circumstances, such as formation of micellar jackets in a silicone/hydrophilic-hydrophobic blend material, the polymer self-organizes, relative to the silicone (e.g., silicone globule(s)) such that the hydrophobic PPO is adjacent to the silicone (which is hydrophobic) and the two PEO groups project away from the silicone (e.g., due to thermodynamic forces). Depending upon the circumstance (e.g., the polymer selected), variations of the micellar jacket structure described above (e.g., opposite orientations) are possible. For example, it is believed that in a mixture of PPO-PEO-PPO and silicone, the PPO groups self-orient toward the silicone and the PEO center is oriented away from the silicone.

In one embodiment, the hydrophilic polymer has a molecular weight of at least about 1000 g/mol, 5,000 g/mol, 8,000 g/mol, 10,000 g/mol, or 15,000 g/mol. In one embodiment, the hydrophilic polymer comprises both a hydrophilic domain and a partially hydrophobic domain (e.g., a copolymer, also referred to herein as a hydrophobic-hydrophilic polymer). The hydrophobic domain(s) facilitate the blending of the hydrophilic polymer with the hydrophobic silicone polymer, such as but not limited to formation of micellar jackets within and/or around the silicone. In one embodiment, the hydrophobic domain is itself a polymer (i.e., a polymeric hydrophobic domain). For example, in one embodiment, the hydrophobic domain is not a simple molecular head group but is rather polymeric. In various embodiments, the molecular weight of any covalently continuous hydrophobic domain within the hydrophilic polymer is at least about 500 g/mol, 700 g/mol, 1000 g/mol, 2000 g/mol, 5000 g/mol, or 8,000 g/mol. In various embodiments, the molecular weight of any covalently continuous hydrophilic domain within the hydrophilic polymer is at least about 500 g/mol, 700 g/mol, 1000 g/mol, 2000 g/mol, 5000 g/mol, or 8,000 g/mol.

In some embodiments, within a particular layer, the ratio of the silicone polymer to hydrophilic polymer is selected to provide an amount of oxygen and water-soluble molecule solubility such that oxygen and water-soluble molecule transport through a domain is optimized according to the desired function of that particular layer. Furthermore, in some embodiments, the ratio of silicone polymer to hydrophilic polymer, as well as the polymeric compositions, are selected such that a layer constructed from the material has interference characteristics that inhibit transport of one or more interfering species through the layer. Some known interfering species for a glucose sensor include, but are not limited to, acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. Accordingly, in some embodiments, a silicone polymer/hydrophilic polymer layer as disclosed herein is less permeable to one or more of these interfering species than to the analyte, e.g., glucose.

In some of these embodiments, the ratio of silicone polymer to hydrophilic polymer (in the layers incorporating the blends) varies according to the desired functionality of each layer. The relative amounts of silicone polymer and hydrophilic polymer described below are based on the respective amounts found in the cured polymeric blend. Upon introduction into an aqueous environment, some of the polymeric components may leach out, thereby changing the relative amounts of silicone polymer and hydrophilic polymer. For example, substantial amounts of the portions of the hydrophilic polymer that are not cross-linked may leach out, for example, depending on the hydrophilic polymer's molecular weight and how tortuous it the diffusion path out of the membrane.

In some embodiments, the silicone and hydrophilic polymers form a substantial blend. Namely, the amount of any cross-linking between the silicone polymer and the hydrophilic polymer is substantially limited. In various embodiments, at least about 75%, 85%, 95%, or 99% of the silicone polymer is not covalently linked to the hydrophilic polymer. In some embodiments, the silicone polymer and the hydrophilic polymer do not cross-link at all unless a cross-linking agent is used (e.g., such as described below). Similarly, in some embodiments, the amount of any entanglement (e.g., blending on a molecular level) between the silicone polymer and the hydrophilic polymer is substantially limited. In one embodiment, the silicone polymer and hydrophilic polymers form microdomains. For example, in one embodiment, the silicone polymer forms micellar jacket structures surrounded by a network of hydrophilic polymer.

The silicone polymer for use in the silicone/hydrophilic polymer blend may be any suitable silicone polymer. In some embodiments, the silicone polymer is a liquid silicone rubber that may be vulcanized using a metal—(e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-si loxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

The hydrophilic polymer for use in the blend may be any suitable hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, diblock, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. Some PLURONIC® polymers are triblock copolymers of poly(ethylene oxide)-poly(propylene oxide)-poly(ethylene oxide) having the general molecular structure:

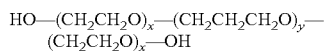

where the repeat units x and y vary between various PLURONIC® products. The poly(ethylene oxide) blocks act as a hydrophilic domain allowing the dissolution of aqueous agents in the polymer. The poly(propylene oxide) block acts as a hydrophobic domain facilitating the blending of the PLURONIC® polymer with a silicone polymer. In one embodiment, PLURONIC® F-127 is used having x of approximately 100 and y of approximately 65. The molecular weight of PLURONIC® F-127 is approximately 12,600 g/mol as reported by the manufacture. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The polyether structure of PLURONIC® polymers is relatively inert. Accordingly, without being bound by any particular theory, it is believed that the PLURONIC® polymers do not substantially react with the components in MED-4840 or other silicone polymer precursors.

Those of skill in the art will appreciate that other copolymers having hydrophilic and hydrophobic domains may be used. For example, in one alternative embodiment, a triblock copolymer having the structure hydrophobic-hydrophilic-hydrophobic may be used. In another alternative embodiment, a diblock copolymer having the structure hydrophilic-hydrophobic is used. Additional devices, methods and compositions can be found in U.S. Patent Publication No. US-2006-0270923-A1, and U.S. patent application Ser. No. 11/404,417, filed on Apr. 14, 2006, and entitled "SILICONE BASED MEMBRANES FOR USE IN IMPLANTABLE GLUCOSE SENSORS," both of which are incorporated herein by reference.

Layers and/or domains that include a silicone polymer-hydrophilic polymer blend can be made using any of the methods of forming polymer blends known in the art. In one embodiment, a silicone polymer precursor (e.g., MED-4840) is mixed with a solution of a hydrophilic polymer (e.g., PLURONIC® F-127 dissolved in a suitable solvent such as acetone, ethyl alcohol, or 2-butanone). The mixture may then be drawn into a film or applied in a multi-layer membrane structure using any method known in the art (e.g., spraying, painting, dip coating, vapor depositing, molding, 3-D printing, lithographic techniques (e.g., photolithograph), micro- and nano-pipetting printing techniques, etc.). The mixture may then be cured under high temperature (e.g., 50-150° C.). Other suitable curing methods include ultraviolet or gamma radiation, for example. During curing, the silicone polymer precursor will vulcanize and the solvent will evaporate. In one embodiment, after the mixture is drawn into a film, another preformed layer of the membrane system is placed on the film. Curing of the film then provides bonding between the film and the other preformed layer. In one embodiment, the preformed layer is the cell disruptive layer. In one embodiment, the cell disruptive domain comprises a preformed porous silicone membrane. In other embodiments, the cell disruptive domain is also formed from a silicone polymer/hydrophilic polymer blend. In some embodiments, multiple films are applied on top of the preformed layer. Each film may posses a finite interface with adjacent films or may together form a physically continuous structure having a gradient in chemical composition.

Some amount of cross-linking agent may also be included in the mixture to induce cross-linking between hydrophilic polymer molecules. For example, when using a PLURONIC® polymer, a cross-linking system that reacts with pendant or terminal hydroxy groups or methylene, ethylene, or propylene hydrogen atoms may be used to induce cross linking. Non-limiting examples of suitable cross-linking agents include ethylene glycol diglycidyl ether (EGDE), poly (ethylene glycol) diglycidyl ether (PEGDE), or dicumyl peroxide (DCP). While not being bound by any particular theory, at low concentrations, these cross-linking agents are believed to react primarily with the PLURONIC® polymer with some amount possibly inducing cross-linking in the silicone polymer or between the PLURONIC® polymer and the silicone polymer. In one embodiment, enough cross-linking agent is added such that the ratio of cross-linking agent molecules to hydrophilic polymer molecules added when synthesizing the blend is about 10 to about 30 (e.g., about 15 to about 20). In one embodiment, from about 0.5% to about 15% w/w of cross-linking agent is added relative to the total dry weights of cross-linking agent, silicone polymer, and hydrophilic polymer added when blending the ingredients (in one example, from about 1% to about 10%). In one embodiment, from about 5% to about 30% of the dry ingredient weight is the PLURONIC® polymer. During the curing process, substantially all of the cross-linking agent is believed to react, leaving substantially no detectable unreacted cross-linking agent in the final film.

In some embodiments, other agents may be added to the mixture to facilitate formation of the blend. For example, a small amount of butylhydroxy toluene (BHT) (e.g., about 0.01% w/w) or other suitable antioxidant may be mixed with a PLURONIC® to stabilize it.

In some alternative embodiments, precursors of both the silicone polymer and hydrophilic polymer may be mixed prior to curing such that polymerization of both the silicone polymer and the hydrophilic polymer occur during curing. In another embodiment, already polymerized silicone polymer is mixed with a hydrophilic polymer such that no significant polymerization occurs during curing.

While not wishing to be bound by theory, it is believed that a micelle-like structure, referred to herein as a micellar jacket structure, can be formed by combining certain hydrophobic polymers (e.g., silicone) with certain amphipathic polymers (e.g., hydrophilic polymers such as PLURONIC® polymers), which, when substantially blended, create a mechanism by which glucose and other analytes are transported at a limited rate. One example of a limited rate is diffusion of oxygen and glucose into the membrane at a ratio of 50:1 (50 oxygen molecules for every one glucose molecule). In a preferred embodiment, oxygen and glucose diffuse into the membrane at the limited rate of 100:1. In a more preferred embodiment, oxygen and glucose diffuse into the membrane at the limited rate of 200:1.

In a first mechanism of limited analyte transport, it is believed that the PLURONIC® hydrophilic and hydrophobic constituents can promote self-organization of the PLURONIC® molecules, in conjunction with the silicone, into micellar jackets. The micellar jackets provide a contiguous channel (e.g., a tortuous path) though the silicone, through which the analyte travels. For example, at a first side of a membrane/domain, glucose dissolves into the hydrophilic component of the micellar jackets (e.g., within the membrane/domain) and diffuses through the hydrophilic portion of adjacent micellar jackets, to reach the opposite side of the membrane/domain.

In a second mechanism of limited analyte transport, it is believed that micellar jackets can provide a hydrophilic phase within the silicone membrane/domain structure. There is an energetic barrier to diffusion of the analyte (e.g., glucose) into the silicone. However, an energetic, thermodynamic force (e.g., an analyte concentration gradient) drives the analyte to pass across/through the membrane by "jumping" from one micellar jacket to another. For example, a glucose concentration gradient can provide the energy for a glucose molecule to pass into the membrane domain or layer (e.g., the cell impermeable domain formed of a substantial blend of silicone and PLURONIC®), to the first micellar jacket, then to "jump" to the next micellar jacket, and so on, until the molecule reaches the opposite side of the membrane domain/layer.

In one exemplary embodiment, a silicone-hydrophilic polymer (e.g., wherein the hydrophilic polymer is an amphipathic polymer, such as but not limited to PLURONIC®) blend is believed to promote the macromolecular self-organization of micellar jackets that clothe colloidal silicone globules (e.g., silicone granules that form a three-dimensional contiguous macromolecular structure having silicone-to-silicone contacts between the silicone granules, coated with the hydrophilic polymer), within the membrane domain. The hydrophilic groups of the micellar jackets orient toward the silicone, with the hydrophobic portions of the polymer oriented away from the silicone core of the structure. For example, in the case of silicone globules clothed with PLURONIC® (PEO-PPO-PEO), it is believed that it is thermodynamically favorable for a PLURONIC® molecule to orient itself such that the PPO "lies against" the silicone and the PEO to bends away from the silicone, for example, in a U-like shape. Inverse micellar jackets are also possible, for example, inverted micellar jackets (e.g., with the hydrophobic PPO facing outward toward the silicone and the hydrophilic PEO facing inward) within the silicone. Additionally, the micellar jackets may not be in direct, physical contact with each other, which would provide a thermodynamic barrier to molecules entering the membrane layer and traveling through/across the layer by energetically "jumping" from one micellar jacket to the next.

In addition to facilitating analyte passage through the membrane domain, it has been found that the micellar jacket structure blocks diffusion of small, reactive oxygen and nitrogen interferents (e.g., $H_2O_2$, oxygen radicals, peroxynitrates, etc.) that can cause non-constant noise. While not wishing to be bound by theory, it is believed that the micellar jacket structure sufficiently slows the diffusion of the reactive oxygen and nitrogen interferents such that these molecules self-annihilate before reaching the electroactive surface(s). In contrast, it is believed that large molecular weight interferents (e.g., acetaminophen and ascorbate) are sterically and/or thermodynamically blocked and/or trapped by the micellar jackets, and thus do not reach the electroactive surface(s). Accordingly, non-constant noise produced by both small and large molecular weight interferents is attenuated, with improved sensor function as a result.

In one exemplary embodiment, the sensor is configured to block non-constant, non-analyte-related noise and comprises first and second working electrodes separated by a spacer (as described elsewhere herein, see FIGS. 1B-1C or 7F-7G) and a membrane system (e.g., FIGS. 2A-2B) comprising at least an enzyme domain and a silicone-hydrophilic polymer blend that includes a micellar jacket structure. In some further embodiments, the membrane system includes at least one additional domain, such as but not limited to an electrode domain, an interference domain, a resistance domain and a cell disruptive domain (e.g., a most distal domain comprising a silicone-hydrophilic polymer blend and a micellar jacket structure). In one preferred embodiment, the membrane system includes a combined resistance-interference domain formed of a silicone-hydrophilic polymer blend having a micellar jacket structure, whereby the combined silicone-hydrophilic polymer blend resistance-interference domain can modulate the flux of the analyte into the membrane system and reduce noise by blocking the passage of at least one interferent (e.g., acetaminophen) into the membrane system. In a further preferred embodiment, the sensor is configured for transcutaneous insertion into the host. In another further preferred embodiment, the sensor is configured for insertion into a host's vessel, such as but not limited to a blood vessel.

Fluid Pocket Formation to Reduce Noise

While not wishing to be bound by theory, it is believed that non-constant, non-analyte-related noise can be decreased by diluting and/or removing interferents, such as by increasing fluid bulk (e.g., a fluid pocket), increasing bulk fluid flow and/or increasing diffusion rate around at least a portion of the sensor, such as the sensing portion of the sensor. Furthermore, a physical spacer can reduce the effect of lymph pooling (e.g., build-up of interferents in the tissue surrounding an implanted sensor) due to local compression (described elsewhere herein) by mechanically maintaining a fluid pocket. Since a spacer can maintain the fluid bulk around the sensor during local compression, the effect of interferant concentration increases can be suppressed or reduced, thereby reducing noise and promoting optimal sensor function. One preferred embodiment provides a device with reduced noise (e.g., during intermittent host sedentary periods) having an architecture that allows and/or promotes increased fluid bulk and/or increased bulk fluid flow in the area surrounding at least a portion of an implanted sensor in vivo.

A variety of structures can be incorporated into the sensor configuration as an interference domain to allow and/or promote increased (e.g., to stimulate or to promote) fluid bulk, bulk fluid flow, and/or diffusion rate, such as by forming a fluid pocket, which can reduce noise. These structures can include but are not limited to spacers, meshes, shedding layers, roughened surfaces, machineable materials, nanoporous materials, shape-memory materials, porous memory materials, self-assembly materials, collapsible materials, biodegradable materials, combinations thereof, and the like. Structures that promote increased fluid bulk and/or increased bulk fluid flow can also include but are not limited to structures that promote fluid influx or efflux (e.g., fluid influx-promoting architecture, fluid efflux-promoting architecture), that promote vasodilation (e.g., vasodilating architecture), that promote inflammation (e.g., inflammatory architecture), that promote wound healing or perpetuate wounding (e.g., wound-healing architecture and wounding architecture, respectively), that promote angiogenesis (e.g., angiogenic architecture), that suppress inflammation (e.g., an anti-inflammatory architecture) or combinations thereof.

In certain embodiments, the device includes a physical spacer between the sensor and the surrounding tissue. A spacer allows for a liquid sheath to form around at least a portion of the sensor, such as the area surrounding the electrodes, for example. A fluid sheath can provide a fluid bulk that dilutes or buffers interferants while promoting glucose and oxygen transport to the sensor.

In some embodiments, the spacer is a mesh or optionally a fibrous structure. Suitable mesh materials are known in the art and include open-weave meshes fabricated of biocompatible materials such as but not limited to PLA, PGA, PP, nylon and the like. Mesh spacers can be applied directly to the sensing mechanism or over a biointerface membrane, such as a porous biointerface membrane disclosed elsewhere herein. Mesh spacers can act as a fluid influx- or efflux-promoting structure and provides the advantage of relatively more rapid fluid movement, mixing and/or diffusion within the mesh to reduce local interferant concentrations and increasing glucose and oxygen concentrations. The increased fluid volume within the mesh can also promote increased fluid movement in and out of the area, which brings in glucose and oxygen while removing or diluting interferants.

In one exemplary embodiment, the sensor is wrapped with a single layer of open weave polypropylene (PP) biocompatible mesh. When the sensor is inserted, the mesh holds the surrounding tissue away from the sensor surface and allows an influx of extracellular fluid to enter the spaces within the mesh, thereby creating a fluid pocket around the sensor. Within the fluid pocket, fluid can mix substantially rapidly as extracellular fluid enters and leaves the fluid pocket or due to host movement. Interferants are carried by the fluid and therefore can be mixed and/or diluted. Since the host can wear the sensor for a plurality of days, sedentary periods will inevitably occur. During these periods interferants can accumulate. However, the increased fluid volume provided by the mesh can substantially buffer accumulated interferants until the sedentary period ends. When the sedentary period is over, any accumulated interferants can be diluted or carried away by an influx or efflux of fluid.

In an alternative embodiment, a mesh can be applied to a sensor either symmetrically or asymmetrically. For example, the mesh can be tightly wrapped around the sensor. In another example, a strip of mesh can be applied to only one side of the sensor. In yet another example, the mesh can form a flat envelope about a few millimeters to about a centimeter wide, with the sensor sandwiched within the envelope. In some embodiments, the mesh can cover only a portion of the sensor, such as the portion containing the electrochemically reactive surface(s). In other embodiments, the mesh can cover the entire sensor.

In another alternative embodiment, noise can be reduced by inclusion of a hydrogel on the surface of at least a portion of the sensor, such as the sensing region. A hydrogel is a network of super absorbent (they can contain 20%-99% or weight % water, preferably 80% to over 99% weight % water) natural or synthetic polymer chains. Hydrogels are sometimes found as a colloidal gel in which water is the dispersion medium. Since hydrogels are nonporous, fluid and interferants within the hydrogel move by diffusion. Accordingly, the movement of molecules within hydrogels is relatively slower than that possible within mesh-based fluid pockets as described above. Optionally, the hydrogel can be biodegradable. A biodegradable hydrogel can provide a fluid pocket that gradually diminishes and is eventually eliminated by the surrounding tissue.

In a further embodiment, a hydrogel includes a flexible, water-swellable, film (as disclosed elsewhere herein) having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques. The hydrogel material can be applied to the entire sensor or a portion of it, using any method known in the art, such as but not limited to dipping, painting, spraying, wrapping, and the like.

In certain embodiments, scavenging agents (e.g., bioactive agents that can scavenge, bind-up or substantially inactivate interferants) can be incorporated into the hydrogel or other aspect of the device (e.g., membrane system). Scavenging agents can suppress prolonged wounding and inflammation by removing signal associated with irritating substances from the locality of the sensor and/or internally generated hydrogen peroxide.

One exemplary scavenging agent embodiment incorporates an $H_2O_2$-degrading enzyme, such as but not limited to glutathione peroxidase (GSH peroxidase), heme-containing peroxidases, eosinophil peroxidase, thyroid peroxidase or horseradish peroxidase (IRP) into the hydrogel to degrade the available $H_2O_2$ and produce oxygen. The scavenging agent can act within the hydrogel or can be released into the local environment to act outside the hydrogel.

In a further embodiment, a mesh and a hydrogel can be used in combination to provide greater mechanical support (to hold the surrounding tissue away from the sensor) while slowing down the diffusion rate within the mesh-hydrogel layer. For example, a PP mesh can be applied to the sensor followed by spraying a dry hydrogel material onto the PP-wrapped sensor. Alternatively, the hydrogel can be dried within the mesh before application to the sensor. Upon sensor implantation, the hydrogel can absorb fluid from the surrounding tissue, expand and fill the mesh pores. In a further example, the hydrogel can be biodegradable. In this example, the hydrogel can initially slow fluid movement. But as the hydrogel is biodegraded, the pores of the mesh are opened up and fluid movement can speed up or increase.

A variety of alternative materials can be used to create architectures that create a fluid pocket. For example, shape-memory materials can be used as an alternative to a mesh, to form a fluid pocket around the sensor. Shape-memory materials are metals or polymers that "remember" their geometries. Shape-memory metals (e.g., memory metals or smart wire) include copper-zinc-aluminum, copper-aluminum-nickel, and nickel-titanium (NiTi) alloys. Shape-memory polymers include materials such as polynorbornene, segmented poly(epsilon-caprolactone) polyurethanes, poly(ethylene glycol)-poly(epsilon-caprolactone) diblock copolymers, and the like, for example. A shape-memory material can be deformed from its "original" conformation and regains its original geometry by itself in response to a force, such as temperature or pressure.

In one embodiment, a porous memory material that has been collapsed into a flat, nonporous sheet can be applied to the exterior of the sensor as a flat film. After insertion into the body, increased temperature or moisture exposure can stimulate the memory material to transform to a 3-dimensional, porous architecture that promotes fluid pocket formation, for example.

In an alternative embodiment, nanoporous materials, which act as molecular sieves, can be used to exclude interferants surrounding the sensor. In another alternative embodiment, a swellable material (e.g., a material having an initial volume that absorbs fluid, such as water, when it contacts the fluid to become a second volume that is greater than the initial volume) or collapsible material (e.g., a material having an initial volume that collapse to a second volume that is smaller than the initial volume) can produce or maintain a fluid pocket.

In yet another embodiment, materials with differing characteristics can be applied in combination, such as alternating bands or layers, to suppress uniform capsule formation. For example, alternating bands of collapsible and non-collapsible swellable material can be applied around a portion of the sensor. Upon implantation, both materials swell with fluid from the surrounding tissue. However, only the segments of collapsible material can deform. Since the material surrounding the sensor will be irregular, it can disrupt formation of a continuous cell layer, thereby reducing noise and extending sensor life.

In addition to providing a physical spacer, mesh, porous material or the like, irritating sensor configurations can reduce noise by promoting fluid pocket formation and/or increased bulk fluid flow. Accordingly, one embodiment of an irritating biointerface includes a structure having a roughened surface, which can rub or poke adjacent cells in vivo. The sensor surface can be roughened by coating the sensor with a machineable material that is or can be etched to form ridges, bristles, spikes, grids, grooves, circles, spirals, dots, bumps, pits or the like, for example. The material can be any convenient, biocompatible material, such as machined porous structures that are overlaid on the sensor, such as but not limited to machineable metal matrix composites, bone substrates such as hydroxyapatite, coral hydroxyapatite and β-tricalcium phosphate (TCP), porous titanium (Ti) mixtures made by sintering of elemental powders, bioglasses (calcium and silicon-based porous glass), ceramics and the like. The material can be "machined" by any convenient means, such as but not limited to scraping, etching, lathing or lasering, for example.

Micro-motion of the sensor can increase the irritating effect of a roughened surface. Micro-motion is an inherent property of any implanted device, such as an implanted glucose sensor. Micro-motion of the device (e.g., minute movements of the device within the host) is caused by host movements, ranging from breathing and small local muscle movements to gross motor movements, such as walking, running or even getting up and sitting down. External forces, such as external pressure application, can also cause micro-motion. Micro-motion includes movement of the sensor back and forth, rotation, twisting and/or turning. Accordingly, as the sensor is moved by micro-motion, the sensor's rough surface can rub more vigorously against the surrounding tissue, causing increased or extended wounding, resulting in additional stimulation of the wound healing process and increases in fluid bulk, bulk fluid flow and/or fluid pocket formation, with a concomitant reduction in noise.

In another embodiment, an irritating architecture is formed from self-assembly materials. Self-assembly biomaterials comprise specific polypeptides that are designed a priori to self-assemble into targeted nano- and microscopic structures. Intramolecular self-assembling molecules are often complex polymers with the ability to assemble from the random coil conformation into a well-defined stable structure (secondary and tertiary structure). A variety of self-assembly materials known in the art can find use in the present embodiment. For example, PuraMatrix™ (3DM Inc., Cambridge, Mass., USA) can be used to create synthetic self-assembling peptide nanofiber scaffolds and defined 3-D microenvironments.

In an exemplary embodiment of an irritating biointerface, an irritating superstructure is applied to the working electrode or the completed sensor. A "superstructure," as used herein is a broad term and used in its ordinary sense, including, without limitation, to refer to any structure built on something else, such as but not limited to the overlying portion of a structure. An irritating superstructure can include any substantial structure that prevents cell attachment and is irritating to the surrounding tissue in vivo. In one example, an irritating superstructure can include large spaces, such as at least about 50 µm wide and at least about 50 µm deep. Cells surrounding the sensor can be prevented from attachment in the spaces within the superstructure, allowing fluid to fill these spaces. In some exemplary embodiments, an irritating superstructure takes advantage of sensor micromotion, to prevent cell attachment and stimulate fluid pocket formation.

In one exemplary embodiment, an irritating superstructure is comprised of ridges at least about 0.25 to 0.50 µm in diameter and about 50 µm high, and separated by at least about 0.25 to 0.50 µm. In another exemplary embodiment, an exposed silver wire, at least about 0.25 to 0.50 µm in diameter, is applied to the sensor exterior to form grooves about 50 µm wide and about 50 µm deep. Since silver is pro-inflammatory and stimulates fluid influx from the surrounding tissues, the combination of an irritating superstructure and a chemical irritant could promote an increased rate of fluid influx or prolong irritation and fluid influx. In yet another exemplary embodiment, with reference to the embodiment shown in FIG. 1C, the configuration (e.g., diameter) of the reference electrode 20 can be changed (e.g., increased in size and/or coil spacing) such that the reference electrode, itself, becomes an irritating superstructure, with or without a coating 22 as disclosed elsewhere herein.

Porous Membrane

In addition to the devices described above, fluid bulk and or bulk fluid flow at and/or adjacent to the sensor can be increased by incorporating a porous membrane into the sensor system, such that noise is substantially reduced and sensor accuracy and/or sensitivity are improved. A porous membrane can be referred to as a "bioprotective domain" or a "cell disruptive domain." In some embodiments, the sensor includes a porous material disposed over some portion thereof, which modifies the host's tissue response to the sensor and thereby reduces noise (e.g., due to a local build up of interferents). For example, in some embodiments, the porous material surrounding the sensor advantageously enhances and extends sensor performance and lifetime in the short-term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long-term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lacetic acid), hydroxyethylmethacrylate, hydroxyapeptide, alumina, zirconia, carbon fiber, aluminum, calcium phosphate, titanium, titanium alloy, nintinol, stainless steel, and CoCr alloy, or the like, such as are described in U.S. Patent Publication No. US-2005-0031689-A1 and U.S. Patent Publication No. US-2005-0112169-A1.

In some embodiments, the porous material surrounding the sensor provides unique advantages in the short-term (e.g. one to 14 days) that can be used to enhance and extend sensor performance and lifetime. However, such materials can also provide advantages in the long-term too (e.g. greater than 14 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short-term advantages). It is believed that this reduces or slows the sensitivity loss normally observed in a short-term sensor over time.

In an embodiment wherein the porous material is a high oxygen solubility material, such as porous silicone, the high oxygen solubility porous material surrounds some of or the entire in vivo portion of the sensor. In some embodiments, a lower ratio of oxygen-to-glucose can be sufficient to provide excess oxygen by using a high oxygen soluble domain (for example, a silicone- or fluorocarbon-based material) to enhance the supply/transport of oxygen to the enzyme membrane and/or electroactive surfaces. It is believed that some signal noise normally seen by a conventional sensor can be attributed to an oxygen deficit. Silicone has high oxygen permeability, thus promoting oxygen transport to the enzyme layer. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess. While not being bound by any particular theory, it is believed that silicone materials provide enhanced bio-stability when compared to other polymeric materials such as polyurethane.

In certain aspects, modifying a sensor with a biointerface structure, material, matrix, and/or membrane that creates a space appropriate for filling with fluid in vivo can enhance sensor performance. In some embodiments, the sensor includes a porous biointerface material, which allows fluid from the surrounding tissues to form a fluid-filled pocket around at least a portion of the sensor. It is believed that the fluid-filled pocket provides a sufficient source of analyte-containing fluid for accurate sensor measurement in the short-term. Additionally or alternatively, inclusion of bioactive agents can modify the host's tissue response, for example to reduce or eliminate tissue ingrowth or other cellular responses into the biointerface.

In some aspects, modifying a sensor with a structure, material, and/or membrane/matrix that allows tissue ingrowth without barrier cell formation can enhance sensor performance. For example, a vascularized bed of tissue for long-term analyte sensor measurement. In some embodiments, a porous biointerface membrane, including a plurality of interconnected cavities and a solid portion, covering at least the sensing portion of a sensor allows vascularized tissue ingrowth therein. Vascularized tissue ingrowth provides a sufficient source of analyte-containing tissue in the long-term. Additionally or alternatively, inclusion of bioactive agents can modify the host's tissue response, for example to reduce or eliminate barrier cell layer formation within the membrane.

When used herein, the terms "membrane" and "matrix" are meant to be interchangeable. In these embodiments first domain is provided that includes an architecture, including cavity size, configuration, and/or overall thickness, that modifies the host's tissue response, for example, by creating a fluid pocket, encouraging vascularized tissue ingrowth, disrupting downward tissue contracture, resisting fibrous tissue growth adjacent to the device, and/or discouraging barrier cell formation. The biointerface preferably covers at least the sensing mechanism of the sensor and can be of any shape or size, including uniform, asymmetrically, or axi-symmetrically covering or surrounding a sensing mechanism or sensor.

In some embodiments, a second domain is optionally provided that is impermeable to cells and/or cell processes. A bioactive agent is optionally provided that is incorporated into the at least one of the first domain, the second domain, the sensing membrane, or other part of the implantable device, wherein the bioactive agent is configured to modify a host tissue response.

In one embodiment, a porous material that results in increased fluid bulk, bulk fluid flow and/or diffusion rate, as well as formation of close vascular structures, is a porous polymer membrane, such as but not limited to polytetrafluoroethylene (PTFE), polysulfone, polyvinylidene difluoride, polyacrylonitrile, silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lacetic acid), and hydroxyethylmethacrylate, having an average nominal pore size of at least about 0.6 to 20 µm, using conventional methods for determination of pore size in the trade. In one embodiment, at least approximately 50% of the pores of the membrane have an average size of approximately 0.6 to about 20 µm, such as described in U.S. Pat. No. 5,882, 354. In this exemplary embodiment, the structural elements, which provide the three-dimensional conformation, can include fibers, strands, globules, cones or rods of amorphous or uniform geometry that is smooth or rough. These elements, hereafter referred to as "strands," have in general one dimension larger than the other two and the smaller dimensions do not exceed five microns.

In another further embodiment, the porous polymer membrane material, as described above, consists of strands that define "apertures" formed by a frame of the interconnected strands. The apertures have an average size of no more than about 20 µm in any but the longest dimension. The apertures of the material form a framework of interconnected apertures, defining "cavities" that are no greater than an average of about 20 µm in any but the longest dimension. In another embodiment the porous polymer membrane material has at least some apertures having a sufficient size to allow at least some vascular structures to be created within the cavities. At least some of these apertures, while allowing vascular structures to form within the cavities, prevent connective tissue from forming therein because of size restrictions.

In a further embodiment, the porous membrane has frames of elongated strands of material that are less than 5 microns in all but the longest dimension and the frames define apertures which interconnect to form three-dimensional cavities which permit substantially all inflammatory cells migrating into the cavities to maintain a rounded morphology. Additionally, the porous material promotes vascularization adjacent but not substantially into the porous material upon implantation into a host. Exemplary materials include but are not limited to polyethylene, polypropylene, polytetrafluoroethylene (PTFE), cellulose acetate, cellulose nitrate, polycarbonate, polyester, nylon, polysulfone, mixed esters of cellulose, polyvinylidene difluoride, silicone, polyacrylonitrile, and the like.

In some embodiments, a short-term sensor is provided with a spacer adapted to provide a fluid pocket between the sensor and the host's tissue. It is believed that this spacer, for example a biointerface material, matrix, mesh, hydrogel and like structures and the resultant fluid pocket provide for oxygen and/or glucose transport to the sensor.

In one exemplary embodiment, the sensor includes a biointerface membrane configured to prevent adipose cell contact with an inserted transcutaneous sensor or an implanted sensor. Preferably, a porous biointerface membrane surrounds the sensor, covering the sensing mechanism (e.g., at least a working electrode) and is configured to fill with fluid in vivo, thereby creating a fluid pocket surrounding the sensor. Accordingly, the adipose cells surrounding the sensor are held a distance away (such as the thickness of the porous biointerface membrane, for example) from the sensor surface. Accordingly, as the porous biointerface membrane fills with fluid (e.g., creates a fluid pocket), oxygen and glucose are transported to the sensing mechanism in quantities sufficient to maintain accurate sensor function. Additionally, as discussed elsewhere herein, interferants are diluted, suppressing or reducing interference with sensor function.

In another exemplary embodiment, a short-term sensor (or short-term function of a long-term sensor) including a biointerface, including but not limited to, for example, porous biointerface materials, mesh cages, and the like, all of which are described in more detail elsewhere herein, can be employed to improve sensor function in the short-term (e.g., first few hours to days), such as by reducing noise on the sensor signal. Porous biointerface membranes need not necessarily include interconnected cavities for creating a fluid pocket in the short-term.

Bioactive Agents

A variety of bioactive agents are known to promote fluid influx or efflux. Accordingly, incorporation of bioactive agents into the membrane can increasing fluid bulk, bulk fluid flow and/or diffusion rates (and promoting glucose and oxygen influx), thereby decrease non-constant noise. In some embodiments, fluid bulk and/or bulk fluid flow are increased at (e.g., adjacent to the sensor exterior surface) the sensor by incorporation of one or more bioactive agents. In some embodiments, the sensor is configured to include a bioactive agent that irritates the wound and stimulates the release of soluble mediators that are known to cause a local fluid influx at the wound site. In some embodiments, the sensor is configured to include a vasodilating bioactive agent, which can cause a local influx of fluid from the vasculature.

A variety of bioactive agents can be found useful in preferred embodiments. Exemplary bioactive agents include but are not limited to blood-brain barrier disruptive agents and vasodilating agents, vasodilating agents, angiogenic factors, and the like. Useful bioactive agents include but are not limited to mannitol, sodium thiosulfate, VEGF/VPF, NO, NO-donors, leptin, bradykinin, histamines, blood components, platelet rich plasma (PRP), matrix metalloproteinases (MMT), Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lacetic Acid, Insulin, Leptin, Copper Sulphate, Estradiol, prostaglandins, cox inhibitors, endothelial cell binding agents (for example, decorin or vimentin), glenipin, hydrogen peroxide, nicotine, and Growth Hormone. Still other useful bioactive agents include enzymes, cytotoxic or necrosing agents (e.g., pactataxyl, actinomycin, doxorubicin, daunorubicin, epirubicin, bleomycin, plicamycin, mitomycin), cyclophosphamide, chlorambucil, uramustine, melphalan, bryostatins, inflammatory bacterial cell wall components, histamines, pro-inflammatory factors and the like.

Bioactive agents can be added during manufacture of the sensor by incorporating the desired bioactive agent in the manufacturing material for one or more sensor layers or into an exterior biomaterial, such as a porous silicone membrane. For example, bioactive agents can be mixed with a solution during membrane formation, which is subsequently applied onto the sensor during manufacture. Alternatively, the completed sensor can be dipped into or sprayed with a solution of a bioactive agent, for example. The amount of bioactive agent can be controlled by varying its concentration, varying the indwell time during dipping, applying multiple layers until a desired thickness is reached, and the like, as disclosed elsewhere herein. In an alternative embodiment, the bioactive agent is microencapsulated before application to the sensor. For example, microencapsulated bioactive agent can be sprayed onto a completed sensor or incorporated into a structure, such as an outer mesh layer or a shedding layer. Microencapsulation can offer increased flexibility in controlling bioactive agent release rate, time of release occurrence and/or release duration.

Chemical systems/methods of irritation can be incorporated into an exterior sensor structure, such as the biointerface membrane (described elsewhere herein) or a shedding layer that releases the irritating agent into the local environment. For example, in some embodiments, a "shedding layer" releases (e.g., sheds or leaches) molecules into the local vicinity of the sensor and can speed up osmotic fluid shifts. In some embodiments, a shedding layer can provide a mild irritation and encourage a mild inflammatory/foreign body response, thereby preventing cells from stabilizing and building up an ordered, fibrous capsule and promoting fluid pocket formation.

A shedding layer can be constructed of any convenient, biocompatible material, include but not limited to hydrophilic, degradable materials such as polyvinylalcohol (PVA), PGC, Polyethylene oxide (PEO), polyethylene glycol-polyvinylpyrrolidone (PEG-PVP) blends, PEG-sucrose blends, hydrogels such as polyhydroxyethyl methacrylate (pHEMA), polymethyl methacrylate (PMMA) or other polymers with quickly degrading ester linkages. In certain embodiment, absorbable suture materials, which degrade to compounds with acid residues, can be used. The acid residues are chemical irritants that stimulate inflammation and wound healing. In certain embodiments, these compounds include glycolic acid and lacetic acid based polymers, polyglactin, polydioxone, polydyconate, poly(dioxanone), poly(trimethylene carbonate) copolymers, and poly (-caprolactone) homopolymers and copolymers, and the like.

In other exemplary embodiments, the shedding layer can be a layer of materials listed elsewhere herein for the first domain, including copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. Nos. 4,803,243 and 4,686,044, hereby incorporated by reference). In one preferred embodiment, the shedding layer is comprised of polyurethane and a hydrophilic polymer. For example, the hydrophilic polymer can be polyvinylpyrrolidone. In one preferred embodiment, the shedding layer is polyurethane comprising not less than 5 weight percent polyvinylpyrrolidone and not more than 45 weight percent polyvinylpyrrolidone. Preferably, the shedding layer comprises not less than 20 weight percent polyvinylpyrrolidone and not more than 35 weight percent polyvinylpyrrolidone and, most preferably, polyurethane comprising about 27 weight percent polyvinylpyrrolidone.

In other exemplary embodiments, the shedding layer can include a silicone elastomer, such as a silicone elastomer and a poly(ethylene oxide) and poly(propylene oxide) co-polymer blend, as disclosed in copending U.S. patent application Ser. No. 11/404,417, filed Apr. 14, 2006 and entitled "SILICONE BASED MEMBRANES FOR USE IN IMPLANTABLE GLUCOSE SENSORS." In one embodiment, the silicone elastomer is a dimethyl- and methylhydrogen-siloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC® polymer. In one embodiment, the co-polymer is PLURONIC® F-127. In one embodiment, at least a portion of the co-polymer is cross-linked. In one embodiment, from about 5% w/w to about 30% w/w of the membrane is the co-polymer.

A shedding layer can take any shape or geometry, symmetrical or asymmetrical, to promote fluid influx in a desired location of the sensor, such as the sensor head or the electrochemically reactive surfaces, for example. Shedding layers can be located on one side of sensor or both sides. In another example, the shedding layer can be applied to only a small portion of the sensor or the entire sensor.

In one exemplary embodiment, a shedding layer comprising polyethylene oxide (PEO) is applied to the exterior of the sensor, where the tissue surrounding the sensor can directly access the shedding layer. PEO leaches out of the shedding layer and is ingested by local cells that release pro-inflammatory factors. The pro-inflammatory factors diffuse through the surrounding tissue and stimulate an inflammation response that includes an influx of fluid. Accordingly, early noise can be reduced or eliminated and sensor function can be improved.

In another exemplary embodiment, the shedding layer is applied to the sensor in combination with an outer porous layer, such as a mesh or a porous biointerface as disclosed elsewhere herein. In one embodiment, local cells access the shedding layer through the through pores of a porous silicone biointerface. In one example, the shedding layer material is applied to the sensor prior to application of the porous silicone. In another example, the shedding layer material can be absorbed into the lower portion of the porous silicone (e.g., the portion of the porous silicone that will be proximal to the sensor after the porous silicone has been applied to the sensor) prior to application of the porous silicone to the sensor.

Wound Suppression

Non-constant noise can be decreased by wound suppression (e.g., during sensor insertion), in some embodiments. Wound suppression includes any systems or methods by which an amount of wounding that occurs upon sensor insertion is reduced and/or eliminated. While not wishing to be bound by theory, it is believed that if wounding is suppressed or at least significantly reduced, the sensor will be surrounded by substantially normal tissue (e.g., tissue that is substantially similar to the tissue prior to sensor insertion). Substantially normal tissue is believed to have a lower metabolism than wounded tissue, producing fewer interferants and reducing early noise.

Wounds can be suppressed or minimized by adaptation of the sensor's architecture to one that either suppresses wounding or promotes rapid healing, such as an architecture that does not cause substantial wounding (e.g., an architecture configured to prevent wounding), an architecture that promotes wound healing, an anti-inflammatory architecture, and the like. In one exemplary embodiment, the sensor is configured to have a low profile, a zero-footprint or a smooth surface. For example, the sensor can be formed of substantially thin wires, such as wires about 50-150 μm in diameter, for example. Preferably, the sensor is small enough to fit within a very small gauge needle, such as a 30, 31, 32, 33, 34, or 35-gauge needle (or smaller) on the Stubs scale, for example. In general, a smaller needle, the more reduces the amount of wounding during insertion. For example, a very small needle can reduce the amount of tissue disruption and thereby reduce the subsequent wound healing response. In an alternative embodiment, the sensor's surface is smoothed with a lubricious coating, to reduce wounding upon sensor insertion.

Wounding can also be reduced by inclusion of wound-suppressive agents (bioactive agents) that either reduce the amount of initial wounding or suppress the wound healing process. While not wishing to be bound by theory, it is believed that application of a wound-suppressing agent, such as an anti-inflammatory, an immunosuppressive agent, an anti-infective agent, or a scavenging agent, to the sensor can create a locally quiescent environment and suppress wound healing. In a quiescent environment, bodily processes, such as the increased cellular metabolism associated with wound healing, can minimally affect the sensor. If the tissue surrounding the sensor is undisturbed, it can continue its normal metabolism and promote sensor function.

In some embodiment, useful compounds and/or factors for suppressing wounding include but are not limited to first-generation $H_1$-receptor antagonists: ethylenediamines (e.g., mepyramine (pyrilamine), antazoline), ethanolamines (e.g., diphenhydramine, carbinoxamine, doxylamine, clemastine, and dimenhydrinate), alkylamines (pheniramine, chlorphenamine (chlorpheniramine), dexchlorphenamine, brompheniramine, and triprolidine), piperazines (cyclizine, hydroxyzine, and meclizine), and tricyclics (promethazine, alimemazine (trimeprazine), cyproheptadine, and azatadine); second-generation $H_1$-receptor antagonists such as acrivastine, astemizole, cetirizine, loratadine, mizolastine, azelastine, levocabastine, and olopatadine; mast cell stabilizers such as cromoglicate (cromolyn) and nedocromil; anti-inflammatory agents, such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (e.g., L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone; immunosuppressive and/or immuno-modulatory agents such as anti-proliferative, cell-cycle inhibitors (e.g., paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings; anti-infective agents, such as anthelmintics (mebendazole); antibiotics such as aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim; interferant scavengers, such as superoxide dismutase (SOD), thioredoxin, glutathione peroxidase and catalase, anti-oxidants, such as uric acid and vitamin C, iron compounds, Heme compounds, and some heavy metals; artificial protective coating components, such as albumin, fibrin, collagen, endothelial cells, wound closure chemicals, blood products, platelet-rich plasma, growth factors and the like.

In some embodiments, wounding can be suppressed by inclusion of a silicone coating (e.g., silicon-hydrophilic polymer blend) or a hydrophilic shedding layer can be applied to the sensor. While not wishing to be bound by theory, it is believed that a silicone bioprotective coating or shedding layer can promote formation and maintenance of a fluid pocket around the sensor, to enhance glucose and fluid transport as well as clearance of interferants. A silicone bioprotective coating can create a local environment with enhanced vascular permeability and/or vascularization. Such a coating is believed to speed up the inflammatory response to achieve a substantially consistent wound environment more quickly than without the coating. Furthermore, a silicone bioprotective coating is believed to be able to subdue the inflammatory response to reduce production of cellular byproducts that are believed to be electrochemical interferants.

In one embodiment, a silicone bioprotective coating can consist of one or more layer(s) formed from a composition that, in addition to providing high oxygen solubility, allows for the transport of glucose or other such water-soluble molecules (for example, drugs). In one embodiment, these layers comprise a blend of a silicone polymer with a hydrophilic polymer. For additional description, see the section entitled "Noise Reduction by silicon/Hydrophilic Polymer Blend Materials," and co-pending U.S. patent application Ser. No. 11/404,417, filed Apr. 14, 2006 and entitled "SILICONE BASED MEMBRANES FOR USE IN IMPLANTABLE GLUCOSE SENSORS," co-pending U.S. patent application Ser. No. 11/675,063, filed Feb. 14, 2007 and entitled "ANALYTE SENSOR," U.S. Patent Publication No. US-2005-0090607-A1, U.S. Patent Publication No. US-2006-0270923-A1, and U.S. Patent Publication No. US-2007-0027370-A1, each of which are incorporated by reference herein in their entirety.

Many of the above disclosed methods and structures for forming a fluid pocket, diluting interferants, reducing noise and the like can be used in combination to facilitate a desired effect or outcome. For example, in one embodiment, a shedding layer composed of a hydrophilic silicone film and a necrosing agent can be applied in combination to at least a portion of the sensor. The silicone film can suppress protein adherence to the sensor surface while the necrosing agent can devitalize a small portion of tissue adjacent to the sensor, stimulating formation of a fluid pocket around the hydrophilic silicone film. Preferably, the increased volume of fluid surrounding the sensor dilutes interferants while the shedding layer provides a physical separation between the sensor and the surrounding tissue.

In another exemplary embodiment, a mesh sprayed with dexamethasone is wrapped around the exterior of the sensor. The mesh can provide a physical spacer for a fluid pocket while the dexamethasone inhibits inflammation. Preferably, fluid can fill the mesh and the dexamethasone can promote normal tissue metabolism around the sensor by inhibiting an influx of inflammatory cells. Consequently, glucose and oxygen can travel freely between the tissue and the sensor through the fluid filled mesh without a buildup of interferants, even during periods of tissue compression, thereby promoting sensor sensitivity and thereby reducing noise.

Additional description of increasing fluid bulk, by adapting the sensor's configuration can be found in co-pending U.S. Patent Publication No. US-2006-0229512-A1 and co-pending U.S. patent application Ser. No. 11/654,140, filed on Jan. 17, 2007 and entitled "MEMBRANES FOR ANALYTE SENSOR," both of which are incorporated herein in their entirety.

Auxiliary Electrode

In some circumstances, non-constant noise can be reduced by incorporating into the sensor system an auxiliary electrode configured to electrochemically modify (for example, oxidize or reduce) electrochemical interferants to render them substantially non-electroactively reactive at the electroactive sensing surface(s) in order to overcome the effects of interferants on the working electrode. It is known that many electrochemical interferants can be reduced at a potential of from about +0.1V to +1.2V or more; for example, acetaminophen is reduced at a potential of about +0.4 V. It is noted that one challenge to generating oxygen electrochemically in this way is that while an auxiliary electrode does produce excess oxygen, the placement of the auxiliary electrode in proximity to the analyte-measuring working electrode can cause oxidation of hydrogen peroxide at the auxiliary electrode, resulting in reduced signals at the working electrode. Accordingly, the sensors of preferred embodiments place an auxiliary electrode above the electrode system, or other electroactive sensing surface, thereby reducing or eliminating the problem of inaccurate signals as described above.

Preferably, the auxiliary electrode is located within or adjacent to the membrane system, for example, between the enzyme and other domains, although the auxiliary electrode can be placed anywhere between the electroactive sensing surface and the outside fluid. The auxiliary electrode is formed from known working electrode materials (for example, platinum, palladium, graphite, gold, carbon, conductive polymer, or the like) and has a voltage setting that produces oxygen (for example, from about +0.6 V to +1.2 V or more) and/or that electrochemically modifies (for example, reduces) electrochemical interferants to render them substantially non-reactive at the electroactive sensing surface(s) (for example, from about +0.1 V to +1.2 V or more). The auxiliary electrode can be a mesh, grid, plurality of spaced wires or conductive polymers, or other configurations designed to allow analytes to penetrate therethrough.

In another aspect of the preferred embodiments, the auxiliary electrode is configured to electrochemically modify (for example, oxidize or reduce) electrochemical interferants to render them substantially non-reactive at the electroactive sensing surface(s). In these embodiments, which can be in addition to or alternative to the above-described oxygen-generating embodiments, a polymer coating is chosen to selectively allow interferants (for example, urate, ascorbate, and/or acetaminophen such as described in U.S. Pat. No. 6,579,690 to Bonnecaze, et al.) to pass through the coating and electrochemically react with the auxiliary electrode, which effectively pre-oxidizes the interferants, rendering them substantially non-reactive at the working electrode. In one exemplary embodiment, silicone materials can be synthesized to allow the transport of oxygen, acetaminophen and other interferants, but not allow the transport of glucose. In some embodiments, the polymer coating material can be chosen with a molecular weight that blocks glucose and allows the transport of oxygen, urate, ascorbate, and acetaminophen. In another exemplary embodiment, silicone materials can be synthesized to allow the transport of oxygen, glucose, acetaminophen, and other interferants. In some embodiments, the polymer coating material is chosen with a molecular weight that allows the transport of oxygen, glucose, urate, ascorbate, and acetaminophen. The voltage setting necessary to react with interfering species depends on the target electrochemical interferants, for example, from about +0.1 V to about +1.2 V. In some embodiments, wherein the auxiliary electrode is set at a potential of from about +0.6 to about +1.2 V, both oxygen-generation and electrochemical interferant modification can be achieved. In some embodiments, wherein the auxiliary electrode is set at a potential below about +0.6 V, the auxiliary electrode will function mainly to electrochemically modify interferants, for example. Additional description can be found in U.S. Pat. No. 7,074,307, to Simpson, which is incorporated herein by reference.

Interferent Affinity Domain

Incorporating an affinity domain (e.g., affinity for an interferent) into the membrane can reduce non-constant noise by preventing the passage of an interferent (to which the affinity domain has affinity) therethrough. For example, an affinity domain can be configured to preferentially bind acetaminophen and thereby remove the acetaminophen from the cellular milieu surrounding an implanted sensor. In preferred embodiments, the affinity domain can be configured to include an affinity for numerous other interferants. For example, optical glucose sensors suffer from interference from species such as triglyceride, albumin, and gamma globulin. In general, the effects of any known interferants on sensor signals may be reduced using the concepts described herein.

Figure 16:
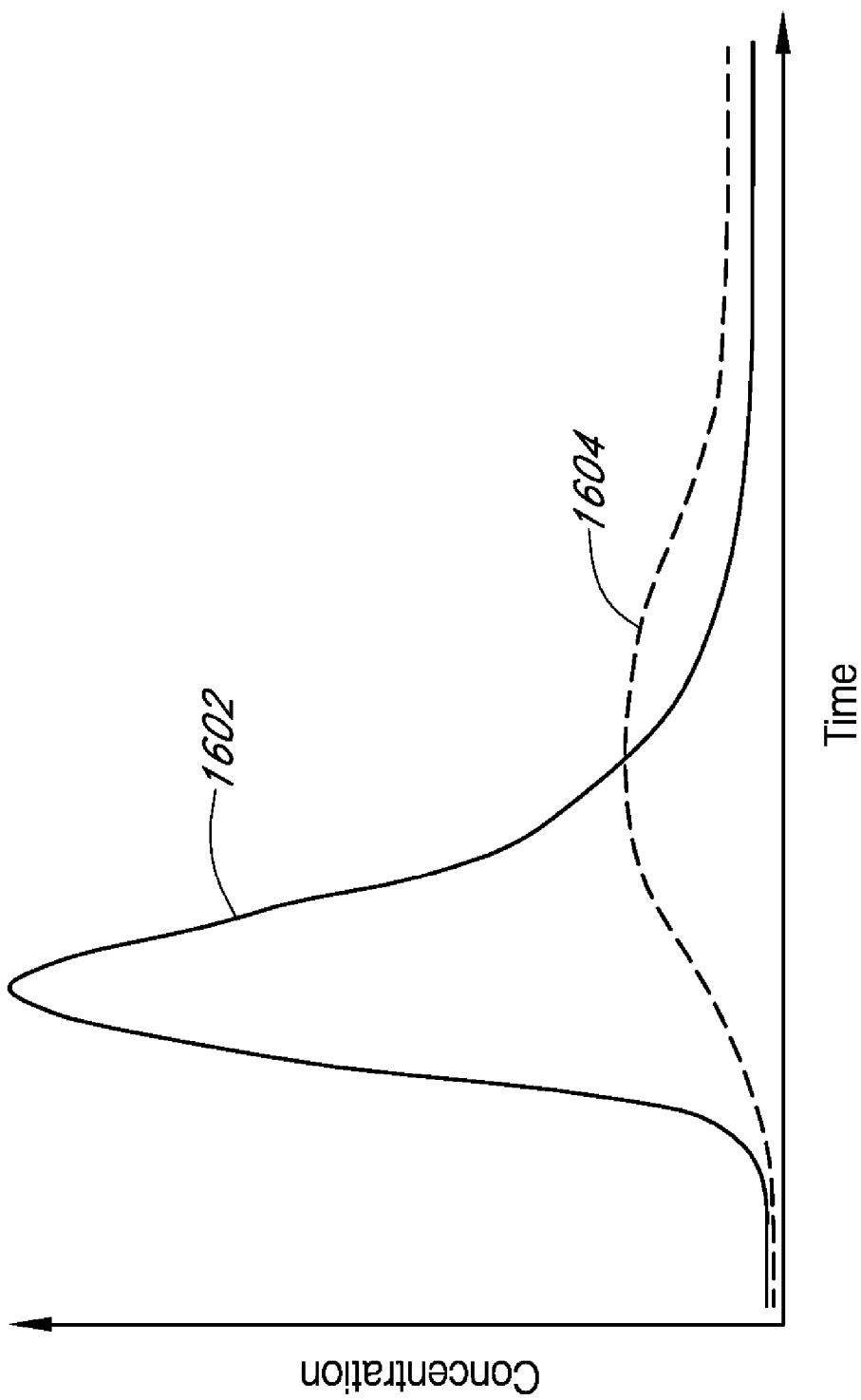
FIG. 16 is a graph of interferant concentration versus time.

FIG. 16 is a graph of interferant concentration (relative) versus time (relative), which illustrates the rise and fall of a transient interferant concentration exposed to a sensor in a host's body. For example, when acetaminophen is taken orally, the systemic concentration rises quickly and then decreases roughly logarithmically as the species is cleared by the system, such as illustrated in FIG. 16, line 1602. It is noted that medication such as acetaminophen is typically taken transiently (e.g., rather than continually) and therefore produces transient, non-glucose related signal artifacts on a glucose-measuring device. Because an elevated acetaminophen concentration is a transient event in the host, moderating acetaminophen concentration is generally only required for discrete periods of time.

According to the preferred embodiments, the affinity domain has an "affinity" for the interferant to be blocked, and therefore sorbs that interferant; by sorbing the interferant into the membrane system, the effects on the resulting signal are reduced. Consequently, the local concentration of interferant presented to the electrochemically reactive surface of the sensor is moderated as illustrated in FIG. 16, line 1604.

While not wishing to be bound to theory, it is believed that the area under both curves is substantially equal, however the local concentration of interfering species at the sensor with the affinity domain of the preferred embodiments is sufficiently lowered over time (e.g., line 1604), as compared to a membrane system without the affinity domain (e.g., line 1602). In other words, the affinity domain of the preferred embodiments slows the diffusion of the interfering species on the signal, such that the signal deviation due to the interferant is below a level that may substantially interfere with sensor accuracy.

The preferred embodiments provide a membrane system, particularly for use on an electrochemical sensor, wherein the membrane system includes an affinity domain. The affinity domain can be layer, surface, region, and/or portion of the membrane system and manufactured using a variety of methods. In general, the affinity domain is formed using sorbents with an affinity for the target interferant(s). Sorbents include any substance (e.g., molecule, particle, coating, or the like) that has a stronger affinity for a particular molecule or compound (e.g., interfering species) than another (e.g., measured analyte or substance). The sorbents of the preferred embodiments provide for the retention of an interfering species, such that the interfering species will be at least temporarily immobilized, and will take a longer time to pass through the affinity domain.

In some embodiments, the sorbents are polymeric adsorbents, such as chromatography-packing materials. The chromatography-packing materials can be selected, modified, or otherwise adapted to possess an affinity for a target interferant, for example, phenol-containing species. Some examples of chromatography-packing materials include Optipore L-493 (Dow Chemical Company, Providence, R.I.), SP-850 (Mitsubishi Chemical America, White Plains, N.Y.), Amberlite XAD-4 (Rohm and Haas, Philadelphia, Pa.), and LC-18 (Supleco, Bellefonte, Pa.).

In some embodiments, fused silica, Amberlite XAD-2, Amberlite IRC-50, Discovery DPA-6s, C-6 Bulk Phenyl, and other affinity-based packings or adsorbents synthesized from fused silica and/or TEOS with different phenyl derivatized silanes, can be used as the sorbents. In some embodiments, the sorbents are formed from carbon-based solids.

In some embodiments, sorbents are coated onto an inert support material, such as treated diatomaceous earth or other silica based materials (for example, solid silica support particles can have an organic coating bonded to their surface, wherein the bonding is produced by reacting a halogen substituted organosilane with the surface —OH groups present on the silica support). Generally, these coatings are non-polar in nature and therefore retention of the interfering species is produced by dispersion forces, making them useful for separation of organic compounds based on slight differences in their backbone or side chain configuration.

In some embodiments, the affinity domain can be manufactured using molecular imaging technology. In this embodiment, a sorbent is selected or prepared that is useful for binding a pre-determined interferant on the surface of a material by complementary functional group interaction. For example, a cross-linked styrene divinyl benzene material can be prepared that is imprinted with acetaminophen. U.S. Pat. Nos. 5,453,199 and 5,872,198, both of which are incorporated by reference herein in their entirety, describe molecular imaging technology that can be used for imprinting acetaminophen or other interferants on the surface of a material. Complementary functional group interaction provides a selective, reversible association between the interferant and the material surface. Such methods for making binding surfaces are referred to hereinafter as "molecular imaging" methods and form surfaces referred to hereinafter as "imaged surfaces."

Molecular imaging provides a high surface area chromatography matrix material with molecular-specific sorbents. The imaged surfaces bind with interferants by covalently adhering, in a way that is geometrically controlled at least in the direction parallel, and preferably also in a direction normal to an underlying surface plane, a plurality of charged groups, hydrophobic groups, and various combinations thereof, to form a mirror image of groups complementary to them on a molecular surface of a target molecule, for example acetaminophen. These groups are preferably spaced about a hydrophilic undersurface rich in hydrogen containing groups and electronegative atoms such as oxygen, nitrogen, phosphorus, or sulfur that take part in formation of hydrogen bonds.

In some embodiments, a silica-like sol-gel material is imaged similarly to that described above with reference to molecular imaging. U.S. Pat. No. 6,057,377, which is incorporated herein by reference in its entirety, describes a method for molecularly imprinting the surface of a sol-gel material, by forming a solution including a sol-gel material, a solvent, an imprinting molecule, and a functionalizing siloxane monomer of the form $Si(OR)_3\text{-}nX_n$, wherein n is an integer between zero and three and X is a functional group capable of reacting or associating with the imprinting molecule. In some embodiments, the phenyl silane is phenyldimethylpropytrimethoxysilane, N-phenylaminopropyltrimethoxysilane, phenyldiethoxysilane, or phenyltriethoxysilane, for example.

The resulting sol-gel structure would include a three dimensional material imprinted with acetaminophen or other interferant. In this embodiment, the solvent is evaporated, and the imprinting molecule removed to form the molecularly imprinted sol-gel material. The removal of the imprinting molecule creates a pocket, which has the correct geometry and hydrogen binding to bind the interfering species as it passes through the structure. This sol-gel structure can then be ground using a mortar-pestal, or the like, and added to the membrane system as the affinity domain.

The use of sol-gel materials advantageously allow the material porosity, pore size, density, surface area, hardness, electrostatic charge, polarity, optical density, and surface hydrophobicity to be tailored to suit the affinity domain useful in the preferred embodiments.

Additional description can be found in U.S. Patent Publication Number US-2005-0176136-A1, which is incorporated herein by reference.

Interferent Blocking Compounds

In some embodiments, constant and/or non-constant noise can be decreased by including one or more layers comprising an interferent-blocking compound in an interference domain of the membrane system. A variety of interferent-blocking compounds can be used, such as but not limited to sulfonated polyether sulfone, polyamino-phenol or polypyrrole. In one embodiment, the membrane system includes 3-amino-phenol, which allows the diffusion of $H_2O_2$ while blocking the transport of acetaminophen. Interferent-blocking compounds can be applied to the electrodes using any method know in the art, such as but not limited to dipping, spraying, electropolymerization, spin coating and the like, as are discussed elsewhere herein. In one exemplary embodiment, the sensor is a glucose sensor comprising two working electrodes, wherein a solution of 3-amino-phenol is sprayed onto the working electrodes and dried prior to the application of the membrane enzyme domain. In a further embodiment, the sensor includes additional membrane layers. Additional methods and devices can be found in U.S. Pat. No. 7,120,483, to Russell, which is incorporated herein by reference in its entirety.

Interferent Scavenging

In some embodiments, one or more layers of the membrane system include an interferent scavenger. Depending upon the nature of the interferent, the interferent scavenger can be incorporated into a membrane layer either more distal or proximal to the electroactive surfaces than the enzyme domain; in some embodiments, the scavenger can be incorporated into the membrane's enzyme layer. For example, some interferents are ionic and bind to ionic interferents. Accordingly, incorporating interferent-scavenging ionic components, such as Nafion®, into one or more layers of the membrane system can substantially block and/or slow diffusion of an interferent having the same charge as the ionic component through the membrane system, in some embodiments. Thus, less interferent reaches the electroactive surfaces and noise is reduced.

An interferent-scavenging enzyme can be incorporated into one or more layers of the membrane system. Useful enzymes include but are not limited to peroxidases and/or oxidases. In general, a peroxidase catalyzes the reduction of a compound using $H_2O_2$. Exemplary peroxidases include horseradish peroxidase, glutathione peroxidase, cytochrome C peroxidase, myeloperoxidase, and the like. Horseradish peroxidase is a preferred peroxidase because interferents present in biological fluids, such as ascorbate, urate, acetaminophen, bilirubin and cysteine, are rapidly oxidized by hydrogen peroxide in the presence of horseradish peroxidase. In general, an oxidase catalyzes the oxidation/reduction of a compound using molecular $O_2$. Exemplary oxidases include glucose oxidase, monoamine oxidase, cytochrome P450 oxidase, NADPH oxidase, cytochrome C oxidase, Xanthine oxidase, L-gulonolactone oxidase, lactate oxidase, lysyl oxidase and the like. In some embodiments, the peroxidase can be crosslinked to one or more membrane domains using known protein cross-linking techniques, such as but not limited to glutaraldehyde cross-linking, $NaIO_4$, oxidation of enzyme oligosaccharide groups followed by coupling to the matrix. Some useful coupling methods are described in U.S. Pat. Nos. 5,262,305 and 5,356,786, incorporated herein by reference.

In one exemplary embodiment, a peroxidase is incorporated into a distal membrane domain (e.g., above the enzyme domain) to remove $H_2O_2$ derived from external sources (e.g., from macrophages during wound healing). In one exemplary embodiment, the resistance domain 30 comprises horseradish-peroxidase. In a preferred embodiment, the sensor is a glucose sensor comprising two working electrodes and a resistance domain comprising horseradish peroxidase. Additional scavenging techniques are described in U.S. Pat. No. 5,356,786 to Heller, U.S. Pat. No. 6,284,478 to Heller and U.S. Pat. No. 7,003,341 to Say, which are incorporated herein by reference in their entirety.

Other systems and methods for reducing or eliminating interference species that can be applied to the membrane system of the preferred embodiments are described in U.S. Patent Publication No. US-2005-0115832-A1, U.S. Patent Publication No. US-2005-0176136-A1, U.S. Patent Publication No. US-2005-0161346-A1, and U.S. Patent Publication No. US-2005-0143635-A1, each of which are incorporated herein by reference. In some alternative embodiments, a distinct interference domain is not included.

Enzyme Domain

In preferred embodiments, the membrane system further includes an enzyme domain 28 disposed more distally from the electroactive surfaces than the interference domain; however other configurations can be desirable (FIGS. 2A-2B). In the preferred embodiments, the enzyme domain provides an enzyme to catalyze the reaction of the analyte and its co-reactant, as described in more detail below. In the preferred embodiments of a glucose sensor, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase (GOx), are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See, e.g., U.S. Patent Publication No. US-2005-0054909-A1.

In preferred embodiments, the enzyme domain is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. However in some embodiments, the enzyme domain can be deposited directly onto the electroactive surfaces. Preferably, the enzyme domain is deposited by spray or dip coating. In one embodiment of needle-type (transcutaneous) sensor such as described herein, the enzyme domain is formed by dip coating the interference domain coated sensor into an enzyme domain solution and curing the domain for from about 15 to about 30 minutes at a temperature of from about 40° C. to about 55° C. (and can be accomplished under vacuum (e.g. 20 to 30 mmHg)). In embodiments wherein dip coating is used to deposit the enzyme domain at room temperature, a preferred insertion rate of from about 0.25 inch per minute to about 3 inches per minute, with a preferred dwell time of from about 0.5 minutes to about 2 minutes, and a preferred withdrawal rate of from about 0.25 inch per minute to about 2 inches per minute provides a functional coating. However, values outside of those set forth above can be acceptable or even desirable in certain embodiments, for example, depending upon viscosity and surface tension, as is appreciated by one skilled in the art. In one embodiment, the enzyme domain is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Resistance Domain

In preferred embodiments, the membrane system includes a resistance domain 30 disposed more distal from the electroactive surfaces than the enzyme domain (FIGS. 2A-2B). Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21(1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semipermeable membrane that controls the flux of oxygen and glucose to the underlying enzyme domain, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Patent Publication No. US-2005-0090607-A1, which is incorporated by reference herein.

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In some embodiments, the resistance domain is formed from a silicone polymer modified to allow analyte (e.g., glucose) transport.

In some embodiments, the resistance domain is formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

In preferred embodiments, the resistance domain is deposited onto the enzyme domain to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. Preferably, the resistance domain is deposited onto the enzyme domain by vapor deposition, spray coating, or dip coating. In one preferred embodiment, spray coating is the preferred deposition technique. The spraying process atomizes and mists the solution, and therefore most or all of the solvent is evaporated prior to the coating material settling on the underlying domain, thereby minimizing contact of the solvent with the enzyme.

In a preferred embodiment, the resistance domain is deposited on the enzyme domain by spray coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Preferably, each exemplary sensor design (e.g., FIGS. 1A, 2A, and 7A through 9B) includes electronic connections, for example, one or more electrical contacts configured to provide secure electrical contact between the sensor and associated electronics. In some embodiments, the electrodes and membrane systems of the preferred embodiments are coaxially formed, namely, the electrodes and/or membrane system all share the same central axis. While not wishing to be bound by theory, it is believed that a coaxial design of the sensor enables a symmetrical design without a preferred bend radius. Namely, in contrast to prior art sensors comprising a substantially planar configuration that can suffer from regular bending about the plane of the sensor, the coaxial design of the preferred embodiments do not have a preferred bend radius and therefore are not subject to regular bending about a particular plane (which can cause fatigue failures and the like). However, non-coaxial sensors can be implemented with the sensor system of the preferred embodiments.

In addition to the above-described advantages, the coaxial sensor design of the preferred embodiments enables the diameter of the connecting end of the sensor (proximal portion) to be substantially the same as that of the sensing end (distal portion) such that a needle is able to insert the sensor into the host and subsequently slide back over the sensor and release the sensor from the needle, without slots or other complex multi-component designs, as described in detail in U.S. Patent Publication No. US-2006-0063142-A1 and U.S. application Ser. No. 11/360,250 filed Feb. 22, 2006 and entitled "ANALYTE SENSOR," which are incorporated in their entirety herein by reference.

Exemplary Continuous Sensor Configurations

Figure 10:
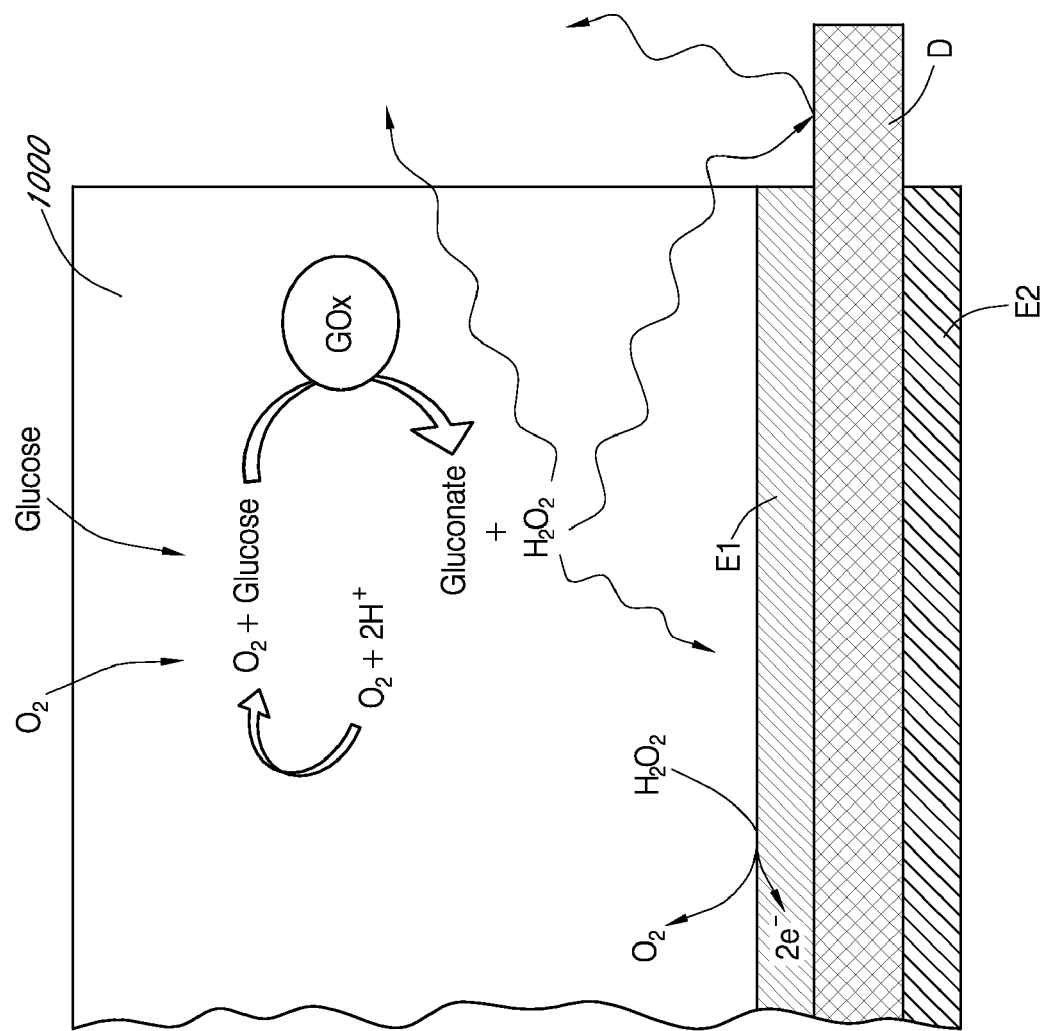
FIG. 10 is a schematic illustrating metabolism of glucose by Glucose Oxidase (GOx) and one embodiment of a diffusion barrier D that substantially prevents the diffusion of $H_2O_2$ produced on a first side of the sensor (e.g., from a first electrode that has active GOx) to a second side of the sensor (e.g., to the second electrode that lacks active GOx).

In some embodiments, the sensor is an enzyme-based electrochemical sensor, wherein the glucose-measuring working electrode 16 (e.g., FIGS. 1A-1B) measures the hydrogen peroxide produced by the enzyme catalyzed reaction of glucose being detected and creates a measurable electronic current (for example, detection of glucose utilizing glucose oxidase produces hydrogen peroxide ($H_2O_2$) as a by product, $H_2O_2$ reacts with the surface of the working electrode producing two protons ($2H^+$), two electrons ($2e^-$) and one molecule of oxygen ($O_2$) which produces the electronic current being detected, see FIG. 10), such as described in more detail elsewhere herein and as is appreciated by one skilled in the art. Preferably, one or more potentiostat is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrodes. The output signal is typically a raw data stream that is used to provide a useful value of the measured analyte concentration in a host to the patient or doctor, for example.

Some alternative analyte sensors that can benefit from the systems and methods of the preferred embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al., for example. All of the above patents are incorporated in their entirety herein by reference and are not inclusive of all applicable analyte sensors; in general, it should be understood that the disclosed embodiments are applicable to a variety of analyte sensor configurations.

Although some exemplary glucose sensor configurations are described in detail below, it should be understood that the systems and methods described herein can be applied to any device capable of continually or continuously detecting a concentration of analyte of interest and providing an output signal that represents the concentration of that analyte, for example oxygen, lactose, hormones, cholesterol, medicaments, viruses, or the like.

FIG. 1A is a perspective view of an analyte sensor, including an implantable body with a sensing region including a membrane system disposed thereon. In the illustrated embodiment, the analyte sensor 10a includes a body 12 and a sensing region 14 including membrane and electrode systems configured to measure the analyte. In this embodiment, the sensor 10a is preferably wholly implanted into the subcutaneous tissue of a host, such as described in U.S. Patent Publication No. US-2006-0015020-A1; U.S. Patent Publication No. US-2005-0245799-A1; U.S. Patent Publication No. US-2005-0192557-A1; U.S. Patent Publication No. US-2004-0199059-A1; U.S. Patent Publication No. US-2005-0027463-A1; and U.S. Pat. No. 6,001,067, each of which are incorporated herein by reference in their entirety.

The body 12 of the sensor 10a can be formed from a variety of materials, including metals, ceramics, plastics, or composites thereof. In one embodiment, the sensor is formed from thermoset molded around the sensor electronics. U.S. Patent Publication No. US-2004-0199059-A1 discloses suitable configurations for the body, and is incorporated by reference in its entirety.

In some embodiments, the sensing region 14 includes a glucose-measuring working electrode 16, an optional auxiliary working electrode 18, a reference electrode 20, and a counter electrode 24. Generally, the sensing region 14 includes means to measure two different signals, 1) a first signal associated with glucose and non-glucose related electroactive compounds having a first oxidation potential, wherein the first signal is measured at the glucose-measuring working electrode disposed beneath an active enzymatic portion of a membrane system, and 2) a second signal associated with the baseline and/or sensitivity of the glucose sensor. In some embodiments, wherein the second signal measures sensitivity, the signal is associated with at least one non-glucose constant data point, for example, wherein the auxiliary working electrode 18 is configured to measure oxygen. In some embodiments, wherein the second signal measures baseline, the signal is associated with non-glucose related electroactive compounds having the first oxidation potential, wherein the second signal is measured at an auxiliary working electrode 18 and is disposed beneath a non-enzymatic portion of the membrane system, such as described in more detail elsewhere herein.

Preferably, a membrane system (see FIG. 2A) is deposited over the electroactive surfaces of the sensor 10a and includes a plurality of domains or layers, such as described in more detail below, with reference to FIGS. 2A and 2B. In general, the membrane system may be disposed over (deposited on) the electroactive surfaces using methods appreciated by one skilled in the art. See U.S. Patent Publication No. US-2006-0015020-A1.

The sensing region 14 comprises electroactive surfaces, which are in contact with an electrolyte phase (not shown), which is a free-flowing fluid phase disposed between the membrane system 22 and the electroactive surfaces. In this embodiment, the counter electrode is provided to balance the current generated by the species being measured at the working electrode. In the case of glucose oxidase based analyte sensors, the species being measured at the working electrode is $H_2O_2$. Glucose oxidase catalyzes the conversion of oxygen and glucose to hydrogen peroxide and gluconate according to the following reaction:

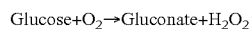

Glucose+$O_2$→Gluconate+$H_2O_2$

The change in $H_2O_2$ can be monitored to determine glucose concentration because for each glucose molecule metabolized, there is a proportional change in the product $H_2O_2$ (see FIG. 10). Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of the working electrode and produces two protons ($2H^+$), two electrons ($2e^-$), and one oxygen molecule ($O_2$). Preferably, one or more potentiostats are employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrodes. The output signal is typically a raw data stream that is used to provide a useful value of the measured analyte concentration in a host to the patient or doctor, for example.

FIG. 1B is a schematic view of an alternative exemplary embodiment of a continuous analyte sensor 10b, also referred to as an in-dwelling or transcutaneous analyte sensor in some circumstances, particularly illustrating the in vivo portion of the sensor. In this embodiment, the in vivo portion of the sensor 10b is the portion adapted for insertion under the host's skin, in a host's blood stream, or other biological sample, while an ex vivo portion of the sensor (not shown) is the portion that remains above the host's skin after sensor insertion and operably connects to an electronics unit. In the illustrated embodiment, the analyte sensor 10b is coaxial and includes three electrodes: a glucose-measuring working electrode 16, an optional auxiliary working electrode 18, and at least one additional electrode 20, which may function as a counter and/or reference electrode, hereinafter referred to as the reference electrode 20. Generally, the sensor 10b may include the ability to measure two different signals, 1) a first signal associated with glucose and non-glucose related electroactive compounds having a first oxidation potential, wherein the first signal is measured at the glucose-measuring working electrode disposed beneath an active enzymatic portion of a membrane system, and 2) a second signal associated with the baseline and/or sensitivity of the glucose sensor, such as described in more detail above with reference to FIG. 1A.

One skilled in the art appreciates that the analyte sensor of FIG. 1B can have a variety of configurations. In one exemplary embodiment, the sensor is generally configured of a first working electrode, a second working electrode, and a reference electrode. In one exemplary configuration, the first working electrode 16 is a central metal wire or plated non-conductive rod/filament/fiber and the second working and reference electrodes (20 and 18, respectively or 18 and 20, respectively) are coiled around the first working electrode 16. In another exemplary configuration, the first working electrode is a central wire, as depicted in FIG. 1B, the second working electrode is coiled around the first working electrode, and the reference electrode is disposed remotely from the sensor, as described herein. In another exemplary configuration, the first and second working electrodes (20 and 18) are coiled around a supporting rod 16 of insulating material. The reference electrode (not shown) can be disposed remotely from the sensor, as described herein, or disposed on the non-conductive supporting rod 16. In still another exemplary configuration, the first and second working electrodes (20 and 18) are coiled around a reference electrode 16 (not to scale).

Preferably, each electrode is formed from a fine wire, with a diameter in the range of 0.001 to 0.010 inches, for example, and may be formed from plated wire or bulk material, however the electrodes may be deposited on a substrate or other known configurations as is appreciated by one skilled in the art.

In one embodiment, the glucose-measuring working electrode 16 comprises a wire formed from a conductive material, such as platinum, palladium, graphite, gold, carbon, conductive polymer, or the like. Alternatively, the glucose-measuring working electrode 16 can be formed of a non-conductive fiber or rod that is plated with a conductive material. The glucose-measuring working electrode 16 is configured and arranged to measure the concentration of glucose. The glucose-measuring working electrode 16 is covered with an insulating material, for example a non-conductive polymer. Dip-coating, spray-coating, or other coating or deposition techniques can be used to deposit the insulating material on the working electrode, for example. In one preferred embodiment, the insulating material comprises Parylene, which can be an advantageous conformal coating for its strength, lubricity, and electrical insulation properties, however, a variety of other insulating materials can be used, for example, fluorinated polymers, polyethyleneterephthalate, polyurethane, polyimide, or the like.

In this embodiment, the auxiliary working electrode 18 comprises a wire formed from a conductive material, such as described with reference to the glucose-measuring working electrode 16 above. Preferably, the reference electrode 20, which may function as a reference electrode alone, or as a dual reference and counter electrode, is formed from silver, Silver/Silver chloride, or the like.

Preferably, the electrodes are juxtapositioned and/or twisted with or around each other; however other configurations are also possible. In one example, the auxiliary working electrode 18 and reference electrode 20 may be helically wound around the glucose-measuring working electrode 16 as illustrated in FIG. 1B. Alternatively, the auxiliary working electrode 18 and reference electrode 20 may be formed as a double helix around a length of the glucose-measuring working electrode 16. In some embodiments, the working electrode, auxiliary working electrode and reference electrodes may be formed as a triple helix. The assembly of wires may then be optionally coated together with an insulating material, similar to that described above, in order to provide an insulating attachment. Some portion of the coated assembly structure is then stripped, for example using an excimer laser, chemical etching, or the like, to expose the necessary electroactive surfaces. In some alternative embodiments, additional electrodes may be included within the assembly, for example, a three-electrode system (including separate reference and counter electrodes) as is appreciated by one skilled in the art.

FIGS. 2A and 2B are schematic views membrane systems in some embodiments that may be disposed over the electroactive surfaces of an analyte sensors of FIGS. 1A and 1B, respectively, wherein the membrane system includes one or more of the following domains: a resistance domain 30, an enzyme domain 28, an interference domain 26, and an electrolyte domain 24, such as described in more detail below. However, it is understood that the membrane system 22 can be modified for use in other sensors, by including only one or more of the domains, additional domains not recited above, or for other sensor configurations. For example, the interference domain can be removed when other methods for removing interferants are utilized, such as an auxiliary electrode for measuring and subtracting out signal due to interferants. As another example, an "oxygen antenna domain" composed of a material that has higher oxygen solubility than aqueous media so that it concentrates oxygen from the biological fluid surrounding the biointerface membrane can be added. The oxygen antenna domain can then act as an oxygen source during times of minimal oxygen availability and has the capacity to provide on demand a higher rate of oxygen delivery to facilitate oxygen transport to the membrane. This enhances function in the enzyme reaction domain and at the counter electrode surface when glucose conversion to hydrogen peroxide in the enzyme domain consumes oxygen from the surrounding domains. Thus, this ability of the oxygen antenna domain to apply a higher flux of oxygen to critical domains when needed improves overall sensor function.

In some embodiments, the membrane system generally provides one or more of the following functions: 1) protection of the exposed electrode surface from the biological environment, 2) diffusion resistance (limitation) of the analyte, 3) a catalyst for enabling an enzymatic reaction, 4) optionally limitation or blocking of interfering species, and 5) hydrophilicity at the electrochemically reactive surfaces of the sensor interface, such as described in U.S. Patent Publication No. US-2005-0245799-A1. In some embodiments, the membrane system additionally includes a cell disruptive domain, a cell impermeable domain, and/or an oxygen domain (not shown), such as described in more detail in U.S. Patent Publication No. US-2005-0245799-A1. However, it is understood that a membrane system modified for other sensors, for example, by including fewer or additional domains is within the scope of the preferred embodiments.

One aspect of the preferred embodiments provides for a sensor (for transcutaneous, wholly implantable, or intravascular short-term or long-term use) having integrally formed parts, such as but not limited to a plurality of electrodes, a membrane system and an enzyme. For example, the parts may be coaxial, juxtapositioned, helical, bundled and/or twisted, plated and/or deposited thereon, extruded, molded, held together by another component, and the like. In another example, the components of the electrode system are integrally formed, (e.g., without additional support, such as a supporting substrate), such that substantially all parts of the system provide essential functions of the sensor (e.g., the sensing mechanism or "in vivo" portion). In a further example, a first electrode can be integrally formed directly on a second electrode (e.g. electrically isolated by an insulator), such as by vapor deposition of a conductive electrode material, screen printing a conductive electrode ink or twisting two electrode wires together in a coiled structure.

Some embodiments provide an analyte sensor that is configured for insertion into a host and for measuring an analyte in the host, wherein the sensor includes a first working electrode disposed beneath an active enzymatic portion of a membrane (e.g., membrane system) on the sensor and a second working electrode disposed beneath an inactive- or non-enzymatic portion of the membrane on the sensor. In these embodiments, the first and second working electrodes integrally form at least a portion of the sensor.

Exemplary Sensor Configurations

FIG. 1B is a schematic view of a sensor in one embodiment. In some preferred embodiments, the sensor is configured to be integrally formed and coaxial. In this exemplary embodiment, one or more electrodes are helically wound around a central core, all of which share axis A-A. The central core 16 can be an electrode (e.g., a wire or metal-plated insulator) or a support made of insulating material. The coiled electrodes 18, 20 are made of conductive material (e.g., plated wire, metal-plated polymer filaments, bulk metal wires, etc.) that is helically wound or twisted about the core 16. Generally, at least the working electrodes are coated with an insulator I of non-conductive or dielectric material.

One skilled in the art will recognize that various electrode combinations are possible. For example, in one embodiment, the core 16 is a first working electrode and can be substantially straight. One of the coiled electrodes (18 or 20) is a second working electrode and the remaining coiled electrode is a reference or counter electrode. In a further embodiment, the reference electrode can be disposed remotely from the sensor, such as on the host's skin or on the exterior of the sensor, for example. Although this exemplary embodiment illustrates an integrally formed coaxial sensor, one skilled in the art appreciates a variety of alternative configurations. In one exemplary embodiment, the arrangement of electrodes is reversed, wherein the first working electrode is helically wound around the second working electrode core 16. In another exemplary embodiment, the reference electrode can form the central core 16 with the first and second working electrodes coiled there around. In some exemplary embodiments, the sensor can have additional working, reference and/or counter electrodes, depending upon the sensor's purpose. Generally, one or more of the electrode wires are coated with an insulating material, to prevent direct contact between the electrodes. Generally, a portion of the insulating material can be removed (e.g., etched, scraped or grit-blasted away) to expose an electroactive surface of the electrode. An enzyme solution can be applied to the exposed electroactive surface, as described herein.

The electrodes each have first and second ends. The electrodes can be of any geometric solid shape, such as but not limited to a cylinder having a circular or oval cross-section, a rectangle (e.g., extruded rectangle), a triangle (e.g., extruded triangle), an X-cross section, a Y-cross section, flower petal-cross sections, star-cross sections, melt-blown fibers loaded with conductive material (e.g., conductive polymers) and the like. The first ends (e.g., an in vivo portion, "front end") of the electrodes are configured for insertion in the host and the second ends (e.g., an ex vivo portion, "back end") are configured for electrical connection to sensor electronics. In some embodiments, the sensor includes sensor electronics that collect data from the sensor and provide the data to the host in various ways. Sensor electronics are discussed in detail elsewhere herein.

Figure 7B:
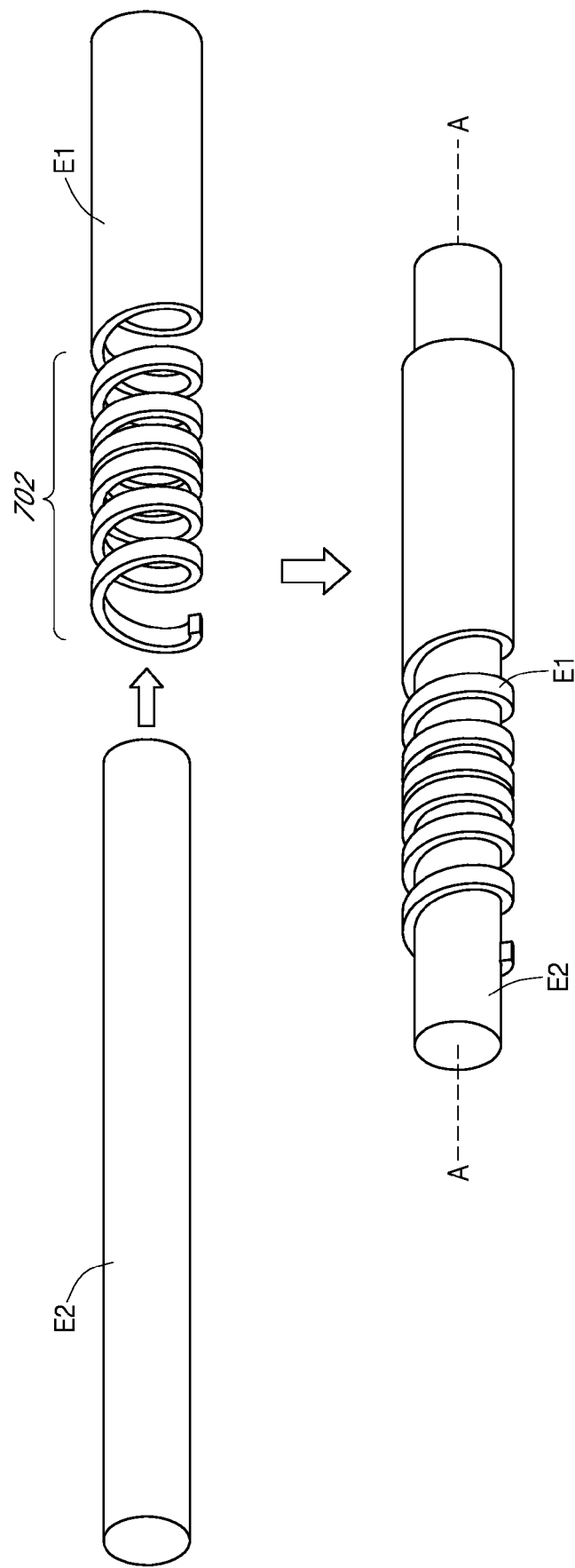
FIG. 7B is a schematic of another embodiment of a coaxial sensor.

FIGS. 7A1 and 7A2 are schematics of an analyte sensor in another embodiment. FIG. 7A1 is a side view and FIG. 7A2 is a side-cutaway view. In some preferred embodiments, the sensor is configured to be integrally formed and coaxial, with an optional stepped end. In this exemplary embodiment, the sensor includes a plurality of electrodes E1, E2, E3 to En, wherein n equals any number of electrode layers. Layers of insulating material I (e.g., non-conductive material) separate the electrode layers. All of the electrode and insulating material layers share axis A-A. The layers can be applied by any technique known in the art, such as but not limited to spraying, dipping, spraying, etc. For example, a bulk metal wire electrode E1 can be dipped into a solution of insulating polymer that is vulcanized to form a layer of non-conductive, electrically insulating material I. A second electrode E2 can be plated (e.g., by electroplating or other plating technique used in the art) on the first insulating layer, followed by application of a second insulating layer I applied in the same manner as the first layer. Additional electrode layers (e.g., E3 to En) and insulating layers can be added to the construct, to create the desired number of electrodes and insulating layers. As an example, multiple sensors can be formed from a long wire (with insulating and electrode layers applied) that can be cut to yield a plurality of sensors of the desired length. After the sensor has been cut to size, it can be polished or otherwise treated to prepare the electrodes for use. In some embodiments, the various electrode and/or insulator layers can be applied by dipping, spraying, printing, vapor deposition, plating, spin coating or any other method known in the art. Although this exemplary embodiment illustrates an integrally formed coaxial sensor, one skilled in the art appreciates a variety of alternative configurations. For example, in some embodiments, the sensor can have two, three, four or more electrodes separated by insulating material I. In another embodiment, the analyte sensor has two or more electrodes, such as but not limited to a first working electrode, an auxiliary working electrode, a reference electrode and/or counter electrode. FIG. 7B is a schematic view of an integrally formed, coaxial sensor in another embodiment. In this exemplary embodiment, a coiled first electrode E1 is manufactured from an electrically conductive tube or cylinder, such as but not limited to a silver Hypotube. A portion of the Hypotube is trimmed or carved into a helix or coil 702. A second electrode E2 that is sized to fit (e.g., with minimal tolerance) within the first electrode E1 mates (e.g., slides into) with the first electrode E1, to form the sensor. In general, the surfaces of the electrodes are coated with an insulator, to prevent direct contact between the electrodes. As described herein, portion of the insulator can be stripped away to expose the electroactive surfaces. Although this exemplary embodiment illustrates one configuration of a coaxial, integrally formed sensor, one skilled in the art appreciates a variety of alternative configurations. For example, in some embodiments, the first electrode E1 is a reference or auxiliary electrode, and the second electrode E2 is a working electrode. However, the first electrode E1 can be a working electrode and the second electrode E2 can be a reference or auxiliary electrode. In some embodiments, additional electrodes are applied to the construct (e.g., after E2 is inserted into E1). One advantage of this configuration is that the silver Hypotube can be cut to increase or decrease the flexibility of the sensor. For example, the spiral cut can space the coils farther apart to increase the sensor's flexibility. Another example of this configuration is that it is easier to construct the sensor in this manner, rather than winding one electrode around another (e.g., as is done for the embodiment shown in FIG. 1B).

Figure 7C:
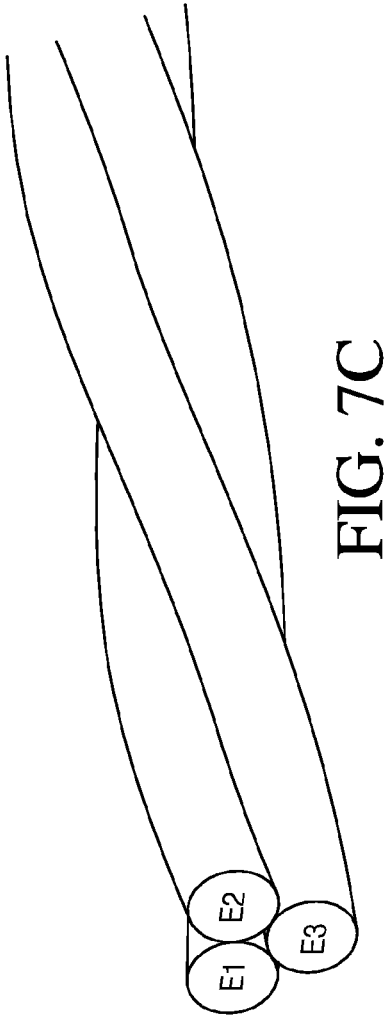
FIG. 7C is a schematic of one embodiment of a sensor having three electrodes.
Figure 7E:
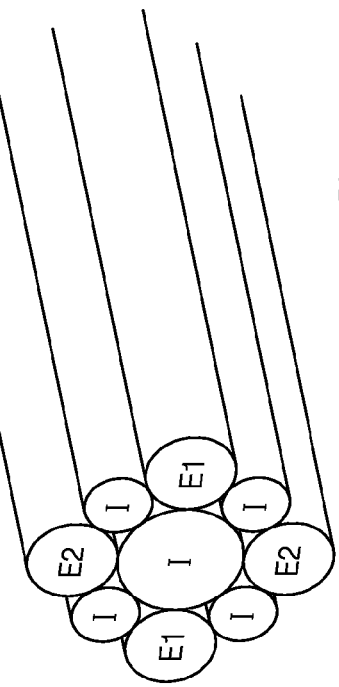
FIG. 7E is a schematic of one embodiment of a sensor having two pairs of electrodes and insulating material.
Figure 7D:
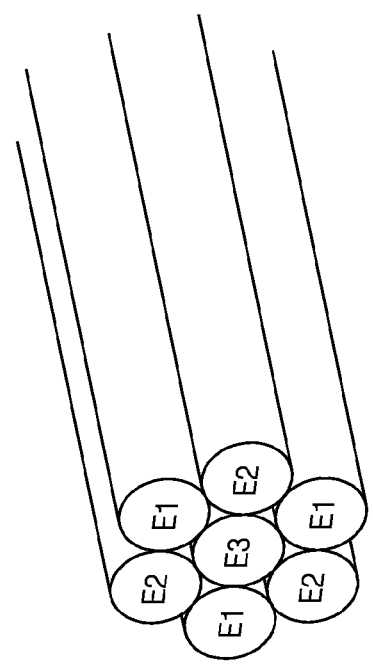
FIG. 7D is a schematic of one embodiment of a sensor having seven electrodes.

FIGS. 7C to 7E are schematics of three embodiments of bundled analyte sensors. In these embodiments, of the sensors are configured to be integrally formed sensors, wherein a plurality (E1, E2, E3, to En) of electrodes are bundled, coiled or twisted to form a portion of the sensor. In some embodiments, the electrodes can be twisted or helically coiled to form a coaxial portion of the sensor, which share the same axis. In one embodiment, the first and second working electrodes are twisted or helically wound together, to form at least a portion of the sensor (e.g., a glucose sensor). For example, the electrodes can be twisted in a double helix. In some embodiments, additional electrodes are provided and twisted, coiled or wound with the first and second electrodes to form a larger super helix, such as a triple helix, a quadruple helix, or the like. For example, three wires (E1, E2, and E3) can be twisted to form a triple helix. In still other embodiments, at least one reference electrode can be disposed remotely from the working electrodes, as described elsewhere herein. In some embodiments, the tip of the sensor can be cut at an angle (90° or other angle) to expose the electrode tips to varying extents, as described herein.

FIG. 7C is a schematic of an exemplary embodiment of a sensor having three bundled electrodes E1, E2, and E3. In some preferred embodiments of the sensor, two or all of the electrodes can be identical. Alternatively, the electrodes can be non-identical. For example, the sensor can have a glucose-sensing electrode, an oxygen-sensing electrode and a reference electrode. Although this exemplary embodiment illustrates a bundled sensor, one skilled in the art appreciates a variety of alternative sensor configurations. For example, only two electrodes can be used or more than three electrodes can be used. In another example, holding one end of the bundled wires in a clamp and twisting the other end of the wires, to form a cable-like structure, can coil the electrodes together. Such a coiled structure can hold the electrodes together without additional structure (e.g., bound by a wire or coating). In another example, non-coiled electrodes can be bundled and held together with a wire or fiber coiled there around, or by applying a coating of insulating material to the electrode bundle. In still another example, the reference electrode can be disposed remotely from the working electrodes, as described elsewhere herein.

FIG. 7D is a schematic view of a sensor in one embodiment. In some preferred embodiments, the sensor is designed to be integrally formed and bundled and/or coaxial. In this exemplary embodiment, the sensor includes seven electrodes, wherein three electrodes of a first type (e.g., 3×E1) and three electrodes of a second type (e.g., 3×E2) are bundled around one electrode of a third type (e.g., E3). Those skilled in the art appreciate a variety of configurations possible with this embodiment. For example, the different types of electrodes can be alternated or not alternated. For example, in FIG. 7D, the two types of electrodes are alternately disposed around E3. However, the two types of electrodes can be grouped around the central structure. As described herein, some or all of the electrodes can be coated with a layer of insulating material, to prevent direct contact between the electrodes. The electrodes can be coiled together, as in a cable, or held together by a wire or fiber wrapping or a coating of insulating material. The sensor can be cut, to expose the electroactive surfaces of the electrodes, or portions of the insulating material coating can be stripped away, as described elsewhere herein. In another example, the sensor can include additional (or fewer) electrodes. In one exemplary embodiment, the E1 and E2 electrodes are bundled around a non-conductive core (e.g., instead of electrode E3), such as an insulated fiber. In another embodiment, different numbers of E1, E2, and E3 electrodes can be used (e.g., two E1 electrodes, two E2 electrodes, and three E3 electrodes). In another embodiment, additional electrode type can be included in the sensor (e.g., an electrode of type E4, E5 or E6, etc.). In still another exemplary embodiment, three glucose-detecting electrodes (e.g., E1) and three reference electrodes (e.g., E2) are bundled and (optionally) coiled around a central auxiliary working electrode (e.g., E3).

FIG. 7E is a schematic of a sensor in another embodiment. In this exemplary embodiment of an integrally formed sensor, two pairs of electrodes (e.g., 2×E1 and 2×E2) are bundled around a core of insulating material I. Fibers or strands of insulating material I also separate the electrodes from each other. Although this exemplary embodiment illustrates an integrally formed sensor, one skilled in the art appreciates a variety of alternative configurations. For example, the pair of E1 electrodes can be working electrodes and the pair of E2 electrodes can be reference and/or auxiliary electrodes. In one exemplary embodiment, the E1 electrodes are both glucose-detecting electrodes, a first E2 electrode is a reference electrode and a second E2 electrode is an auxiliary electrode. In another exemplary embodiment, one E1 electrode includes active GOx and measures a glucose-related signal; the other E1 electrode lacks active GOx and measures a non-glucose-related signal, and the E2 electrodes are reference electrodes. In yet another exemplary embodiment, one E1 electrode detects glucose and the other E1 electrode detects urea, and both E2 electrodes are reference electrodes. One skilled in the art of electrochemical sensors will recognized that the size of the various electrodes can be varied, depending upon their purpose and the current and/or electrical potential used. Electrode size and insulating material size/shape are not constrained by their depiction of relative size in the Figures, which are schematic schematics intended for only illustrative purposes.

Figure 7F:
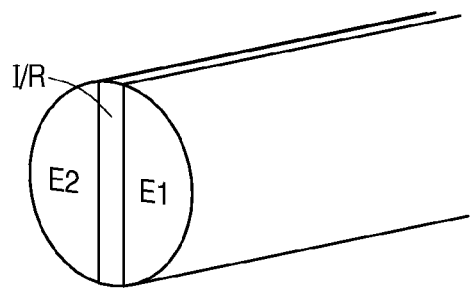
FIG. 7F is a schematic of one embodiment of a sensor having two electrodes separated by a reference electrode or insulating material.

FIG. 7F is a schematic view of a cross-section of an integrally formed sensor in another embodiment. In some preferred embodiments, the sensor is configured to be bifunctional. In this exemplary embodiment, the sensor includes two working electrodes E1/E2 separated by either a reference electrode R or an insulating material I. The electrodes E1, E2 and optionally the reference electrode R are conductive and support the sensor's shape. In addition, the reference electrode R (or the insulating material I) can act as a diffusion barrier (D, described herein) between the working electrodes E1, E2 and support the sensor's structure. Although this exemplary embodiment illustrates one configuration of an integrally formed sensor having bifunctional components, one skilled in the art appreciates a variety of alternative configurations. Namely, FIG. 7F is not to scale and the working electrodes E1, E2 can be relatively larger or smaller in scale, with regard to the reference electrode/insulator R/I separating them. For example, in one embodiment, the working electrodes E1, E2 are separated by a reference electrode that has at least 6-times the surface area of the working electrodes, combined. While the working electrodes E1, E2 and reference electrode/insulator R/I are shown and semi-circles and a rectangle, respectively, one skilled in the art recognizes that these components can take on any geometry know in the art, such as but not limited to rectangles, cubes, cylinders, cones, and the like.

Figure 7G:
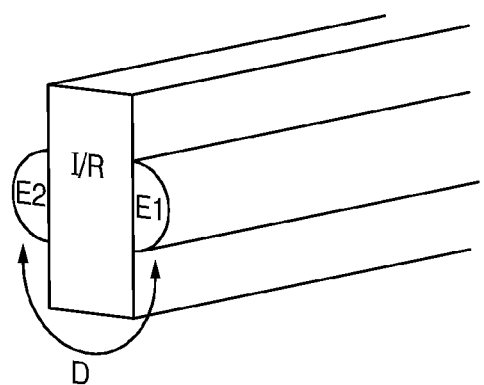
FIG. 7G is a schematic of another embodiment of a sensor having two electrodes separated by a reference electrode or insulating material.

FIG. 7G is a schematic view of a sensor in yet another embodiment. In some preferred embodiments, the sensor is configured to be integrally formed with a diffusion barrier D, as described herein. In this exemplary embodiment, the working electrodes E1, E2 (or one working electrode and one counter electrode) are integrally formed on a substantially larger reference electrode R or an insulator I that substantially prevents diffusion of analyte or other species from one working electrode to another working electrode (e.g., from the enzymatic electrode (e.g., coated with active enzyme) to the non-enzymatic electrode (e.g., no enzyme or inactive enzyme)). Although this exemplary embodiment illustrates an integrally formed sensor having a diffusion barrier, one skilled in the art appreciates a variety of alternative configurations. For example, in one embodiment, the reference electrode is designed to include an exposed electroactive surface area that is at least equal to, greater than, or more than about 2, 3, 4, 5, 6, 7, 8, 9, 10 or more times greater than the surface area of the working electrodes (e.g., combined). In other embodiments, the surface of the reference electrode is about 6 (e.g., about 6 to 20) or more times greater than the working electrodes. In some embodiments, each working electrode detects a separate analyte (e.g., glucose, oxygen, uric acid, nitrogen, pH, and the like). In other embodiments, one of the working electrodes is a counter electrode. In still another exemplary embodiment, an enzyme solution containing active GOx is applied to the E1 electroactive surface, while an enzyme solution containing inactive GOx (or no GOx at all) is applied to the E2 electroactive surface. As described herein, this configuration allows the measurement of two signals. Electrode E1 measures both a signal related to glucose concentration and a signal that is not related to glucose concentration. Electrode E2 measures a signal that is not related to glucose concentration. The sensor electronics, as described herein, can use these data to calculate glucose concentration without signal due to non-glucose-related contributions.

Figure 7H:
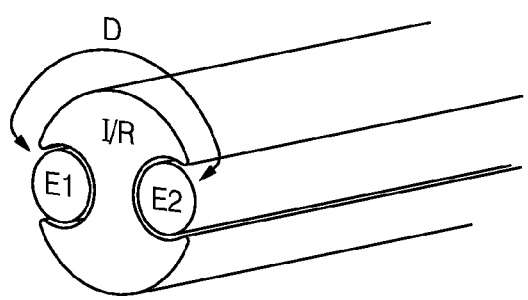
FIG. 7H is a schematic of another embodiment of a sensor having two electrodes separated by a reference electrode or insulating material.

FIG. 7H is a schematic view of a sensor in another embodiment. In some preferred embodiments, the sensor is configured of a geometric solid (e.g., cylindrical) reference electrode R having two or more working electrodes E1, E2 to En disposed within two or more grooves or channels carved in the sides of the reference electrode R (parallel to the axis of the reference electrode R). The grooves are sized such that the electrodes E1, E2 can snuggly fit therein. Additionally, the depth of the grooves can be configured that the electrode placed therein is externally exposed to a greater or lesser degree. For example, the opening to the groove may be wider or narrower. In some embodiments, a portion of an electrode protrudes from the groove in which the electrode has been disposed. In some embodiments, an insulator (e.g., I) takes the place of a reference electrode (which can be disposed elsewhere, such remotely as described in more detail elsewhere herein). The reference electrode/insulator R/I can take any geometric structure known in the art, such as but not limited to cylinders, rectangles, cones, and the like. Similarly, the relative sizes of the working electrodes E1, E2 and the reference electrode/insulator R/I can be varied to achieve a desired signal level, to enable the use of the desired voltage (e.g., to bias the sensor), and the like, as described herein.

In one exemplary embodiment, a diffusion barrier D (described in greater detail below) separates the working electrodes. The diffusion barrier can be spatial, physical, or temporal. For example, the distance around the reference electrode (e.g., from the first working electrode E1 to the second working electrode E2, around a portion of the circumference of the reference electrode R) acts as a spatial diffusion barrier. In one exemplary embodiment, the working electrodes are coated with a layer of insulating material I (e.g., non-conductive material or dielectric) to prevent direct contact between the working electrodes E1, E2 and the reference electrode R. A portion of the insulator I on an exterior surface of each working electrode is etched away, to expose the electrode's electroactive surface. In some embodiments, an enzyme solution (e.g., containing active GOx) is applied to the electroactive surfaces of both electrodes, and dried. Thereafter, the enzyme applied to one of the electroactive surfaces is inactivated. As is known in the art, enzymes can be inactivated by a variety of means, such as heat, treatment with inactivating (e.g., denaturing) solvents, proteolysis, laser irradiation or UV irradiation (e.g., at 254-320 nm). For example, the enzyme coating one of the electroactive surfaces can be inactivated by masking one of the electroactive surfaces/electrodes (e.g., E1, temporarily covered with a UV-blocking material); irradiating the sensor with UV light (e.g., 254-320 nm; a wavelength that inactivates the enzyme, such as by cross-linking amino acid residues) and removing the mask. Accordingly, the GOx on E2 is inactivated by the UV treatment, but the E1 GOx is still active due to the protective mask. In other embodiments, an enzyme solution containing active enzyme is applied to a first electroactive surface (e.g., E1) and an enzyme solution containing either inactivated enzyme or no enzyme is applied to the second electroactive surface (e.g., E2). Accordingly, the enzyme-coated first electroactive surface (e.g., E1) detects analyte-related signal and non-analyte-related signal; while the second electroactive surface (e.g., E2), which lacks active enzyme, detects non-analyte-related signal. As described herein, the sensor electronics can use the data collected from the two working electrodes to calculate the analyte-only signal.

Figure 7I:
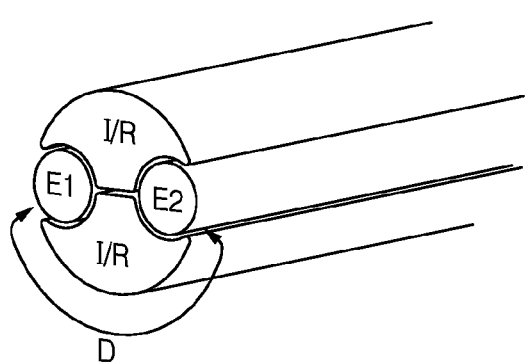
FIG. 7I is a schematic of another embodiment of a sensor having two electrodes separated by reference electrodes or insulating material.

Although this exemplary embodiment illustrates one embodiment of an integrally-formed sensor having a diffusion barrier D, one skilled in the art appreciates a variety of alternative configurations, such as but not limited to the embodiment shown in FIG. 7I. In this exemplary embodiment, the reference electrode is formed of at least two adjacent pieces shaped such that the working electrodes fill at least some space between them. The at least two pieces can be any shape known in the art, as described herein. In some embodiments, the at least two pieces are symmetrical and/or mirror images of each other, but one skilled in the art will recognize that this is not a requirement. In various embodiments, an insulating material can be coated on the working electrodes and/or the reference electrode(s) to prevent contact there between. As described elsewhere herein, the working electrodes can detect the same analyte or separate analytes, or one of the working electrodes may act as a counter electrode (e.g., auxiliary electrode). Although this exemplary embodiment illustrates one example of a sensor having a reference electrode R that is formed of at least two pieces shaped such that the working electrodes fill at least some space between the pieces, one skilled in the art appreciates that a variety of sensor configurations are possible. For example, the reference electrode can be formed of three or more pieces. In other example, the sensor can be configured with more than two working electrodes (e.g., 3, 4, or 5 working electrodes, or more).

Figure 7J:
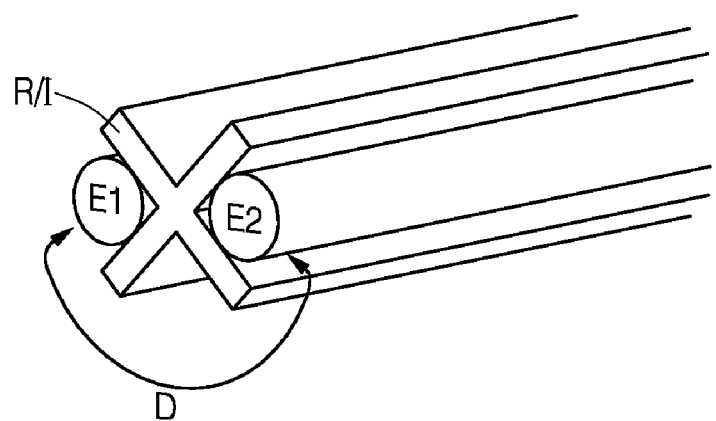
FIG. 7J is a schematic of one embodiment of a sensor having two electrodes separated by a substantially X-shaped reference electrode or insulating material.
Figure 7K:
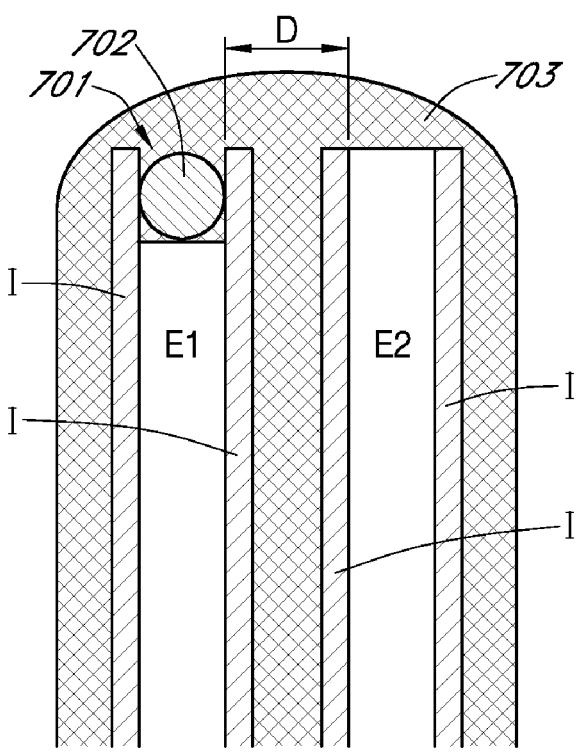
FIG. 7K is a schematic of one embodiment of a sensor having two electrodes coated with insulating material, wherein one electrode has a space for enzyme, the electrodes are separated by a distance D and covered by a membrane system.

FIG. 7J is a schematic view of an integrally formed sensor in yet another embodiment. In this exemplary embodiment, the reference electrode R is formed in any desired extruded geometry, such as an approximate X-shape. Two or more working electrodes E1, E2 are disposed on substantially opposing sides of the reference electrode, with a diffusion barrier D between them. In this embodiment, the diffusion barrier is a physical diffusion barrier, namely the distance between the two working electrodes (e.g., around the reference electrode). In some embodiments, the electrodes are bundled and held together by a wrapping of wire or fiber. In other embodiments, the electrodes are twisted around the lengthwise axis of the extruded X-shaped reference electrode, to form a coaxial sensor. Although this exemplary embodiment illustrates an integrally formed sensor, one skilled in the art appreciates a variety of alternative configurations. For example, furthering some embodiments, three or four working electrodes can be disposed around the reference electrode (e.g., in the indentations between the legs/arms of the X-shaped electrode). In other embodiments, the reference electrode can be Y-shapes, star-shaped, flower-shaped, scalloped, or any other convenient shape with multiple substantially isolated sides. In some embodiments, an insulating material I takes the place of the reference electrode of FIG. 7J, which is remotely located. In an alternative embodiment, a working electrode is replaced with a counter electrode. As described elsewhere herein, the sensor components are bifunctional. Namely, the electrodes and reference electrode provide electrical conduction and the sensor's structure. The reference electrode (or insulating material) provides a physical diffusion barrier D. In addition to providing shape to the sensor, the insulating material acts as insulator by preventing direct electrical contact between the electrodes. Similarly, the materials selected to construct the sensor determine the sensor's flexibility. As described elsewhere, active enzyme is applied to the electroactive surface of at least one working electrode (e.g., E1). In some embodiments, no enzyme (or inactivated enzyme) is applied to the electroactive surface of a second working electrode (e.g., E2). In an alternative embodiment, a second enzyme is applied to the second working electrode (e.g., E2) such that the sensor can measure the signals of two different analytes (e.g., glucose and aureate or oxygen). FIG. 7K is a schematic of a sensor in another embodiment. In some preferred embodiments, the sensor is configured to be integrally formed of two working electrodes. In this exemplary embodiment, the sensor includes two electrodes E1, E2 (e.g., metal wires), wherein each electrode is coated with a non-conductive material I (e.g., and insulator). As is shown in FIG. 7K, the first working electrode E1 formed within the insulator I leaving space for an enzyme. For example, an enzyme solution 702 (e.g., GOx for detecting glucose) is disposed within the space 701. In contrast, the second working electrode E2 extends substantially flush with the insulator I. A membrane system 703 coats the electrodes. A diffusion barrier D separates the working electrodes. In some embodiments, the first and second electrodes are separated by a distance D that substantially prevents diffusion of $H_2O_2$ from the first electrode (e.g., with active enzyme) to the second electrode (e.g., without active enzyme). Although this exemplary embodiment illustrates one integrally formed sensor, one skilled in the art appreciates a variety of alternative configurations. For example, the use of more than two working electrodes and wrapping the construct with a reference electrode wire R or disposing the reference electrode remotely from the sensor.

Figure 7L:
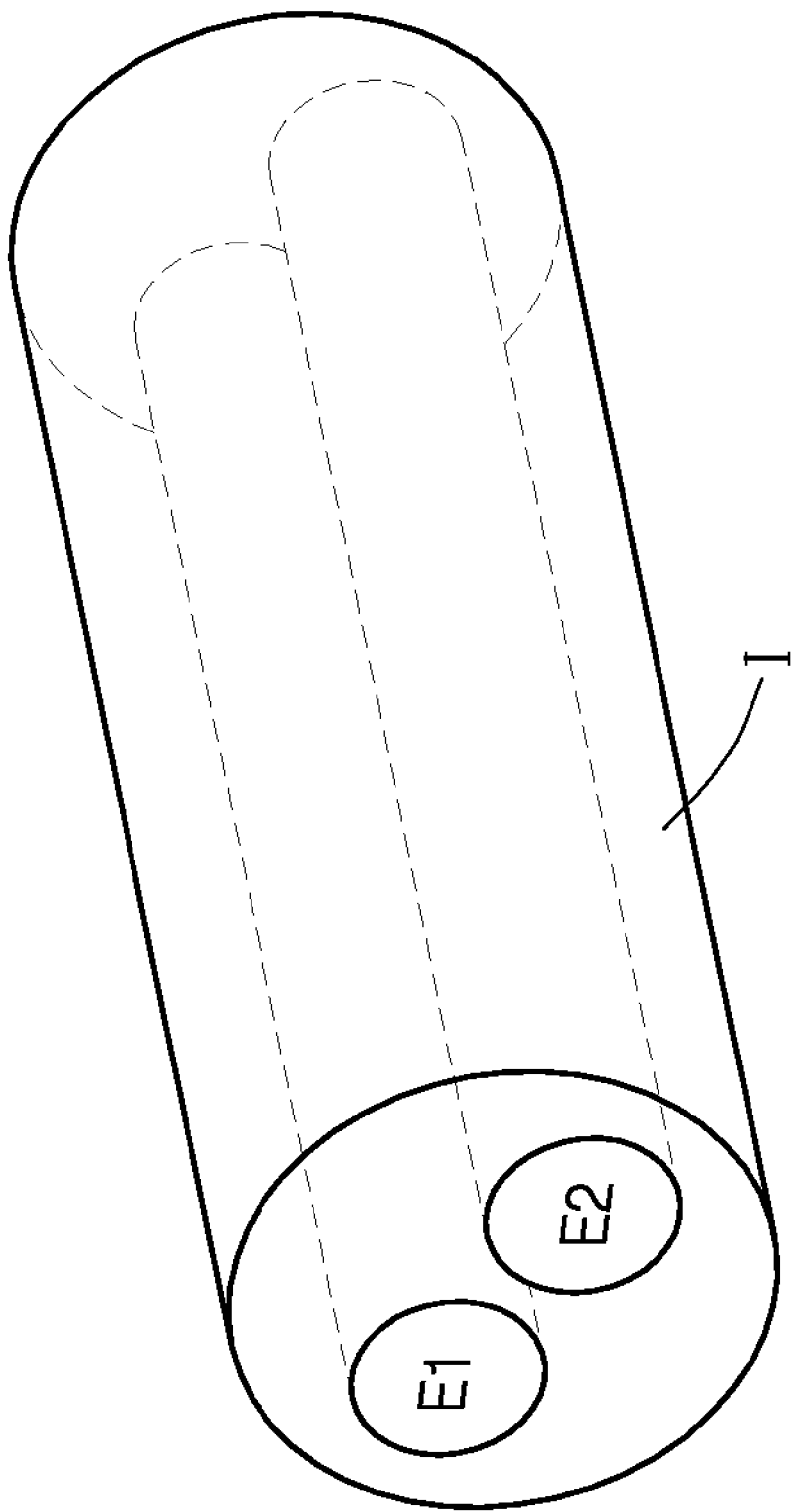
FIG. 7L is a schematic of one embodiment of a sensor having two electrodes embedded in an insulating material.

FIG. 7L is a schematic of a sensor in one embodiment. In some preferred embodiments, the sensor is designed to be integrally formed. In this exemplary embodiment, two electrodes E1, E2 are embedded within an insulator I. The sensor can be formed by embedding conductive wires within a dielectric, curing the dielectric and then cutting sensors of the desired length. The cut end provides the exposed electroactive electrode surfaces and can be polished or otherwise treated. Although this exemplary embodiment illustrates one integrally formed sensor, one skilled in the art appreciates a variety of alternative configurations. For example, additional electrode wires can be embedded in the dielectric material. In another example, a reference electrode (e.g., wire or cylinder) can be coiled or wrapped around the sensor (e.g., on the surface of the insulator). Alternatively, as described elsewhere herein, the reference electrode can be disposed remotely from the working electrodes E1, E2, such as on the host's skin or on another portion of the sensor. One advantage of this configuration is that it is relatively simple to embed electrode wires in a long cylinder of insulating material and then cut the sensors to any desired size and/or shape.

Figure 7M:
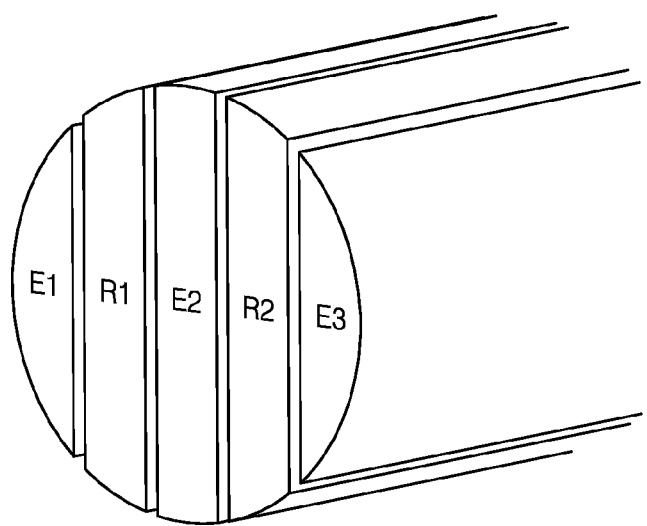
FIG. 7M is a schematic of one embodiment of a sensor having multiple working electrodes and multiple reference electrodes.

FIG. 7M is a schematic cross-sectional view of a sensor having multiple working and reference electrodes, in one embodiment. In some preferred embodiments, the sensor is integrally formed. In this exemplary embodiment, the sensor includes a plurality of working electrodes (e.g., E1, E2, E3) that are layered with a plurality of reference electrodes (e.g., R1, R2, Rn). In some embodiments, the working electrodes are coated with an insulating material to prevent direct contact with adjacent reference electrodes. In some embodiments, the reference electrodes are also coated with insulative material. In some embodiments, layers of insulating material separate the layers. In some embodiments, at least one of the working electrodes is a counter electrode. As described herein, in some embodiments, electroactive surfaces are exposed on one or more electrodes, such as by stripping away a portion of an insulating coating, such as on the sides of the sensor. In other embodiments, an extended electrode structure (e.g., a long sandwich of electrode layers) that is cut to the desired length, and the cut end includes the exposed electroactive surfaces of the electrodes. An enzyme layer can be applied to one or more of the electroactive surfaces, as described herein. Depending upon the desired sensor function, the working electrodes can be configured to detect the same analyte (e.g., all electroactive surfaces coated with GOx glucose) or different analytes (e.g., one working electrode detects glucose, another detects oxygen and the third detects ureate), as described herein. Although this exemplary embodiment illustrates a sensor having a plurality of working and reference electrodes, one skilled in the art appreciates a variety of alternative configurations. For example, in some embodiments, the electrodes can be of various sizes, depending upon their purpose. For example, in one sensor, it may be preferred to use a 3 mm oxygen electrode, a 10 mm glucose electrode and a 4 mm counter electrode, all separated by reference electrodes. In another embodiment, each reference electrode can be functionally paired with a working electrode. For example, the electrodes can be pulsed on and off, such that a first reference electrode R1 is active only when the first working electrode E1 is active, and a second reference electrode R2 is active only when the second working electrode E2 is active. In another embodiment, a flat sensor (e.g., disk-shaped) can be manufactured by sandwiching reference electrodes between working electrodes, cutting the sandwich into a cylinder, and the cutting the cylinder cross-wise (perpendicularly or at an angle) into disks.

Figure 7N:
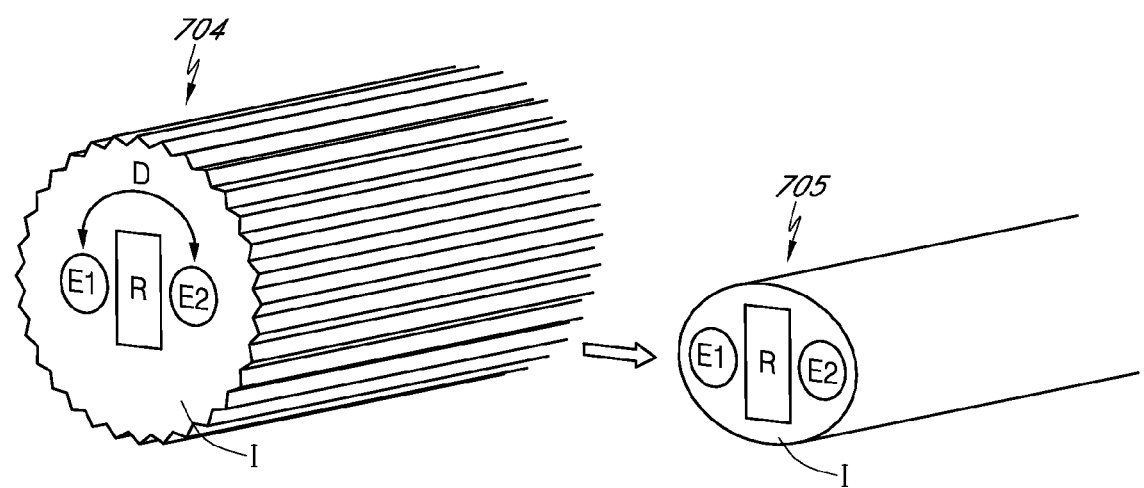
FIG. 7N is a schematic of one step of the manufacture of one embodiment of a sensor having, embedded in insulating material, two working electrodes separated by a reference electrode, wherein the sensor is trimmed to a final size and/or shape.

FIG. 7N is a schematic cross-sectional view of the manufacture of an integrally formed sensor, in one embodiment. In some preferred embodiments, at least two working electrodes (E1, E2) and optionally a reference electrode R are embedded in a quantity 704 of insulating material I. The working electrodes are separated by a diffusion barrier D. After the insulator has been cured (e.g., vulcanized or solidified) the structure is shaped (e.g., carved, scraped or cut etc.) to the final sensor shape 705, such that excess insulation material is removed. In some embodiments, multiple sensors can be formed as an extended structure of electrode wires embedded in insulator, which is subsequently cut to the desired length, wherein the exposed electrode ends (e.g., at the cut surface) become the electroactive surfaces of the electrodes. In other embodiments, portions of the insulator adjacent to the electrodes (e.g., windows) can be removed (e.g., by cutting or scraping, etc.) to expose the electroactive surfaces. Depending upon the sensor's configuration and purpose, an enzyme solution can be applied to one or more of the electroactive surfaces, as described elsewhere herein. Although this exemplary embodiment illustrates one technique of manufacturing a sensor having insulation-embedded electrodes, one skilled in the art appreciates a variety of alternative configurations. For example, a diffusion barrier D, can comprise both the reference electrode R and the insulating material I, or only the reference electrode. In another example, windows exposing the electroactive surfaces can be formed adjacent to each other (e.g., on the same side of the reference electrode) or on opposite sides of the reference electrode. Still, in other embodiments, more working or reference electrodes can be included, and the working and reference electrodes can be of relatively larger or smaller size, depending upon the sensor's configuration and operating requirements (e.g., voltage and/or current requirements).

Figure 8A:
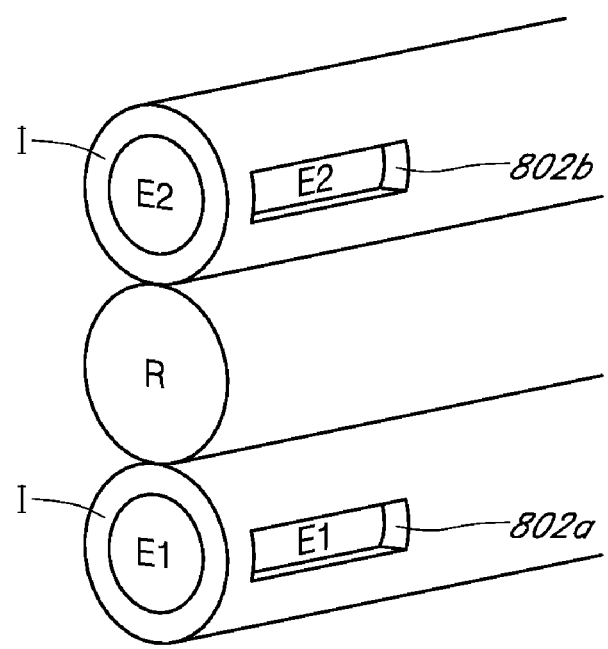
FIG. 8A is a schematic on one embodiment of a sensor having two working electrodes coated with insulating material, and separated by a reference electrode.
Figure 8B:
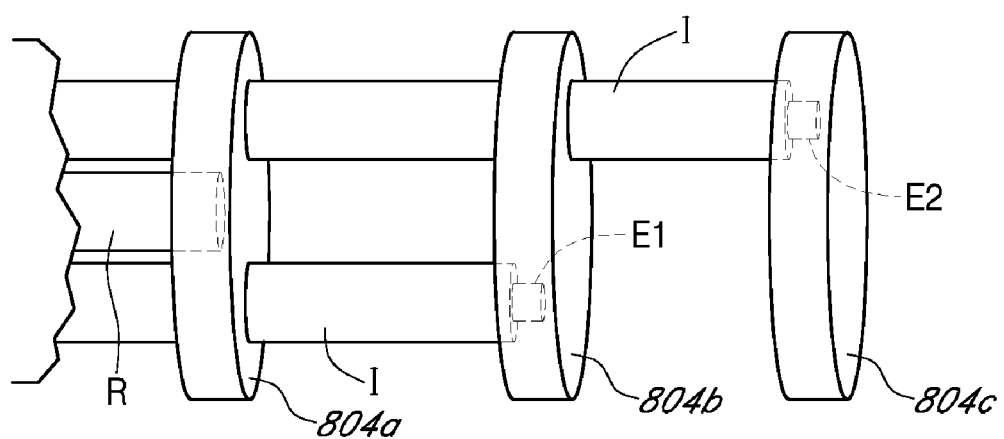
FIG. 8B is a schematic of the second end (e.g., ex vivo terminus) of the sensor of FIG. 8A having a stepped connection to the sensor electronics.

FIGS. 8A and 8B are schematic views of a sensor in yet another embodiment. FIG. 8A is a view of the cross-section and side of an in vivo portion of the sensor. FIG. 8B is a side view of the ex vivo portion of the sensor (e.g., the portion that is connected to the sensor electronics, as described elsewhere herein). Namely, two working electrodes E1, E2 that are coated with insulator I and then disposed on substantially opposing sides of a reference electrode R, such as a silver or silver/silver chloride electrode (see FIG. 8A). The working electrodes are separated by a diffusion barrier D that can include a physical barrier (provided by the reference electrode and/or the insulating material coatings), a spatial barrier (provided by staggering the electroactive surfaces of the working electrodes), or a temporal barrier (provided by oscillating the potentials between the electrodes). In some embodiments, the reference electrode R has a surface area at least 6-times the surface area of the working electrodes. Additionally, the reference electrode substantially can act as a spatial diffusion barrier between the working electrodes due to its larger size (e.g., the distance across the reference electrode, from one working electrode to another).

The electrodes can be held in position by wrapping with wire or a non-conductive fiber, a non-conductive sheath, a biointerface membrane coating, or the like. The electroactive surfaces of the working electrodes are exposed. In some embodiments, the end of the sensor is cut off, to expose the ends of the wires. In other embodiments, the ends of the wires are coated with insulating material; and the electroactive surfaces are exposed by removing a portion of the insulating material (e.g., a window 802 cut into the side of the insulation coating the electrode). In some embodiments, the windows exposing the electroactive surfaces of the electrodes can be staggered (e.g., spaced such that one or more electrodes extends beyond the other one or more electrodes), symmetrically arranged or rotated to any degree; for example, to substantially prevent diffusion of electroactive species from one working electrode (e.g., 802a) to the other working electrode (e.g., 802b), as will be discussed in greater detail elsewhere herein. In various embodiments, the reference electrode is not coated with a nonconductive material. The reference electrode can have a surface area that is at least 6 times the surface area of the exposed working electrode electroactive surfaces. In some embodiments, the reference electrode R surface area is 7-10 times (or larger) than the surface area of the working electrode electroactive surfaces. In still other embodiments, the reference electrode can be only 1-5 times the surface area of working electrode electroactive surfaces (e.g., (E1+E2)× 1=R or (E1+E2)×2=R, etc.).

The ex vivo end of the sensor is connected to the sensor electronics (not shown) by electrical connectors 804a, 804b, 804c. In some embodiments, the ex vivo end of the sensor is stepped. For example, the ex vivo end of the reference electrode R terminates within electrical connector 804a. The ex vivo end of the first working electrode E1 is exposed (e.g., nonconductive material removed therefrom) and terminates a small distance past the reference electrode R, within electrical connector 804b. Similarly, the ex vivo end of the second working electrode E2 is exposed (e.g., nonconductive material removed therefrom) and terminates a small distance past the termination of the first working electrode E1, within electrical connector 804c.

Although this exemplary embodiment illustrates one configuration of an integrally formed sensor, one skilled in the art appreciates a variety of alternative configurations. For example, in some embodiments, a portion of the in vivo portion of the sensor can be twisted and/or stepped. More working, reference, and/or counter electrodes, as well as insulators, can be included. The electrodes can be of relatively larger or smaller size, depending upon the sensor's intended function. In some embodiments, the electroactive surfaces can be staggered. In still other embodiments, the reference electrode can be disposed remotely from the sensor, as described elsewhere herein. For example, the reference electrode shown in FIG. 8A can be replaced with a non-conductive support and the reference electrode disposed on the host's skin.

With reference to the ex vivo portion of the sensor, one skilled in the art appreciates additional alternative configurations. For example, in one embodiment, a portion of the ex vivo portion of the sensor can be twisted or coiled. In some embodiments, the working and reference electrodes can be of various lengths and configurations not shown in FIG. 8B. For example, the reference electrode R can be the longest (e.g., connect to electrical contact 804c) and the first second working electrode E2 can be the shortest (e.g., connect to electrical contact 804a). In other embodiments, the first working electrode E1 may be either the longest electrode (e.g., connect to electrical contact 804c) or the shortest electrode (e.g., connect to electrical contact 804a).

Figure 9A:
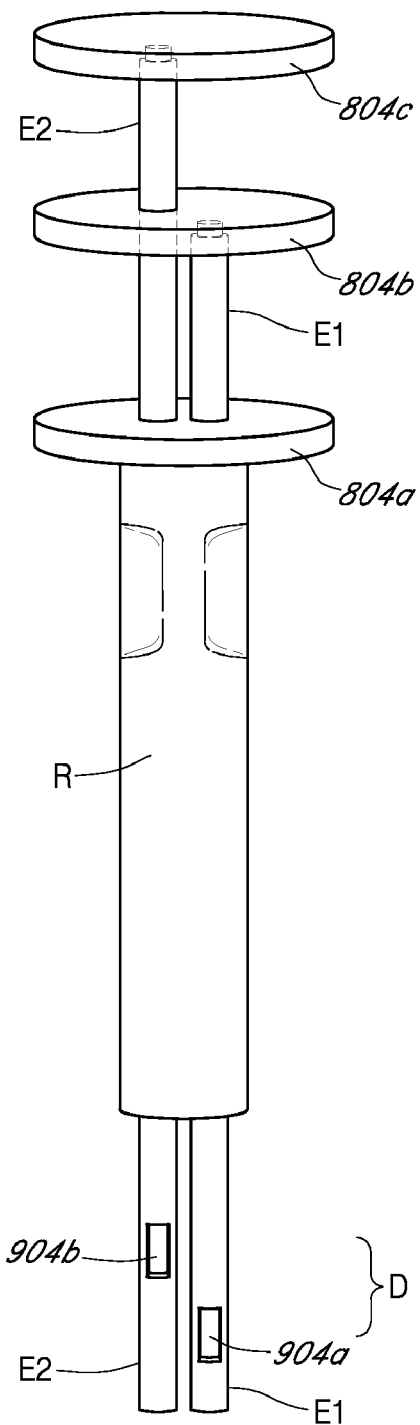
FIG. 9A is a schematic of one embodiment of a sensor having two working electrodes and a substantially cylindrical reference electrode there around, wherein the second end (the end connected to the sensor electronics) of the sensor is stepped.

FIG. 9A is a schematic view that illustrates yet another exemplary embodiment of an integrally formed analyte sensor. Namely, two working electrodes E1, E2 are bundled together and substantially encircled with a cylindrical silver or silver/silver chloride reference electrode R (or the like). The reference electrode can be crimped at a location 902, to prevent movement of the working electrodes E1, E2 within the reference electrode R cylinder. In alternative embodiments, a reference electrode can be rolled or coiled around the working electrodes E1, E2, to form the reference electrode R. Preferably, the working electrodes are at least partially insulated as described in more detail elsewhere herein; such as by coating with a non-conductive material, such as but not limited to Parylene. One skilled in the art appreciates that a variety of alternative configurations are possible.

Figure 9B:
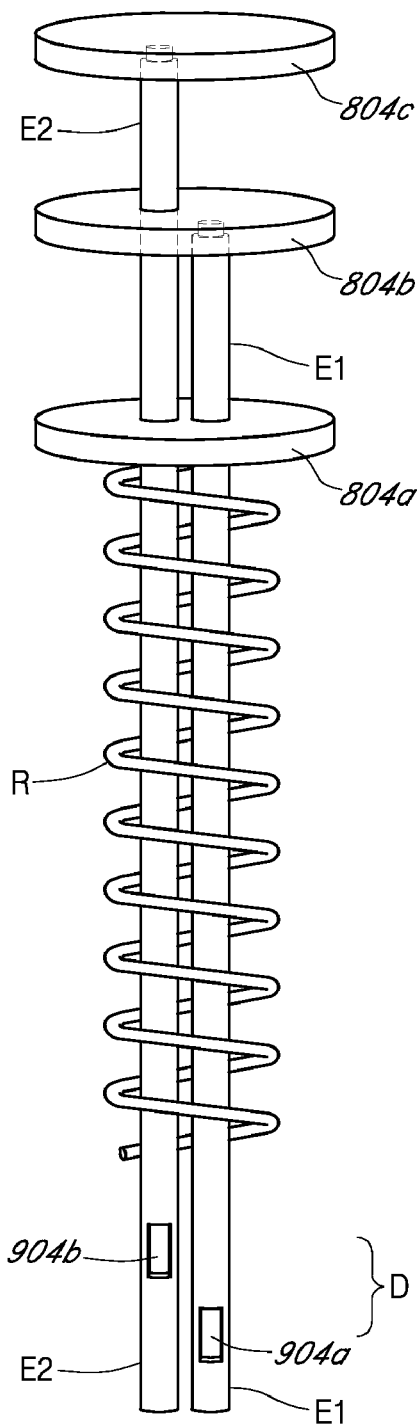
FIG. 9B is a schematic of one embodiment of a sensor having two working electrodes and an electrode coiled there around, wherein the second end (the end connected to the sensor electronics) of the sensor is stepped.

FIG. 9B illustrates another embodiment of an integrally formed analyte sensor. Namely, two working electrodes E1, E2 are bundled together with a silver or silver/silver chloride wire reference electrode R coiled there around. The reference electrode can be coiled tightly, to prevent movement of the working electrodes E1, E2 within the reference electrode R coil.

Referring again to FIGS. 9A to 9B, near the tip of the in vivo portion of the sensor, windows 904a and 904b are formed on the working electrodes E1, E2. Portions of the non-conductive material (e.g., insulator) coating each electrode is removed to form windows 904a and 904b. The electroactive surfaces of the electrodes are exposed via windows 904a and 904b. As described elsewhere herein, the electrode electroactive surfaces exposed through windows 904a and 904b are coated with a membrane system. An active enzyme (e.g., GOx is used if glucose is the analyte) is disposed within or beneath or within the membrane covering one of the windows (e.g., 904a or 904b). The membrane covering the other window can include inactivated enzyme (e.g., GOx inactivated by heat, solvent, UV or laser irradiation, etc., as described herein) or no enzyme. The electrode having active enzyme detects a signal related to the analyte concentration and non-analyte related signal (e.g., due to background, etc.). In contrast, the electrode having inactive enzyme or no enzyme detects substantially only the non-analyte related signal. These signals are transmitted to sensor electronics (discussed elsewhere herein) to calculate an analyte concentration based on only the signal component related to only the analyte (described elsewhere herein).

In general, the windows 904a and 904b are separated or staggered by a distance D, which is selected to be sufficiently large that electroactive species (e.g., $H_2O_2$) do not substantially diffuse from one window to the other (e.g., from 904a to 904b). In an exemplary embodiment of a glucose-oxidase-based sensor, active enzyme is included in the membrane covering window 904a and inactive enzyme is included in the membrane covering window 904b. Distance D is configured to be large enough that $H_2O_2$ cannot diffuse from window 904a to window 904b, which lacks active enzyme (as discussed elsewhere herein). In some embodiments, the distance D is at least about 0.020 inches or less to about 0.120 inches or more. In some embodiments, D is at least about 0.030 to about 0.050 inches. In other embodiments, D is at least about 0.090 to about 0.095 inches. One skilled in the art appreciates alternative embodiments of the diffusion barrier D. Namely, the diffusion barrier D can be spatial (discussed herein with relation to FIGS. 9A and 9B), physical or temporal (see discussion of Diffusion Barriers herein and FIG. 10). In some embodiments, a physical diffusion barrier D, such as but not limited to an extended non-conductive structure placed between the working electrodes (e.g., FIG. 8A), substantially prevents diffusion of $H_2O_2$ from one working electrode (having active enzyme) to another working electrode (having no active enzyme). In other embodiments, a temporal diffusion barrier D is created by pulsing or oscillating the electrical potential, such that only one working electrode is activated at a time.

In various embodiments, one of the windows 904a or 904b comprises an enzyme system configured to detect the analyte of interest (e.g., glucose or oxygen). The other window comprises no active enzyme system (e.g., wherein the enzyme system lacks enzyme or wherein the enzyme has been deactivated). In some embodiments, wherein the "enzyme system lacks enzyme," a layer may be applied, similar to an active enzyme layer, but without the actual enzyme included therein. In some embodiments, wherein "the enzyme has been de-activated" the enzyme can be inactivated (e.g., by heat or solvent) prior to addition to the enzyme system solution or the enzyme can be inactivated after application to the window.

In one exemplary embodiment, an enzyme is applied to both windows 904a and 904b followed by deactivation of the enzyme in one window. For example, one window can be masked (e.g., to protect the enzyme under the mask) and the sensor then irradiated (to deactivate the enzyme in the unmasked window). Alternatively, one of the enzyme-coated windows (e.g., the first window but not the second window) can be sprayed or dipped in an enzyme-deactivating solvent (e.g., treated with a protic acid solution such a hydrochloric acid or sulfuric acid). For example, a window coated with GOx can be dipped in dimethyl acetamide (DMAC), ethanol, or tetrahydrofuran (THF) to deactivate the GOx. In another example, the enzyme-coated window can be dipped into a hot liquid (e.g., water or saline) to deactivate the enzyme with heat.

In these embodiments, the design of the active and inactive enzyme window is at least partially dependent upon the sensor's intended use. In some embodiments, it is preferred to deactivate the enzyme coated on window 904a. In other embodiments, it is preferred to deactivate the enzyme coated on window 904b. For example, in the case of a sensor to be used in a host's blood stream, the choice depends upon whether the sensor will be inserted pointing upstream (e.g., against the blood flow) or pointing downstream (e.g., with the blood flow).

In one exemplary embodiment, an intravascular sensor is inserted into the host's vein pointing upstream (against the blood flow), an enzyme coating on electrode E1 (window 904a) is inactivated (e.g., by dipping in THF and rinsing) and an enzyme coating on electrode E2 (in window 904b) is not inactivated (e.g., by not dipping in THF). Because the enzyme on the first electrode E1 (e.g., in window 904a) is inactive, electroactive species (e.g., $H_2O_2$) will not be substantially generated at window 904a (e.g., the first electrode E1 generates substantially no $H_2O_2$ to effect the second electrode E2). In contrast, the active enzyme on the second electrode E2 (in window 904b) generates $H_2O_2$ which at least partially diffuses down stream (away from the windows) and thus has no effect on the first electrode E1, other features and advantages of spatial diffusion barriers are described in more detail elsewhere herein.

In another exemplary embodiment, an intravascular sensor is inserted into the host's vein pointing downstream (with the blood flow), the enzyme coating on electrode E1 (window 904a) is active and the enzyme coating on electrode E2 (in window 904b) is inactive. Because window 904a is located further downstream than window 904b, the $H_2O_2$ produced by the enzyme in 904a diffuses downstream (away from window 904b), and therefore does not affect substantially electrode E2. In a preferred embodiment, the enzyme is GOx, and the sensor is configured to detect glucose. Accordingly, $H_2O_2$ produced by the GOx in window 904a does not affect electrode E2, because the sensor is pointing downstream and the blood flow carries away the $H_2O_2$ produced on electrode E1.

FIGS. 9A and 9B illustrate two embodiments of a sensor having a stepped second end (e.g., the back end, distal end or ex vivo end, described with reference to FIG. 8B) that connects the sensor to the sensor electronics. Namely, each electrode terminates within an electrical connector 804 such as but not limited to an elastomeric electrical connector. Additionally, each electrode is of a different length, such that each electrode terminates within one of a plurality of sequential electrical connectors. For example, with reference to FIG. 9A, the reference electrode R is the shortest in length and terminates within the first electrical connector 804. The first working electrode E1 is longer than the reference electrode R, and terminates within the second electrical connector 804. Finally, the second working electrode E2 is the longest electrode and terminates within the third electrical connector 804. One skilled in the art appreciates that other configurations are possible. For example, the first working electrode E1 can be longer than the second working electrode E2. Accordingly, the second working electrode E2 would terminate within the second (e.g., middle) electrical connector 804 and the first working electrode E1 would terminate within the third (e.g., last) electrical connector 804. With reference to FIG. 9B, additional stepped second end configurations are possible. In alternative embodiments, the second ends of the sensor may be separated from each other to connect to non-parallel, non-sequential electrical connectors.

Figure 11:
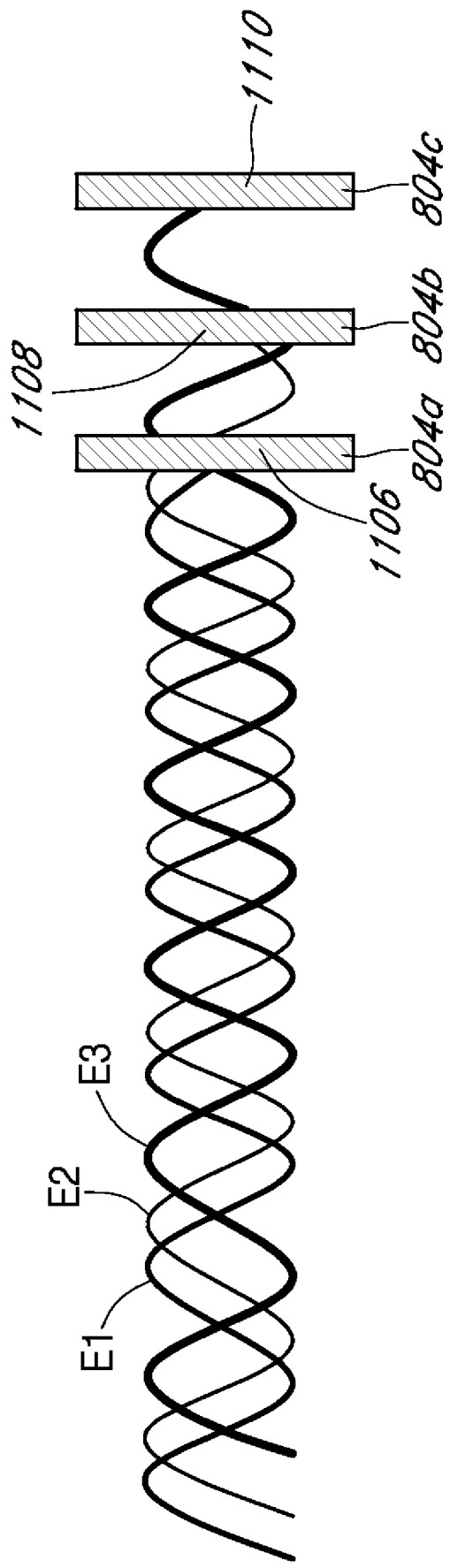
FIG. 11 is a schematic illustrating one embodiment of a triple helical coaxial sensor having a stepped second terminus for engaging the sensor electronics.

FIG. 11 is a schematic view of a sensor in yet another embodiment. In preferred embodiments, the sensor is integrally formed, coaxial, and has a stepped ex vivo end (e.g., back or second end). Electrodes E1, E2 and E3 are twisted to form a helix, such as a triple helix. Additionally, at the back end of the sensor, the electrodes are stepped and each electrode is individually connected to the sensor electronics by an electrical connector 804. At each electrode's second end, the electrode engages an electrical connector 804 that joins the electrode to the sensor electronics. For example, the second end of electrode E1 electrically connects electrical connector 1106. Similarly, the second end of electrode E2 electrically connects electrical connector 1108 and the second end of electrode E3 electrically connects electrical connector 1110. As described elsewhere herein, each sensor component is difunctional, and provides electrical conductance, structural support, a diffusion barrier, or insulation (see description elsewhere herein). Although this exemplary embodiment illustrates an integrally formed, coaxial sensor having a stepped back end, one skilled in the art appreciates a variety of alternative configurations. For example, one of the electrodes E1, E2 or E3 can be a reference electrode, or the reference electrode can be disposed remotely from the sensor, such as but not limited to on the host's skin. In another example, the sensor can have only two electrodes or more than three electrodes.

One skilled in the art recognizes a variety of alternative configurations for the embodiments described herein. For example, in any embodiment of an analyte sensor, the reference electrode (and optionally a counter electrode) can be disposed remotely from the working electrodes. For example, in FIGS. 7A1 through 9B and FIG. 11, the reference electrode R can be replaced with a non-conductive material, such as an insulator I. Depending upon the sensor's configuration and location of use, the reference electrode R can then be inserted into the host in a location near to the sensor, applied to the host's skin, be disposed within a fluid connector, be disposed on the ex-vivo portion of the sensor or even disposed on the exterior of the sensor electronics.

FIG. 7L illustrates an embodiment in which the reference and/or counter electrode is located remotely from the first and second working electrodes E1 and E2, respectively. In one exemplary embodiment, the sensor is a needle-type sensor such as described with reference to FIG. 1B, and the working electrodes E1, E2 are integrally formed together with a substantially X-shaped insulator I and the reference electrode (and/or counter electrode) is placed on the host's skin (e.g., a button, plate, foil or wire, such as under the housing) or implanted transcutaneously in a location separate from the working electrodes.

As another example, in one embodiment of a sensor configured to measure a host's blood, such as described in co-pending U.S. patent application Ser. No. 11/543,396, filed on Oct. 4, 2006 and entitled "ANALYTE SENSOR", and which is incorporated herein by reference in its entirety; one or more working electrodes can be inserted into the host's blood via a catheter and the reference and/or counter electrode can be placed within the a fluid connector (on the sensor) configured to be in fluid communication with the catheter; in such an example, the reference and/or counter electrode is in contact with fluid flowing through the fluid connector but not in direct contact with the host's blood. In still other embodiments, the reference and/or counter electrodes can be placed exterior to the sensor, in bodily contact for example.

With reference to the analyte sensor embodiments disclosed herein, the surface area of the electroactive portion of the reference (and/or counter) electrode is at least six times the surface area of one or more working electrodes. In other embodiments, the reference (and/or counter) electrode surface is 1, 2, 3, 4, 5, 7, 8, 9 or 10 times the surface area of the working electrodes. In other embodiments, the reference (and/or counter) electrode surface area is 11, 12, 13, 14, 15, 16, 17, 18, 19 or 20 times the surface area of the working electrodes. For example, in a needle-type glucose sensor, similar to the embodiment shown in FIG. 1B, the surface area of the reference electrode (e.g., 18 or 20) includes the exposed surface of the reference electrode, such as but not limited to the electrode surface facing away from the working electrode 16.

In various embodiments, the electrodes can be stacked or grouped similar to that of a leaf spring configuration, wherein layers of electrode and insulator (or individual insulated electrodes) are stacked in offset layers. The offset layers can be held together with bindings of non-conductive material, foil, or wire. As is appreciated by one skilled in the art, the strength, flexibility, and/or other material property of the leaf spring-configured or stacked sensor can be either modified (e.g., increased or decreased), by varying the amount of offset, the amount of binding, thickness of the layers, and/or materials selected and their thicknesses, for example.

In some embodiments, the sensor (e.g., a glucose sensor) is configured for implantation into the host. For example, the sensor may be wholly implanted into the host, such as but not limited to in the host's subcutaneous tissue (e.g., the embodiment shown in FIG. 1A). In other embodiments, the sensor is configured for transcutaneous implantation in the host's tissue. For example, the sensor can have a portion that is inserted through the host's skin and into the underlying tissue, and another portion that remains outside the host's body (e.g., such as described in more detail with reference to FIG. 1B). In still other embodiments, the sensor is configured for indwelling in the host's blood stream. For example, a needle-type sensor can be configured for insertion into a catheter dwelling in a host's vein or artery. In another example, the sensor can be integrally formed on the exterior surface of the catheter, which is configured to dwell within a host's vein or artery. Examples of indwelling sensors can be found in co-pending U.S. patent application Ser. No. 11/543,396 filed on Oct. 4, 2006 and entitled "ANALYTE SENSOR." In various embodiments, the in vivo portion of the sensor can take alternative configurations, such as but not limited to those described in more detail with reference to FIGS. 7A-9B and 11.

In preferred embodiments, the analyte sensor substantially continuously measures the host's analyte concentration. In some embodiments, for example, the sensor can measure the analyte concentration every fraction of a second, about every fraction of a minute or every minute. In other exemplary embodiments, the sensor measures the analyte concentration about every 2, 3, 4, 5, 6, 7, 8, 9, or 10 minutes. In still other embodiments, the sensor measures the analyte concentration every fraction of an hour, such as but not limited to every 15, 30 or 45 minutes. Yet in other embodiments, the sensor measures the analyte concentration about every hour or longer. In some exemplary embodiments, the sensor measures the analyte concentration intermittently or periodically. In one preferred embodiment, the analyte sensor is a glucose sensor and measures the host's glucose concentration about every 4-6 minutes. In a further embodiment, the sensor measures the host's glucose concentration every 5 minutes.

In one exemplary embodiment, the analyte sensor is a glucose sensor having a first working electrode configured to generate a first signal associated with both glucose and non-glucose related electroactive compounds that have a first oxidation potential. Non-glucose related electroactive compounds can be any compound, in the sensor's local environment that has an oxidation potential substantially overlapping with the oxidation potential of $H_2O_2$, for example. While not wishing to be bound by theory, it is believed that the glucose-measuring electrode can measure both the signal directly related to the reaction of glucose with GOx (produces $H_2O_2$ that is oxidized at the working electrode) and signals from unknown compounds that are in the extracellular milieu surrounding the sensor. These unknown compounds can be constant or non-constant (e.g., intermittent or transient) in concentration and/or effect. In some circumstances, it is believed that some of these unknown compounds are related to the host's disease state. For example, it is know that blood chemistry changes dramatically during/after a heart attack (e.g., pH changes, changes in the concentration of various blood components/protein, and the like). Other compounds that can contribute to the non-glucose related signal are believed to be related to the wound healing process that is initiated by implantation/insertion of the sensor into the host, which is described in more detail with reference to U.S. Patent Publication No. US-2007-0027370-A1, which is incorporated herein by reference in its entirety. For example, transcutaneously inserting a needle-type sensor initiates a cascade of events that includes the release of various reactive molecules by macrophages.

In some embodiments, the glucose sensor includes a second (e.g., auxiliary) working electrode that is configured to generate a second signal associated with non-glucose related electroactive compounds that have the same oxidation potential as the above-described first working electrode (e.g., para supra). In some embodiments, the non-glucose related electroactive species includes at least one of interfering species, non-reaction-related $H_2O_2$, and other electroactive species. For example, interfering species includes any compound that is not directly related to the electrochemical signal generated by the glucose-GOx reaction, such as but not limited to electroactive species in the local environment produces by other bodily processes (e.g., cellular metabolism, wound healing, a disease process, and the like). Non-reaction-related $H_2O_2$ includes $H_2O_2$ from sources other than the glucose-GOx reaction, such as but not limited to $H_2O_2$ released by nearby cells during the course of the cells' metabolism, $H_2O_2$ produced by other enzymatic reactions (e.g., extracellular enzymes around the sensor or such as can be released during the death of nearby cells or such as can be released by activated macrophages), and the like. Other electroactive species includes any compound that has an oxidation potential similar to or overlapping that of $H_2O_2$.

The non-analyte (e.g., non-glucose) signal produced by compounds other than the analyte (e.g., glucose) obscured the signal related to the analyte, contributes to sensor inaccuracy, and is considered background noise. As described in greater detail in the section entitled "Noise Reduction," background noise includes both constant and non-constant components and must be removed to accurately calculate the analyte concentration. While not wishing to be bound by theory, it is believed that the sensor of the preferred embodiments are designed (e.g., with symmetry, coaxial design and/or integral formation) such that the first and second electrodes are influenced by substantially the same external/environmental factors, which enables substantially equivalent measurement of both the constant and non-constant species/noise. This advantageously allows the substantial elimination of noise (including transient biologically related noise that has been previously seen to affect accuracy of sensor signal due to it's transient and unpredictable behavior) on the sensor signal (using electronics described elsewhere herein) to substantially reduce or eliminate signal effects due to noise, including non-constant noise (e.g., unpredictable biological, biochemical species or the like) known to effect the accuracy of conventional continuous sensor signals. Preferably, the sensor includes electronics operably connected to the first and second working electrodes. The electronics are configured to provide the first and second signals that are used to generate glucose concentration data substantially without signal contribution due to non-glucose-related noise. Preferably, the electronics include at least a potentiostat that provides a bias to the electrodes. In some embodiments, sensor electronics are configured to measure the current (or voltage) to provide the first and second signals. The first and second signals are used to determine the glucose concentration substantially without signal contribution due to non-glucose-related noise such as by but not limited to subtraction of the second signal from the first signal or alternative data analysis techniques. In some embodiments, the sensor electronics include a transmitter that transmits the first and second signals to a receiver, where additional data analysis and/or calibration of glucose concentration can be processed. U.S. Patent Publication No. US-2005-0027463-A1, U.S. Patent Publication No. US-2005-0203360-A1, and U.S. Patent Publication No. US-2006-0036142-A1 describe systems and methods for processing sensor analyte data and are incorporated herein by reference in their entirety.

In preferred embodiments, the sensor electronics (e.g., electronic components) are operably connected to the first and second working electrodes. The electronics are configured to calculate at least one analyte sensor data point. For example, the electronics can include a potentiostat, A/D converter, RAM, ROM, transmitter, and the like. In some embodiments, the potentiostat converts the raw data (e.g., raw counts) collected from the sensor to a value familiar to the host and/or medical personnel. For example, the raw counts from a glucose sensor can be converted to milligrams of glucose per deciliter of glucose (e.g., mg/dl). In some embodiments, the electronics are operably connected to the first and second working electrodes and are configured to process the first and second signals to generate a glucose concentration substantially without signal contribution due to non-glucose noise artifacts. The sensor electronics determine the signals from glucose and non-glucose related signal with an overlapping measuring potential (e.g., from a first working electrode) and then non-glucose related signal with an overlapping measuring potential (e.g., from a second electrode). The sensor electronics then use these data to determine a substantially glucose-only concentration, such as but not limited to subtracting the second electrode's signal from the first electrode's signal, to give a signal (e.g., data) representative of substantially glucose-only concentration, for example. In general, the sensor electronics may perform additional operations, such as but not limited to data smoothing and noise analysis.

Bifunctionality

In some embodiments, the components of at least a portion (e.g., the in vivo portion or the sensing portion) of the sensor possess bifunctional properties (e.g., provide at least two functions to the sensor). These properties can include electrical conductance, insulative properties, structural support, and diffusion barrier properties.

In one exemplary embodiment, the analyte sensor is designed with two working electrodes, a membrane system and an insulating material disposed between the working electrodes. An active enzymatic membrane is disposed above the first working electrode, while an inactive- or non-enzymatic membrane is disposed above the second working electrode. Additionally, the working electrodes and the insulating material are configured provide at least two functions to the sensor, including but not limited to electrical conductance, insulative properties, structural support, and diffusion barrier. For example, in one embodiment of a glucose sensor, the two working electrodes support the sensor's structure and provide electrical conductance; the insulating material provides insulation between the two electrodes and provides additional structural support and/or a diffusional barrier.

In some embodiments, a component of the sensor is configured to provide both electrical conductance and structural support. In an exemplary embodiment, the working electrode(s) and reference electrode are generally manufactured of electrically conductive materials, such as but not limited silver or silver/silver chloride, copper, gold, platinum, iridium, platinum-iridium, palladium, graphite, carbon, conductive polymers, alloys, and the like. Accordingly, the electrodes are both conductive and they give the sensor its shape (e.g., are supportive).

Referring to FIG. 1B, all three electrodes 16, 18, and 20 are manufactured from plated insulator, a plated wire, or electrically conductive material, such as but not limited to a metal wire. Accordingly, the three electrodes provide both electrical conductance (to measure glucose concentration) and structural support. Due to the configuration of the electrodes (e.g., the wires are about 0.001 inches in diameter or less, to about 0.01 inches or more), the sensor is needle-like and only about 0.003 inches or less to about 0.015 inches or more.

Similarly, the electrodes of FIG. 7A through FIG. 9 provide electrical conductance, to detect the analyte of interest, as well as structural support for the sensor. For example, the sensors depicted in FIGS. 7A through 7L embodiments that are substantially needle-like. Additionally, these sensors are substantially resilient, and therefore able to flex in response to mechanical pressure and then to regain their original shapes. FIG. 7M depicts a cross-section of another sensor embodiment, which can be a composite (e.g., built up of layers of working and reference electrode materials) needle-like sensor or the composite "wire" can be cut to produce pancake-shaped sensors [describe its bifunctionality without unnecessary characterizations (e.g., not "pancake-shaped"). FIG. 7N through FIG. 9 illustrate additional sensor embodiments, wherein the electrodes provide electrical conductance and support the sensor's needle-like shape.

In some embodiments, the first and second working electrodes are configured to provide both electrical conductance and structural support. For example, in a needle-type sensor, the working electrodes are often manufactured of bulk metal wires (e.g., copper, gold, platinum, iridium, platinum-iridium, palladium, graphite, carbon, conductive polymers, alloys, and the like). The reference electrode, which can function as a reference electrode alone, or as a dual reference and counter electrode, are formed from silver or silver/silver chloride, or the like. The metal wires are conductive (e.g., can conduct electricity) and give the sensor its shape and/or structural support. For example, one electrode metal wire may be coiled around the other electrode metal wire (e.g., FIG. 1B or FIG. 7B). In a further embodiment, the sensor includes a reference electrode that is also configured to provide electrical conductance and structural support (e.g., FIG. 1B, FIGS. 7C to 7E). In general, reference electrodes are made of metal, such as bulk silver or silver/silver chloride wires. Like the two working electrodes, the reference electrode both conducts electricity and supports the structure of the sensor.

In some embodiments, the first and second working electrode and the insulating material are configured provide at least two functions, such as but not limited to electrical conductance, insulative properties, structural support, and diffusion barrier. As described elsewhere herein, the working electrodes are electrical conductors and also provide support for the sensor. The insulating material (e.g., I) acts as an insulator, to prevent electrical communication between certain parts of the various electrodes. The insulating material also provides structural support or substantially prevents diffusion of electroactive species from one working electrode to the other, which is discussed in greater detail elsewhere herein.

In preferred embodiments, the sensor has a diffusion barrier disposed between the first and second working electrodes. The diffusion barrier is configured to substantially block diffusion of the analyte or a co-analyte (e.g., $H_2O_2$) between the first and second working electrodes. For example, a sheet of a polymer through which $H_2O_2$ cannot diffuse can be interposed between the two working electrodes. Diffusion barriers are discussed in greater detail elsewhere herein.

In some embodiments of the preferred embodiments, the analyte sensor includes a reference electrode that is configured to provide electrical conductance and a diffusion barrier. Electrical conductance is an inherent property of the metal used to manufacture the reference electrode. However, the reference electrode can be configured to prevent species (e.g., $H_2O_2$) from diffusing from the first working electrode to the second working electrode. For example, a sufficiently large reference electrode can be placed between the two working electrodes. In some embodiments, the reference electrode projects further than the two working electrodes. In other embodiments, the reference electrode is so broad that a substantial portion of the $H_2O_2$ produced at the first working electrode cannot diffuse to the second working electrode, and thereby significantly affect the second working electrode's function.

In a further embodiment, the reference electrode is configured to provide a diffusion barrier and structural support. As described elsewhere herein, the reference electrode can be constructed of a sufficient size and/or shape that a substantial portion of the $H_2O_2$ produced at a first working electrode cannot diffuse to the second working electrode and affect the second working electrode's function. Additionally, metal wires are generally resilient and hold their shape, the reference electrode can also provide structural support to the sensor (e.g., help the sensor to hold its shape).

In some embodiments of the analyte sensor described elsewhere herein, the insulating material is configured to provide both electrical insulative properties and structural support. In one exemplary embodiment, portions of the electrodes are coated with a non-conductive polymer. Inherently, the non-conductive polymer electrically insulates the coated electrodes from each other, and thus substantially prevents passage of electricity from one coated wire to another coated wire. Additionally, the non-conductive material (e.g., a non-conductive polymer or insulating material) can stiffen the electrodes and make them resistant to changes in shape (e.g., structural changes).

In some embodiments, a sensor component is configured to provide electrical insulative properties and a diffusion barrier. In one exemplary embodiment, the electrodes are coated with the non-conductive material that substantially prevents direct contact between the electrodes, such that electricity cannot be conducted directly from one electrode to another. Due to the non-conductive coatings on the electrodes, electrical current must travel from one electrode to another through the surrounding aqueous medium (e.g., extracellular fluid, blood, wound fluid, or the like). Any non-conductive material (e.g., insulator) known in the art can be used to insulate the electrodes from each other. In exemplary embodiments, the electrodes can be coated with non-conductive polymer materials (e.g., parylene, PTFE, ETFE, polyurethane, polyethylene, polyimide, silicone and the like) by dipping, painting, spraying, spin coating, or the like.

Non-conductive material (e.g., insulator, as discussed elsewhere herein) applied to or separating the electrodes can be configured to prevent diffusion of electroactive species (e.g., $H_2O_2$) from one working electrode to another working electrode. Diffusion of electroactive species from one working electrode to another can cause a false analyte signal. For example, electroactive species (e.g., $H_2O_2$) that are created at a first working electrode having active enzyme (e.g., GOx) can diffuse to a nearby working electrode (e.g., without active GOx). When the electroactive species arrives at the second working electrode, the second electrode registers a signal (e.g., as if the second working electrode comprised active GOx). The signal registered at the second working electrode due to the diffusion of the $H_2O_2$ is aberrant and can cause improper data processing in the sensor electronics. For example, if the second electrode is configured to measure a substantially non-analyte related signal (e.g., background) the sensor will record a higher non-analyte related signal than is appropriate, possibly resulting in the sensor reporting a lower analyte concentration than actually is present in the host. This is discussed in greater detail elsewhere herein.

In preferred embodiments, the non-conductive material is configured to provide a diffusion barrier and structural support to the sensor. Diffusion barriers are described elsewhere herein. Non-conductive materials can be configured to support the sensor's structure. In some, non-conductive materials with relatively more or less rigidity can be selected. For example, if the electrodes themselves are relatively flexible, it may be preferred to select a relatively rigid non-conductive material, to make the sensor stiffer (e.g., less flexible or bendable). In another example, if the electrodes are sufficiently resilient or rigid, a very flexible non-conductive material may be coated on the electrodes to bind the electrodes together (e.g., keep the electrodes together and thereby hold the sensor's shape).

Referring now to FIGS. 7C to 7J, the non-conductive material can be coated on or wrapped around the grouped or bundled electrodes, to prevent the electrodes from separating and also to prevent the electrodes from directly touching each other. For example, with reference to FIG. 7C, each electrode can be individually coated by a first non-conductive material and then bundled together. Then the bundle of individually insulated electrodes can be coated with a second layer of the first non-conductive material or with a layer or a second non-conductive material. In an embodiment of a sensor having the structure shown in FIG. 7K, each electrode E1, E2 is coated with a non-conductive material/insulator I, and then coated with a second non-conductive material 703 (e.g., instead of a biointerface membrane). Similarly, in FIG. 7L, the non-conductive material I prevents electrodes E1 and E2 from making direct contact with each other as well as giving the needle-like sensor its overall dimensions and shape.

FIG. 7N illustrates one method of configuring a sensor having a non-conductive material I that both provides electrical insulation between the electrodes E1, E2, R and provides structural support to the sensor. Namely, the electrodes are embedded in a non-conductive polymer I, which is subsequently vulcanized (704=before shaping). After vulcanization, the excess non-conductive polymer I is trimmed away (e.g., cutting or scraping, etc.) to produce a sensor having the final desired sensor shape 705=after shaping).

In some embodiments, a component of the sensor is configured to provide both insulative properties and a diffusion barrier. Diffusion barriers are discussed elsewhere herein. In one exemplary embodiment, the working electrodes are separated by a non-conductive material/insulator that is configured such that electroactive species (e.g., $H_2O_2$) cannot diffuse around it (e.g., from a first electrode to a second electrode). For example, with reference to the embodiment shown in FIG. 7H, the electrodes E1, E2 are placed in the groves carved into a cylinder of non-conductive material I. The distance D from E1 to E2 (e.g., around I) is sufficiently great that $H_2O_2$ produced at E1 cannot diffuse to E2 and thereby cause an aberrant signal at E2.

In some preferred embodiments, in addition to two working electrodes and a non-conductive material/insulator, the sensor includes at least a reference or a counter electrode. In preferred embodiments, the reference and/or counter electrode, together with the first and second working electrodes, integrally form at least a portion of the sensor. In some embodiments, the reference and/or counter electrode is located remote from the first and second working electrodes. For example, in some embodiments, such as in the case of a transcutaneous sensor, the reference and/or counter electrodes can be located on the ex vivo portion of the sensor or reside on the host's skin, such as a portion of an adhesive patch. In other embodiments, such as in the case of an intravascular sensor, the reference and/or counter electrode can be located on the host's skin, within or on the fluid connector (e.g., coiled within the ex vivo portion of the device and in contact with fluid within the device, such as but not limited to saline) or on the exterior of the ex vivo portion of the device. In preferred embodiments, the surface area of the reference and/or counter electrode is as least six times the surface area of at least one of the first and second working electrodes. In a further embodiment, the surface area of the reference and/or counter electrode is at least ten times the surface area of at least one of the first and second electrodes.

In preferred embodiments, the sensor is configured for implantation into the host. The sensor can be configured for subcutaneous implantation in the host's tissue (e.g., transcutaneous or wholly implantable). Alternatively, the sensor can be configured for indwelling in the host's blood stream (e.g., inserted through an intravascular catheter or integrally formed on the exterior surface of an intravascular catheter that is inserted into the host's blood stream).

In some embodiments, the sensor is a glucose sensor that has a first working electrode configured to generate a first signal associated with glucose (e.g., the analyte) and non-glucose related electroactive compounds (e.g., physiological baseline, interferents, and non-constant noise) having a first oxidation potential. For example, glucose has a first oxidation potential. The interferents have an oxidation potential that is substantially the same as the glucose oxidation potential (e.g., the first oxidation potential). In a further embodiment, the glucose sensor has a second working electrode that is configured to generate a second signal associated with noise of the glucose sensor. The noise of the glucose sensor is signal contribution due to non-glucose related electroactive compounds (e.g., interferents) that have an oxidation potential that substantially overlaps with the first oxidation potential (e.g., the oxidation potential of glucose, the analyte). In various embodiments, the non-glucose related electroactive species include an interfering species, non-reaction-related hydrogen peroxide, and/or other electroactive species.

In preferred embodiments, the glucose sensor has electronics that are operably connected to the first and second working electrodes and are configured to provide the first and second signals to generate glucose concentration data substantially without signal contribution due to non-glucose-related noise. For example, the sensor electronics analyze the signals from the first and second working electrodes and calculate the portion of the first electrode signal that is due to glucose concentration only. The portion of the first electrode signal that is not due to the glucose concentration can be considered to be background, such as but not limited to noise.

In preferred embodiments, the glucose sensor has a non-conductive material (e.g., insulative material) positioned between the first and second working electrodes. The non-conductive material substantially prevents cross talk between the first and second working electrodes. For example, the electrical signal cannot pass directly from a first insulated electrode to a second insulated electrode. Accordingly, the second insulated electrode cannot aberrantly record an electrical signal due to electrical signal transfer from the first insulated electrode.

In preferred embodiments, the first and second working electrodes and the non-conductive material integrally form at least a portion of the sensor (e.g., a glucose sensor). The first and second working electrodes integrally form a substantial portion of the sensor configured for insertion in the host (e.g., the in vivo portion of the sensor). In a further embodiment, the sensor (e.g., a glucose sensor) includes a reference electrode that, in addition to the first and second working electrodes, integrally forms a substantial portion of the sensor configured for insertion in the host (e.g., the in vivo portion of the sensor). In yet a further embodiment, the sensor (e.g., a glucose sensor) has an insulator (e.g., non-conductive material), wherein the first and second working electrodes and the insulator integrally form a substantial portion of the sensor configured for insertion in the host (e.g., the in vivo portion of the sensor).

In preferred embodiments, the sensor (e.g., a glucose sensor) includes a diffusion barrier configured to substantially block diffusion of the analyte (e.g., glucose) or a co-analyte (e.g., $H_2O_2$) between the first and second working electrodes. For example, as described with reference to FIG. 10, a diffusion barrier D (e.g., spatial, physical and/or temporal) blocks diffusion of a species (e.g., glucose and/or $H_2O_2$) from the first working electrode E1 to the second working electrode E2. In some embodiments, the diffusion barrier D is a physical diffusion barrier, such as a structure between the working electrodes that blocks glucose and $H_2O_2$ from diffusing from the first working electrode E1 to the second working electrode E2. In other embodiments, the diffusion barrier D is a spatial diffusion barrier, such as a distance between the working electrodes that blocks glucose and $H_2O_2$ from diffusing from the first working electrode E1 to the second working electrode E2. In still other embodiments, the diffusion barrier D is a temporal diffusion barrier, such as a period of time between the activity of the working electrodes such that if glucose or $H_2O_2$ diffuses from the first working electrode E1 to the second working electrode E2, the second working electrode E2 will not substantially be influenced by the $H_2O_2$ from the first working electrode E1.

With reference to FIG. 7H, if the diffusion barrier is spatial, a distance D separates the working electrodes, such that the analyte or co-analyte substantially cannot diffuse from a first electrode E1 to a second electrode E2. In some embodiments, the diffusion barrier is physical and configured from a material that substantially prevents diffusion of the analyte or co-analyte there through. Again referring to FIG. 7H, the insulator I and/or reference electrode R is configured from a material that the analyte or co-analyte cannot substantially pass through. For example, $H_2O_2$ cannot substantially pass through a silver/silver chloride reference electrode. In another example, a parylene insulator can prevent $H_2O_2$ diffusion between electrodes. In some embodiments, wherein the diffusion barrier is temporal, the two electrodes are activated at separate, non-overlapping times (e.g., pulsed). For example, the first electrode E1 can be activated for a period of one second, followed by activating the second electrode E2 three seconds later (e.g., after E1 has been inactivated) for a period of one second.

In additional embodiments, a component of the sensor is configured to provide both a diffusional barrier and a structural support, as discussed elsewhere herein. Namely, the diffusion barrier can be configured of a material that is sufficiently rigid to support the sensor's shape. In some embodiments, the diffusion barrier is an electrode, such as but not limited to the reference and counter electrodes (e.g., FIG. 7G to 7J and FIG. 8A). In other embodiments, the diffusion barrier is an insulating coating (e.g., parylene) on an electrode (e.g., FIG. 7K to 7L) or an insulating structure separating the electrodes (e.g., FIG. 8A and FIG. 10).

One preferred embodiment provides a glucose sensor configured for insertion into a host for measuring a glucose concentration in the host. The sensor includes a first working electrode configured to generate a first signal associated with glucose and non-glucose related electroactive compounds having a first oxidation potential. The sensor also includes a second working electrode configured to generate a second signal associated with noise of the glucose sensor comprising signal contribution due to non-glucose related electroactive compounds that have an oxidation potential that substantially overlaps with the first oxidation potential (e.g., the oxidation potential of $H_2O_2$). Additionally, the glucose sensor includes a non-conductive material located between the first and second working electrodes. Each of the first working electrode, the second working electrode, and the non-conductive material are configured to provide at least two functions selected from the group consisting of: electrical conductance, insulative properties, structural support, and diffusion barrier.

In some embodiments of the glucose sensor, each of the first working electrode and the second working electrode are configured to provide electrical conductance and structural support. For example, the metal plated wire of electrodes conducts electricity and helps maintain the sensor's shape. In a further embodiment, the glucose sensor includes a reference electrode that is configured to provide electrical conductance and structural support. For example, the silver/silver chloride reference electrode is both electrically conductive and supports the sensor's shape. In some embodiments of the glucose sensor includes a reference electrode that is configured to provide electrical conductance and a diffusion barrier. For example, the silver/silver chloride reference electrode can be configured as a large structure or protruding structure, which separates the working electrodes by the distance D (e.g., FIG. 7G). Distance "D" is sufficiently large that glucose and/or $H_2O_2$ cannot substantially diffuse around the reference electrode. Accordingly, $H_2O_2$ produced at a first working electrode does not substantially contribute to signal at a second working electrode. In some embodiments of the glucose sensor includes a reference electrode that is configured to provide a diffusion barrier and structural support. In some embodiments of the glucose sensor, the non-conductive material is configured to provide electrical insulative properties and structural support. For example, non-conductive dielectric materials can insulate an electrode and can be sufficiently rigid to stiffen the sensor. In still other embodiments, the non-conductive material is configured to provide electrical insulative properties and a diffusion barrier. For example, a substantially rigid, non-conductive dielectric can coat the electrodes and provide support, as shown in FIG. 7L. In other embodiments, the non-conductive material is configured to provide diffusion barrier and structural support. For example, a dielectric material can protrude between the electrodes, to act as a diffusion barrier and provide support to the sensor's shape, as shown in FIG. 10.

Noise Reduction

In another aspect, the sensor is configured to reduce noise, including non-constant non-analyte related noise with an overlapping measuring potential with the analyte. A variety of noise can occur when a sensor has been implanted in a host. Generally, implantable sensors measure a signal (e.g., counts) that generally comprises at least two components, the background signal (e.g., background noise) and the analyte signal. The background signal is composed substantially of signal contribution due to factors other than glucose (e.g., interfering species, non-reaction-related hydrogen peroxide, or other electroactive species with an oxidation potential that overlaps with the analyte or co-analyte). The analyte signal (e.g., glucose) is composed substantially of signal contribution due to the analyte. Consequently, because the signal includes these two components, a calibration is performed in order to determine the analyte (e.g., glucose) concentration by solving for the equation $y=mx+b$, where the value of b represents the background of the signal.

There are a variety of ways noise can be recognized and/or analyzed. In preferred embodiments, the sensor data stream is monitored, signal artifacts are detected, and data processing is based at least in part on whether or not a signal artifact has been detected, such as described in U.S. Patent Publication No. US-2005-0043598-A1 and U.S. Patent Publication No. US-2007-0027370-A1, herein incorporated by reference in their entirety.

Accordingly, if a sensor is designed such that the signal contribution due to baseline and noise can be removed, then more accurate analyte concentration data can be provided to the host or a healthcare professional.

One embodiment provides an analyte sensor (e.g., glucose sensor) configured for insertion into a host for measuring an analyte (e.g., glucose) in the host. The sensor includes a first working electrode disposed beneath an active enzymatic portion of a membrane on the sensor; a second working electrode disposed beneath an inactive- or non-enzymatic portion of the membrane on the sensor; and electronics operably connected to the first and second working electrode and configured to process the first and second signals to generate an analyte (e.g., glucose) concentration substantially without signal contribution due to non-glucose related noise artifacts.

Referring now to FIG. 9B, in another embodiment, the sensor has a first working electrode E1 and a second working electrode E2. The sensor includes a membrane system (not shown) covering the electrodes, as described elsewhere herein. A portion of the membrane system on the first electrode contains active enzyme, which is depicted schematically as oval 904a (e.g., active GOx). A portion of the membrane system on the second electrode is non-enzymatic or contains inactivated enzyme, which is depicted schematically as oval 904b (e.g., heat- or chemically-inactivated GOx or optionally no GOx). A portion of the sensor includes electrical connectors 804. In some embodiments, the connectors 804 are located on an ex vivo portion of the sensor. Each electrode (e.g., E1, E2, etc.) is connected to sensor electronics (not shown) by a connector 804. Since the first electrode E1 includes active GOx, it produces a first signal that is related to the concentration of the analyte (in this case glucose) in the host as well as other species that have an oxidation potential that overlaps with the oxidation potential of the analyte or co-analyte (e.g., non-glucose related noise artifacts, noise-causing compounds, background). Since the second electrode E2 includes inactive GOx, it produces a second signal that is not substantially related to the analyte or co-analyte. Instead, the second signal is substantially related to noise-causing compounds and other background noise. The sensor electronics process the first and second signals to generate an analyte concentration that is substantially free of the non-analyte related noise artifacts. Elimination or reduction of noise (e.g., non-constant background) is attributed at least in part to the configuration of the electrodes in the preferred embodiments, e.g., the locality of first and second working electrode, the symmetrical or opposing design of the first and second working electrodes, and/or the overall sizing and configuration of the exposed electroactive portions. Accordingly, the host is provided with improved analyte concentration data, upon which he can make medical treatment decisions (e.g., if he should eat, if he should take medication or the amount of medication he should take). Advantageously, in the case of glucose sensors, since the sensor can provide improved quality of data, the host can be maintained under tighter glucose control (e.g., about 80 mg/dl to about 120 mg/dl) with a reduced risk of hypoglycemia and hypoglycemia's immediate complications (e.g., coma or death). Additionally, the reduced risk of hypoglycemia makes it possible to avoid the long-term complications of hyperglycemia (e.g., kidney and heart disease, neuropathy, poor healing, loss of eye sight) by consistently maintaining tight glucose control (e.g., about 80 mg/dl to about 120 mg/dl).

In one embodiment, the sensor is configured to substantially eliminate (e.g., subtract out) noise due to mechanical factors. Mechanical factors include macro-motion of the sensor, micro-motion of the sensor, pressure on the sensor, local tissue stress, and the like. Since both working electrodes are constructed substantially symmetrically and identically, and due to the sensor's small size, the working electrodes are substantially equally affected by mechanical factors impinging upon the sensor. For example, if a build-up of noise-causing compounds occurs (e.g., due to the host pressing upon and manipulating (e.g., fiddling with) the sensor, for example) both working electrodes will measure the resulting noise to substantially the same extend, while only one working electrode (the first working electrode, for example) will also measure signal due to the analyte concentration in the host's body. The sensor then calculates the analyte signal (e.g., glucose-only signal) by removing the noise that was measured by the second working electrode from the total signal that was measured by the first working electrode.

Non-analyte related noise can also be caused by biochemical and/or chemical factors (e.g., compounds with electroactive acidic, amine or sulfhydryl groups, urea, lacetic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing). As with noise due to mechanical factors, noise due to biochemical/chemical factors will impinge upon the two working electrodes of the preferred embodiments (e.g., with and without active GOx) about the same extent, because of the sensor's small size and symmetrical configuration. Accordingly, the sensor electronics can use these data to calculate the glucose-only signal, as described elsewhere herein.

In one exemplary embodiment, the analyte sensor is a glucose sensor that measures a first signal associated with both glucose and non-glucose related electroactive compounds having a first oxidation potential. For example, the oxidation potential of the non-glucose related electroactive compounds substantially overlaps with the oxidation potential of $H_2O_2$, which is produced according to the reaction of glucose with GOx and subsequently transfers electrons to the first working electrode (e.g., E1; FIG. 10). The glucose sensor also measures a second signal, which is associated with background noise of the glucose sensor. The background noise is composed of signal contribution due to noise-causing compounds (e.g., interferents), non-reaction-related hydrogen peroxide, or other electroactive species with an oxidation potential that substantially overlaps with the oxidation potential of $H_2O_2$ (the co-analyte). The first and second working electrodes integrally form at least a portion of the sensor, such as but not limited to the in vivo portion of the sensor, as discussed elsewhere herein. Additionally, each of the first working electrode, the second working electrode, and a non-conductive material/insulator are configured provide at least two functions (to the sensor), such as but not limited to electrical conductance, insulative properties, structural support, and diffusion barrier (described elsewhere herein). Furthermore, the sensor has a diffusion barrier that substantially blocks diffusion of glucose or $H_2O_2$ between the first and second working electrodes.

Diffusion Barrier

Another aspect of the sensor is a diffusion barrier, to prevent an undesired species, such as $H_2O_2$ or the analyte, from diffusing between active (with active enzyme) and inactive (without active enzyme) electrodes. In various embodiments, the sensor includes a diffusion barrier configured to be physical, spatial, and/or temporal.

FIG. 10 is a schematic illustrating one embodiment of a sensor (e.g., a portion of the in vivo portion of the sensor, such as but not limited to the sensor electroactive surfaces) having one or more components that act as a diffusion barrier (e.g., prevent diffusion of electroactive species from one electrode to another). The first working electrode E1 is coated with an enzyme layer 1000 comprising active enzyme. For example, in a glucose sensor, the first working electrode E1 is coated with glucose oxidase enzyme (GOx). A second working electrode E2 is separated from the first working electrode E1 by a diffusion barrier D, such as but not limited to a physical diffusion barrier (e.g., either a reference electrode or a layer of non-conductive material/insulator). The diffusion barrier can also be spatial or temporal, as discussed elsewhere herein.

Glucose and oxygen diffuse into the enzyme layer 1000, where they react with GOx, to produce gluconate and $H_2O_2$. At least a portion of the $H_2O_2$ diffuses to the first working electrode E1, where it is electrochemically oxidized to oxygen and transfers two electrons (e.g., 2e⁻) to the first working electrode E1, which results in a glucose signal that is recorded by the sensor electronics (not shown). The remaining $H_2O_2$ can diffuse to other locations in the enzyme layer or out of the enzyme layer (illustrated by the wavy arrows). Without a diffusion barrier D, a portion of the $H_2O_2$ can diffuse to the second working electrode E2, which results in an aberrant signal that can be recorded by the sensor electronics as a non-glucose related signal (e.g., background).

Preferred embodiments provide for a substantial diffusion barrier D between the first and second working electrodes (E1, E2) such that the $H_2O_2$ cannot substantially diffuse from the first working electrode E1 to the second working electrode E2. Accordingly, the possibility of an aberrant signal produced by $H_2O_2$ from the first working electrode E1 (at the second working electrode E2) is reduced or avoided.

In some alternative embodiments, the sensor is provided with a spatial diffusion barrier between electrodes (e.g., the working electrodes). For example, a spatial diffusion barrier can be created by separating the first and second working electrodes by a distance that is too great for the $H_2O_2$ to substantially diffuse between the working electrodes. In some embodiments, the spatial diffusion barrier is about 0.010 inches to about 0.120 inches. In other embodiments, the spatial diffusion barrier is about 0.020 inches to about 0.050 inches. Still in other embodiments, the spatial diffusion barrier is about 0.055 inches to about 0.095 inches. A reference electrode R (e.g., a silver or silver/silver chloride electrode) or a non-conductive material I (e.g., a polymer structure or coating such as Parylene) can be configured to act as a spatial diffusion barrier.

FIGS. 9A and 9B illustrate two exemplary embodiments of sensors with spatial diffusion barriers. In each embodiment, the sensor has two working electrodes E1 and E2. Each working electrode includes an electroactive surface, represented schematically as windows 904a and 904b, respectively. The sensor includes a membrane system (not shown). Over one electroactive surface (e.g., 904a) the membrane includes active enzyme (e.g., GOx). Over the second electroactive surface (e.g., 904b) the membrane does not include active enzyme. In some embodiments, the portion of the membrane covering the second electroactive surface contains inactivated enzyme (e.g., heat- or chemically-inactivated GOx) while in other embodiments, this portion of the membrane does not contain any enzyme (e.g., non-enzymatic). The electroactive surfaces 904a and 904b are separated by a spatial diffusion barrier that is substantially wide such that $H_2O_2$ produced at the first electroactive surface 904a cannot substantially affect the second electroactive surface 904b. In some alternative embodiments, the diffusion barrier can be physical (e.g., a structure separating the electroactive surfaces) or temporal (e.g., oscillating activity between the electroactive surfaces).

In another embodiment, the sensor is an indwelling sensor, such as configured for insertion into the host's circulatory system via a vein or an artery. In some exemplary embodiments, an indwelling sensor includes at least two working electrodes that are inserted into the host's blood stream through a catheter. The sensor includes at least a reference electrode that can be disposed either with the working electrodes or remotely from the working electrodes. The sensor includes a spatial, a physical, or a temporal diffusion barrier. A spatial diffusion barrier can be configured as described elsewhere herein, with reference to FIG. 7A through FIG. 8A.

FIG. 9B provides one exemplary embodiment of an indwelling analyte sensor, such as but not limited to an intravascular glucose sensor to be used from a few hours to ten days or longer. Namely, the sensor includes two working electrodes. One working electrode detects the glucose-related signal (due to active GOx applied to the electroactive surface) as well as non-glucose related signal. The other working electrode detects only the non-glucose related signal (because no active GOx is applied to its electroactive surface). $H_2O_2$ is produced on the working electrode with active GOx. If the $H_2O_2$ diffuses to the other working electrode (the no GOx electrode) an aberrant signal will be detected at this electrode, resulting in reduced sensor activity. Accordingly, it is desirable to separate the electroactive surfaces with a diffusion barrier, such as but not limited to a spatial diffusion barrier. Indwelling sensors are described in more detail in copending U.S. patent application Ser. No. 11/543,396 filed on Oct. 4, 2006 and entitled "ANALYTE SENSOR," herein incorporated in its entirety by reference.

To configure a spatial diffusion barrier between the working electrodes, the location of the active enzyme (e.g., GOx) is dependent upon the orientation of the sensor after insertion into the host's artery or vein. For example, in an embodiment configured for insertion upstream in the host's blood flow (e.g., against the blood flow), active GOx would be applied to electroactive surface 904b and inactive GOx (or no GOx) would be applied to electroactive surface 904a (e.g., upstream from 904b, relative to the direction of blood flow). Due to this configuration, $H_2O_2$ produced at electroactive surface 904b would be carrier down stream (e.g., away from electroactive surface 904a) and thus not affect electrode E1.

Alternatively, the indwelling electrode can also be configured for insertion of the sensor into the host's vein or artery in the direction of the blood flow (e.g., pointing downstream). In this configuration, referred to as a spatial diffusion barrier, or as a flow path diffusion barrier, the active GOx can be advantageously applied to electroactive surface 904a on the first working electrode E1. The electroactive surface 904b on the second working electrode E2 has no active GOx. Accordingly, $H_2O_2$ produced at electroactive surface 904a is carried away by the blood flow, and has no substantial effect on the second working electrode E2.

In another embodiment of an indwelling analyte sensor, the reference electrode, which is generally configured of silver/silver chloride, can extend beyond the working electrodes, to provide a physical barrier around which the $H_2O_2$ generated at the electrode comprising active GOx cannot pass the other working electrode (that has active GOx). In some embodiments, the reference electrode has a surface area that is at least six times larger than the surface area of the working electrodes. In other embodiments, a 2-working electrode analyte sensor includes a counter electrode in addition to the reference electrode. As is generally know in the art, the inclusion of the counter electrode allows for a reduction in the reference electrode's surface area, and thereby allows for further miniaturization of the sensor (e.g., reduction in the sensor's diameter and/or length, etc.).

FIG. 7H provides one exemplary embodiment of a spatial diffusion barrier, wherein the reference electrode/non-conductive insulating material R/I is sized and shaped such that $H_2O_2$ produced at the first working electrode E1 (e.g., with enzyme) does not substantially diffuse around the reference electrode/non-conductive material R/I to the second working electrode E2 (e.g., without enzyme). In another example, shown in FIG. 7J, the X-shaped the reference electrode/non-conductive material R/I substantially prevents diffusion of electroactive species from the first working electrode E1 (e.g., with enzyme) to the second working electrode E2 (e.g., without enzyme). In another embodiment, such as the sensor shown in FIG. 7A, the layer of non-conductive material I (between the electrodes) is of a sufficient length that the $H_2O_2$ produced at one electrode cannot substantially diffuse to another electrode. (e.g., from E1 to either E2 or E3; or from E2 to either E1 or E3, etc.).

In some embodiments, a physical diffusion barrier is provided by a physical structure, such as an electrode, insulator, and/or membrane. For example, in the embodiments shown in FIGS. 7G to 7J, the insulator (I) or reference electrode (R) act as a diffusion barrier. As another example, the diffusion barrier can be a bioprotective membrane (e.g., a membrane that substantially resists or blocks the transport of a species (e.g., hydrogen peroxide), such as CHRONOTHANE®-H (a polyetherurethaneurea based on polytetramethylene glycol, polyethylene glycol, methylene diisocyanate, and organic amines). As yet another example, the diffusion barrier can be a resistance domain, as described in more detail elsewhere herein; namely, a semipermeable membrane that controls the flux of oxygen and an analyte (e.g., glucose) to the underlying enzyme domain. Numerous other structures and membranes can function as a physical diffusion barrier as is appreciated by one skilled in the art.

In other embodiments, a temporal diffusion barrier is provided (e.g., between the working electrodes). By temporal diffusion barrier is meant a period of time that substantially prevents an electroactive species (e.g., $H_2O_2$) from diffusing from a first working electrode to a second working electrode. For example, in some embodiments, the differential measurement can be obtained by switching the bias potential of each electrode between the measurement potential and a non-measurement potential. The bias potentials can be held at each respective setting (e.g., high and low bias settings) for as short as milliseconds to as long as minutes or hours. Pulsed amperometric detection (PED) is one method of quickly switching voltages, such as described in Bisenberger, M.; Brauchle, C.; Hampp, N. A triple-step potential waveform at enzyme multisensors with thick-film gold electrodes for detection of glucose and sucrose. *Sensors and Actuators* 1995, B. 181-189, which is incorporated herein by reference in its entirety. In some embodiments, bias potential settings are held long enough to allow equilibration.

One preferred embodiment provides a glucose sensor configured for insertion into a host for measuring glucose in the host. The sensor includes first and second working electrodes and an insulator located between the first and second working electrodes. The first working electrode is disposed beneath an active enzymatic portion of a membrane on the sensor and the second working electrode is disposed beneath an inactive- or non-enzymatic portion of the membrane on the sensor. The sensor also includes a diffusion barrier configured to substantially block diffusion of glucose or hydrogen peroxide between the first and second working electrodes.

In a further embodiment, the glucose sensor includes a reference electrode configured integrally with the first and second working electrodes. In some embodiments, the reference electrode can be located remotely from the sensor, as described elsewhere herein. In some embodiments, the surface area of the reference electrode is at least six times the surface area of the working electrodes. In some embodiments, the sensor includes a counter electrode that is integral to the sensor or is located remote from the sensor, as described elsewhere herein.

In a further embodiment, the glucose sensor detects a first signal associated with glucose and non-glucose related electroactive compounds having a first oxidation potential (e.g., the oxidation potential of $H_2O_2$). In some embodiments, the glucose sensor also detects a second signal is associated with background noise of the glucose sensor comprising signal contribution due to interfering species, non-reaction-related hydrogen peroxide, or other electroactive species with an oxidation potential that substantially overlaps with the oxidation potential of hydrogen peroxide; the first and second working electrodes integrally form at least a portion of the sensor; and each of the first working electrode, the second working electrode and the non-conductive material/insulator are configured provide at least two functions such as but not limited to electrical conductance, insulation, structural support, and a diffusion barrier In further embodiments, the glucose sensor includes electronics operably connected to the first and second working electrodes. The electronics are configured to calculate at least one analyte sensor data point using the first and second signals described above. In still another further embodiment, the electronics are operably connected to the first and second working electrode and are configured to process the first and second signals to generate a glucose concentration substantially without signal contribution due to non-glucose noise artifacts.

Additional Membrane Configurations

Figure 3A:
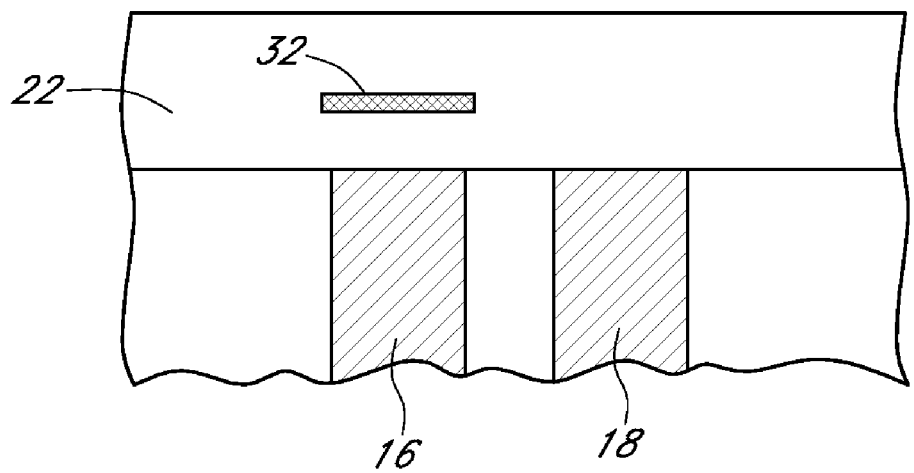
FIG. 3A which is a cross-sectional exploded schematic view of a sensing region of a continuous glucose sensor in one embodiment wherein an active enzyme of an enzyme domain is positioned only over the glucose-measuring working electrode.
Figure 3B:
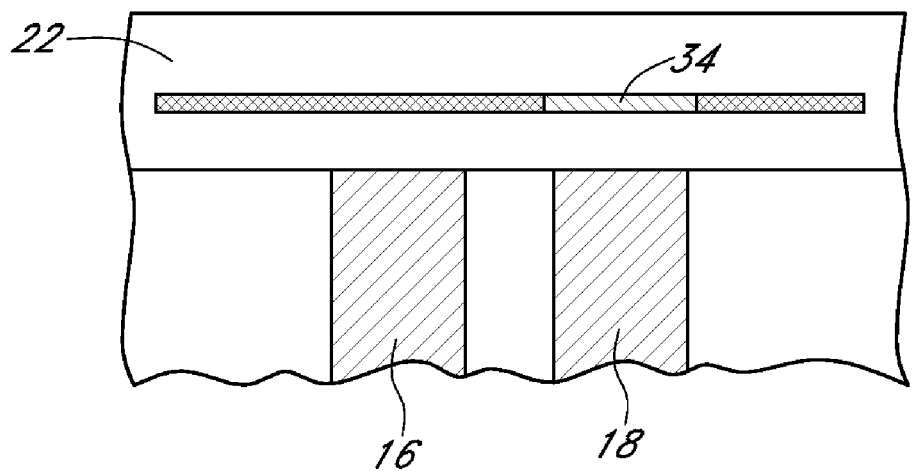
FIG. 3B is a cross-sectional exploded schematic view of a sensing region of a continuous glucose sensor in another embodiment, wherein an active portion of the enzyme within the enzyme domain positioned over the auxiliary working electrode has been deactivated.

Depending upon the sensor configuration, additional membrane configurations can be desirable. FIGS. 3A to 3B are cross-sectional exploded schematic views of the sensing region of a glucose sensor 10, which show architectures of the membrane system 22 disposed over electroactive surfaces of glucose sensors in some embodiments. In the illustrated embodiments of FIGS. 3A and 3B, the membrane system 22 is positioned at least over the glucose-measuring working electrode 16 and the optional auxiliary working electrode 18; however the membrane system may be positioned over the reference and/or counter electrodes 20, 20a in some embodiments.

Reference is now made to FIG. 3A, which is a cross-sectional exploded schematic view of the sensing region in one embodiment wherein an active enzyme 32 of the enzyme domain is positioned only over the glucose-measuring working electrode 16. In this embodiment, the membrane system is formed such that the glucose oxidase 32 only exists above the glucose-measuring working electrode 16. In one embodiment, during the preparation of the membrane system 22, the enzyme domain coating solution can be applied as a circular region similar to the diameter of the glucose-measuring working electrode 16. This fabrication can be accomplished in a variety of ways such as screen-printing or pad printing. Preferably, the enzyme domain is pad printed during the enzyme domain fabrication with equipment as available from Pad Print Machinery of Vermont (Manchester, Vt.). This embodiment provides the active enzyme 32 above the glucose-measuring working electrode 16 only, so that the glucose-measuring working electrode 16 (and not the auxiliary working electrode 18) measures glucose concentration. Additionally, this embodiment provides an added advantage of eliminating the consumption of $O_2$ above the counter electrode (if applicable) by the oxidation of glucose with glucose oxidase.

FIG. 3B is a cross-sectional exploded schematic view of a sensing region of the preferred embodiments, and wherein the portion of the active enzyme within the membrane system 22 positioned over the auxiliary working electrode 18 has been deactivated 34. In one alternative embodiment, the enzyme of the membrane system 22 may be deactivated 34 everywhere except for the area covering the glucose-measuring working electrode 16 or may be selectively deactivated only over certain areas (for example, auxiliary working electrode 18, counter electrode 20a, and/or reference electrode 20) by irradiation, heat, proteolysis, solvent, or the like. In such a case, a mask (for example, such as those used for photolithography) can be placed above the membrane that covers the glucose-measuring working electrode 16. In this way, exposure of the masked membrane to ultraviolet light deactivates the glucose oxidase in all regions except that covered by the mask.

In some alternative embodiments, the membrane system is disposed on the surface of the electrode(s) using known deposition techniques. The electrode-exposed surfaces can be inset within the sensor body, planar with the sensor body, or extending from the sensor body. Although some examples of membrane systems have been provided above, the concepts described herein can be applied to numerous known architectures not described herein.

Sensor Electronics

In some embodiments, the sensing region may include reference and/or electrodes associated with the glucose-measuring working electrode and separate reference and/or counter electrodes associated with the optional auxiliary working electrode(s). In yet another embodiment, the sensing region may include a glucose-measuring working electrode, an auxiliary working electrode, two counter electrodes (one for each working electrode), and one shared reference electrode. In yet another embodiment, the sensing region may include a glucose-measuring working electrode, an auxiliary working electrode, two reference electrodes, and one shared counter electrode. However, a variety of electrode materials and configurations can be used with the implantable analyte sensor of the preferred embodiments.

In some alternative embodiments, the working electrodes are interdigitated. In some alternative embodiments, the working electrodes each comprise multiple exposed electrode surfaces; one advantage of these architectures is to distribute the measurements across a greater surface area to overcome localized problems that may occur in vivo for example, with the host's immune response at the biointerface. Preferably, the glucose-measuring and auxiliary working electrodes are provided within the same local environment, such as described in more detail elsewhere herein.

Figure 4:
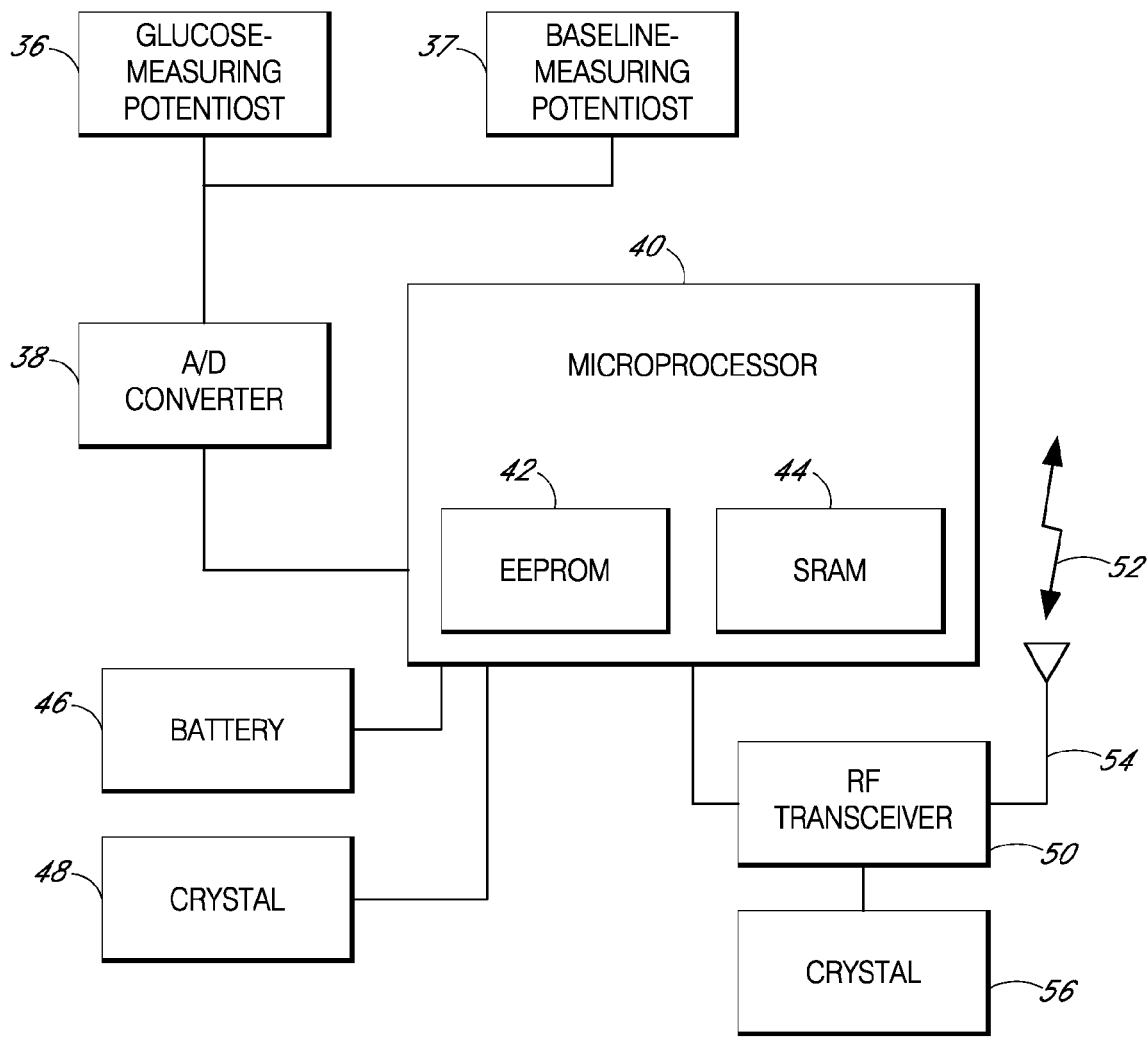
FIG. 4 is a block diagram that illustrates continuous glucose sensor electronics in one embodiment.

FIG. 4 is a block diagram that illustrates the continuous glucose sensor electronics in one embodiment. In this embodiment, a first potentiostat 36 is provided that is operatively associated with the glucose-measuring working electrode 16. The first potentiostat 36 measures a current value at the glucose-measuring working electrode and preferably includes a resistor (not shown) that translates the current into voltage. An optional second potentiostat 37 is provided that is operatively associated with the optional auxiliary working electrode 18. The second potentiostat 37 measures a current value at the auxiliary working electrode 18 and preferably includes a resistor (not shown) that translates the current into voltage. It is noted that in some embodiments, the optional auxiliary electrode can be configured to share the first potentiostat with the glucose-measuring working electrode. An A/D converter 38 digitizes the analog signals from the potentiostats 36, 37 into counts for processing. Accordingly, resulting raw data streams (in counts) can be provided that are directly related to the current measured by each of the potentiostats 36 and 37.

A microprocessor 40, also referred to as the processor module, is the central control unit that houses EEPROM 42 and SRAM 44, and controls the processing of the sensor electronics. It is noted that certain alternative embodiments can utilize a computer system other than a microprocessor to process data as described herein. In other alternative embodiments, an application-specific integrated circuit (ASIC) can be used for some or all the sensor's central processing. The EEPROM 42 provides semi-permanent storage of data, for example, storing data such as sensor identifier (ID) and programming to process data streams (for example, such as described in U.S. Patent Publication No. US-2005-0027463-A1, which is incorporated by reference herein in its entirety. The SRAM 44 can be used for the system's cache memory, for example for temporarily storing recent sensor data. In some alternative embodiments, memory storage components comparable to EEPROM and SRAM may be used instead of or in addition to the preferred hardware, such as dynamic RAM, non-static RAM, rewritable ROMs, flash memory, or the like.

A battery 46 is operably connected to the microprocessor 40 and provides the necessary power for the sensor 10a. In one embodiment, the battery is a Lithium Manganese Dioxide battery, however any appropriately sized and powered battery can be used (for example, AAA, Nickel-cadmium, Zinc-carbon, Alkaline, Lithium, Nickel-metal hydride, Lithium-ion, Zinc-air, Zinc-mercury oxide, Silver-zinc, and/or hermetically-sealed). In some embodiments the battery is rechargeable. In some embodiments, a plurality of batteries can be used to power the system. In some embodiments, one or more capacitors can be used to power the system. A Quartz Crystal 48 may be operably connected to the microprocessor 40 to maintain system time for the computer system as a whole.

An RF Transceiver 50 may be operably connected to the microprocessor 40 to transmit the sensor data from the sensor 10 to a receiver (see FIGS. 4 and 5) within a wireless transmission 52 via antenna 54. Although an RF transceiver is shown here, some other embodiments can include a wired rather than wireless connection to the receiver. In yet other embodiments, the receiver can be transcutaneously powered via an inductive coupling, for example. A second quartz crystal 56 can provide the system time for synchronizing the data transmissions from the RF transceiver. It is noted that the transceiver 50 can be substituted with a transmitter in other embodiments. In some alternative embodiments other mechanisms such as optical, infrared radiation (IR), ultrasonic, or the like may be used to transmit and/or receive data.

Receiver

Figure 5:
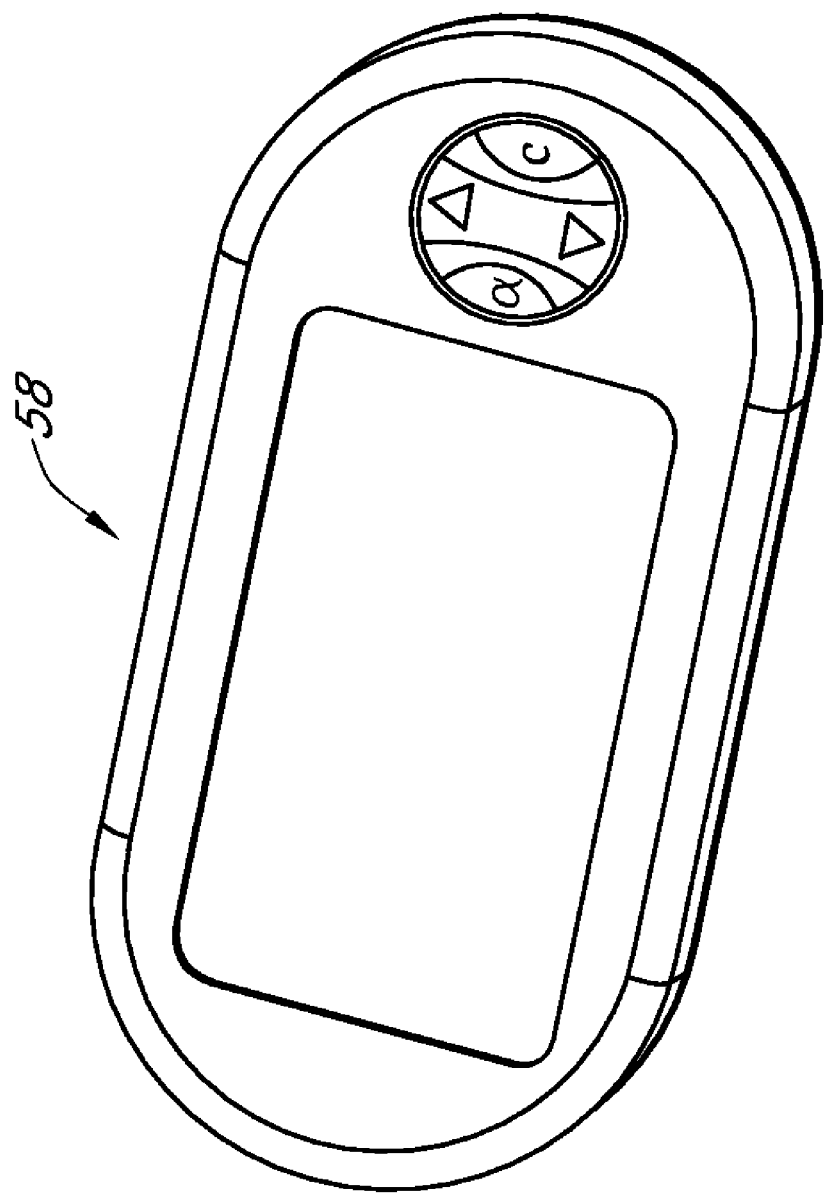
FIG. 5 is a drawing of a receiver for the continuous glucose sensor in one embodiment.

FIG. 5 is a schematic drawing of a receiver for the continuous glucose sensor in one embodiment. The receiver 58 comprises systems necessary to receive, process, and display sensor data from the analyte sensor, such as described in more detail elsewhere herein. Particularly, the receiver 58 may be a pager-sized device, for example, and house a user interface that has a plurality of buttons and/or keypad and a liquid crystal display (LCD) screen, and which may include a backlight. In some embodiments the user interface may also include a speaker, and a vibrator such as described with reference to FIG. 6.

Figure 6:
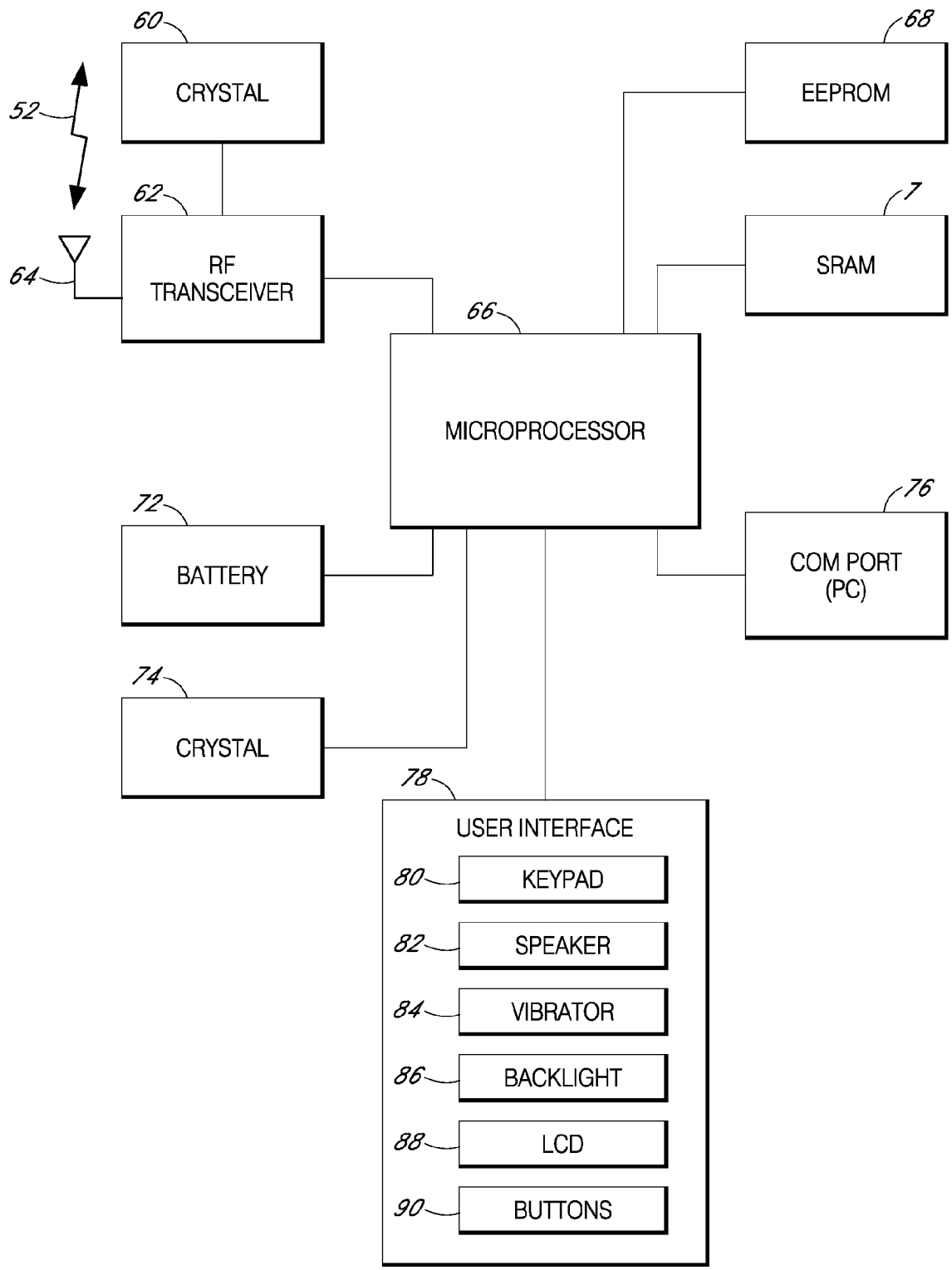
FIG. 6 is a block diagram of the receiver electronics in one embodiment.

FIG. 6 is a block diagram of the receiver electronics in one embodiment. In some embodiments, the receiver comprises a configuration such as described with reference to FIG. 5, above. However, the receiver may comprise any reasonable configuration, including a desktop computer, laptop computer, a personal digital assistant (PDA), a server (local or remote to the receiver), or the like. In some embodiments, a receiver may be adapted to connect (via wired or wireless connection) to a desktop computer, laptop computer, a PDA, a server (local or remote to the receiver), or the like in order to download data from the receiver. In some alternative embodiments, the receiver may be housed within or directly connected to the sensor in a manner that allows sensor and receiver electronics to work directly together and/or share data processing resources. Accordingly, the receiver, including its electronics, may be generally described as a "computer system."

A quartz crystal 60 may be operably connected to an RF transceiver 62 that together function to receive and synchronize data streams via an antenna 64 (for example, transmission 52 from the RF transceiver 50 shown in FIG. 4). Once received, a microprocessor 66 can process the signals, such as described below.

The microprocessor 66, also referred to as the processor module, is the central control unit that provides the processing, such as storing data, calibrating sensor data, downloading data, controlling the user interface by providing prompts, messages, warnings and alarms, or the like. The EEPROM 68 may be operably connected to the microprocessor 66 and provides semi-permanent storage of data, storing data such as receiver ID and programming to process data streams (for example, programming for performing calibration and other algorithms described elsewhere herein). SRAM 70 may be used for the system's cache memory and is helpful in data processing. For example, the SRAM stores information from the continuous glucose sensor for later recall by the patient or a doctor; a patient or doctor can transcribe the stored information at a later time to determine compliance with the medical regimen or a comparison of glucose concentration to medication administration (for example, this can be accomplished by downloading the information through the pc com port 76). In addition, the SRAM 70 can also store updated program instructions and/or patient specific information. In some alternative embodiments, memory storage components comparable to EEPROM and SRAM can be used instead of or in addition to the preferred hardware, such as dynamic RAM, non-static RAM, rewritable ROMs, flash memory, or the like.

A battery 72 may be operably connected to the microprocessor 66 and provides power for the receiver. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 84 may be operably connected to the microprocessor 66 and maintains system time for the system as a whole.

A PC communication (com) port 76 can be provided to enable communication with systems, for example, a serial communications port, allows for communicating with another computer system (for example, PC, PDA, server, or the like). In one exemplary embodiment, the receiver is able to download historical data to a physician's PC for retrospective analysis by the physician. The PC communication port 76 can also be used to interface with other medical devices, for example pacemakers, implanted analyte sensor patches, infusion devices, telemetry devices, or the like.

A user interface 78 comprises a keypad 80, speaker 82, vibrator 84, backlight 86, liquid crystal display (LCD) 88, and one or more buttons 90. The components that comprise the user interface 78 provide controls to interact with the user. The keypad 80 can allow, for example, input of user information about himself/herself, such as mealtime, exercise, insulin administration, and reference glucose values. The speaker 82 can provide, for example, audible signals or alerts for conditions such as present and/or predicted hyper- and hypoglycemic conditions. The vibrator 84 can provide, for example, tactile signals or alerts for reasons such as described with reference to the speaker, above. The backlight 94 can be provided, for example, to aid the user in reading the LCD in low light conditions. The LCD 88 can be provided, for example, to provide the user with visual data output. In some embodiments, the LCD is a touch-activated screen. The buttons 90 can provide for toggle, menu selection, option selection, mode selection, and reset, for example. In some alternative embodiments, a microphone can be provided to allow for voice-activated control.

The user interface 78, which is operably connected to the microprocessor 70, serves to provide data input and output for the continuous analyte sensor. In some embodiments, prompts can be displayed to inform the user about necessary maintenance procedures, such as "Calibrate Sensor" or "Replace Battery." In some embodiments, prompts or messages can be displayed on the user interface to convey information to the user, such as malfunction, outlier values, missed data transmissions, or the like. Additionally, prompts can be displayed to guide the user through calibration of the continuous glucose sensor, for example when to obtain a reference glucose value.

Keypad, buttons, touch-screen, and microphone are all examples of mechanisms by which a user can input data directly into the receiver. A server, personal computer, personal digital assistant, insulin pump, and insulin pen are examples of external devices that can be connected to the receiver via PC com port 76 to provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input and can be helpful in data processing as will be understood by one skilled in the art.

Electronic Identification and Removal Noise

In addition blocking and/or diluting interfering species before they can cause noise on the sensor signal, a non-constant noise signal component can be electronically identified, such that the identified noise component can be removed from the signal by algorithmic/mathematical means, in some embodiments. For example, in a glucose sensor (e.g., as described herein) that catalyzes the conversion of oxygen and glucose to hydrogen peroxide and gluconate (e.g., by GOX incorporated into the membrane system), for each glucose molecule metabolized there is an equivalent change in molecular concentration in the co-reactant $O_2$ and the product $H_2O_2$. Consequently, one can use an electrode (for example, working electrode 16) to monitor the concentration-induced current change in either the co-reactant or the product (for example, $H_2O_2$) to determine glucose concentration. However, if an interfering species exists with an oxidation or reduction potential that overlaps with the co-reactant or the product (for example, $H_2O_2$), then the current change does not accurately reflect glucose concentration. Additionally, if an oxygen deficiency exists, such that insufficient oxygen is present to react with an analyte at the enzyme for example, then the current change similarly does not accurately reflect glucose concentration.

It is noted that a glucose sensor signal obtained from glucose when the bias potential is set between about +0.35V and about +0.75V is substantially constant under standard physiologic conditions. In contrast, a glucose sensor signal obtained from interfering species when the same bias potentials are set (between about +0.35V and about +0.75V) is not substantially constant under standard physiologic conditions. Current-voltage curves are known for various analytes and are available in the literature, for example such as described by Lerner, H.; Giner, J.; Soeldner, J. S.; Colton, C. K. An implantable electrochemical glucose sensor. *Ann NY Acad Sci* 1984, 428, 263-278, which is incorporated herein by reference in its entirety.

Figure 17:
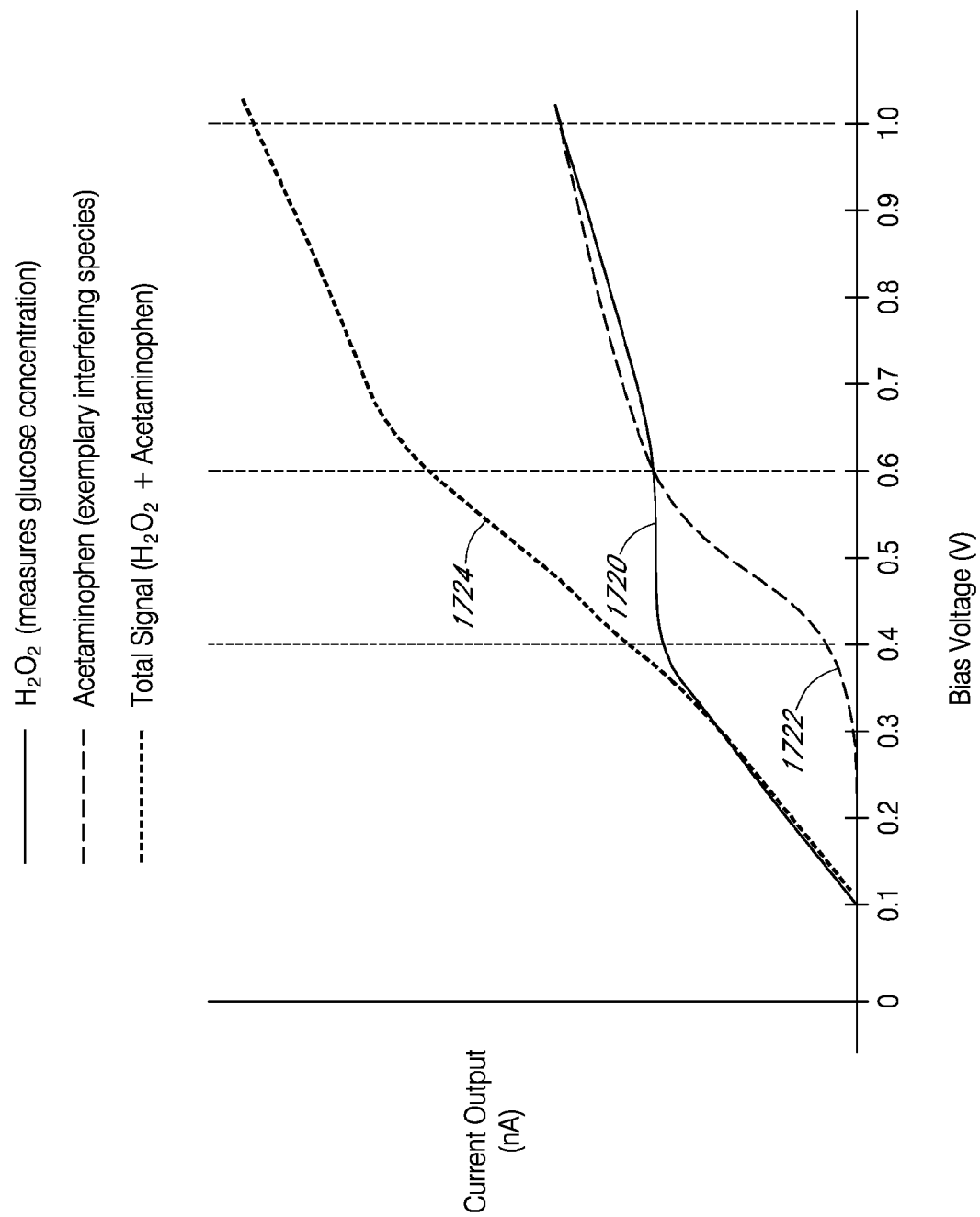
FIG. 17 is a schematic graph of current vs. voltage obtained from cyclic voltammetry for hydrogen peroxide and acetaminophen.

FIG. 17 is a schematic graph of current vs. voltage obtained from cyclic voltammetry (also known as a CV-curve) for hydrogen peroxide and acetaminophen. The x-axis represents bias potential applied to an electrochemical cell in Volts (V); the y-axis represents current output measured by the working electrode of the electrochemical cell in nanoAmps (nA). The schematic graph generally shows current output of an electrochemical enzyme-based glucose sensor as the bias potential is varied from about 0.1V to about 1.0V. Current output is shown without units because it is the differential response, rather than the actual measurement, of signal output that is being generally taught herein. As illustrated by the graph, acetaminophen 1722 increases the total signal 1724, resulting in an inaccurate glucose measurement that is significantly higher than the actual value.

The hydrogen peroxide curve 1720 can be obtained by exposing an electrochemical sensor to glucose (without acetaminophen) and varying the bias potential from about 0.1V to about 1.0V. The graph shows the response of the glucose sensor to hydrogen peroxide; generally, the current increases at a relatively constant rate from about 0.1V to about 0.4V, after which it plateaus until about 0.6V, and then continues to increase at a slightly slower rate.

The acetaminophen curve 1722 can be obtained by exposing an electrochemical sensor to acetaminophen (without glucose), and varying the bias potential from about 0.1V to about 1.0V. The graph shows the response of the glucose sensor to acetaminophen; generally, the acetaminophen curve 1722 increases relatively slowly from about 0.1V to about 0.4V, showing a minimal current output of the acetaminophen signal (at 0.4V) relative to the higher glucose signal (at 4.0V). From 0.4V to 0.6V, the acetaminophen curve 1722 increases to a value at 0.6V approximately equal to the value of the hydrogen peroxide signal at that same bias potential, after which the acetaminophen curve 1722 continues to increase at a slightly slower rate.

The total signal 1724 shows the curve that can be obtained by exposing an electrochemical sensor to glucose and acetaminophen. It is particularly noted that at 0.6 V, acetaminophen adds significantly to the signal output, which cause erroneously high readings of the glucose concentration when a presence or amount of acetaminophen is unknowingly introduced. In other words, the output signal of an electrochemical sensor may not be indicative of the actual glucose concentration due to signal interference from acetaminophen. Therefore, the preferred embodiments provide systems and methods for identifying the presence of an interfering species and optionally deriving and analyte value therefrom.

In general, the preferred embodiments measure the difference between the sensor signal at low and high bias potential settings, hereinafter referred to as the "differential measurement," which at the minimum enables identification of signal contribution from the interfering species. A differential measurement that is relatively low or shows substantial equivalence (for example, below a set threshold) identifies a substantially glucose-only signal. In contrast, a differential measurement that is relatively higher or does not show substantial equivalence (for example, above a set threshold) identifies the presence of interfering species (for example, acetaminophen) on a glucose signal.

In some embodiments, the differential measurement can be obtained from a single analyte-measuring device with multiple sensors. In one such example, the first sensor can be biased at a voltage of about +0.4V and the second sensor can be biased at a voltage about +0.6V. The two sensors can be provided under the same membrane system or separate membrane systems. The two sensors can share the same reference and/or counter electrodes or can utilize separate reference and/or counter electrodes.

In some embodiments, the differential measurement can be obtained by switching the bias potential of a single sensor between the two measurement potentials. The bias potentials can be held at each respective setting (high and low bias settings) for as short as milliseconds to as long as minutes or hours. Pulsed amperometric detection (PED) is one method of quickly switching voltages, such as described in Bisenberger, M.; Brauchle, C.; Hampp, N. A triple-step potential waveform at enzyme multisensors with thick-film gold electrodes for detection of glucose and sucrose. *Sensors and Actuators* 1995, B. 181-189, which is incorporated herein by reference in its entirety. In some embodiments, bias potential settings are held long enough to allow equilibration.

Additional description can be found in U.S. Pat. No. 7,081, 195, to Simpson, which is incorporated by reference herein in its entirety.

Calibration Systems and Methods

As described above in the "Overview" section, continuous analyte sensors define a relationship between sensor-generated measurements and a reference measurement that is meaningful to a user (for example, blood glucose in mg/dL). This defined relationship must be monitored to ensure that the continuous analyte sensor maintains a substantially accurate calibration and thereby continually provides meaningful values to a user. Unfortunately, both sensitivity m and baseline b of the calibration are subject to changes that occur in vivo over time (for example, hours to months), requiring updates to the calibration. Generally, any physical property that influences diffusion or transport of molecules through the membrane can alter the sensitivity (and/or baseline) of the calibration. Physical properties that can alter the transport of molecules include, but are not limited to, blockage of surface area due to foreign body giant cells and other barrier cells at the biointerface, distance of capillaries from the membrane, foreign body response/capsule, disease, tissue ingrowth, thickness of membrane system, or the like.

In one example of a change in transport of molecules, an implantable glucose sensor is implanted in the subcutaneous space of a human, which is at least partially covered with a biointerface membrane, such as described in U.S. Patent Publication No. US-2005-0112169-A1, which is incorporated by reference herein in its entirety. Although the body's natural response to a foreign object is to encapsulate the sensor, the architecture of this biointerface membrane encourages tissue ingrowth and neo-vascularization over time, providing transport of solutes (for example, glucose and oxygen) close to the membrane that covers the electrodes. While not wishing to be bound by theory, it is believed that ingrowth of vascularized tissue matures (changes) over time, beginning with a short period of high solute transport during the first few days after implantation, continuing through a time period of significant tissue ingrowth a few days to a week or more after implantation during which low solute transport to the membrane has been observed, and into a mature state of vascularized tissue during which the bed of vascularized tissue provides moderate to high solute transport, which can last for months and even longer after implantation. In some embodiments, this maturation process accounts for a substantial portion of the change in sensitivity and/or baseline of the calibration over time due to changes in solute transport to the membrane.

Accordingly, in one aspect of the preferred embodiments, systems and methods are provided for measuring changes in sensitivity, also referred to as changes in solute transport or biointerface changes, of an analyte sensor 10 implanted in a host over a time period. Preferably, the sensitivity measurement is a signal obtained by measuring a constant analyte other than the analyte being measured by the analyte sensor. For example, in a glucose sensor, a non-glucose constant analyte is measured, wherein the signal is measured beneath the membrane system 22 on the glucose sensor 10. While not wishing to be bound by theory, it is believed that by monitoring the sensitivity over a time period, a change associated with solute transport through the membrane system 22 can be measured and used as an indication of a sensitivity change in the analyte measurement. In other words, a biointerface monitor is provided, which is capable of monitoring changes in the biointerface surrounding an implantable device, thereby enabling the measurement of sensitivity changes of an analyte sensor over time.

In some embodiments, the analyte sensor 10 is provided with an auxiliary electrode 18 configured as a transport-measuring electrode disposed beneath the membrane system 22. The transport-measuring electrode can be configured to measure any of a number of substantially constant analytes or factors, such that a change measured by the transport-measuring electrode can be used to indicate a change in solute (for example, glucose) transport to the membrane system 22. Some examples of substantially constant analytes or factors that can be measured include, but are not limited to, oxygen, carboxylic acids (such as urea), amino acids, hydrogen, pH, chloride, baseline, or the like. Thus, the transport-measuring electrode provides an independent measure of changes in solute transport to the membrane, and thus sensitivity changes over time.

In some embodiments, the transport-measuring electrode measures analytes similar to the analyte being measured by the analyte sensor. For example, in some embodiments of a glucose sensor, water soluble analytes are believed to better represent the changes in sensitivity to glucose over time than non-water soluble analytes (due to the water-solubility of glucose), however relevant information may be ascertained from a variety of molecules. Although some specific examples are described herein, one skilled in the art appreciates a variety of implementations of sensitivity measurements that can be used as to qualify or quantify solute transport through the biointerface of the analyte sensor.

In one embodiment of a glucose sensor, the transport-measuring electrode is configured to measure urea, which is a water-soluble constant analyte that is known to react directly or indirectly at a hydrogen peroxide sensing electrode (similar to the working electrode of the glucose sensor example described in more detail above). In one exemplary implementation wherein urea is directly measured by the transport-measuring electrode, the glucose sensor comprises a membrane system as described in more detail above, however, does not include an active interference domain or active enzyme directly above the transport-measuring electrode, thereby allowing the urea to pass through the membrane system to the electroactive surface for measurement thereon. In one alternative exemplary implementation wherein urea is indirectly measured by the transport-measuring electrode, the glucose sensor comprises a membrane system as described in more detail above, and further includes an active uricase oxidase domain located directly above the transport-measuring electrode, thereby allowing the urea to react at the enzyme and produce hydrogen peroxide, which can be measured at the electroactive surface thereon.

In some embodiments, the change in sensitivity is measured by measuring a change in oxygen concentration, which can be used to provide an independent measurement of the maturation of the biointerface, and to indicate when recalibration of the system may be advantageous. In one alternative embodiment, oxygen is measured using pulsed amperometric detection on the glucose-measuring working electrode 16 (eliminating the need for a separate auxiliary electrode). In another embodiment, the auxiliary electrode is configured as an oxygen-measuring electrode. In another embodiment, an oxygen sensor (not shown) is added to the glucose sensor, as is appreciated by one skilled in the art, eliminating the need for an auxiliary electrode.

In some embodiments, a stability module is provided; wherein the sensitivity measurement changes can be quantified such that a co-analyte concentration threshold is determined. A co-analyte threshold is generally defined as a minimum amount of co-analyte required to fully react with the analyte in an enzyme-based analyte sensor in a non-limiting manner. The minimum co-analyte threshold is preferably expressed as a ratio (for example, a glucose-to-oxygen ratio) that defines a concentration of co-analyte required based on a concentration of analyte available to ensure that the enzyme reaction is limited only by the analyte. While not wishing to be bound by theory, it is believed that by determining a stability of the analyte sensor based on a co-analyte threshold, the processor module can be configured to compensate for instabilities in the glucose sensor accordingly, for example by filtering the unstable data, suspending calibration or display, or the like.

In one such embodiment, a data stream from an analyte signal is monitored and a co-analyte threshold set, whereby the co-analyte threshold is determined based on a signal-to-noise ratio exceeding a predetermined threshold. In one embodiment, the signal-to-noise threshold is based on measurements of variability and the sensor signal over a time period, however one skilled in the art appreciates the variety of systems and methods available for measuring signal-to-noise ratios. Accordingly, the stability module can be configured to set determine the stability of the analyte sensor based on the co-analyte threshold, or the like.

In some embodiments, the stability module is configured to prohibit calibration of the sensor responsive to the stability (or instability) of the sensor. In some embodiments, the stability module can be configured to trigger filtering of the glucose signal responsive to a stability (or instability) of the sensor.

In some embodiments, sensitivity changes can be used to trigger a request for one or more new reference glucose values from the host, which can be used to recalibrate the sensor. In some embodiments, the sensor is re-calibrated responsive to a sensitivity change exceeding a preselected threshold value. In some embodiments, the sensor is calibrated repeatedly at a frequency responsive to the measured sensitivity change. Using these techniques, patient inconvenience can be minimized because reference glucose values are generally only requested when timely and appropriate (namely, when a sensitivity or baseline shift is diagnosed).

In some alternative embodiments, sensitivity changes can be used to update calibration. For example, the measured change in transport can be used to update the sensitivity m in the calibration equation. While not wishing to be bound by theory, it is believed that in some embodiments, the sensitivity m of the calibration of the glucose sensor is substantially proportional to the change in solute transport measured by the transport-measuring electrode.

It should be appreciated by one skilled in the art that in some embodiments, the implementation of sensitivity measurements of the preferred embodiments typically necessitate an addition to, or modification of, the existing electronics (for example, potentiostat configuration or settings) of the glucose sensor and/or receiver.

In some embodiments, the signal from the oxygen measuring electrode may be digitally low-pass filtered (for example, with a passband of $0\text{-}10^{-5}$ Hz, dc-24 hour cycle lengths) to remove transient fluctuations in oxygen, due to local ischemia, postural effects, periods of apnea, or the like. Since oxygen delivery to tissues is held in tight homeostatic control, this filtered oxygen signal should oscillate about a relatively constant. In the interstitial fluid, it is thought that the levels are about equivalent with venous blood (40 mmHg). Once implanted, changes in the mean of the oxygen signal (for example, >5%) may be indicative of change in transport through the biointerface (change in sensor sensitivity and/or baseline due to changes in solute transport) and the need for system recalibration.

The oxygen signal may also be used in its unfiltered or a minimally filtered form to detect or predict oxygen deprivation-induced artifact in the glucose signal, and to control display of data to the user, or the method of smoothing, digital filtering, or otherwise replacement of glucose signal artifact. In some embodiments, the oxygen sensor may be implemented in conjunction with any signal artifact detection or prediction that may be performed on the counter electrode or working electrode voltage signals of the electrode system. U.S. Patent Publication No. US-2005-0043598-A1, which is incorporated by reference in its entirety herein, describes some methods of signal artifact detection and replacement that may be useful such as described herein.

Preferably, the transport-measuring electrode is located within the same local environment as the electrode system associated with the measurement of glucose, such that the transport properties at the transport-measuring electrode are substantially similar to the transport properties at the glucose-measuring electrode.

In a second aspect the preferred embodiments, systems and methods are provided for measuring changes baseline, namely non-glucose related electroactive compounds in the host. Preferably the auxiliary working electrode is configured to measure the baseline of the analyte sensor over time. In some embodiments, the glucose-measuring working electrode 16 is a hydrogen peroxide sensor coupled to a membrane system 22 containing an active enzyme 32 located above the electrode (such as described in more detail with reference to FIGS. 1 to 4, above). In some embodiments, the auxiliary working electrode 18 is another hydrogen peroxide sensor that is configured similar to the glucose-measuring working electrode however a portion 34 of the membrane system 22 above the base-measuring electrode does not have active enzyme therein, such as described in more detail with reference to FIGS. 3A and 3B. The auxiliary working electrode 18 provides a signal substantially comprising the baseline signal, b, which can be (for example, electronically or digitally) subtracted from the glucose signal obtained from the glucose-measuring working electrode to obtain the signal contribution due to glucose only according to the following equation:

$$\text{Signal}_{glucose\ only} = \text{Signal}_{glucose\text{-}measuring\ working\ electrode} - \text{Signal}_{baseline\text{-}measuring\ working\ electrode}$$

In some embodiments, electronic subtraction of the baseline signal from the glucose signal can be performed in the hardware of the sensor, for example using a differential amplifier. In some alternative embodiments, digital subtraction of the baseline signal from the glucose signal can be performed in the software or hardware of the sensor or an associated receiver, for example in the microprocessor.

One aspect the preferred embodiments provides for a simplified calibration technique, wherein the variability of the baseline has been eliminated (namely, subtracted). Namely, calibration of the resultant differential signal ($\text{Signal}_{glucose\ only}$) can be performed with a single matched data pair by solving the following equation:

$$y = mx$$

While not wishing to be bound by theory, it is believed that by calibrating using this simplified technique, the sensor is made less dependent on the range of values of the matched data pairs, which can be sensitive to human error in manual blood glucose measurements, for example. Additionally, by subtracting the baseline at the sensor (rather than solving for the baseline b as in conventional calibration schemes), accuracy of the sensor may increase by altering control of this variable (baseline b) from the user to the sensor. It is additionally believed that variability introduced by sensor calibration may be reduced.

In some embodiments, the glucose-measuring working electrode 16 is a hydrogen peroxide sensor coupled to a membrane system 22 containing an active enzyme 32 located above the electrode, such as described in more detail above; however the baseline signal is not subtracted from the glucose signal for calibration of the sensor. Rather, multiple matched data pairs are obtained in order to calibrate the sensor (for example using y=mx+b) in a conventional manner, and the auxiliary working electrode 18 is used as an indicator of baseline shifts in the sensor signal. Namely, the auxiliary working electrode 18 is monitored for changes above a certain threshold. When a significant change is detected, the system can trigger a request (for example, from the patient or caregiver) for a new reference glucose value (for example, SMBG), which can be used to recalibrate the sensor. By using the auxiliary working electrode signal as an indicator of baseline shifts, recalibration requiring user interaction (namely, new reference glucose values) can be minimized due to timeliness and appropriateness of the requests. In some embodiments, the sensor is re-calibrated responsive to a baseline shifts exceeding a preselected threshold value. In some embodiments, the sensor is calibrated repeatedly at a frequency responsive to the rate-of-change of the baseline.

In yet another alternative embodiment, the electrode system of the preferred embodiments is employed as described above, including determining the differential signal of glucose less baseline current in order to calibrate using the simplified equation (y=mx), and the auxiliary working electrode 18 is further utilized as an indicator of baseline shifts in the sensor signal. While not wishing to be bound by theory, it is believed that shifts in baseline may also correlate and/or be related to changes in the sensitivity m of the glucose signal. Consequently, a shift in baseline may be indicative of a change in sensitivity m. Therefore, the auxiliary working electrode 18 is monitored for changes above a certain threshold. When a significant change is detected, the system can trigger a request (for example, from the patient or caregiver) for a new reference glucose value (for example, SMBG), which can be used to recalibrate the sensor. By using the auxiliary signal as an indicator of possible sensitivity changes, recalibration requiring user interaction (new reference glucose values) can be minimized due to timeliness and appropriateness of the requests.

It is noted that infrequent new matching data pairs may be useful over time to recalibrate the sensor because the sensitivity m of the sensor may change over time (for example, due to maturation of the biointerface that may increase or decrease the glucose and/or oxygen availability to the sensor). However, the baseline shifts that have conventionally required numerous and/or regular blood glucose reference measurements for updating calibration (for example, due to interfering species, metabolism changes, or the like) can be consistently and accurately eliminated using the systems and methods of the preferred embodiments, allowing reduced interaction from the patient (for example, requesting less frequent reference glucose values such as daily or even as infrequently as monthly).

An additional advantage of the sensor of the preferred embodiments includes providing a method of eliminating signal effects of interfering species, which have conventionally been problematic in electrochemical glucose sensors. Namely, electrochemical sensors are subject to electrochemical reaction not only with the hydrogen peroxide (or other analyte to be measured), but additionally may react with other electroactive species that are not intentionally being measured (for example, interfering species), which cause an increase in signal strength due to this interference. In other words, interfering species are compounds with an oxidation potential that overlap with the analyte being measured. Interfering species such as acetaminophen, ascorbate, and urate, are notorious in the art of glucose sensors for producing inaccurate signal strength when they are not properly controlled. Some glucose sensors utilize a membrane system that blocks at least some interfering species, such as ascorbate and urate. Unfortunately, it is difficult to find membranes that are satisfactory or reliable in use, especially in vivo, which effectively block all interferants and/or interfering species (for example, see U.S. Pat. Nos. 4,776,944, 5,356,786, 5,593,852, 5,776,324B1, and 6,356,776).

The preferred embodiments are particularly advantageous in their inherent ability to eliminate the erroneous transient and non-transient signal effects normally caused by interfering species. For example, if an interferant such as acetaminophen is ingested by a host implanted with a conventional implantable electrochemical glucose sensor (namely, one without means for eliminating acetaminophen), a transient non-glucose related increase in signal output would occur. However, by utilizing the electrode system of the preferred embodiments, both working electrodes respond with substantially equivalent increased current generation due to oxidation of the acetaminophen, which would be eliminated by subtraction of the auxiliary electrode signal from the glucose-measuring electrode signal.

In summary, the system and methods of the preferred embodiments simplify the computation processes of calibration, decreases the susceptibility introduced by user error in calibration, and eliminates the effects of interfering species. Accordingly, the sensor requires less interaction by the patient (for example, less frequent calibration), increases patient convenience (for example, few reference glucose values), and improves accuracy (via simple and reliable calibration).

In another aspect of the preferred embodiments, the analyte sensor is configured to measure any combination of changes in baseline and/or in sensitivity, simultaneously and/or iteratively, using any of the above-described systems and methods. While not wishing to be bound by theory, the preferred embodiments provide for improved calibration of the sensor, increased patient convenience through less frequent patient interaction with the sensor, less dependence on the values/range of the paired measurements, less sensitivity to error normally found in manual reference glucose measurements, adaptation to the maturation of the biointerface over time, elimination of erroneous signal due to non-constant analyte-related signal so interfering species, and/or self-diagnosis of the calibration for more intelligent recalibration of the sensor.

Sensors Having Multiple Working Electrodes and Interferent-Blocking Membranes

In general, for a sensor configured with first and second working electrodes (e.g., enzyme-including and active-enzyme-lacking) the signal from the enzyme-lacking electrode, b, can be subtracted from the enzyme-including signal, y, and if the sensors are co-located and have equal diffusion properties (equal sensitivities to peroxide and other reactive species), the difference signal (y−b) is specific to the analyte and contains no baseline. Ideally, this difference signal also subtracts out noise and interference (for example, acetaminophen). In operation, however, it is likely that the two sensors will have somewhat different diffusion properties. For example, in some circumstances, differences in diffusion properties can arise from a variety of factors, such as but not limited to, small differences in manufacturing of each electrode, or because the membranes over the two working electrodes are not identical (e.g., because of differences in the enzyme content or lack there of). Additionally, in some circumstances, the local environment adjacent to one working electrode can be substantially different from the local environment adjacent to the other working electrode. For example, a blood vessel (which improves interferent removal) can be adjacent to one working electrode while the other working electrode can be pressed against adipose tissue (which reduces interferent removal). Thus, in some circumstances, the difference signal (y−b) can contain some baseline, some noise and/or some interference.

Additionally, a sensor having two or more working electrodes can be affected by sensor error, depending upon the amplitude of the baseline (e.g., non-analyte-related signal) relative to the analyte-related signal. In other words, the higher the noise amplitude relative to the analyte-related signal, the greater the error; accordingly small differences in noise amplitude can induce error during calculation of the analyte concentration using the methods described above. Conversely, the lower noise amplitude relative to the analyte-related signal, the less the error produced, which corresponds to small changes in noise amplitude having substantially little effect on the calibrated analyte concentration. As an extreme example to illustrate this problem, the signal measured by the enzyme-including electrode is equal to the analyte-related signal plus non-analyte-related signal. If the non-analyte-related signal is very high (e.g., 1000 counts) relative to the analyte-related signal (e.g., 100 counts), a small change in the non-analyte-related signal can induce substantial error when determining the analyte concentration. If on the other hand, the non-analyte-related signal (e.g., 10 counts) is reduced relative to the analyte-related signal (e.g., 100 counts), less error occurs when determining the analyte concentration.

It is desirable to reduce noise, such that differences in enzyme and no-enzyme electrodes does not substantially not affect sensor function and/or sensor accuracy. While not wishing to be bound by theory, it is believed that variability caused by baseline, noise and/or interference sometimes observed on the difference signal (y−b) can be substantially eliminated by applying at least one interference domain, including constant and/or non-constant noise reducing mechanisms and methods as described above, to a sensor having two or more working electrodes, as described elsewhere herein. In other words, an interference domain can substantially prevent noise-causing interferents from affecting the working electrodes, such that substantially little error is induced (e.g., when determining analyte concentration), thereby allowing improved signal processing and greater reliability of the data.

Accordingly, in one preferred embodiment, the sensor is a sensor having first and second working electrodes and a membrane system configured to substantially block and/or dilute interfering species (e.g., CA/CAB, Polyurethane, silicone-Pluronics blend, fluid-pocket forming configuration including a wound-suppressing bioagent, interferent scavengers, etc., as described elsewhere herein), wherein the first working electrode is enzyme-including (e.g., with GOX) and the second working electrode is enzyme-lacking (e.g., either no enzyme added or deactivated/inactive enzyme added); wherein the signal on the enzyme-lacking electrode is configured to determine signal due to non-analyte-related signal; and further wherein the signals from the first and second working electrodes can be processed to determine the signal that is substantially analyte-related.

In one exemplary embodiment, the sensor is a sensor including an enzyme-including working electrode, and enzyme-lacking working electrode and an interference domain, wherein the interference domain includes one or more cellulosic derivatives, such as but not limited to cellulose acetate, cellulose acetate butyrate, 2-hydroxyethyl cellulose, cellulose acetate phthalate, cellulose acetate propionate, cellulose acetate trimellitate, and the like, as well as their copolymers and terpolymers with other cellulosic or non-cellulosic monomers, as described in the section entitled "Interference Domain." In addition to forming an interference domain from only cellulose acetate(s) or only cellulose acetate butyrate(s), the interference domain can be formed from combinations or blends of cellulosic derivatives, such as but not limited to cellulose acetate and cellulose acetate butyrate, or combinations of layer(s) of cellulose acetate and layer(s) of cellulose acetate butyrate.

In another exemplary embodiment, the sensor is a sensor including an enzyme-including working electrode, and enzyme-lacking working electrode and an interference domain, wherein the interference domain includes a blend of a silicone material and a hydrophilic polymer (e.g., a hydrophilic-hydrophobic polymer, such as but not limited to a PLURONIC® polymer). In a preferred embodiment, the blend is a substantial blend. For example, the ratio of silicone polymer to hydrophilic polymer, as well as the polymeric compositions, can be selected such that a layer constructed from the material has interference characteristics that inhibit transport of one or more interfering species (described above) through the layer.

In yet another exemplary embodiment, the sensor is a sensor including an enzyme-including working electrode, and enzyme-lacking working electrode and an interference domain, wherein the interference domain includes polyurethanes, polymers having pendant ionic groups, and/or polymers having controlled pore size. In a further embodiment, the interference domain includes a thin, hydrophobic membrane that is non-swellable and restricts diffusion of low molecular weight species. Additionally, the interference domain is permeable to relatively low molecular weight substances, such as hydrogen peroxide, but restricts the passage of higher molecular weight substances, including glucose and ascorbic acid.

In still another exemplary embodiment, the sensor is a sensor including an enzyme-including working electrode, and enzyme-lacking working electrode and an interferent blocking membrane system, wherein the membrane system includes one or more interferent-blocking configurations, such as but not limited to an interferent-blocking interference layer, an interferent-blocking resistance domain, a porous membrane configured to suppress interferent build-up, an interferent-eliminating auxiliary electrode, an interferent-scavenger and the like.

EXAMPLES

Example 1

Dual-Electrode Sensor with Coiled Reference Electrode

Dual-electrode sensors (having a configuration similar to the embodiment shown in FIG. 9B) were constructed from two platinum wires, each coated with non-conductive material/insulator. Exposed electroactive windows were cut into the wires by removing a portion thereof. The platinum wires were laid next to each other such that the windows are offset (e.g., separated by a diffusion barrier). The bundle was then placed into a winding machine & silver wire was wrapped around the platinum electrodes. The silver wire was then chloridized to produce a silver/silver chloride reference electrode. The sensor was trimmed to length, and a glucose oxidase enzyme solution applied to both windows (e.g., enzyme applied to both sensors). To deactivate the enzyme in one window (e.g., window 904a, FIG. 9B) the window was dipped into dimethylacetamide (DMAC) and rinsed. After the sensor was dried, a resistance layer was sprayed onto the sensor and dried.

Figure 12:
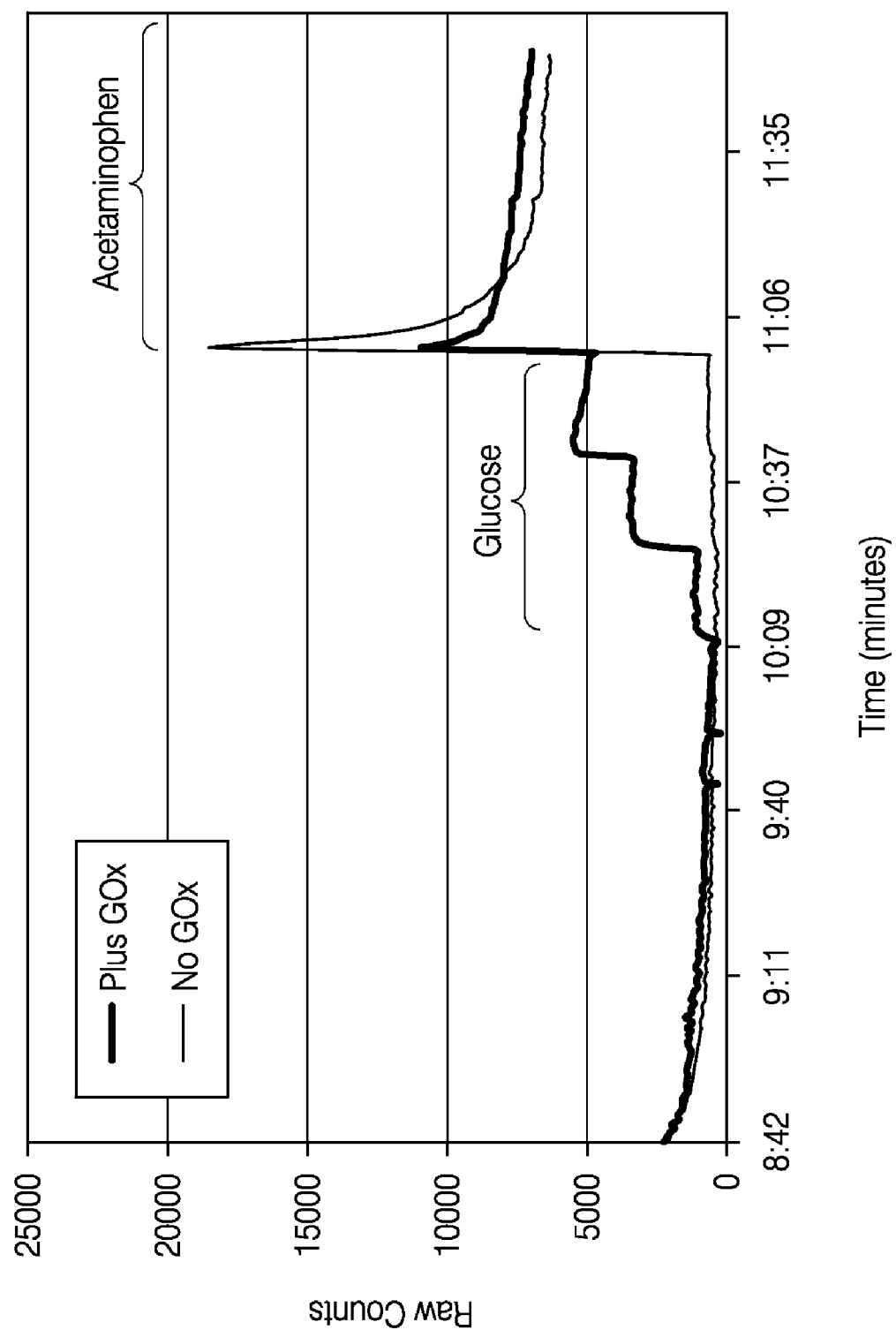
FIG. 12 is a graph that illustrates in vitro signal (raw counts) detected from a sensor having three bundled wire electrodes with staggered working electrodes. Plus GOx (thick line)=the electrode with active GOx. No GOx (thin line)=the electrode with inactive or no GOx.

FIG. 12 shows the results from one experiment, comparing the signals from the two electrodes of the dual-electrode sensor having a coiled silver/silver chloride wire reference electrode described above. The "Plus GOx" electrode included active GOx in its window. The "No GOx" electrode included DMAC-inactivated GOx in its window. To test, the sensor was incubated in room temperature phosphate buffered saline (PBS) for 30 minutes. During this time, the signals from the two electrodes were substantially equivalent. Then the sensor was moved to a 40-mg/dl solution of glucose in PBS. This increase in glucose concentration resulting in an expected rise in signal from the "Plus GOx" electrode but no significant increase in signal from the "No GOx" electrode. The sensor was then moved to a 200-mg/dl solution of glucose in PBS. Again, the "Plus GOx" electrode responded with a characteristic signal increase while no increase in signal was observed for the "No GOx" electrode. The sensor was then moved to a 400-mg/dl solution of glucose in PBS. The "Plus GOx" electrode signal increased to about 5000 counts while no increase in signal was observed for the "No GOx" electrode. As a final test, the sensor was moved to a solution of 400 mg/dl glucose plus 0.22 mM acetaminophen (a known interferant) in PBS. Both electrodes recorded similarly dramatic increases in signal (raw counts). These data indicate that the "No GOx" electrode is measuring sensor background (e.g., noise) that is substantially related to non-glucose factors.

Example 2

Dual-Electrode Sensor with X-Shaped Reference Electrode

This sensor was constructed similarly to the sensor of Example 1, except that the configuration was similar to the embodiment shown in FIG. 7J. Two platinum electrode wires were dipped into non-conductive material and then electroactive windows formed by removing portions of the nonconductive material. The two wires were then bundled with an X-shaped silver reference electrode therebetween. An additional layer of non-conductive material held the bundle together.

Figure 13:
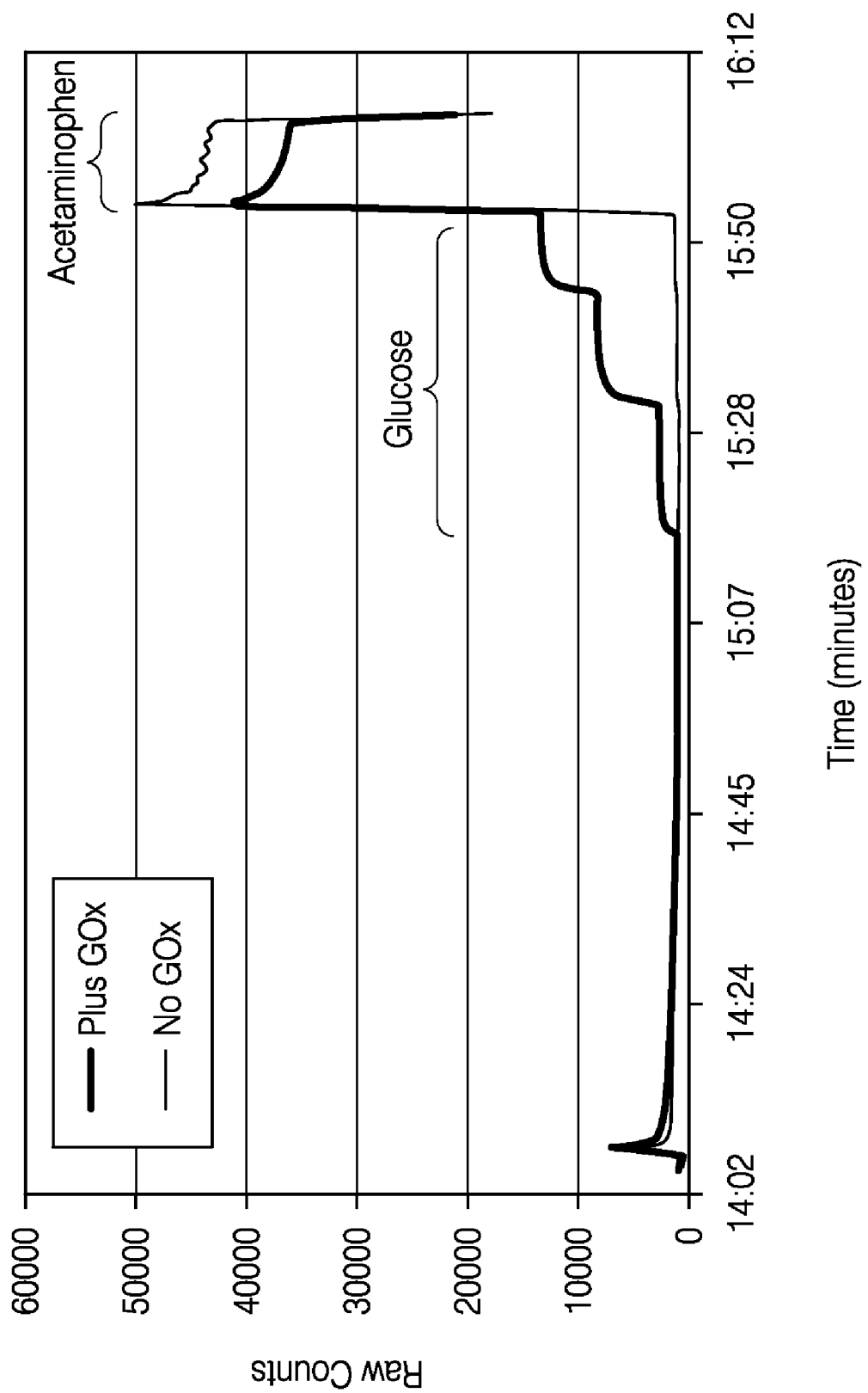
FIG. 13 is a graph that illustrates in vitro signal (counts) detected from a sensor having the configuration of the embodiment shown in FIG. 7J (silver/silver chloride X-wire reference electrode separating two platinum wire working electrodes). Plus GOx (thick line)=the electrode with active GOx. No GOx (thin line)=the electrode with inactive or no GOx.

FIG. 13 shows the results from one experiment, comparing the signals from the two electrodes of a dual-electrode sensor having an X-shaped reference electrode. The "Plus GOx" electrode has active GOx in its window. The "No GOx" electrode has DMAC-inactivated GOx in its window. The sensor was tested as was described for Experiment 1, above. Signal from the two electrodes were substantially equivalent until the sensor was transferred to the 40-mg/dl glucose solution. As this point, the "Plus GOx" electrode signal increased but the "No GOx" electrode signal did not. Similar increases were observed in the "Plus GOx" signal when the sensor was moved consecutively to 200-mg/dl and 400-mg/dl glucose solution, but still not increase in the "No GOx" signal was observed. When sensor was moved to a 400-mg/dl glucose solution containing 0.22 mM acetaminophen, both electrodes recorded a similar increase in signal (raw counts). These data indicate that the "No GOx" electrode measures sensor background (e.g., noise) signal that is substantially related to non-glucose factors.

Example 3

Dual-Electrode Challenge with Hydrogen Peroxide, Glucose, and Acetaminophen

A dual-electrode sensor was assembled similarly to the sensor of Example 1, with a bundled configuration similar to that shown in FIG. 7C (two platinum working electrodes and one silver/silver chloride reference electrode, not twisted). The electroactive windows were staggered by 0.085 inches, to create a diffusion barrier.

Figure 14:
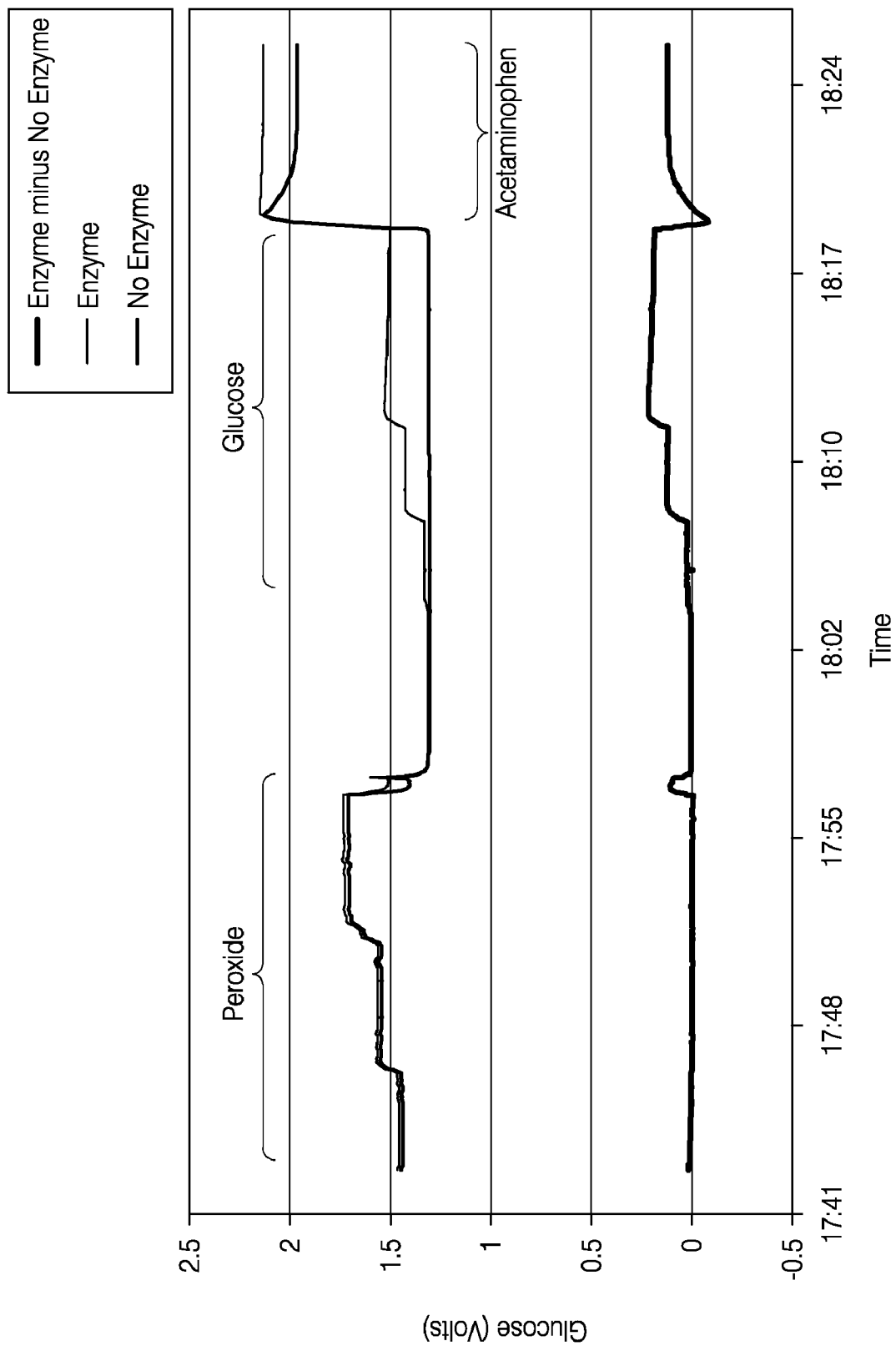
FIG. 14 is a graph that illustrates an in vitro signal (counts) detected from a dual-electrode sensor with a bundled configuration similar to that shown in FIG. 7C (two platinum working electrodes and one silver/silver chloride reference electrode, not twisted).

FIG. 14 shows the experimental results. The Y-axis shows the glucose signal (volts) and the X-axis shows time. The "Enzyme" electrode included active GOx. The "No Enzyme" electrode did not include active GOx. The "Enzyme minus No Enzyme" represents a simple subtraction of the "Enzyme" minus the "NO Enzyme." The "Enzyme" electrode measures the glucose-related signal and the non-glucose-related signal. The "No Enzyme" electrode measures only the non-glucose-related signal. The "Enzyme minus No Enzyme" graph illustrates the portion of the "Enzyme" signal related to only the glucose-related signal.

The sensor was challenged with increasing concentrations of hydrogen peroxide in PBS. As expected, both the "Enzyme" and "No Enzyme" electrodes responded substantially the same with increases in signal corresponding increased in $H_2O_2$ concentration (~50 µM, 100 µM and 250 µM $H_2O_2$). When the "No Enzyme" signal was subtracted from the "Enzyme" signal, the graph indicated that the signal was not related to glucose concentration.

The sensor was challenged with increasing concentrations of glucose (~20 mg/dl, 200 mg/dl, 400 mg/dl) in PBS. As glucose concentration increased, the "Enzyme" electrode registered a corresponding increase in signal. In contrast, the "No Enzyme" electrode did not record an increase in signal. Subtracting the "No Enzyme" signal from the "Enzyme" signal shows a step-wise increase in signal related to only glucose concentration.

The sensor was challenged with the addition of acetaminophen (~0.22 mM) to the highest glucose concentration. Acetaminophen is known to be an interferent (e.g., produces non-constant noise) of the sensors built as described above, e.g., due to a lack of acetaminophen-blocking membrane and/or mechanism formed thereon or provided therewith. Both the "Enzyme" and "No Enzyme" electrodes showed a substantial increase in signal. The "Enzyme minus No Enzyme" graph substantially shows the portion of the signal that was related to glucose concentration.

From these data, it is believed that a dual-electrode system can be used to determine the analyte-only portion of the signal.

Example 4

IV Dual-Electrode Sensor in Dogs

An intravascular dual-electrode sensor was built substantially as described in co-pending U.S. patent application Ser. No. 11/543,396 filed on Oct. 4, 2006, and entitled "ANALYTE SENSOR." Namely, the sensor was built by providing two platinum wires (e.g., dual working electrodes) and vapor-depositing the platinum wires with Parylene to form an insulating coating. A portion of the insulation on each wire was removed to expose the electroactive surfaces (e.g., 904a and 904b). The wires were bundled such that the windows were offset to provide a diffusion barrier, as described herein, cut to the desired length, to form an "assembly." A silver/silver chloride reference electrode was disposed remotely from the working electrodes (e.g., coiled inside the sensor's fluid connector).

An electrode domain was formed over the electroactive surface areas of the working electrodes by dip coating the assembly in an electrode solution (comprising BAYHYDROL® 123 with PVP and added EDC) and drying.

An enzyme domain was formed over the electrode domain by subsequently dip coating the assembly in an enzyme domain solution (BAYHYDROL 140AQ mixed with glucose oxidase and glutaraldehyde) and drying. This dip coating process was repeated once more to form an enzyme domain having two layers and subsequently drying. Next an enzyme solution containing active GOx was applied to one window; and an enzyme solution without enzyme (e.g., No GOx) was applied to the other window.

A resistance domain was formed over the enzyme domain by subsequently spray coating the assembly with a resistance domain solution (Chronothane H and Chronothane 1020) and drying.

After the sensor was constructed, it was placed in a protective sheath and then threaded through and attached to a fluid coupler, as described in co-pending U.S. patent application Ser. No. 11/543,396 filed on Oct. 4, 2006 and entitled "ANALYTE SENSOR." Prior to use, the sensors were sterilized using electron beam radiation.

The forelimb of an anesthetized dog (2 years old, 40 pounds) was cut down to the femoral artery and vein. An arterio-venous shunt was placed from the femoral artery to the femoral vein using 14 gauge catheters and ⅛-inch IV tubing. A pressurized arterial fluid line was connected to the sensor systems at all times. The test sensor system included a 20 gauge×1.25-inch catheter and took measurements every 30 seconds. The catheter was aseptically inserted into the shunt, followed by insertion of the sensor into the catheter. As controls, the dog's glucose was checked with an SMBG, as well as removing blood samples and measuring the glucose concentration with a Hemocue.

Figure 15:
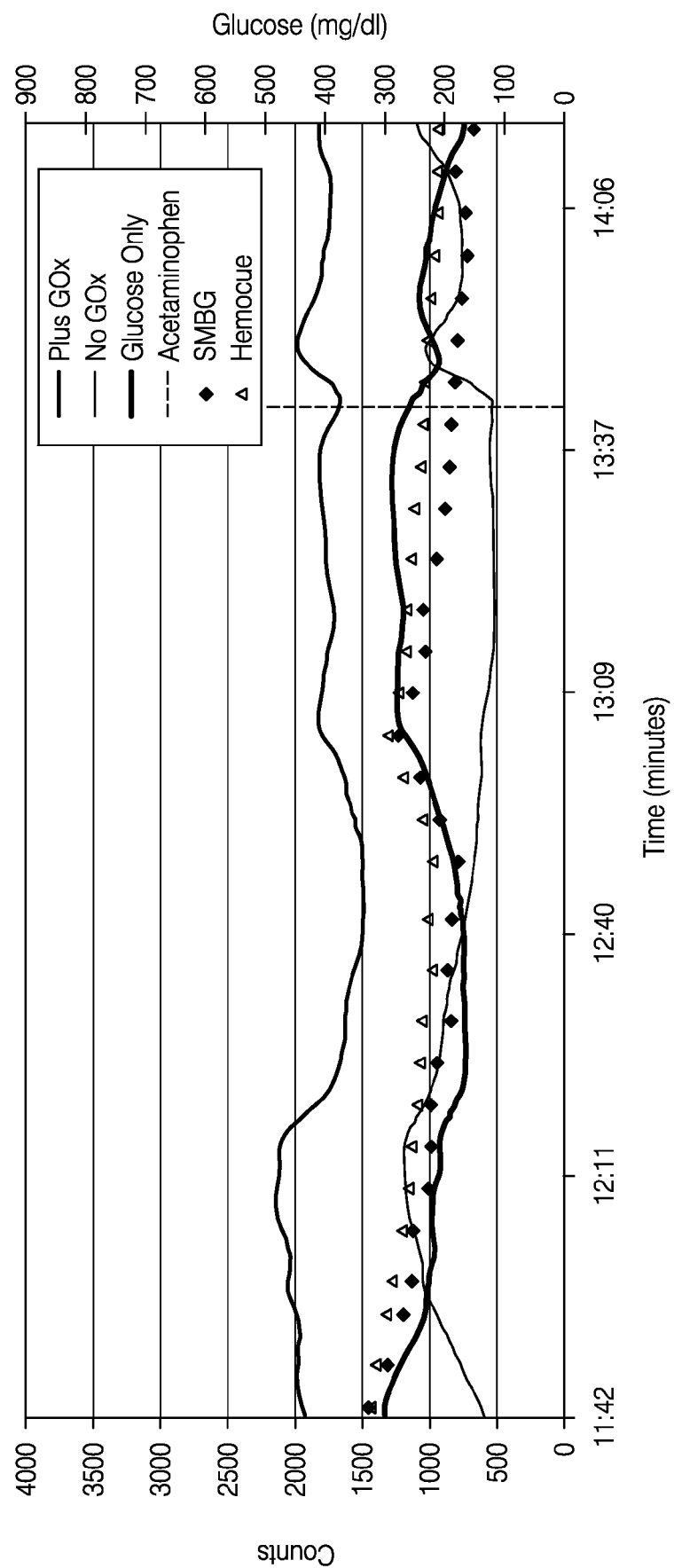
FIG. 15 is a graph that illustrates an in vivo signal (counts) detected from a dual-electrode sensor with a bundled configuration similar to that shown in FIG. 7C (two platinum working electrodes, not twisted, and one remotely disposed silver/silver chloride reference electrode).

FIG. 15 shows the experimental results. Glucose test data (counts) is shown on the left-hand Y-axis, glucose concentration for the controls (SMBG and Hemocue) are shown on the right-hand y-axis and time is shown on the X-axis. Each time interval on the X-axis represents 29-minutes (e.g., 12:11 to 12:40 equals 29 minutes). An acetaminophen challenge is shown as a vertical line on the graph.

The term "Plus GOx" refers to the signal from the electrode coated with active GOx, which represents signal due to both the glucose concentration and non-glucose-related electroactive compounds as described elsewhere herein (e.g., glucose signal and background signal, which includes both constant and non-constant noise). "No GOx" is signal from the electrode lacking GOx, which represents non-glucose related signal (e.g., background signal, which includes both constant and non-constant noise). The "Glucose Only" signal (e.g., related only to glucose concentration) is determined during data analysis (e.g., by sensor electronics). In this experiment, the "Glucose Only" signal was determined by a subtraction of the "No GOx" signal from the "Plus GOx" signal.

During the experiment, the "No GOx" signal (thin line) substantially paralleled the "Plus GOx" signal (medium line). The "Glucose Only" signal substantially paralleled the control tests (SMBG/Hemocue).

Acetaminophen is known to be an interferent (e.g., produces non-constant noise) of the sensors built as described above, e.g., due to a lack of acetaminophen-blocking membrane and/or mechanism formed thereon or provided therewith. The SMBG or Hemocue devices utilized in this experiment, however, do include mechanisms that substantially block acetaminophen from the signal (see FIG. 15). When the dog was challenged with acetaminophen, the signals from both working electrodes ("Plus GOx" and "No GOx") increased in a substantially similar manner. When the "Glucose Only" signal was determined, it substantially paralleled the signals of the control devices and was of a substantially similar magnitude.

From these experimental results, it is believed that an indwelling, dual-electrode glucose sensor system (as described herein) in contact with the circulatory system can provide substantially continuous glucose data that can be used to calculate a glucose concentration that is free from background components (e.g., constant and non-constant noise), in a clinical setting.

Methods and devices that are suitable for use in conjunction with aspects of the preferred embodiments are disclosed in U.S. Pat. No. 4,994,167; 4,757,022; 6,001,067; 6,741,877; 6,702,857; 6,558,321; 6,931,327; 6,862,465; 7,074,307; 7,081,195; 7,108,778; and 7,110,803.

Methods and devices that are suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0112169-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2003-0217966-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0020189-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No.

US-2007-0016381-A1; U.S. Patent Publication No. US-2007-0027370-A1; U.S. Patent Publication No. US-2007-0027384-A1; U.S. Patent Publication No. US-2007-0032717-A1; and U.S. Patent Publication No. US-2007-0032718 A1.

Methods and devices that are suitable for use in conjunction with aspects of the preferred embodiments are disclosed in U.S. application Ser. No. 09/447,227 filed Nov. 22, 1999 and entitled "DEVICE AND METHOD FOR DETERMINING ANALYTE LEVELS"; U.S. application Ser. No. 11/515,342 filed Sep. 1, 2006 and entitled "SYSTEMS AND METHODS FOR PROCESSING ANALYTE SENSOR DATA"; U.S. application Ser. No. 11/654,135 filed Jan. 17, 2007 and entitled "POROUS MEMBRANES FOR USE WITH IMPLANTABLE DEVICES"; U.S. application Ser. No. 11/675,063 filed Feb. 14, 2007 and entitled "ANALYTE SENSOR"; U.S. application Ser. No. 11/543,734 filed Oct. 4, 2006 and entitled "DUAL ELECTRODE SYSTEM FOR A CONTINUOUS ANALYTE SENSOR"; U.S. application Ser. No. 11/654,140 filed Jan. 17, 2007 and entitled "MEMBRANES FOR AN ANALYTE SENSOR"; U.S. application Ser. No. 11/654,327 filed Jan. 17, 2007 and entitled "MEMBRANES FOR AN ANALYTE SENSOR"; U.S. application Ser. No. 11/543,396 filed Oct. 4, 2006 and entitled "ANALYTE SENSOR"; U.S. application Ser. No. 11/543,490 filed Oct. 4, 2006 and entitled "ANALYTE SENSOR"; U.S. application Ser. No. 11/543,404 filed Oct. 4, 2006 and entitled "ANALYTE SENSOR"; U.S. application Ser. No. 11/681,145 filed Mar. 1, 2007 and entitled "ANALYTE SENSOR"; and U.S. application Ser. No. 11/690,752 filed Mar. 23, 2007 and entitled "TRANSCUTANEOUS ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An analyte sensor configured for measuring an analyte in a host, the sensor comprising:
   a first working electrode disposed beneath an active enzymatic portion of a sensor membrane, wherein the sensor membrane comprises a first interference domain located over the first working electrode, and wherein the first interference domain is configured to substantially block flow of at least one interfering species; and
   a second working electrode disposed beneath an inactive-enzymatic portion of a sensor membrane or a non-enzymatic portion of a sensor membrane, wherein the sensor membrane comprises a second interference domain located over the second working electrode, wherein the second interference domain is configured to substantially block flow of at least one interfering species, and wherein the first interference domain is distinct from the second interference domain.

2. The analyte sensor of claim 1, wherein the interference domain is configured to substantially block at least one interferent selected from the group consisting of acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

3. The analyte sensor of claim 1, wherein the interference domain is configured to substantially block at least one interferent selected from the group consisting of hydrogen peroxide, reactive oxygen species, and reactive nitrogen species.

4. The analyte sensor of claim 1, wherein the interference domain is configured to substantially block at least one non-constant noise causing interferent.

5. The analyte sensor of claim 1, wherein the sensor membrane further comprises a blend of at least one hydrophilic component and at least one hydrophobic component, wherein the interference domain is configured such that the sensor provides an equivalent analyte signal response to at least one interferent that does not substantially affect accuracy of an in vivo analyte concentration measurement, and wherein the sensor is configured to provide a linear response to analyte concentration, in vivo, within in a physiological range.

6. The analyte sensor of claim 5, wherein the hydrophilic component and the hydrophobic component each comprise at least one cellulosic derivative.

7. The analyte sensor of claim 1, wherein the sensor membrane further comprises a silicone material configured to allow transport of an analyte therethrough.

8. The analyte sensor of claim 7, wherein the silicone material comprises a blend of a silicone elastomer and a hydrophilic copolymer.

9. The analyte sensor of claim 1, wherein the sensor membrane further comprises a polyurethane.

10. The analyte sensor of claim 1, wherein the sensor membrane further comprises a polymer having pendant ionic groups.

11. The analyte sensor of claim 1, wherein the sensor membrane further comprises a polymer membrane having a predetermined pore size that restricts diffusion of high molecular weight species.

12. The analyte sensor of claim 11, wherein the high molecular weight species comprise at least one of glucose and ascorbic acid.

13. The analyte sensor of claim 1, wherein the sensor is configured to be subcutaneously implanted.

14. The analyte sensor of claim 1, wherein the sensor is configured to be intravascularly implanted.

15. The analyte sensor of claim 1, wherein the sensor comprises an architecture with at least one dimension less than about 1 mm.

16. The analyte sensor of claim 1, wherein the first interference domain and second interference domain are individually formed on each of the first electrode and the second electrode.

17. The analyte sensor of claim 1, wherein the sensor comprises a diffusion barrier between the first electrode and the second electrode.

18. The analyte sensor of claim 1, wherein the sensor comprises a diffusion barrier between the first interference domain and the second interference domain.

19. The analyte sensor of claim 1, wherein the first and second interference domains are each configured to substantially block passage therethrough of at least one interferent such that an equivalent glucose signal response of the interferent is less than about 60 mg/dl.

20. The analyte sensor of claim 1, wherein the interference domain is configured to substantially block at least one interferent selected from the group consisting of ureate, ascorbate, and acetaminophen.

21. The analyte sensor of claim 1, wherein the interference domain is configured to substantially block at least one interferent having an oxidation potential that overlaps with the analyte to be measured.

* * * * *

UNITED STATES PATENT AND TRADEMARK OFFICE
CERTIFICATE OF CORRECTION

PATENT NO.       : 7,761,130 B2
APPLICATION NO.  : 11/692154
DATED            : July 20, 2010
INVENTOR(S)      : Simpson et al.

It is certified that error appears in the above-identified patent and that said Letters Patent is hereby corrected as shown below:

| Issued Patent | | 1. Description of Discrepancy |
|---|---|---|
| Column | Line | |
| Page 1 (Item 75) (Inventors) | 3-5 | After "(US);" delete "Paul V. Goode, Cherry Hill, NJ (US); Apurv U. Kamath, San Diego, CA (US);". |
| Page 1 (Item 75) (Inventors) | 10-12 | After "(US);" delete "John Burd, San Diego, CA (US); Rathbun K. Rhodes, Madison, WI (US);". |
| (Item 56) Page 3 Col. 2 | 51 | Under U.S. Patent Documents, change "Berner et al." to --Kim et al.--. |
| (Item 56) Page 3 Col. 2 | 70 | Under U.S. Patent Documents, change "van" to --Van--. |
| (Item 56) Page 4 Col. 1 | 49 | Under U.S. Patent Documents, change "McIvor" to --McIvor--. |
| (Item 56) Page 5 Col. 2 | 66 | Under Other Publications, change "amperometeric" to --amperometric--. |
| (Item 56) Page 6 Col. 2 | 49 | Under Other Publications, change "Senso" to --Sensor--. |
| (Item 56) Page 6 Col. 2 | 61 | Under Other Publications, change "reliablity" to --reliability--. |
| (Item 56) Page 7 Col. 1 | 4 | Under Other Publications, change "inactiviation" to --inactivation--. |

Signed and Sealed this
Fifteenth Day of February, 2011

David J. Kappos
*Director of the United States Patent and Trademark Office*

CERTIFICATE OF CORRECTION (continued)
U.S. Pat. No. 7,761,130 B2

| Column | Line | |
|---|---|---|
| (Item 56) Page 7 Col. 1 | 50 | Under Other Publications, change "Membran," to --Membrane,--. |
| (Item 56) Page 7 Col. 2 | 58 | Under Other Publications, change "2008, 2008" to --2008--. |
| Sheet 5 of 24 (Reference Numeral 36) (FIG. 4) | 3 | Change "POTENTIOST" to --POTENTIOSTAT--. |
| Sheet 5 of 24 (Reference Numeral 37) (FIG. 4) | 3 | Change "POTENTIOST" to --POTENTIOSTAT--. |
| Sheet 7 of 24 (Below Reference Numeral 68) (FIG. 6) | 1 | Change "7" to --70--. |
| 2 | 43 | Change "electrode" to --electrode.--. |
| 2 | 59 | Change "vivo" to --vivo,--. |
| 4 | 52 | Change "thereon" to --thereon.--. |
| 7 | 4 | Change "andrenostenedione;" to --androstenedione;--. |
| 7 | 5-6 | Change "biotimidase;" to --biotinidase;--. |
| 7 | 19 | Change "diptheria" to --diphtheria--. |
| 7 | 25 | Change "perioxidase;" to --peroxidase;--. |
| 7 | 31 | Change "phenyloin;" to --phenytoin;--. |
| 7 | 38-39 | Change "duodenalisa," to --duodenalis,--. |
| 7 | 46 | Change "Trepenoma pallidium," to --Treponema pallidum,--. |
| 7 | 47 | Change "stomatis" to --stomatitis--. |
| 8 | 1 | Change "(barbituates," to --(barbiturates,--. |
| 10 | 26 | Change "(GOX)" to --(GOx)--. |
| 10 | 35 | Change "(GOX)" to --(GOx)--. |
| 14 | 20 | Change "lacetic" to --lactic--. |
| 16 | 19 | Change "(e.g." to --(e.g.,--. |
| 19 | 30 | Change "lacetic" to --lactic--. |
| 20 | 33 | Change "he" to --the--. |
| 21 | 33 | Change "vivo" to --vivo,--. |

CERTIFICATE OF CORRECTION (continued)
U.S. Pat. No. 7,761,130 B2

| Column | Line | |
|---|---|---|
| 22 | 45 | Change "e.g." to --e.g.,--. |
| 22 | 53 | Change "(e.g." to --(e.g.,--. |
| 22 | 54 | Change "(e.g." to --(e.g.,--. |
| 22 | 56 | Change "(e.g." to --(e.g.,--. |
| 22 | 58 | Change "(e.g." to --(e.g.,--. |
| 22 | 60 | Change "(e.g." to --(e.g.,--. |
| 23 | 2 | Change "(GOX)" to --(GOx)--. |
| 23 | 28 | Change "(e.g." to --(e.g.,--. |
| 23 | 58 | Change "Bellafonte," to --Bellefonte,--. |
| 23 | 65 | Change "(e.g." to --(e.g.,--. |
| 24 | 7 | Change "(e.g." to --(e.g.,--. |
| 24 | 8 | Change "(e.g." to --(e.g.,--. |
| 26 | 49 (Approx.) | Change "(e.g." to --(e.g.,--. |
| 27 | 55 | Change "e.g." to --e.g.,--. |
| 28 | 20 | Change "(e.g." to --(e.g.,--. |
| 28 | 31 | Change "(e.g." to --(e.g.,--. |
| 28 | 43 | Change "(e.g." to --(e.g.,--. |
| 28 | 45 | Change "e.g." to --e.g.,--. |
| 29 | 2 | Change "(e.g." to --(e.g.,--. |
| 30 | 7 | Change "(e.g." to --(e.g.,--. |
| 30 | 15 | Change "(e.g." to --(e.g.,--. |
| 30 | 21 | Change "(e.g." to --(e.g.,--. |
| 30 | 24 | Change "(e.g." to --(e.g.,--. |
| 30 | 26 | Change "(e.g." to --(e.g.,--. |
| 30 | 45 | Change "(e.g." to --(e.g.,--. |
| 30 | 47 | Change "(e.g." to --(e.g.,--. |
| 30 | 49 | Change "(e.g." to --(e.g.,--. |
| 30 | 52 | Change "(e.g." to --(e.g.,--. |
| 30 | 62 | Change "(e.g." to --(e.g.,--. |
| 31 | 44 | Change "(e.g." to --(e.g.,--. |
| 31 | 56 | Change "(e.g." to --(e.g.,--. |
| 31 | 65 | Change "(e.g." to --(e.g.,--. |
| 32 | 48 | Change "(e.g." to --(e.g.,--. |
| 32 | 51 | Change "(e.g." to --(e.g.,--. |
| 32 | 58 | Change "(e.g." to --(e.g.,--. |
| 32 | 58 | Change "e.g." to --e.g.,--. |
| 33 | 58 | Change "(e.g." to --(e.g.,--. |
| 34 | 8 | Change "(e.g." to --(e.g.,--. |
| 34 | 20 | Change "(e.g." to --(e.g.,--. |
| 34 | 42 | Change "(e.g." to --(e.g.,--. |
| 38 | 30 | Change "posses" to --possess--. |
| 42 | 45 | Change "(IRP)" to --(HRP)--. |

CERTIFICATE OF CORRECTION (continued)
U.S. Pat. No. 7,761,130 B2

| Column | Line | |
|---|---|---|
| 44 | 56 | Change "and or" to --and/or--. |
| 45 | 25 | Change "(L-lacetic" to --(L-lactic--. |
| 45 | 26 | Change "hydroxyapeptite," to --hydroxyapatite,--. |
| 45 | 28 | Change "nintinol," to --nitinol,--. |
| 45 | 33 | Change "(e.g." to --(e.g.,--. |
| 45 | 36 | Change "(e.g." to --(e.g.,--. |
| 47 | 16 | Change "(L-lacetic" to --(L-lactic--. |
| 48 | 47 | Change "(MMT)," to --(MMP),--. |
| 48 | 60 | Change "Lacetic" to --Lactic--. |
| 48 | 63 | Change "glenipin," to --genipin,--. |
| 49 | 48 | Change "lacetic" to --lactic--. |
| 49 | 48-49 | Change "polydioxone," to --polydioxanone,--. |
| 51 | 60 | Change "betamethesone," to --betamethasone,--. |
| 52 | 2 | Change "infiximab)," to --infliximab),--. |
| 52 | 5 | Change "methothrexate," to --methotrexate,--. |
| 52 | 8 | Change "batimstat," to --batimastat,--. |
| 52 | 12 | Change "Tesosentan," to --Tezosentan,--. |
| 52 | 13 | Change "Cerivasttin)," to --Cerivastatin),--. |
| 52 | 16 | Change "aminoclycosides" to --aminoglycosides--. |
| 55 | 54 | Change "(Supleco," to --(Supelco,--. |
| 56 | 46-47 (Approx.) | Change "phenyldimethylpropytrimethoxysilane," to --phenyldimethylpropyltrimethoxysilane,--. |
| 56 | 58 (Approx.) | Change "pestal," to --pestle,--. |
| 58 | 61 | Change "(e.g." to --(e.g.,--. |
| 66 | 18 | Change "(e.g." to --(e.g.,--. |
| 71 | 58 | Change "there between." to --therebetween.--. |
| 77 | 57 | Change "further" to --farther--. |
| 79 | 15 | Change "the a" to --the--. |
| 83 | 54 | Change "further" to --farther--. |
| 85 | 24 | Change "705" to --(705--. |
| 90 | 9 | Change "lacetic" to --lactic--. |
| 92 | 29 | Change "GOX" to --GOx--. |
| 93 | 44 | Change "B." to --B,--. |

CERTIFICATE OF CORRECTION (continued)
U.S. Pat. No. 7,761,130 B2

| Column | Line | |
|---|---|---|
| 94 | 16 | Change "barrier" to --barrier.--. |
| 95 | 43 | Change "vivo" to --vivo,--. |
| 97 | 34 | Change "corn" to --com--. |
| 98 | 31 | Change "corn" to --com--. |
| 98 | 56 | Change "GOX" to --GOx--. |
| 100 | 29 | Change "B." to --B,--. |
| 106 | 38 | Change "there of)." to --thereof).--. |
| 107 | 26 | Change "GOX)" to --GOx)--. |
| 110 | 66 | Change "40" to --~40--. |
| 111 | 57 | Change "No." to --Nos.--. |

UNITED STATES PATENT AND TRADEMARK OFFICE
CERTIFICATE OF CORRECTION

PATENT NO. : 7,761,130 B2
APPLICATION NO. : 11/692154
DATED : July 20, 2010
INVENTOR(S) : Peter C. Simpson et al.

Page 1 of 1

It is certified that error appears in the above-identified patent and that said Letters Patent is hereby corrected as shown below:

On the Title Page

Item (63) under "Related U.S. Application Data" after "Provisional application No. 60/527,323, filed on Dec. 5, 2003, provisional application No. 60/587,787, filed on Jul. 13, 2004", please insert --, provisional application No. 60/614,683, filed on Sep. 30, 2004--.

Signed and Sealed this
Tenth Day of April, 2012

David J. Kappos
*Director of the United States Patent and Trademark Office*